(12) United States Patent
Furuya et al.

(10) Patent No.: US 7,569,570 B2  
(45) Date of Patent: Aug. 4, 2009

(54) THIENOPYRIMIDINES, PROCESS FOR PREPARING THE SAME AND USE THEREOF

(75) Inventors: Shuichi Furuya, Kobe (JP); Takashi Imada, Takarazuka (JP); Takenori Hitaka, Takarazuka (JP); Kazuhiro Miwa, Kyoto (JP); Masami Kusaka, Kobe (JP); Nobuhiro Suzuki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 235 days.

(21) Appl. No.: 10/502,903

(22) PCT Filed: Jan. 29, 2003

(86) PCT No.: PCT/JP03/00828

§ 371 (c)(1), (2), (4) Date: Jul. 28, 2004

(87) PCT Pub. No.: WO03/064429

PCT Pub. Date: Aug. 7, 2003

(65) Prior Publication Data

US 2005/0222174 A1  Oct. 6, 2005

(30) Foreign Application Priority Data

Jan. 30, 2002  (JP) ............... 2002-022034

(51) Int. Cl.  
*A61K 31/519* (2006.01)  
*C07D 495/04* (2006.01)

(52) U.S. Cl. .................... 514/260.1; 544/278

(58) Field of Classification Search ........... 544/278; 514/260.1  
See application file for complete search history.

(56) References Cited

U.S. PATENT DOCUMENTS

| | | |
|---|---|---|
| 5,817,819 A | 10/1998 | Furuya et al. |
| 6,048,863 A | 4/2000 | Furuya et al. |
| 6,262,267 B1 | 7/2001 | Furuya et al. |
| 6,297,255 B1 | 10/2001 | Furuya et al. |
| 6,297,379 B1 * | 10/2001 | Furuya et al. ............ 544/278 |
| 6,329,388 B2 | 12/2001 | Furuya et al. |
| 6,340,686 B1 * | 1/2002 | Furuya et al. ............ 514/260.1 |
| 2003/0134863 A1 | 7/2003 | Furuya et al. |
| 2003/0176360 A1 | 9/2003 | Igari et al. |
| 2004/0034039 A1 | 2/2004 | Nakano et al. |

FOREIGN PATENT DOCUMENTS

| | | |
|---|---|---|
| EP | 1266898 A1 | 12/2002 |
| EP | 1291023 A1 | 3/2003 |
| JP | 09208496 A2 | 8/1997 |
| JP | 2003026601 A2 | 1/2003 |

OTHER PUBLICATIONS

Jones et al, "British Society of Gastroenterology guidelines for the management of the irritable bowel syndrome." Gut 2000, (Suppl II)47:ii1-ii19.*

S. Sasaki, et al., "Discovery of a Thieno[2,3-d]pyrimidine-2,4-dione Bearing a p-Methoxyureidophenyl Moiety at the 6-Position: A Highly Potent and Orally Bioavailable Non-Peptide Antagonist for the Human Luteinizing Hormone-Releasing Hormone Receptor", J. Med. Chem. (2003), pp. 113-124, vol. 46.

* cited by examiner

*Primary Examiner*—Brenda L Coleman  
*Assistant Examiner*—Susanna Moore  
(74) *Attorney, Agent, or Firm*—Sughrue Mion, PLLC

(57) ABSTRACT

The present invention provides a thienopyrimidine compound, represented by the formula

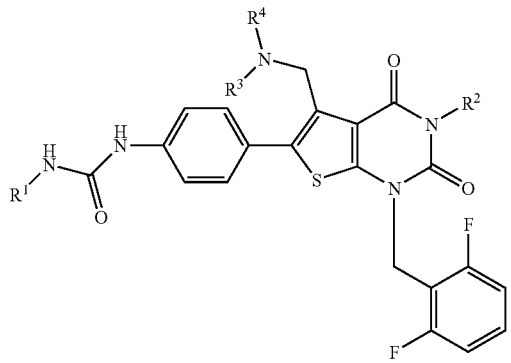

[wherein, $R^1$ is $C_{1-4}$ alkyl, $R^2$ is (1) phenyl optionally having a substituent such as amino, mono $C_{1-4}$ alkylamino and di $C_{1-4}$ alkylamino, or (2) a heterocyclic group optionally having a substituent such as amino, mono $C_{1-4}$ alkylamino and di $C_{1-4}$ alkylamino and the like, $R^3$ is a hydrogen atom or $C_{1-4}$ alkyl, $R^4$ is $C_{1-4}$ alkyl optionally having a substituent such as $C_{1-4}$ alkoxy-carbonyl, carboxyl, mono $C_{1-4}$ alkylamino and N—$C_{1-4}$ alkyl-N—$C_{7-10}$ aralkylamino and the like] or a salt thereof, which has antagonistic action for gonadotropin-releasing hormone.

11 Claims, No Drawings

THIENOPYRIMIDINES, PROCESS FOR PREPARING THE SAME AND USE THEREOF

This application is the National Phase filing of International Patent Application No. PCT/JP03/00828, filed Jan. 29, 2003.

TECHNICAL FIELD

The present invention relates to thieno[2,3-d]pyrimidine compounds exhibiting gonadotropin releasing hormone (GnRH) antagonizing activity, their production and use.

BACKGROUND ART

Secretion of anterior pituitary hormones undergoes feedback control by peripheral hormones secreted from target organs of the respective hormones and by secretion-regulating hormones from the hypothalamus, which is the upper central organ of the anterior lobe of the pituitary (hereinafter, these hormones are collectively called "hypothalamic hormones" in this specification). So far, the existence of nine kinds of hypothalamic hormones including, for example, thyrotropin releasing hormone (TRH), gonadotropin releasing hormone [GnRH, sometimes called LH-RH (luteinizing hormone releasing hormone)] and the like has been confirmed. These hypothalamic hormones are believed to show their actions via the receptors which are considered to exist in the anterior lobe of the pituitary, and analysis of the receptor-gene specific to these hormones, including for humans, has been made. Accordingly, antagonists or agonists specifically and selectively acting on these receptors should control the action of the hypothalamic hormone and the secretion of anterior pituitary hormone. As a result, such antagonists or agonists are expected to be useful in preventing or treating anterior pituitary hormone-dependent diseases.

Known compounds possessing GnRH-antagonizing activity include GnRH-derived linear peptides (U.S. Pat. Nos. 5,140,009 and 5,171,835), a cyclic hexapeptide derivative (JP-A-61-191698), a bicyclic peptide derivative [Journal of Medicinal Chemistry, Vol. 36, pp. 3265-3273 (1993)] and the like. Non-peptide compounds possessing GnRH-antagonizing activity include compounds described in WO 95/28405 (JP-A-8-295693), WO 96/24597 (JP-A-9-169768), WO 97/14682 (JP-A-9-169735), WO 97/14697 (JP-A-9-169767), WO 99/33831 (JP-A-11-315079), WO 00/00493 (JP-A-2000-219691), WO 00/56739 (JP-A-2001-278884) and JP-A-2002-30087 etc.

Peptide compounds have many problems to be resolved with respect to oral absorbability, dosage form, dose volume, drug stability, duration of action, stability to metabolism and the like. There is a strong demand for a GnRH antagonist, especially one based on a non-peptide compound, that has excellent therapeutic effect on hormone-dependent cancers, e.g., prostatic cancer, endometriosis, precocious puberty and the like, and further that does not show transient pituitary-gonadotropic action (acute action) and that has excellent oral absorption.

DISCLOSURE OF INVENTION

The present inventors have studied extensively and, as a result, have synthesized a novel compound of the formula (I) below, or a salt thereof, which is characterized in the chemical structure that 3-$C_{1-4}$ alkylureide is substituted on the para-position of the phenyl group of the 6-position of the thieno [2,3-d]pyrimidine skeleton:

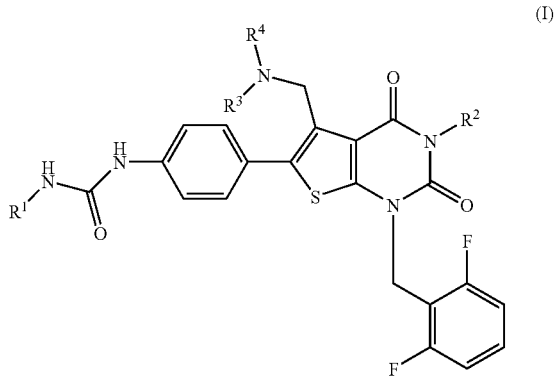

wherein $R^1$ is $C_{1-4}$ alkyl, $R^2$ is (I) phenyl optionally having 1 to 3 substituents selected from (1) amino, (2) mono $C_{1-4}$ alkylamino, (3) di $C_{1-4}$ alkylamino, (4) —$NR^5COR^6$ ($R^5$ is a hydrogen atom or $C_{1-4}$ alkyl, and $R^6$ is $C_{1-4}$ alkyl, mono $C_{1-4}$ alkylamino or di $C_{1-4}$ alkylamino), (5) —$NR^7SO_2R^8$ ($R^7$ is a hydrogen atom or $C_{1-4}$ alkyl, and $R^8$ is $C_{1-4}$ alkyl, mono $C_{1-4}$ alkylamino or di $C_{1-4}$ alkylamino), (6) —$CONR^9R^{10}$ ($R^9$ is a hydrogen atom, or $C_{1-4}$ alkyl or $C_{3-8}$ cycloalkyl optionally having $C_{1-4}$ alkoxy, $R^{10}$ is a hydrogen atom or $C_{1-4}$ alkyl, or $R^9$ and $R^{10}$ may form a ring together with the adjacent nitrogen atom), (7) —$SO_2NR^{11}R^{12}$ ($R^{11}$ is a hydrogen atom, or $C_{1-4}$ alkyl or $C_{3-8}$ cycloalkyl optionally having $C_{1-4}$ alkoxy, $R^{12}$ is a hydrogen atom or $C_{1-4}$ alkyl, or $R^{11}$ and $R^{12}$ may form a ring together with the adjacent nitrogen atom), (8) —$CO_2R^{13}$ ($R^{13}$ is $C_{1-4}$ alkyl), (9) $C_{1-4}$ alkoxy optionally having a hydroxyl group, $C_{1-4}$ alkoxy, $C_{1-4}$ alkyl-carbonyloxy, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above) or —$CO_2R^{13}$ ($R^{13}$ is as defined above), (10) $C_{1-4}$ alkyl optionally having a hydroxyl group, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above), —$CO_2R^{13}$ ($R^{13}$ is as defined above) or $C_{1-4}$ alkoxy, (11) a halogen atom, (12) a hydroxyl group and (13) nitro (hereinafter, referred to briefly as substituent group A), (II) a heterocyclic group optionally having 1 to 3 substituents selected from above-mentioned substituent group A and oxo, (III) $C_{3-8}$ cycloalkyl optionally having 1 to 3 substituents selected from above-mentioned substituent group A or (IV) $C_{1-4}$ alkyl optionally having 1 to 3 substituents selected from (1) a 5 to 7-membered nitrogen-containing heterocyclic group, (2) a hydroxyl group and (3) $C_{1-4}$ alkoxy, $R^3$ is a hydrogen atom or $C_{1-4}$ alkyl, $R^4$ is (I) $C_{1-4}$ alkyl optionally having 1 to 3 substituents selected from (1) $C_{1-4}$ alkoxy optionally having $C_{1-4}$ alkoxy, (2) —$NR^{14}COR^{15}$ ($R^{14}$ is a hydrogen atom or $C_{1-4}$ alkyl and $R^{15}$ is $C_{1-4}$ alkyl), (3) —$NR^{16}SO_2R^{17}$ ($R^{16}$ is a hydrogen atom or $C_{1-4}$ alkyl and $R^{17}$ is $C_{1-4}$ alkyl), (4) —$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (5) —$SO_2NR^{20}R^{21}$ ($R^{20}$ is a hydrogen atom or $C_{1-4}$ alkyl, $R^{21}$ is $C_{1-4}$ alkyl optionally having $C_{1-4}$ alkoxy, or $R^{20}$ and $R^{21}$ may form a ring together with the adjacent nitrogen atom), (6) a 5 to 7-membered nitrogen-containing heterocyclic group optionally having (1') hydroxy-$C_{1-4}$ alkyl, (2') $C_{1-4}$ alkoxy-carbonyl, (3') mono $C_{1-4}$ alkyl-carbamoyl or (4') di $C_{1-4}$ alkyl-carbamoyl, (7) $C_{1-4}$ alkoxy-carbonyl, (8) carboxyl, (9) mono $C_{1-4}$ alkylamino and (10) N—$C_{1-4}$ alkyl-N—$C_{7-10}$ aralkylamino (hereinafter, referred to briefly as substituent group B) or (II) $C_{3-8}$ cycloalkyl optionally having 1 to 3 substituents selected from above-mentioned substituent group B (provided that when $R^2$ is phenyl which is mono-substituted with a halogen atom, $R^4$ is not $C_{1-4}$ alkyl which is substituted with $C_{1-4}$ alkoxy) [hereinafter, it may be referred to briefly as Compound (I)]. Further, the inventors also have found for the first time that Compound (I) has an unexpected, excellent GnRH-antagonizing activity, in particular strong antagonist activity, based upon the specific chemical structure, and very low toxicity and is therefore satisfactory as a medi Cine having GnRH-antagonizing activity, and completed the present invention based on this finding.

Accordingly, the present invention relates to:

[1] a compound represented by the formula

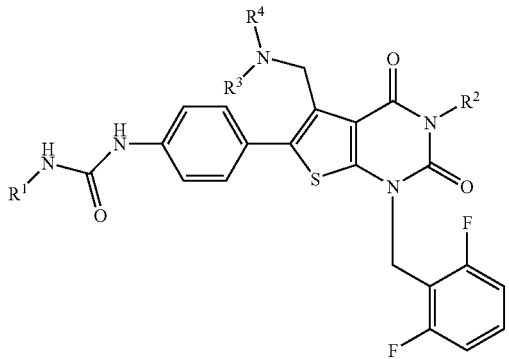

wherein $R^1$ is $C_{1-4}$ alkyl, $R^2$ is (I) phenyl optionally having 1 to 3 substituents selected from (1) amino, (2) mono $C_{1-4}$ alkylamino, (3) di $C_{1-4}$ alkylamino, (4) —$NR^5COR^6$ ($R^5$ is a hydrogen atom or $C_{1-4}$ alkyl, and $R^6$ is $C_{1-4}$ alkyl, mono —$C_{1-4}$ alkylamino or di $C_{1-4}$ alkylamino), (5) —$NR^7SO_2R^8$ ($R^7$ is a hydrogen atom or $C_{1-4}$ alkyl, and $R^8$ is $C_{1-4}$ alkyl, mono $C_{1-4}$ alkylamino or di $C_{1-4}$ alkylamino), (6) —$CONR^9R^{10}$ ($R^9$ is a hydrogen atom, or $C_{1-4}$ alkyl or $C_{3-8}$ cycloalkyl optionally having $C_{1-4}$ alkoxy, $R^{10}$ is a hydrogen atom or $C_{1-4}$ alkyl, or $R^9$ and $R^{10}$ may form a ring together with the adjacent nitrogen atom), (7) —$SO_2NR^{11}R^{12}$ ($R^{11}$ is a hydrogen atom, or $C_{1-4}$ alkyl or $C_{3-8}$ cycloalkyl optionally having $C_{1-4}$ alkoxy, $R^{12}$ is a hydrogen atom or $C_{1-4}$ alkyl, or $R^{11}$ and $R^{12}$ may form a ring together with the adjacent nitrogen atom), (8) —$CO_2R^{13}$ ($R^{13}$ is $C_{1-4}$ alkyl), (9) $C_{1-4}$ alkoxy optionally having a hydroxyl group, $C_{1-4}$ alkoxy, $C_{1-4}$ alkyl-carbonyloxy, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above) or —$CO_2R^{13}$ ($R^{13}$ is as defined above), (10) $C_{1-4}$ alkyl optionally having a hydroxyl group, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above), —$CO_2R^{13}$ ($R^{13}$ is as defined above) or $C_{1-4}$ alkoxy, (11) a halogen atom, (12) a hydroxyl group and (13) nitro (hereinafter, referred to briefly as substituent group A), (II) a heterocyclic group optionally having 1 to 3 substituents selected from above-mentioned substituent group A and oxo, (III) $C_{3-8}$ cycloalkyl optionally having 1 to 3 substituents selected from above-mentioned substituent group A or (IV) $C_{1-4}$ alkyl optionally having 1 to 3 substituents selected from (1) a 5 to 7-membered nitrogen-containing heterocyclic group, (2) a hydroxyl group and (3) $C_{1-4}$ alkoxy, $R^3$ is a hydrogen atom or $C_{1-4}$ alkyl, and $R^4$ is (I) $C_{1-4}$ alkyl optionally having 1 to 3 substituents selected from (1) $C_{1-4}$ alkoxy optionally having $C_{1-4}$ alkoxy, (2) —$NR^{14}COR^{15}$ ($R^{14}$ is a hydrogen atom or $C_{1-4}$ alkyl and $R^{15}$ is $C_{1-4}$ alkyl), (3) —$NR^{16}SO_2R^{17}$ ($R^{16}$ is a hydrogen atom or $C_{1-4}$ alkyl and $R^{17}$ is $C_{1-4}$ alkyl), (4) —$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (5) —$SO_2NR^{20}R^{21}$ ($R^{20}$ is a hydrogen atom or $C_{1-4}$ alkyl, $R^{21}$ is $C_{1-4}$ alkyl optionally having $C_{1-4}$ alkoxy; or $R^{20}$ and $R^{21}$ may form a ring together with the adjacent nitrogen atom), (6) a 5 to 7-membered nitrogen-containing heterocyclic group optionally having (1') hydroxy-$C_{1-4}$ alkyl, (2') $C_{1-4}$ alkoxy-carbonyl, (3') mono $C_{1-4}$ alkyl-carbamoyl or (4') di $C_{1-4}$ alkyl-carbamoyl, (7) $C_{1-4}$ alkoxy-carbonyl, (8) carboxyl, (9) mono $C_{1-4}$ alkylamino and (10) N—$C_{1-4}$ alkyl-N—$C_{7-10}$ aralkylamino (hereinafter, referred to briefly as substituent group B) or (II) $C_{3-8}$ cycloalkyl optionally having 1 to 3 substituents selected from above-mentioned substituent group B (provided that when $R^2$ is phenyl which is mono-substituted with a halogen atom, $R^4$ is not $C_{1-4}$ alkyl which is substituted with $C_{1-4}$ alkoxy) or salt thereof;

[2] the compound as described in above-mentioned [1] wherein $R^1$ is $C_{1-4}$ alkyl, $R^2$ is (I) phenyl optionally having 1 to 3 substituents selected from (1) amino, (2) mono $C_{1-4}$ alkylamino, (3) di $C_{1-4}$ alkylamino, (4) —$NR^5COR^6$ ($R^5$ is a hydrogen atom or $C_{1-4}$ alkyl, and $R^6$ is $C_{1-4}$ alkyl, mono $C_{1-4}$ alkylamino or di $C_{1-4}$ alkylamino), (5) —$NR^7SO_2R^8$ ($R^7$ is a hydrogen atom or $C_{1-4}$ alkyl, and $R^8$ is $C_{1-4}$ alkyl, mono $C_{1-4}$ alkylamino or di $C_{1-4}$ alkylamino), (6) —$CONR^9R^{10}$ ($R^9$ is a hydrogen atom, or $C_{1-4}$ alkyl or $C_{3-8}$ cycloalkyl optionally having $C_{1-4}$ alkoxy, $R^{10}$ is a hydrogen atom or $C_{1-4}$ alkyl, or $R^9$ and $R^{10}$ may form a ring together with the adjacent nitrogen atom), (7) —$SO_2NR^{11}R^{12}$ ($R^{11}$ is a hydrogen atom, or $C_{1-4}$ alkyl or $C_{3-8}$ cycloalkyl optionally having $C_{1-4}$ alkoxy, $R^{12}$ is a hydrogen atom or $C_{1-4}$ alkyl, or $R^{11}$ and $R^{12}$ may form a ring together with the adjacent nitrogen atom), (8) —$CO_2R^{13}$ ($R^{13}$ is $C_{1-4}$ alkyl), (9) $C_{1-4}$ alkoxy optionally having a hydroxyl group, $C_{1-4}$ alkoxy, $C_{1-4}$ alkyl-carbonyloxy, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above) or —$CO_2R^{13}$ ($R^{13}$ is as defined above), (10) $C_{1-4}$ alkyl optionally having a hydroxyl group, —$NR^5COR^6$ ($R^5$ and $R^6$ are as defined above), —$NR^7SO_2R^8$ ($R^7$ and $R^8$ are as defined above), —$CONR^9R^{10}$ ($R^9$ and $R^{10}$ are as defined above), —$SO_2NR^{11}R^{12}$ ($R^{11}$ and $R^{12}$ are as defined above), —$CO_2R^{13}$ ($R^{13}$ is as defined above) or $C_{1-4}$ alkoxy, (11) a halogen atom, (12) a hydroxyl group and (13) nitro (hereinafter, referred to briefly as substituent group A), (II) a heterocyclic group optionally having 1 to 3 substituents selected from above-mentioned substituent group A and oxo or (III) $C_{3-8}$ cycloalkyl optionally having 1 to 3 substituents selected from above-mentioned substituent group A, $R^3$ is a hydrogen atom or $C_{1-4}$ alkyl, and $R^4$ is (I) $C_{1-4}$ alkyl optionally having 1 to 3 substituents selected from (1) $C_{1-4}$ alkoxy optionally having $C_{1-4}$ alkoxy, (2) —NR$^{14}$COR$^{15}$ (R$^{14}$ is a hydrogen atom or C$_{1-4}$ alkyl and R$^{15}$ is C$_{1-4}$ alkyl), (3) —NR$^{16}$SO$_2$R$^{17}$ (R$^{16}$ is a hydrogen atom or C$_{1-4}$ alkyl and R$^{17}$ is C$_{1-4}$ alkyl), (4) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (5) —SO$_2$NR$^{20}$R$^{21}$ (R$^{20}$ is a hydrogen atom or C$_{1-4}$ alkyl, R$^{21}$ is C$_{1-4}$ alkyl optionally having C$_{1-4}$ alkoxy, or R$^{20}$ and R$^{21}$ may form a ring together with the adjacent nitrogen atom), (6) a 5 to 7-membered nitrogen-containing heterocyclic group, (7) C$_{1-4}$ alkoxy-carbonyl, (8) carboxyl, (9) mono C$_{1-4}$ alkylamino and (10) N—C$_{1-4}$ alkyl-N—C$_{7-10}$ aralkylamino (hereinafter, referred to briefly as substituent group B') or (II) C$_{3-8}$ cycloalkyl optionally having 1 to 3 substituents selected from above-mentioned substituent group B';

[3] the compound as described in above-mentioned [1] wherein R$^1$ is C$_{1-4}$ alkyl, R$^2$ is (I) phenyl optionally having 1 to 3 substituents selected from (1) amino, (2) —NHCOR$^{6'}$ (R$^{6'}$ is C$_{1-4}$ alkyl or mono C$_{1-4}$ alkylamino), (3) —CONR$^9$R$^{10}$ (R$^9$ is a hydrogen atom, or C$_{1-4}$ alkyl or C$_{3-8}$ cycloalkyl optionally having C$_{1-4}$ alkoxy, R$^{10}$ is a hydrogen atom or C$_{1-4}$ alkyl, or R$^9$ and R$^{10}$ may form a ring together with the adjacent nitrogen atom), (4) —CO$_2$R$^{13}$ (R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy, —NHSO$_2$R$^{8'}$ (R$^{8'}$ is C$_{1-4}$ alkyl) or —CONR$^9$R$^{10}$ (R$^9$ and R$^{10}$ are as defined above), (6) C$_{1-4}$ alkyl optionally having a hydroxyl group, —CONR$^9$R$^{10}$ (R$^9$ and R$^{10}$ are as defined above) or C$_{1-4}$ alkoxy, (7) a halogen atom, (8) a hydroxyl group and (9) nitro, (II) a 5 to 8-membered nitrogen-containing heterocyclic group optionally having (1) C$_{1-4}$ alkyl optionally having —CONR$^9$R$^{10}$ (R$^9$ and R$^{10}$ are as defined above), (2) C$_{1-4}$ alkoxy optionally having C$_{1-4}$ alkyl-carbonyloxy or —CONR$^9$R$^{10}$ (R$^9$ and R$^{10}$ are as defined above)(3) a halogen atom, (4) a hydroxyl group or (5) oxo, (III) C$_{3-8}$ cycloalkyl optionally having a hydroxyl group or (IV) C$_{1-4}$ alkyl optionally having 1 to 3 substituents selected from (1) a 5 to 7-membered nitrogen-containing heterocyclic group, (2) a hydroxyl group and (3) C$_{1-4}$ alkoxy, R$^3$ is a hydrogen atom or C$_{1-4}$ alkyl, and R$^4$ is (I) C$_{1-4}$ alkyl optionally having 1 to 3 substituents selected from (1) C$_{1-4}$ alkoxy optionally having C$_{1-4}$ alkoxy, (2) —NR$^{14}$COR$^{15}$ (R$^{14}$ is a hydrogen atom or C$_{1-4}$ alkyl and R$^{15}$ is C$_{1-4}$ alkyl), (3) —NR$^{16}$SO$_2$R$^{17}$ (R$^{16}$ is a hydrogen atom or C$_{1-4}$ alkyl and R$^{17}$ is C$_{1-4}$ alkyl), (4) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (5) a 5 to 7-membered nitrogen-containing heterocyclic group optionally having (1') hydroxy-C$_{1-4}$ alkyl, (2') C$_{1-4}$ alkoxy-carbonyl or (3') mono C$_{1-4}$ alkyl-carbamoyl, (6) C$_{1-4}$ alkoxy-carbonyl, (7) carboxyl, (8) mono C$_{1-4}$ alkylamino and (9) N—C$_{1-4}$ alkyl-N—C$_{7-10}$ aralkylamino or (II) C$_{3-8}$ cycloalkyl;

[4] the compound as described in above-mentioned [1] wherein R$^1$ is ethyl;

[5] the compound as described in above-mentioned [1] wherein R$^2$ is phenyl optionally having 1 to 3 substituents selected from (1) amino, (2) —NHCOR$^{6'}$ (R$^{6'}$ is C$_{1-4}$ alkyl or mono C$_{1-4}$ alkylamino), (3) —CONR$^{9'}$R$^{10'}$ (R$^{9'}$ is a hydrogen atom, C$_{1-4}$ alkyl or C$_{3-8}$ cycloalkyl, R$^{10'}$ is a hydrogen atom or C$_{1-4}$ alkyl, or R$^{9'}$ and R$^{10'}$ may form a ring together with the adjacent nitrogen atom), (4) —CO$_2$R$^{13}$ (R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy or —CONR$^{9'}$R$^{10'}$ (R$^{9'}$ and R$^{10'}$ are as defined above), (6) C$_{1-4}$ alkyl optionally having a hydroxyl group or —CONR$^{9'}$R$^{10'}$ (R$^{9'}$ and R$^{10'}$ are as defined above), (7) a halogen atom, (8) a hydroxyl group and (9) nitro;

[6] the compound as described in above-mentioned [1] wherein R$^3$ is methyl;

[7] the compound as described in above-mentioned [1] wherein R$^4$ is C$_{1-4}$ alkyl optionally having 1 to 3 substituents selected from (1) —NR$^{14}$COR$^{15}$ (R$^{14}$ is a hydrogen atom or C$_{1-4}$ alkyl and R$^{15}$ is C$_{1-4}$ alkyl), (2) —NR$^{16}$SO$_2$R$^{17}$ (R$^{16}$ is a hydrogen atom or C$_{1-4}$ alkyl and R$^{17}$ is C$_{1-4}$ alkyl), (3) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (4) a 5 to 7-membered nitrogen-containing heterocyclic group, (5) C$_{1-4}$ alkoxy-carbonyl, (6) carboxyl, (7) mono C$_{1-4}$ alkylamino and (8) N—C$_{1-4}$ alkyl-N—C$_{7-10}$ aralkylamino;

[8] the compound as described in above-mentioned [1] wherein R$^4$ is C$_{1-4}$ alkyl which is substituted with C$_{1-4}$ alkoxy;

[9] the compound as described in above-mentioned [1] wherein R$^4$ is 2-methoxyethyl;

[10] the compound as described in above-mentioned [1] wherein R$^1$ is ethyl;

R$^2$ is phenyl optionally having 1 to 3 substituents selected from (1) amino, (2) —NHCOR$^{6'}$ (R$^{6'}$ is C$_{1-4}$ alkyl or mono C$_{1-4}$ alkylamino), (3) —CONR$^{9'}$R$^{10'}$ (R$^{9'}$ is a hydrogen atom, C$_{1-4}$ alkyl or C$_{3-8}$ cycloalkyl, R$^{10'}$ is a hydrogen atom or C$_{1-4}$ alkyl, or R$^{9'}$ and R$^{10'}$ may form a ring together with the adjacent nitrogen atom), (4) —CO$_2$R$^{13}$ (R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy or —CONR$^{9'}$R$^{10'}$ (R$^{9'}$ and R$^{10'}$ are as defined above), (6) C$_{1-4}$ alkyl optionally having a hydroxyl group or —CONR$^{9'}$R$^{10'}$ (R$^{9'}$ and R$^{10'}$ are as defined above), (7) a halogen atom, (8) a hydroxyl group and (9) nitro, R$^3$ is methyl, and R$^4$ is C$_{1-4}$ alkyl optionally having 1 to 3 substituents selected from (1) —NR$^{14}$COR$^{15}$ (R$^{14}$ is a hydrogen atom or C$_{1-4}$ alkyl and R$^{15}$ is C$_{1-4}$ alkyl), (2) —NR$^{16}$SO$_2$R$^{17}$ (R$^{16}$ is a hydrogen atom or C$_{1-4}$ alkyl and R$^{17}$ is C$_{1-4}$ alkyl), (3) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (4) a 5 to 7-membered nitrogen-containing heterocyclic group, (5) C$_{1-4}$ alkoxy-carbonyl, (6) carboxyl, (7) mono C$_{1-4}$ alkylamino and (8) N—C$_{1-4}$ alkyl-N—C$_{7-10}$ aralkylamino;

[11] the compound as described in above-mentioned [1] wherein R$^1$ is ethyl,

R$^2$ is phenyl optionally having 1 to 3 substituents selected from (1) amino, (2) —NHCOR$^{6'}$ (R$^{6'}$ is C$_{1-4}$ alkyl or mono C$_{1-4}$ alkylamino), (3) —CONR$^{9'}$R$^{10'}$ (R$^{9'}$ is a hydrogen atom, C$_{1-4}$ alkyl or C$_{3-8}$ cycloalkyl, R$^{10'}$ is a hydrogen atom or C$_{1-4}$ alkyl, or R$^{9'}$ and R$^{10'}$ may form a ring together with the adjacent nitrogen atom), (4) —CO$_2$R$^{13}$ (R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy or —CONR$^{9'}$R$^{10'}$ (R$^{9'}$ and R$^{10'}$ are as defined above), (6) C$_{1-4}$ alkyl optionally having a hydroxyl group or —CONR$^{9'}$R$^{10'}$ (R$^{9'}$ and R$^{10'}$ are as defined above), (7) a halogen atom, (8) a hydroxyl group and (9) nitro, R$^3$ is methyl, and R$^4$ is 2-methoxyethyl;

[12] 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3-(2H)-yl)phenyl]-N-methylacetamide, 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3-

(2H)-yl)phenoxy]-N-ethylacetamide, N-{4-[1-(2,6-difluorobenzyl)-5-{[(2-methoxyethyl)(methyl)amino]methyl}-3-(4-methoxy-3-methylphenyl)-2,4-dioxo-1,2,3,4-tetrahydrothieno[2,3-d]pyrimidin-6-yl]phenyl}-N'-ethylurea, N-{4-[1-(2,6-difluorobenzyl)-3-(4-fluorophenyl)-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea, N-{4-[1-(2,6-difluorobenzyl)-3-[4-(2-methoxyethoxy)phenyl]-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea, N-{2-[{[1-(2,6-difluorobenzyl)-6-(4-{[(ethylamino)carbonyl]amino}phenyl)-3-(4-fluorophenyl)-2,4-dioxo-1,2,3,4-tetrahydrothieno[2,3-d]pyrimidin-5-yl]methyl}(methyl)amino]ethyl}-N-methylsulfonamide, N-{2-[({1-(2,6-difluorobenzyl)-6-(4-{[(ethylamino)carbonyl]amino}phenyl)-3-[4-(2-methoxyethoxy)phenyl]-2,4-dioxo-1,2,3,4-tetrahydrothieno[2,3-d]pyrimidin-5-yl}methyl)(methyl)amino]ethyl}-N-methylsulfonamide, N-[4-(1-(2,6-difluorobenzyl)-5-{[[2-(2-methoxyethoxy)ethyl](methyl)amino]methyl}-2,4-dioxo-3-phenyl-1,2,3,4-tetrahydrothieno[2,3-d]pyrimidin-6-yl)phenyl]-N'-ethylurea, N-[4-(1-(2,6-difluorobenzyl)-5-{[(2-methoxyethyl)(methyl)amino]methyl}-2,4-dioxo-3-phenyl-1,2,3,4-tetrahydrothieno[2,3-d]pyrimidin-6-yl)phenyl]-N'-ethylurea, N-[4-(1-(2,6-difluorobenzyl)-5-{[(2-ethoxyethyl)(methyl)amino]methyl}-2,4-dioxo-3-(2-pyridyl)-1,2,3,4-tetrahydrothieno[2,3-d]pyrimidin-6-yl)phenyl]-N'-ethylurea, N-[4-(1-(2,6-difluorobenzyl)-5-{[(2-methoxyethyl)(methyl)amino]methyl}-2,4-dioxo-3-(5-methyl-2-pyridyl)-1,2,3,4-tetrahydrothieno[2,3-d]pyrimidin-6-yl)phenyl]-N'-ethylurea or N-[4-(1-(2,6-difluorobenzyl)-5-{[(2-methoxyethyl)(methyl)amino]methyl}-2,4-dioxo-3-(6-methyl-2-pyridyl)-1,2,3,4-tetrahydrothieno[2,3-d]pyrimidin-6-yl)phenyl]-N'-ethylurea, or a salt thereof;

[13] a prodrug of the compound as described in abovementioned [1];

[14] a pharmaceutical composition comprising the compound as described in above-mentioned [1] or a prodrug thereof;

[15] the pharmaceutical composition as described in above-mentioned [14] which is an antagonist for gonadotropin-releasing hormone,

[16] the pharmaceutical composition as described in above-mentioned [14] which is an agent for preventing or treating a sex hormone-dependent disease;

[17] the pharmaceutical composition as described in above-mentioned [14] which is an agent for preventing or treating sex hormone-dependent cancers, metastasis of the sex hormone-dependent cancers to bone, prostatic hypertrophy, hysteromyoma, endometriosis, uterine fibroid, precocious puberty, amenorrhea, premenstrual syndrome, dysmenorrhea, multilocular ovary syndrome, polycystic ovary syndrome, pimple, alopecia, Alzheimer's disease, infertility, irritable bowel syndrome or LH-RH sensitive benign or malignant tumor which is independent on the hormone, an agent for regulating reproduction, a contraceptive, an ovulation inducer or an agent for preventing recurrence of postoperative sex hormone-dependent cancers;

[18] a method for antagonizing gonadotropin-releasing hormone in a mammal in need thereof which comprises administering to said mammal an effective amount of a compound of above-mentioned [1];

[19] use of a compound of above-mentioned [1] for manufacturing an agent for antagonizing gonadotropin-releasing hormone and the like.

Definition of each substituent in the above formulae is explained in the below.

As used herein, the "$C_{1-4}$ alkyl" includes, for example, straight $C_{1-4}$ alkyl (e.g., methyl, ethyl, propyl, butyl etc.), branched $C_{3-4}$ alkyl (e.g., isopropyl, isobutyl, sec-butyl, tert-butyl etc.) and the like.

As used herein, the "$C_{3-8}$ cycloalkyl" includes cyclopropyl, cyclobutyl, cyclopentyl, cyclohexyl, cycloheptyl, cyclooctyl and the like.

As used herein, the "mono $C_{1-4}$ alkylamino" includes, for example, methylamino, ethylamino, propylamino, isopropylamino, butylamino, isobutylamino, sec-butylamino, tert-butylamino and the like.

As used herein, the "di $C_{1-4}$ alkylamino" includes, for example, dimethylamino, diethylamino, dipropylamino, diisopropylamino, dibutylamino, diisobutylamino, N-ethyl-N-methylamino, N-methyl-N-propylamino, N-ethyl-N-propylamino and the like.

As used herein, the "N—$C_{1-4}$ alkyl-N—$C_{7-10}$ aralkylamino" includes, for example, N-benzyl-N-methylamino, N-benzyl-N-ethylamino, N-benzyl-N-propylamino, N-methyl-N-phenethylamino, N-ethyl-N-phenethylamino and the like.

As used herein, the "$C_{1-4}$ alkoxy" includes, for example, straight $C_{1-4}$ alkoxy (e.g., methoxy, ethoxy, propoxy, butoxy etc.), branched $C_{3-4}$ alkoxy (e.g., isopropoxy, isobutoxy, sec-butoxy, tert-butoxy etc.) and the like.

As used herein, the "$C_{1-4}$ alkyl-carbonyloxy" includes, for example, methylcarbonyloxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy and the like.

As used herein, the "$C_{1-4}$ alkoxy-carbonyl" includes, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like.

As used herein, the "a halogen atom" includes, for example, fluorine, chlorine, bromine, iodine and the like.

As used herein, the "hydroxy-$C_{1-4}$ alkyl" includes, for example, hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl and the like.

As used herein, the "mono $C_{1-4}$ alkyl-carbamoyl" includes, for example, methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl and the like.

As used herein, the "di $C_{1-4}$ alkyl-carbamoyl" includes, for example, methylcarbamoyl, ethylcarbamoyl, propylcarbamoyl, isopropylcarbamoyl, N-ethyl-N-methylcarbamoyl and the like.

As used herein, the "the ring that $R^9$ and $R^{10}$ form together with the adjacent nitrogen atom", "the ring that $R^{11}$ and $R^{12}$ form together with the adjacent nitrogen atom", "the ring that $R^{18}$ and $R^{19}$ form together with the adjacent nitrogen atom" and "the ring that $R^{20}$ and $R^{21}$ form together with the adjacent nitrogen atom" include, for example, 5 or 6-membered nitrogen-containing heterocycle (pyrrolidine, piperidine, morpholine, 2-oxopyrrolidine, 2-oxopiperidine, oxazolidinone etc.).

As used herein, the "a heterocyclic group" represented by $R^2$ includes an aromatic heterocyclic group or a non-aromatic heterocyclic group.

The "aromatic heterocyclic group" includes, for example, a 5 or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and an 8 to 12-membered aromatic fused heterocyclic group such as benzofuranyl, isobenzofuranyl, benzo[b]thienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl (preferably, a hetero ring wherein above-mentioned 5 or 6-membered aromatic monocyclic heterocyclic group is fused with a benzene ring or a hetero ring wherein two rings of above-mentioned 5 or 6-membered aromatic monocyclic heterocyclic group, which are the same or different, are fused with each other, more preferably, a hetero ring wherein above-mentioned 5 or 6-membered aromatic monocyclic heterocyclic group is fused with a benzene ring, especially preferably, benzofuranyl, benzopyranyl, benzo[b]thienyl etc.) and the like.

The "non-aromatic heterocyclic group" includes, for example, a 3 to 8-membered saturated or unsaturated non-aromatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, 3-hexahydrocyclopenta[c]pyrrolyl, homopiperidyl and homopiperazyl, or a non-aromatic heterocyclic group in which all or some double bonds of above-mentioned aromatic monocyclic heterocyclic group or aromatic fused heterocyclic group are saturated such as dihydropyridyl, dihydropyrimidyl, 1,2,3,4-tetrahydroquinolyl and 1,2,3,4-tetrahydroisoquinolyl.

Among others, the "heterocyclic group" represented by $R^2$ is preferably a 5 to 8-membered nitrogen-containing heterocyclic group, more preferably, pyridyl, dihydropyrimidyl, piperidyl, pyrrolyl, morpholyl, 3-hexahydrocyclopenta[c]pyrrolyl, homopiperidyl and the like.

As used herein, the "5 to 7-membered nitrogen-containing heterocyclic group" in the substituent group B includes, for example, pyrrolidin-1-yl, pyrrolidin-2-yl, pyrrolidin-3-yl, 2-oxopyrrolidin-1-yl, 1-methyl-2-oxopyrrolidin-3-yl, 1-methyl sulfonylpyrrolidin-2-yl, 1-methyl sulfonylpyrrolidin-3-yl, 1-methyl-2-oxopyrrolidin-3-yl, 2-oxo-1,3-oxazolidin-3-yl, oxazolidin-3-yl, thiazolidin-3-yl, isoxazolidin-2-yl, isothiazolidin-2-yl, 2-oxo-1,3-thiazolidin-3-yl, 1,1-dioxothiazolidin-3-yl, 1,1-dioxoisothiazolidin-2-yl, 2-oxo-1,3-oxazolin-3-yl, imidazolidin-1-yl, imidazolidin-2-yl, imidazolidin-4-yl, pyrazolidin-2-yl, pyrazolidin-3-yl, pyrazolidin-4-yl, pyrrol-1-yl, pyrrol-2-yl, pyrrol-3-yl, imidazol-1-yl, imidazol-2-yl, imidazol-4-yl, pyrazol-1-yl, pyrazol-3-yl, pyrazol-4-yl, 1,2,3-triazol-1-yl, 1,2,5-triazol-1-yl, tetrazol-1-yl, tetrazol-2-yl, tetrazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, pyridin-2-yl, pyridin-3-yl, pyridin-4-yl, pirazin-2-yl, pyrimidin-2-yl, pyrimidin-4-yl, pyrimidin-5-yl, pyridazin-3-yl, pyridazin-4-yl and the like. Among others, 2-oxopyrrolidin-1-yl, 2-oxo-1,3-oxazolidin-3-yl, 1-methyl-2-oxopyrrolidin-3-yl, 1-methyl sulfonylpyrrolidin-2-yl, 1,1-dioxoisothiazolidin-2-yl, pyridin-2-yl, pyridin-3-yl, pyridin-4-yl, imidazol-1-yl, imidazol-2-yl, imidazol-4-yl, 1,2,3-triazol-1-yl, 1,2,5-triazol-1-yl, tetrazol-1-yl, tetrazol-2-yl, tetrazol-5-yl and the like are preferred. Especially, 1-methylsulfonylpyrrolidin-2-yl, 1,1-dioxo-isothiazolidin-2-yl, 1-methyl-2-oxopyrrolidin-3-yl and the like are preferred.

$R^1$ is preferably straight $C_{1-4}$ alkyl (e.g., methyl, ethyl, propyl, butyl etc.), especially preferably, ethyl.

$R^2$ is preferably (I) phenyl optionally having 1 to 3 substituents selected from (1)amino, (2) —NHCOR$^{6\prime}$ (R$^{6\prime}$ is $C_{1-4}$ alkyl or mono $C_{1-4}$ alkylamino), (3) —CONR$^9$R$^{10}$ (R$^9$ is a hydrogen atom, or $C_{1-4}$ alkyl or $C_{3-8}$ cycloalkyl optionally having $C_{1-4}$ alkoxy, R$^{10}$ is a hydrogen atom or $C_{1-4}$ alkyl, or R$^9$ and R$^{10}$ may form a ring together with the adjacent nitrogen atom), (4)—CO$_2$R$^{13}$ (R$^{13}$ is $C_{1-4}$ alkyl), (5) $C_{1-4}$ alkoxy optionally having a hydroxyl group, $C_{1-4}$ alkoxy, $C_{1-4}$ alkyl-carbonyloxy, —NHSO$_2$R$^{8\prime}$ (R$^{8\prime}$ is $C_{1-4}$ alkyl) or —CONR$^9$R$^{10}$ (R$^9$ and R$^{10}$ are as defined above), (6) $C_{1-4}$ alkyl optionally having a hydroxyl group, —CONR$^9$R$^{10}$ (R$^9$ and R$^{10}$ are as defined above) or $C_{1-4}$ alkoxy, (7) a halogen atom, (8) a hydroxyl group and (9) nitro, (II) a 5 to 8-membered nitrogen-containing heterocyclic group optionally having (1) $C_{1-4}$ alkyl optionally having —CONR$^9$R$^{10}$ (R$^9$ and R$^{10}$ are as defined above), (2) $C_{1-4}$ alkoxy optionally having $C_{1-4}$ alkyl-carbonyloxy or —CONR$^9$R$^{10}$ (R$^9$ and R$^{10}$ are as defined above) (3) a halogen atom, (4) a hydroxyl group or (5) oxo, (III) $C_{3-8}$ cycloalkyl or (IV) $C_{1-4}$ alkyl optionally having 1 to 3 substituents selected from (1) a 5 to 7-membered nitrogen-containing heterocyclic group, (2) a hydroxyl group and (3) $C_{1-4}$ alkoxy.

Among others, $R^2$ is more preferably phenyl optionally having 1 to 3 substituents selected from (1)amino, (2) —NHCOR$^{6\prime}$ (R$^{6\prime}$ is $C_{1-4}$ alkyl or mono $C_{1-4}$ alkylamino), (3) —CONR$^{9\prime}$R$^{10\prime}$ (R$^{9\prime}$ is a hydrogen atom, $C_{1-4}$ alkyl or $C_{3-8}$ cycloalkyl, R$^{10\prime}$ is a hydrogen atom or $C_{1-4}$ alkyl, or R$^{9\prime}$ and R$^{10\prime}$ may form a ring together with the adjacent nitrogen atom), (4) —CO$_2$R$^{13}$ (R$^{13}$ is $C_{1-4}$ alkyl), (5) $C_{1-4}$ alkoxy optionally having a hydroxyl group, $C_{1-4}$ alkoxy, $C_{1-4}$ alkyl-carbonyloxy or —CONR$^{9\prime}$R$^{10\prime}$ (R$^{9\prime}$ and R$^{10\prime}$ are as defined above), (6) $C_{1-4}$ alkyl optionally having a hydroxyl group or —CONR$^{9\prime}$R$^{10\prime}$ (R$^{9\prime}$ and R$^{10\prime}$ are as defined above), (7) a halogen atom, (8) a hydroxyl group and (9) nitro.

In addition, pyridyl optionally having $C_{1-4}$ alkyl is also preferred.

$R^3$ is preferably $C_{1-4}$ alkyl, more preferably straight $C_{1-4}$ alkyl (e.g., methyl, ethyl, propyl, butyl etc.). Especially, methyl is preferred.

$R^4$ is preferably (I) $C_{1-4}$ alkyl optionally having 1 to 3 substituents selected from (1) —NR$^{14}$COR$^{15}$ (R$^{14}$ is a hydrogen atom or $C_{1-4}$ alkyl and R$^{15}$ is $C_{1-4}$ alkyl), (2) —NR$^{16}$SO$_2$R$^{17}$ (R$^{16}$ is a hydrogen atom or $C_{1-4}$ alkyl and R$^{17}$ is $C_{1-4}$ alkyl), (3) —CONR$^{18}$R$^{19}$ (R$^{18}$ is a hydrogen atom or $C_{1-4}$ alkyl, R$^{19}$ is $C_{1-4}$ alkyl optionally having $C_{1-4}$ alkoxy, or R$^{18}$ and R$^{19}$ may form a ring together with the adjacent nitrogen atom), (4) a 5 to 7-membered nitrogen-containing heterocyclic group, (5) $C_{1-4}$ alkoxy-carbonyl, (6) carboxyl, (7) mono $C_{1-4}$ alkylamino and (8) N—$C_{1-4}$ alkyl-N—$C_{7-10}$ aralkylamino or (II) $C_{1-4}$ alkyl which is substituted with $C_{1-4}$ alkoxy (especially, 2-methoxyethyl).

Among the present compounds, preferred are

[1] Compound (I) wherein $R^1$ is ethyl, $R^2$ is phenyl optionally having 1 to 3 substituents selected from (1)amino, (2) —NHCOR$^{6\prime}$ (R$^{6\prime}$ is $C_{1-4}$ alkyl or mono $C_{1-4}$ alkylamino), (3)—CONR$^{9\prime}$R$^{10\prime}$ (R$^{9\prime}$ is a hydrogen atom, $C_{1-4}$ alkyl or $C_{3-8}$ cycloalkyl, R$^{10\prime}$ is a hydrogen atom or $C_{1-4}$ alkyl, or R$^{9\prime}$ and $R^{10'}$ may form a ring together with the adjacent nitrogen atom), (4) —$CO_2R^{13}$ ($R^{13}$ is $C_{1-4}$ alkyl), (5) $C_{1-4}$ alkoxy optionally having a hydroxyl group, $C_{1-4}$ alkoxy, $C_{1-4}$ alkylcarbonyloxy or —$CONR^{9'}R^{10'}$ ($R^{9'}$ and $R^{10'}$ are as defined above), (6) $C_{1-4}$ alkyl optionally having a hydroxyl group or —$CONR^{9'}R^{10'}$ ($R^{9'}$ and $R^{10'}$ are as defined above), (7) a halogen atom, (8) a hydroxyl group and (9) nitro, $R^3$ is methyl, $R^4$ is $C_{1-4}$ alkyl optionally having 1 to 3 substituents selected from (1) —$NR^{14}COR^{15}$ ($R^{14}$ is a hydrogen atom or $C_{1-4}$ alkyl and $R^{15}$ is $C_{1-4}$ alkyl), (2) —$NR^{16}SO_2R^{17}$ ($R^{16}$ is a hydrogen atom or $C_{1-4}$ alkyl and $R^{17}$ is $C_{1-4}$ alkyl), (3) —$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (4) a 5 to 7-membered nitrogen-containing heterocyclic group, (5) $C_{1-4}$ alkoxy-carbonyl, (6) carboxyl, (7) mono $C_{1-4}$ alkylamino and (8) N—$C_{1-4}$ alkyl-N—$C_{7-10}$ aralkylamino, or

[2] Compound (I) wherein $R^1$ is ethyl, $R^2$ is phenyl optionally having 1 to 3 substituents selected from (1)amino, (2) —$NHCOR^{6'}$ ($R^{6'}$ is $C_{1-4}$ alkyl or mono $C_{1-4}$ alkylamino), (3)—$CONR^{9'}R^{10'}$ ($R^{9'}$ is a hydrogen atom, $C_{1-4}$ alkyl or $C_{3-8}$ cycloalkyl, $R^{10'}$ is a hydrogen atom or $C_{1-4}$ alkyl, or $R^{9'}$ and $R^{10'}$ may form a ring together with the adjacent nitrogen atom), (4) —$CO_2R^{13}$ ($R^{13}$ is $C_{1-4}$ alkyl), (5) $C_{1-4}$ alkoxy optionally having a hydroxyl group, $C_{1-4}$ alkoxy, $C_{1-4}$ alkylcarbonyloxy or —$CONR^{9'}R^{10'}$ ($R^{9'}$ and $R^{10'}$ are as defined above), (6) $C_{1-4}$ alkyl optionally having a hydroxyl group or —$CONR^{9'}R^{10'}$ ($R^{9'}$ and $R^{10'}$ are as defined above), (7) a halogen atom, (8) a hydroxyl group and (9) nitro, $R^3$ is methyl and $R^4$ is 2-methoxyethyl.

More specifically, the preferable compound includes, for example, 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3-(2H)-yl)phenyl]-N-methylacetamide, 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenoxy]-N-ethylacetamide, N-{4-[1-(2,6-difluorobenzyl)-5-{[(2-methoxyethyl)(methyl)amino]methyl}-3-(4-methoxy-3-methylphenyl)-2,4-dioxo-1,2,3,4-tetrahydrothieno[2,3-d]pyrimidin-6-yl]phenyl}-N'-ethylurea, N-{4-[1-(2,6-difluorobenzyl)-3-(4-fluorophenyl)-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea, N-{4-[1-(2,6-difluorobenzyl)-3-[4-(2-methoxyethoxy)phenyl]-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea, N-{2-[{[1-(2,6-difluorobenzyl)-6-(4-{[(ethylamino)carbonyl]amino}phenyl)-3-(4-fluorophenyl)-2,4-dioxo-1,2,3,4-tetrahydrothieno[2,3-d]pyrimidin-5-yl]methyl}(methyl)amino]ethyl}-N-methylsulfonamide, N-{2-[({1-(2,6-difluorobenzyl)-6-(4-{[(ethylamino)carbonyl]amino}phenyl)-3-[4-(2-methoxyethoxy)phenyl]-2,4-dioxo-1,2,3,4-tetrahydrothieno[2,3-d]pyrimidin-5-yl}methyl)(methyl)amino]ethyl}-N-methylsulfonamide, N-[4-(1-(2,6-difluorobenzyl)-5-{[[2-(2-methoxyethoxy)ethyl](methyl)amino]methyl}-2,4-dioxo-3-phenyl-1,2,3,4-tetrahydrothieno[2,3-d]pyrimidin-6-yl)phenyl]-N'-ethylurea, N-[4-(1-(2,6-difluorobenzyl)-5-{[(2-methoxyethyl)(methyl)amino]methyl}-2,4-dioxo-3-phenyl-1,2,3,4-tetrahydrothieno[2,3-d]pyrimidin-6-yl)phenyl]-N'-ethylurea, N-[4-(1-(2,6-difluorobenzyl)-5-{[(2-ethoxyethyl)(methyl)amino]methyl}-2,4-dioxo-3-(2-pyridyl)-1,2,3,4-tetrahydrothieno[2,3-d]pyrimidin-6-yl)phenyl]-N'-ethylurea, N-[4-(1-(2,6-difluorobenzyl)-5-{[(2-methoxyethyl)(methyl)amino]methyl}-2,4-dioxo-3-(5-methyl-2-pyridyl)-1,2,3,4-tetrahydrothieno[2,3-d]pyrimidin-6-yl)phenyl]-N'-ethylurea or N-[4-(1-(2,6-difluorobenzyl)-5-{[(2-methoxyethyl)(methyl)amino]methyl}-2,4-dioxo-3-(6-methyl-2-pyridyl)-1,2,3,4-tetrahydrothieno[2,3-d]pyrimidin-6-yl)phenyl]-N'-ethylurea or a salt thereof.

Salts of Compound (I) are preferably physiologically acceptable acid-addition salts. Such salts include, for example, salts with inorganic acids (e.g., hydrochloric acid, hydrobromic acid, nitric acid, sulfuric acid, phosphoric acid etc.), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.) and the like. When Compound (I) has an acidi C group, it may form a physiologically acceptable salt with an inorganic base (e.g., alkali metals or alkaline earth metals such as sodium, potassium, calcium and magnesium, and ammonia) or an organic base (e.g., trimethylamine, triethylamine, pyridine, picoline, ethanolamine, diethanolamine, triethanolamine, di Cyclohexylamine, N,N'-dibenzylethylenediamine etc.).

Compound (I) can be produced by the following Production method 1 and Production method 2. The compounds described in the following reaction formulae may be, for example, in the form of salt. The salt includes the salts as described for Compound (I). Compounds (I) to (VI) described below include their salts.

(Production Method 1)

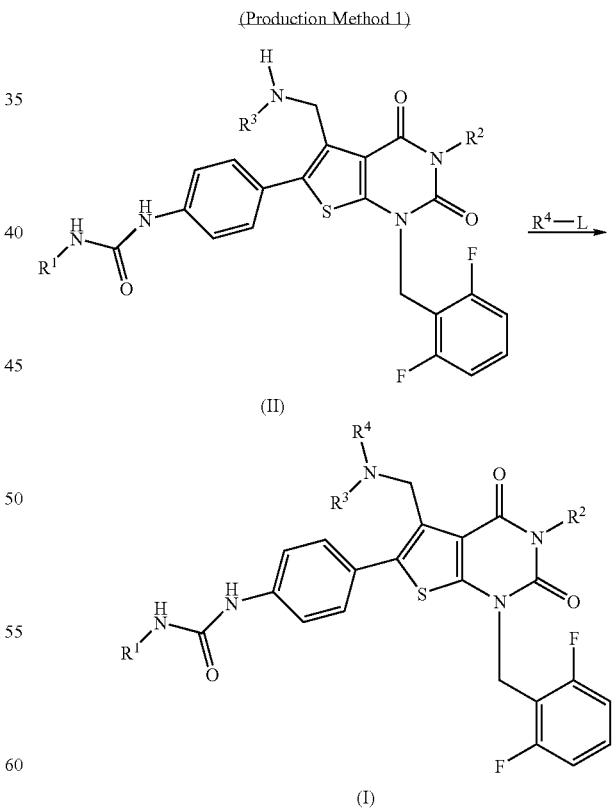

[wherein, L is a leaving group, and other symbols are as defined above.]

The "leaving group" represented by L includes, for example, a halogen atom, $C_{1-4}$ alkyl sulfonyloxy optionally having halogen atom and the like. The "$C_{1-4}$ alkyl sulfonyloxy optionally having halogen atom" includes methane sulfonyloxy, ethane sulfonyloxy, trifluoromethane sulfonyloxy and the like.

Compound (II) can be produced by the methods disclosed in JP-A-2001-278884 or WO00/56739 or analogous methods thereto.

For example, Compound (I) can be produced by reacting Compound (II) and the compound represented by $R^4$-L. Further, this reaction is preferably carried out in the presence of base.

The "base" includes, for example, inorganic bases such as sodium carbonate, sodium hydrogencarbonate, potassium carbonate, potassium hydrogencarbonate, sodium hydroxide, potassium hydroxide and thallium hydroxide, or organic bases such as trimethyl amine, diisopropylethyl amine and pyridine and the like.

The amount of the compound represented by $R^4$-L in the reaction of Compound (II) and the compound represented by $R^4$-L is about 1 to about 3 moles, relative to 1 mole of Compound (II). The amount of the "base" is about 1 to about 3 moles, relative to 1 mole of Compound (II).

This reaction is usually carried out in a suitable solvent inert to the reaction. The solvent includes, for example, ethers (e.g., diethyl ether, dioxane, dimethoxyethane, tetrahydrofuran etc.), aromatic hydrocarbons (e.g., benzene, toluene etc.), amides (e.g., dimethylformamide, dimethylacetamide etc.), halogenated hydrocarbons (e.g., chloroform, dichloromethane etc.) and the like.

The reaction temperature is usually about 0 to about 150° C., preferably about 50 to about 80° C. The reaction time is usually about 1 hour to about 24 hours.

In addition, Compound (II) can be produced by the following method.

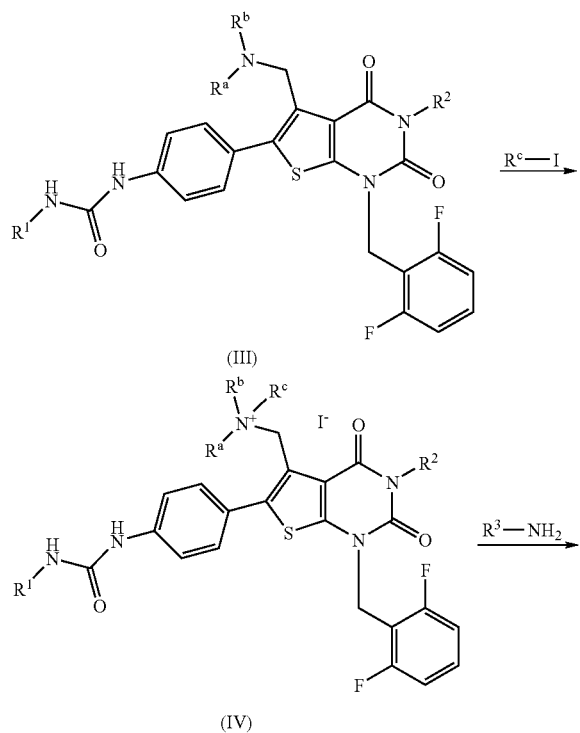

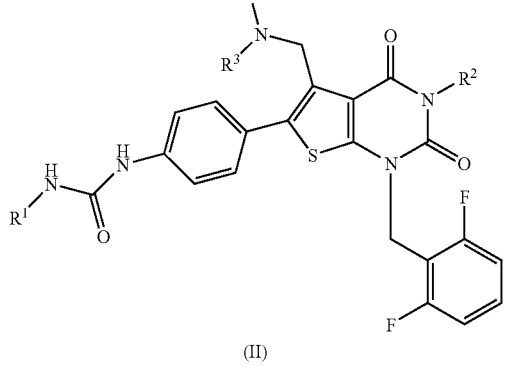

[wherein, $R^a$ is $C_{1-4}$ alkyl, $R^b$ is $C_{1-4}$ alkyl or benzyl, $R^c$ is $C_{1-4}$ alkyl, and other symbols are as defined above.]

"$C_{1-4}$ alkyl" represented by $R^a$, $R^b$ and $R^c$ includes, for example, straight $C_{1-4}$ alkyl (e.g., methyl, ethyl, propyl, butyl etc.), branched $C_{3-4}$ alkyl (e.g., isopropyl, isobutyl, sec-butyl, tert-butyl etc.) and the like.

Compound (III) can be produced by the method described in JP-A-2001-278884, WO00/56739 or analogous methods thereto.

Compound (IV) can be produced by stirring Compound (III) and the compound represented by $R^c$—I in a solvent. The amount of the compound represented by $R^c$—I is about 1 mole to about 3 moles, relative to 1 mole of Compound (III).

This reaction is usually carried out in a suitable solvent inert to the reaction. The solvent includes, for example, ethers (e.g., ethyl ether, dioxane, dimethoxyethane, tetrahydrofuran etc.), aromatic hydrocarbons (e.g., benzene, toluene etc.), amides (e.g., dimethylformamide, dimethylacetamide etc.), halogenated hydrocarbons (e.g., chloroform, dichloromethane etc.) and the like.

The reaction temperature is usually about 0 to about 150° C., preferably about 50 to about 80° C. The reaction time is usually about 1 hour to 24 hours.

Compound (II) can be produced by reacting Compound (IV) and the compound represented by $R^3$—$NH_2$ in the presence of base.

The "base" includes, for example, inorganic bases such as sodium carbonate, sodium hydrogencarbonate, potassium carbonate, potassium hydrogencarbonate, sodium hydroxide, potassium hydroxide and thallium hydroxide, or organic bases such as trimethyl amine, diisopropylethyl amine and pyridine.

The amount of the compound represented by $R^3$—$NH_2$ in the reaction of Compound (IV) and the compound represented by $R^3$—$NH_2$ is about 1 to about 10 moles, relative to 1 mole of Compound (IV). The amount of the "base" is about 1 mole to about 10 moles, relative to 1 mole of Compound (IV).

This reaction is usually carried out in a suitable solvent inert to the reaction.

The solvent includes, for example, ethers (e.g., diethyl ether, dioxane, dimethoxyethane, tetrahydrofuran etc.), aromatic hydrocarbons (e.g., benzene, toluene etc.), amides (e.g., dimethylformamide, dimethylacetamide etc.), halogenated hydrocarbons (e.g., chloroform, dichloromethane etc.) and the like.

The reaction temperature is usually about 0 to about 150° C., preferably about 80 to about 120° C. The reaction time is usually about 1 to 6 hours.

Compound (I), (II) and (IV) may be isolated and purified by per se known means of separation, for example recrystallization, distillation, chromatography and the like.

(Production Method 2)

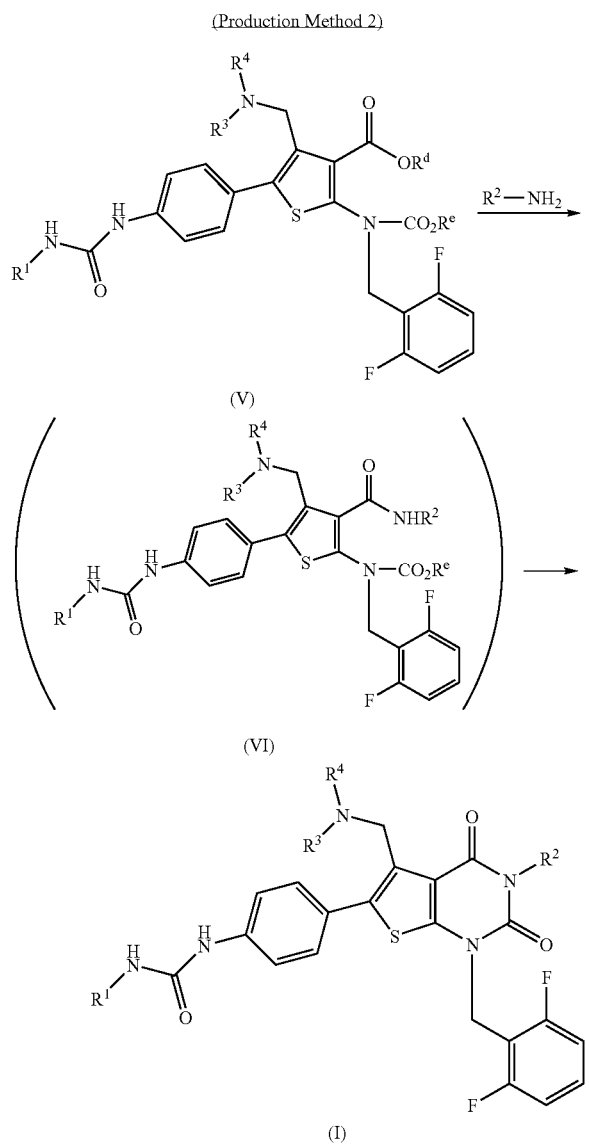

(V)

(VI)

(I)

[wherein, $R^d$ is a hydrogen atom or $C_{1-4}$ alkyl, $R^e$ is $C_{1-4}$ alkyl, and other symbols are as defined above.]

$C_{1-4}$ alkyl represented by $R^d$ and $R^e$ includes, for example, straight $C_{1-4}$ alkyl (e.g., methyl, ethyl, propyl, butyl etc.), branched $C_{3-4}$ alkyl (e.g., isopropyl, isobutyl, sec-butyl, tert-butyl etc.) and the like.

Compound (V) can be produced in any per se known manner, for example, by reacting p-nitrophenyl acetone with a cyanoacetic ester derivative and sulphur [e.g., Chem. Ber., 99, 94-100 (1966) etc.], and subjecting the thus-obtained 2-amino-4-methyl-5-(4-nitrophenyl)thiophene to the methods disclosed in JP-A-9-169768, WO 96/24597 or analogous methods thereto.

(i) When $R^d$ is a hydrogen atom, Compound (I) can be produced by reacting compound (V) with a compound represented by $R^2$—$NH_2$ or a salt thereof in the presence of a condensing agent, to obtain compound (VI), and then subjecting the compound to cyclization.

The "condensing agent" includes, for example, WSC (1-ethyl-3-(3-dimethylaminopropyl)-carbodiimide hydrochloride), DCC (di Cyclohexylcarbodiimide), diethyl cyanophophate, benzotriazol-1-yloxytripyrrolidinophosphonium hexafluorophosphate (PyBOP) and the like.

The amount of the "condensing agent" is about 1 mole to about 3 moles, relative to 1 mole of Compound (V).

This reaction is usually carried out in a suitable solvent inert to the reaction.

The solvent includes, for example, alcohols (e.g., ethanol, methanol etc.), aromatic hydrocarbons (e.g., benzene, toluene etc.), amides (e.g., dimethylformamide, dimethylacetamide etc.), halogenated hydrocarbons (e.g., chloroform, dichloromethane etc.) and the like.

The reaction temperature is usually about 0 to about 150° C., preferably about 0 to about 25° C. The reaction time is usually about 1 hour to about 36 hours.

The product as produced in the manner mentioned above may be applied to the next reaction as a reaction solution or crude product, or may be isolated from the reaction mixture according to a conventional method.

Compound (VI) is subjected to cyclization in the presence of a base.

The "base" includes, for example, inorganic bases such as sodium methoxide, sodium carbonate, sodium hydrogencarbonate, potassium carbonate, potassium hydrogencarbonate, sodium hydroxide, potassium hydroxide and thallium hydroxide, or organic bases such as triethylamine and pyridine.

The amount of the "base" is about 2 to about 20 moles, preferably about 5 to about 12 moles, relative to 1 mole of Compound (VI).

This reaction is usually carried out in a suitable solvent inert to the reaction.

The solvent includes, for example, alcohols (e.g., ethanol, methanol etc.), aromatic hydrocarbons (e.g., benzene, toluene etc.), amides (e.g., dimethylformamide, dimethylacetamide etc.), halogenated hydrocarbons (e.g., chloroform, dichloromethane etc.) and the like.

The reaction temperature is usually about 0 to about 150° C., preferably room temperature (about 15 to about 25° C.). The reaction time is usually about hour 1 to about 36 hours.

(ii) When $R^d$ is an alkyl group, Compound (I) can be produced by activating the compound represented by $R^2$—$NH_2$ and reacting it with Compound (V).

The activation of $R^2$—$NH_2$ can be carried out by any per se known method, for example, by reacting an organo-aluminum reagent with the compound represented by $R^2$—$NH_2$ in a solvent inert to the reaction.

The "organo-aluminum reagent" includes, for example, trimethyl aluminum, dimethyl aluminum chloride and the like, or a solution including them and the like.

The amount of the "organo-aluminum reagent" is about mole 1 to about 5 moles, preferably about 1 mole, relative to 1 mole of the compound represented by $R^2$—$NH_2$.

The solvent preferably includes, for example, halogenated hydrocarbons (e.g., chloroform, dichloromethane etc.) and the like.

The reaction temperature is usually about 0 to about 150° C., preferably about 0 to about 25° C. The reaction time is usually about 1 hour to about 6 hours.

The cyclization can be carried out by activating the compound represented by $R^2$—$NH_2$, and reacting it with Compound (V), to obtain Compound (I).

The amount of "Compound (V)" is preferably about 1/5 volume of a mixture of the compound represented by $R^2$—$NH_2$ and the organo-aluminum reagent.

This reaction is usually carried out in a suitable solvent inert to the reaction.

Such solvent is preferably the same as those used in activating the compound represented by $R^2$—$NH_2$.

The reaction temperature is usually about 0 to 150° C., preferably about 0 to 25° C. The reaction time is usually about 1 hour to 48 hours.

Compound (I) may be isolated and purified by per se known means of separation such as recrystallization, distillation and chromatography.

When Compound (I) is obtained in free form, it can be converted to a desired salt by per se known methods or analogous thereto. When Compound (I) is obtained in salt form, it can be converted to the free form or another desired salt by per se known methods or analogous thereto.

Compound (I) may be a hydrate or a non-hydrate. The hydrate is exemplified by monohydrate, sesquihydrate and dihydrate.

When Compound (I) is obtained as a mixture of optically active configurations, it can be resolved into the (R)- or (S)- forms as desired by the conventional optical resolution techniques.

Compound (I) may be used as a prodrug. The prodrug of Compound (I) means a compound which is converted to Compound (I) under the physiological condition by a reaction due to an enzyme, an gastric acid and the like in vivo, that is, a compound which is converted to Compound (I) by enzymatic oxidation, reduction, hydrolysis and the like; a compound which is converted to Compound (I) by hydrolysis etc. with gastric acid and the like; and the like. The prodrug of Compound (I) includes a compound wherein an amino group of Compound (I) is modified to acyl, alkyl or phosphoric acid (e.g., a compound wherein an amino group of Compound (I) is modified to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl etc.); a compound wherein an hydroxyl group of Compound (I) is modified to acyl, alkyl, phosphoric acid or boric acid (e.g., a compound wherein an hydroxyl group of Compound (I) is modified with acetyl, palmitoyl, propanoyl, pivaloyl, succinyl, fumaryl, alanyl, dimethylaminomethylcarbonyl etc.); a compound wherein a carboxyl group of Compound (I) is modified to ester or amide (e.g., a compound wherein a carboxyl group of Compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide etc.); and the like. These compounds can be produced by per se known method from the compound of the present invention.

In addition, the prodrug of the compound of the present invention may be a compound which is converted into the compound of the present invention under the physiological conditions as described in "Pharmaceutical Research and Development", Vol. 7 (Drug Design), pages 163-198, published in 1990 by Hirokawa Publishing Co.

In addition, Compound (I) may be labeled with an isotype (e.g., $^3H$, $^{14}C$, $^{35}S$) and the like.

In addition, in the above reactions, when the starting compounds have amino group, carboxyl group or hydroxyl group as substituents, these groups may be protected by the protective groups such as those generally employed in peptide chemistry and the like. After the reaction, the protective groups may be removed to obtain the desired compound if necessary.

The amino-protective group includes, for example, an optionally substituted $C_{1-6}$alkylcarbonyl (e.g., acetyl, propionyl, etc.), formyl, phenylcarbonyl, $C_{1-6}$alkyloxycarbonyl (e.g., methoxycarbonyl, ethoxycarbonyl, t-butoxycarbonyl, etc.), phenyloxycarbonyl (e.g., benzoxycarbonyl, etc.), $C_{7-14}$ aralkyloxycarbonyl (e.g., benzyloxycarbonyl, 9-fluorenyl methoxycarbonyl etc.), trityl, phthaloyl and the like. These protective groups may be substituted by approximately 1 to 3 substituents such as halogen atom (e.g., fluorine, chlorine, bromine, iodine, etc.), $C_{1-6}$alkylcarbonyl (e.g., acetyl, propionyl, butyryl, etc.), nitro group and the like.

The carboxyl-protective group includes, for example, an optionally substituted $C_{1-6}$ alkyl (e.g., methyl, ethyl, propyl, isopropyl, butyl, tert-butyl, etc.), phenyl, trityl, silyl and the like. These protective groups may be substituted by approximately 1 to 3 substituents such as halogen atom (e.g., fluorine, chlorine, bromine, iodine, etc.), $C_{1-6}$ alkylcarbonyl (e.g., acetyl, propionyl, butyryl, etc.), formyl, nitro group and the like.

The hydroxy-protective group includes, for example, an optionally substituted $C_{1-6}$ alkyl (e.g., methyl, ethyl, propyl, isopropyl, butyl, tert-butyl, etc.), phenyl, $C_{7-10}$ aralkyl (e.g., benzyl, etc.), $C_{1-6}$ alkylcarbonyl (e.g., acetyl, propionyl, etc.), formyl, phenyloxycarbonyl, $C_{7-10}$ aralkyloxycarbonyl (e.g., benzyloxycarbonyl, etc.), pyranyl, furanyl, silyl and the like. These protective groups may be substituted by approximately 1 to 4 substituents such as halogen atom (e.g., fluorine, chlorine, bromine, iodine, etc.), $C_{1-6}$ alkyl, phenyl, $C_{7-10}$ aralkyl, nitro group and the like.

In addition, the protective groups may be introduced or removed by per se known methods or analogous methods thereto (e.g., a method described in Protective Groups in Organic Chemistry (J. F. W. McOmie et. al.; Plenum Press Inc.). For example, the protective groups may be removed, for example, by a method using an acid, a base, reduction, ultra-violet ray, hydrazine, phenylhydrazine, sodium N-methyldithiocarbamate, tetrabutylammonium fluoride, palladium acetate and the like.

Compound (I) of the present invention and a salt thereof (hereinafter also abbreviated as "the compound of the present invention") possesses excellent GnRH-antagonizing activity and low toxicity. In addition, it is excellent in oral absorption or duration of action, and also in stability or pharmacokinetics. They can therefore be safely used in a mammal (e.g., human, monkey, bovine, horse, dog, cat, rabbit, rat, mouse etc.) for preventing and/or treating diseases depending on male or female hormones, and diseases due to excess of these hormones and the like, by suppressing gonadotropin secretion by its GnRH receptor-antagonizing action to control plasma sex hormone concentrations.

For example, the compound of the present invention is useful as an agent for preventing and/or treating sex hormone-dependent cancers (e.g., prostatic cancer, uterine cancer, breast cancer, pituitary tumor etc.), metastasis of sex hormone-dependent diseases to bone, prostatic hypertrophy, hysteromyoma, endometriosis, precocious puberty, amenorrhea, premenstrual syndrome, dysmenorrhea, multilocular ovary syndrome, polycystic ovary syndrome, pimple, alopecia, Alzheimer's disease (Alzheimer's disease, senile dementia of Alzheimer's type or a combination thereof) and the like. The compound of the present invention is also useful for the regulation of reproduction in males and females (e.g., pregnancy regulators, menstruation cycle regulators etc.). The compound of the present invention also can be used as a male or female contraceptive, or as a female ovulation inducer. Based on its rebound effect after withdrawal, the compound of the present invention can be used to treat infertility. The compound of the present invention also can be used as an agent for preventing and/or treating LH-RH sensitive benign or malignant tumor which is independent on the hormone. The compound of the present invention also can be used as an agent for preventing and/or treating irritable bowel syndrome and an agent for preventing recurrence of post-operative sex hormone-dependent cancers (an agent for preventing recurrence of post-operative prostatic cancer, an agent for preventing recurrence of post-operative breast or ovary cancer in postmenopausal and premenopausal women and the like, preferably an agent for preventing recurrence of post-operative breast or ovary cancer in premenopausal women).

In addition, the compound of the present invention is useful for regulation of animal estrous, improvement of food meat quality, promotion of animal growth and the like in the field of animal husbandry. The compound of the present invention is also useful as a fish spawning promoter.

The compound of the present invention can be used to suppress the transient rise in plasma testosterone concentration (flare phenomenon) observed in administration of a GnRH super-agonist such as leuprorelin acetate. The compound of the present invention can be used in combination with a GnRH super-agonist such as leuprorelin acetate, gonadrelin, buserelin, triptorelin, goserelin, nafarelin, histrelin, deslorelin, meterelin, lecirelin and the like, preferably leuprorelin acetate.

It is also beneficial to use the compound of the present invention in combination with at least one kind selected from the steroidal or nonsteroidal androgen antagonist or antiestrogen, chemotherapeutic agent, GnRH antagonistic peptide, α-reductase inhibitor, α-receptor inhibitor, aromatase inhibitor, 17β-hydroxysteroid dehydrogenase inhibitor, adrenal androgen production inhibitor, kinase inhibitor, drug for hormone therapy, drug antagonizing growth factor or its receptor and the like.

The "chemotherapeutic agent" mentioned above includes ifosfamide, adriamycin, peplomycin, cisplatin, cyclophosphamide, 5-FU, UFT, methotrexate, mitomycin C, mitoxantrone and the like.

The "GnRH antagonistic peptide" mentioned above includes non-oral GnRH antagonistic peptides such as cetrorelix, ganirelix, abarelix and the like.

The "adrenal androgen production inhibitor" mentioned above includes lyase ($C_{17,20}$-lyase) inhibitors and the like.

The "kinase inhibitor" mentioned above includes tyrosine kinase inhibitor and the like.

The "drugs for hormone therapy" includes antiestrogens, progesterons (e.g., MPA etc.), androgens, estrogens, androgen antagonists and the like.

The "growth factor" may be any substance that promotes proliferation of cells and generally includes peptides having molecular weights 20,000 or less which express the action at low concentrations through binding to receptors. Specifically, there can be mentioned (1) EGF (epidermal growth factor) or substances having substantially the same activity (e.g., EGF, heregulin (HER2 ligand) etc.), (2) insulin or substances having substantially the same activity (e.g., insulin, IGF (insulin-like growth factor)-1, IGF-2 etc.), (3) FGF (fibroblast growth factor) or substances having substantially the same activity (aFGF, bFGF, KGF (keratinocyte growth factor), HGF (hepatocyte growth factor), FGF-10 etc.), (4) other growth factors (e.g., CSF (colony stimulating factor), EPO (erythropoietin), IL-2 (interleukin-2), NGF (nerve growth factor), PDGF (platelet-derived growth factor), TGFβ (transforming growth factor β) etc.) and the like.

The "growth factor receptor" mentioned above may be any receptor capable of binding said growth factor, specifically including EGF receptor, heregulin receptor (HER2), insulin receptor-1, insulin receptor-2, IGF receptor, FGF receptor-1, FGF receptor-2 and the like.

The drug inhibiting the action of said growth factor includes herceptin (HER2 receptor antibody) and the like.

The drug inhibiting the action of said growth factor or growth factor receptor includes herbimycin, PD153035 [e.g., Science, 265 (5175) p1093, (1994)] and the like.

The drug inhibiting the action of said growth factor or growth factor receptor also includes HER2 inhibitor. The HER2 inhibitor may be any substance that inhibits the activity of HER2 (e.g., phosphorylating activity), thus including an antibody, a low-molecular compound (a synthetic or natural product), an antisense, an HER2 ligand, heregulin, or any partially modified or mutated substances in the structure thereof. Moreover, it may be a substance which inhibits HER2 activity by antagonizing HER2 receptor (e.g., HER2 receptor antibody). The low molecular compound having HER2 inhibiting activity includes, for example, the compounds described in WO 98/03505, specifically 1-[3-[4-[2-((E)-2-phenylethenyl)-4-oxazolylmethoxy]phenyl]propyl]-1,2,4-triazole and the like.

For prostatic hypertrophy, the compound of the present invention may be used in combination with the GnRH super-agonist, androgen antagonist, antiestrogen, GnRH antagonistic peptide, α-reductase inhibitor, α-receptor inhibitor, aromatase inhibitor, 17β-hydroxysteroid dehydrogenase inhibitor, adrenal androgen production inhibitor, kinase inhibitor and the like.

For prostatic cancer, the compound of the present invention may be used in combination with the GnRH super-agonist, androgen antagonist, antiestrogen, chemotherapeutic agent (e.g., ifosfamide, UFT, adriamycin, peplomycin, cisplatin etc.), GnRH antagonistic peptide, aromatase inhibitor, 17β-hydroxysteroid dehydrogenase inhibitor, adrenal androgen production inhibitor, kinase inhibitor, drug for hormone therapy [e.g., estrogens (e.g., DSB, EMP etc.), androgen antagonist (e.g., CMA etc.) etc.], drug inhibiting growth factor or its receptor and the like.

For breast cancer, the compound of the present invention may be used in combination with the GnRH super-agonist, antiestrogen, chemotherapeutic agent [e.g., cyclophosphamide, 5-FU, UFT, methotrexate, adriamycin, mitomycin C, mitoxantrone etc.], GnRH antagonistic peptide, aromatase inhibitor, adrenal androgen production inhibitor, kinase inhibitor, drug for hormone therapy [e.g., antiestrogen (e.g., tamoxifen etc.), progesterons (e.g., MPA etc.), androgens, estrogens etc.], drug inhibiting growth factor or its receptor and the like.

Dosage forms of the combination drug of the compound of the present invention and other drugs are not specifically limited as long as the compound of the present invention and other drugs are combined when administered. The dosage forms include (1) administration of single preparation obtained by simultaneously formulating the compound of the present invention and other drugs, (2) concurrent administration of two kinds of preparations obtained by separately formulating the compound of the present invention and other drugs via same administration route, (3) time-intervaled administration of two kinds of preparations obtained by separately formulating the compound of the present invention and other drugs via same administration route, (4) concurrent administration of two kinds of preparations obtained by separately formulating the compound of the present invention and other drugs via different administration route, (5) time-intervaled administration of two kinds of preparations obtained by separately formulating the compound of the present invention and other drugs via different administration route (for example, administration in the order from the compound of the present invention to other drugs, or administration reversely) and the like.

When the compound of the present invention is used as a prophylactic and/or therapeutic agent for the above-mentioned diseases or used in the field of animal husbandry or fishery, it can be administered orally or non-orally according to a per se known method, as formulated with a pharmaceutically acceptable carrier, in the form of solid preparations, usually in the form of tablets, capsules, granules, powders and the like for oral administration, or in the form of intravenous, subcutaneous, intramuscular or other injections, suppositories or sublingual tablets for non-oral administration. It may also be sublingually, subcutaneously, intramuscularly or otherwise administered in the form of sustained-release preparations of sublingual tablets, microcapsules and the like. Daily dose is not specifically limited as long as to achieve the object of the present invention, and may vary depending on symptom severity; age, sex, weight and sensitivity of the subject; time and intervals of administration; property, prescription and kinds of pharmaceutical preparation; kinds of active ingredient and the like. For use in the treatment of the above-described sex hormone-dependent cancers (e.g., prostatic cancer, uterine cancer, breast cancer, pituitary tumor etc.), prostatic hypertrophy, hysteromyoma, endometriosis, precocious puberty and the like. For oral preparations, dose of active ingredient (the compound of the present invention) is normally about 0.01 to 30 mg, preferably about 0.02 to 10 mg, and more preferably 0.1 to 10 mg, most preferably 0.1 to 5 mg per kg weight of mammal, normally in 1 to 4 divided dosages per day.

The above doses are applicable to the use of the compound of the present invention in the field of animal husbandry or fishery. For oral preparations, dose of active ingredient (the compound of the present invention) is about 0.01 to 30 mg, preferably about 0.1 to 10 mg, per kg weight of subject organism, normally in 1 to 3 divided dosages per day.

In the pharmaceutical composition of the present invention, the content of Compound (I) is about 0.01 to 100% by weight of the total weight of the composition.

Above-mentioned pharmaceutically acceptable carriers include various organic or inorganic carrier substances which are commonly used as pharmaceutical materials, for example, excipients, lubricants, binders and disintegrants for solid preparations; solvents, dissolution aids, suspending agents, isotonizing agents, buffers, soothing agents and the like for liquid preparations. Other pharmaceutical additives such as preservatives, antioxidants, coloring agents and sweetening agents may be also used as necessary.

Preferable excipients include, for example, lactose, sucrose, D-mannitol, starch, crystalline cellulose, light silicic anhydride and the like. Preferable lubricants include, for example, magnesium stearate, calcium stearate, talc, colloidal silica and the like. Preferable binders include, for example, crystalline cellulose, sucrose, D-mannitol, dextrin, hydroxypropyl cellulose, hydroxypropylmethyl cellulose, polyvinylpyrrolidone and the like. Preferable disintegrants include, for example, starch, carboxymethyl cellulose, carboxymethyl cellulose calcium, crosslinked carmellose sodium, carboxymethyl starch sodium and the like. Preferable solvents include, for example, water for injection, alcohol, propylene glycol, macrogol, sesame oil, corn oil and the like. Preferable dissolution aids include, for example, polyethylene glycol, propylene glycol, D-mannitol, benzyl benzoate, ethanol, trisaminomethane, cholesterol, triethanolamine, sodium carbonate, sodium citrate and the like. Preferable suspending agents include, for example, surfactants such as stearyl triethanolamine, sodium lauryl sulfate, lauryl aminopropionic acid, lecithin, benzalkonium chloride, benzethonium chloride, monostearic glycerol and the like; and hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like; and the like. Preferable isotonizing agents include, for example, sodium chloride, glycerol, D-mannitol and the like. Preferable buffers include, for example, buffer solutions of phosphates, acetates, carbonates, citrates and the like. Preferable soothing agents include, for example, benzyl alcohol and the like. Preferable preservatives include, for example, paraoxybenzoic acid esters, chlorobutanol, benzyl alcohol, phenethyl alcohol, dehydroacetic acid, sorbic acid and the like. Preferable antioxidants include, for example, sulfites, ascorbic acid and the like.

The compound of the present invention can be prepared as an intravenous, subcutaneous or intramuscular injection according to a per se known method by adding a suspending agent, a dissolution aid, a stabilizer, an isotonizing agent, a preservative and the like. In such cases, the compound of the present invention can be freeze-dried as necessary according to a per se known method. When administered to humans, for example, the compound of the present invention can be safely administered orally or non-orally as itself or as a pharmaceutical composition in combination with a pharmacologically acceptable carrier, an excipient or a diluent selected as appropriate.

Such pharmaceutical compositions include oral preparations (e.g., powders, granules, capsules, tablets) and non-oral preparations [e.g., injections, drip infusions, external preparations (e.g., nasal preparations, transdermal preparations and the like) and suppositories (e.g., rectal suppositories, vaginal suppositories etc.) and the like].

These preparations can be produced according to a per se known method which is commonly used for the formulating processes.

The compound of the present invention can be produced as an injection, for example, as an aqueous injection in combination with a dispersing agent (e.g., Tween 80 (produced by Atlas Powder Company, USA), HCO60 (produced by Nikko Chemicals Co., Ltd.), polyethylene glycol, carboxymethyl cellulose, and sodium alginate), a preservative (e.g., methyl paraben, propyl paraben, benzyl alcohol etc.), an isotonizing agent (e.g., sodium chloride, mannitol, sorbitol, glucose etc.) and the like, or as an oily injection as dissolved, suspended or emulsified in a vegetable oil such as olive oil, sesame oil, cottonseed oil and corn oil, propylene glycol and the like.

The compound of the present invention can be produced as an oral preparation according to a per se known method by adding an excipient (e.g., lactose, sucrose, starch etc.), a disintegrant (e.g., starch, calcium carbonate etc.), a binder (e.g., starch, arabic gum, carboxymethyl cellulose, polyvinylpyrrolidone, hydroxypropyl cellulose etc.), a lubricant (e.g., talc, magnesium stearate, polyethylene glycol 6000 etc.) and the like, followed by compressing it and, if necessary, coating the formulated product for the purpose of taste masking, enteric dissolution or sustained release according to a per se known method. Coating agents for this purpose include, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (produced by Rohm Company, Germany; methacrylic acid/acrylic acid copolymer) and dyes (e.g., red iron oxide, titanium dioxide etc.) and the like. For an enteric preparation, an intermediate phase may be provided between the enteric phase and the drug-containing phase for the purpose of separation of the two phases according to a per se known method.

The compound of the present invention can be produced as an external preparation of solid, semi-solid or liquid phase according to a per se known method. The solid composition is produced by, for example, powdering the compound of the present invention as itself or in mixture with an excipient (e.g., glycol, mannitol, starch, microcrystalline cellulose etc.), a thickening agent (e.g., natural gum, cellulose derivative, acrylic acid polymer etc.) and the like. The liquid composition is produced as an oily or aqueous suspension in the nearly same manner as in the injection. The semi-solid composition is preferably an aqueous or oily gel, or an ointment. All these compositions may also contain a pH-adjusting agent (e.g., carbonic acid, phosphoric acid, citric acid, hydrochloric acid, sodium hydroxide etc.), preservatives (e.g., paraoxybenzoic acid esters, chlorobutanol, benzalkonium chloride etc.) and the like.

For example, the compound of the present invention can be produced as a suppository of oily or aqueous solid, semi-solid or liquid phase according to a per se known method. Useful oily bases for the compositions include, for example, glycerides of long-chain fatty acids [e.g., cacao fat, uitepsols (produced by Dynamite Nobel Company, Germany) etc.], medium-chain fatty acids [e.g., MIGLYOL (produced by Dynamite Nobel Company, Germany) etc.], or vegetable oils (e.g., sesame oil, soybean oil, cottonseed oil etc.) and the like. Moreover, the aqueous bases include, for example, polyethylene glycols and propylene glycol. The bases for aqueous gels include, for example, natural gums, cellulose derivatives, vinyl polymers, acrylic acid polymers and the like.

The present invention is hereinafter described in more detail by means of the following reference examples, examples, preparation examples and experimental examples, but is not limited thereto.

$^1$H-NMR spectra are measured with tetramethylsilane as the internal standard, using the Varian GEMINI 200 (200 MHz) spectrometer, the JEOL LAMBDA 300 (300 MHz) spectrometer or the Bruker AM500 (500 MHz) spectrometer. All δ values are shown in ppm. Unless otherwise specifically indicated, "%" indicates weight percent. Yield indicates mol/mol %.

The other symbols used herein have the following definitions:

s: singlet
d: doublet
t: triplet
dt: double triplet
m: multiplet
br: broad
AIBN: 2,2'-azobisisobutyronitrile
DMF: N,N-dimethylformamide
NBS: N-bromosuccinimide
THF: tetrahydrofuran
TFA: trifluoroacetic acid
Me: methyl
Et: ethyl
Ph: phenyl The term "room temperature" indicates the range from about 15 to about 25° C., but is not to be construed as strictly limitative.

EXAMPLES

Reference Example 1

Preparation of N-benzyl[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]-N,N-dimethylmethane aluminum iodide

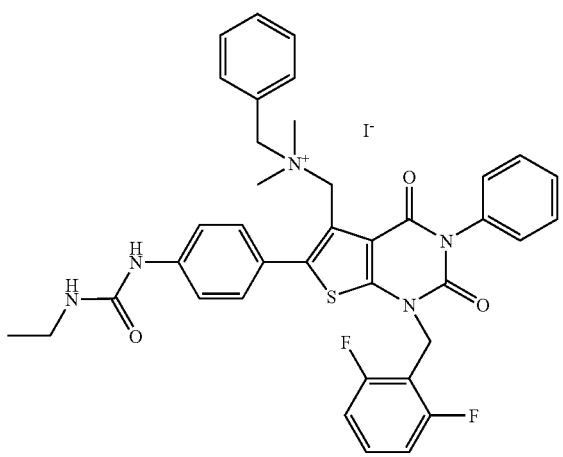

N-(4-(5-{[benzyl(methyl)amino]methyl}-1-(2,6-difluorobenzyl)-3-phenyl-2,4-dioxo-1,2,3,4-tetrahydrothieno[2,3-d]pyrimidin-6-yl}phenyl)-N'-ethylurea (JP-A-2001-278884, WO00/56739) (3.33 g, 0.5 mmol) was dissolved in DMF (6 ml), followed by addition of methyl iodide (0.62 ml, 10 mmol) and the mixture was stirred at 60° C. for 1 hour and a half. The reaction solution was concentrated, followed by addition of ethyl acetate. The precipitate was washed with ethyl acetate and diethyl ether to give the title compound (4.01 g, 99%) as light yellow powder.

$^1$H-NMR(CDCl$_3$) δ: 1.20 (3H, t, J=7.2 Hz), 2.77(6H, brs), 3.25-3.30 (2H, m), 4.55 (2H, brs), 4.9-5.3 (2H, br), 5.3-5.5 (2H, br), 6.2-6.3 (1H, m), 6.94 (2H, t, J=8.4 Hz), 7.2-7.6 (14H, m), 7.70 (1H, d, J=8.4 Hz), 8.73 (1H, s).

IR (KBr): 1711, 1667, 1537, 1470, 1316, 1225, 1032 cm$^{-1}$.

Elemental analysis for $C_{38}H_{36}F_2IN_5O_3S \cdot 1.5H_2O$

Calculated: C, 54.68; H, 4.71; N, 8.39. Found: C, 54.53; H, 4.67; N, 8.25.

mp 185-187° C.

Reference Example 2

Preparation of 3-bromo-N-methylpropanamide

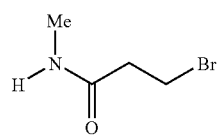

3-Bromopropionic acid (1.52 g, 10 mmol) was dissolved in tetrahydrofuran (20 ml), followed by addition of oxalyl chloride (0.94 ml, 11 mmol) and DMF (2 drops) and the mixture was stirred at room temperature for 1 hour. The reaction solution was concentrated under reduced pressure and then was dissolved in tetrahydrofuran (20 ml), followed by addition of triethylamine (2.08 ml, 15 mmol) and a solution of methylamine in tetrahydrofuran (2 M) (6 ml, 12 mmol) and the mixture was stirred with ice-cooling for 3 hours. Saturated brine was added and the mixture was extracted with ethyl acetate. The reaction solution was dried over magnesium sulfate, and then concentrated under reduced pressure to give the title compound (0.78 g, 47%) as light yellow powder.

$^1$H-NMR(CDCl$_3$) δ: 2.75 (2H, t, J=6.6 Hz), 2.85 (3H, d, J=4.6 Hz), 3.65 (2H, t, J=6.6 Hz), 5.4-5.7 (1H, brm).

Reference Example 3

Preparation of 3-bromo-N,N-dimethylpropanamide

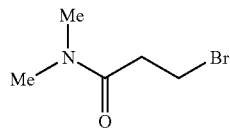

The similar reaction to that of Reference Example 2 was performed using 3-bromopropionic acid (3.06 g, 20 mmol) and a solution of dimethylamine in tetrahydrofuran (2 M) (12 ml, 24 mmol) to give the title compound (2.53 g, 70%) as an orange-colored oily matter.

$^1$H-NMR(CDCl$_3$) δ: 2.91 (2H, t, J=7.2 Hz), 2.97 (3H, s), 2.91 (2H, t, J=7.2 Hz), 3.02 (3H, s), 3.65 (2H, t, J=7.2 Hz).

Reference Example 4

Preparation of 3-[(benzyloxy)methyl]-1-methylpyrrolidin-2-one

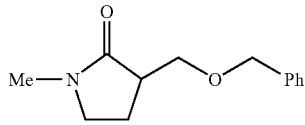

A solution of n-butyllithium in hexane (1.6 M) (13.75 ml, 22 mmol) was added dropwise into a solution of diisopropylamine (3.08 ml, 22 mmol) in tetrahydrofuran (50 ml) with ice-cooling. After stirring at 0° C. for 30 minutes, it was cooled to −78° C., and then a solution of 1-methylpyrrolidin-2-one (1.98 g, 20 mmol) in THF (20 ml) was added dropwise. After stirring at −78° C. for 30 minutes, a solution of benzyl chloromethyl ether (3.76 g, 24 mmol) in THF (30 ml) was added dropwise. After stirring at −78° C., water was added and the mixture was extracted with ethyl acetate. The organic layer was washed with aqueous sodium bicarbonate and brine, dried over magnesium sulfate and then concentrated under reduced pressure. The residue was purified by silica gel column chromatography (eluent: ethyl acetate/hexane; 4/1) to give the title compound (4.14 g, 94%) as a colorless oily matter.

$^1$H-NMR(CDCl$_3$) δ: 1.95-2.3 (2H, m), 2.6-2.8 (1H, m), 2.85 (3H, s), 3.25-3.4 (2H, m), 3.6-3.8 (2H, m), 4.45-4.6 (2H, m), 7.25-7.45 (5H, m).

Reference Example 5

Preparation of 3-(hydroxymethyl)-1-methylpyrrolidin-2-one

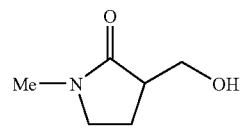

3-[(Benzyloxy)methyl]-1-methylpyrrolidin-2-one (4.14 g, 18.88 mmol) was dissolved in methanol (20 ml), followed by addition of 10% hydrous palladium carbon (1.04 g) and the mixture was stirred at room temperature for 2 hours under hydrogen atmosphere. Palladium carbon was filtered off, and then the filtrate was concentrated under reduced pressure. The residue was purified by silica gel column chromatography (eluent: ethyl acetate/methanol: 10/1) to give the title compound (1.55 g, 64%) as a colorless oily matter.

$^1$H-NMR(CDCl$_3$) δ: 1.7-1.9 (1H, m), 2.05-2.25 (1H, m), 2.6-2.8 (1H, m), 2.86 (3H, s), 3.25-3.45 (3H, m), 3.65-3.95 (2H, m).

Reference Example 6

Preparation of 2-(1,1-dioxideisothiazolin-2-yl)ethyl-methanesulfonate

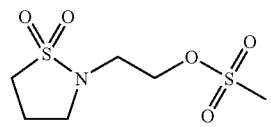

2,2'-Iminodiethanol (1.05 g, 10 mmol) was dissolved in ethyl acetate (30 ml), followed by dropwise addition of triethylamine (4.86 ml, 35 mmol) and methanesulfonyl chloride (2.40 ml, 31 mmol) with ice-cooling and the mixture was stirred for at room temperature for 1 hour. Aqueous sodium bicarbonate was added and the mixture was extracted with ethyl acetate/THF. The organic layers were dried over magnesium sulfate and concentrated under reduced pressure. The precipitate was washed with diethyl ether to give trimesylate product (2.16 g, 64%) as colorless crystals.

$^1$H-NMR(CDCl$_3$) δ: 2.99 (3H, s), 3.08 (6H, s), 3.66 (4H, t, J=5.4 Hz), 4.41 (4H, t, J=5.4 Hz).

The obtained trimesylate product (1.83 g, 5.39 mmol) was suspended in THF (200 ml), followed by dropwise addition of a solution of n-butyllithium (4.04 ml, 6.47 mmol) in hexane (1.6 M). The mixture was stirred at room temperature for 2 hours, followed by addition of a solution of n-butyllithium (4.04 ml, 6.47 mmol) in hexane (1.6 M) and the mixture was stirred at room temperature for 2 hours. Aqueous sodium bicarbonate was added and the mixture was extracted with ethyl acetate/THF. The organic layers were dried over magnesium sulfate and concentrated under reduced pressure. The residue was purified by silica gel column chromatography (eluent: ethyl acetate/hexane; 4/1) to give the title compound (0.71 g, 54%) as a colorless oily matter.

$^1$H-NMR(CDCl$_3$) δ: 2.3-2.5 (2H, m), 3.08 (3H, s), 3.17 (2H, t, J =7.6 Hz), 3.35-3.5 (4H, m), 4.40 (2H, t, J=5.2 Hz).

Reference Example 7

Preparation of 2-[N-(2,6-difluorobenzyl)-N-ethoxycarbonyl]amino-4-[N-(2-methoxyethyl)-N-methylaminomethyl]-5-(4-aminophenyl)thiophene-3-carboxylic acid ethyl ester

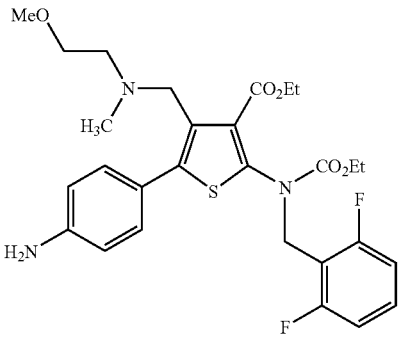

2 N hydrogen chloride/diethyl ether solution (21 ml) and 50% hydrous-10% palladium/carbon (3.73 g) were added to a solution of 2-[N-(2,6-difluorobenzyl)-N-ethoxycarbonyl]amino-4-[N-(2-methoxyethyl)-N-methylaminomethyl]-5-(4-nitrophenyl)thiophene-3-carboxylic acid ethyl ester (12.43 g) (JP-A-2001-278884, WO00/56739) in ethanol (315 ml) and the mixture was stirred thoroughly under hydrogen atmosphere for 1 hour. The filtrate except a catalyst was neutralized with aqueous sodium bicarbonate, and then the solvent was distilled off. The obtained residue was partitioned between ethyl acetate and water, and then the organic layer was washed with saturated brine and then was dried over anhydride magnesium sulfate. The residue obtained by distilling off the solvent under reduced pressure, was subject to NH-silica gel (manufactured by Fuji Silysia Chemical Ltd.) chromatography to give the title compound (11.44 g) as an oily matter.

$^1$H-NMR (CDCl$_3$) δ: 1.12-1.30 (3H, br), 2.05 (3H, s), 2.39 (2H, t, J=6.3 Hz), 3.27 (3H, s), 3.32 (3H, t, J=6.3 Hz), 3.59 (2H, s), 3.78 (2H, s), 4.20 (2H, q, J=7.1 Hz), 4.10-4.23 (2H, br), 5.00 (2H, s), 6.66 (2H, d, J=8.6 Hz), 6.84 (2H, t, J=8.2 Hz), 7.18 (2H, d, J=8.6 Hz), 7.15-7.30 (1H, m).

IR (KBr): 1717, 1626, 1609, 1472, 1406, 1300, 1246 cm$^{-1}$.

Reference Example 8

Preparation of 2-[N-(2,6-difluorobenzyl)-N-ethoxycarbonyl]amino-4-[N-(2-methoxyethyl)-N-methylaminomethyl]-5-[4-(ethylaminocarbonyl)aminophenyl]thiophene-3-carboxylic acid ethyl ester

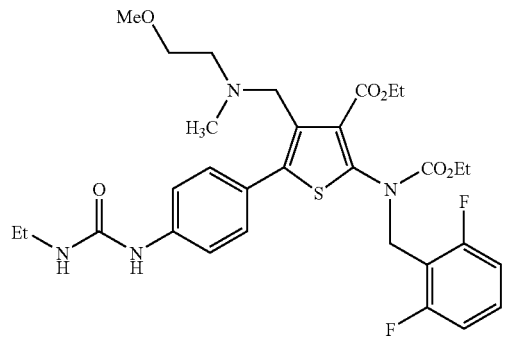

Ethyl isocyanate (2.26 ml) was added to a solution of the compound of Reference Example 7 (8.05 g) in pyridine (143 ml) while stirring with ice-cooling and the mixture was allowed to return to room temperature slowly and was stirred for 18 hours. The residue obtained by distilling off the solvent, was subject to NH-silica gel (manufactured by Fuji Silysia Chemical Ltd.) chromatography to give the title compound (9.25 g) as an oily matter.

$^1$H-NMR (CDCl$_3$) δ: 1.11-1.26 (6H, m), 1.30 (3H, t, J=7.1 Hz), 2.02 (3H, s), 2.38 (2H, t, J=6.3 Hz), 3.26 (3H, s), 3.25-3.35 (4H, m), 3.58 (2H, s), 4.11-4.26 (4H, m), 4.91-5.02 (1H, br), 5.00 (2H, s), 6.71-6.82 (1H, br), 6.84 (2H, t, J=7.7 Hz), 7.20-7.39 (5H, m).

IR (KBr): 1721, 1593, 1541, 1472, 1408, 1310, 1231 cm$^{-1}$.

Reference Example 9

Preparation of 2-[N-(2,6-difluorobenzyl)-N-ethoxycarbonyl]amino-4-[N-(2-methoxyethyl)-N-methylaminomethyl]-5-[4-(ethylaminocarbonyl)aminophenyl]thiophene-3-carboxylic acid

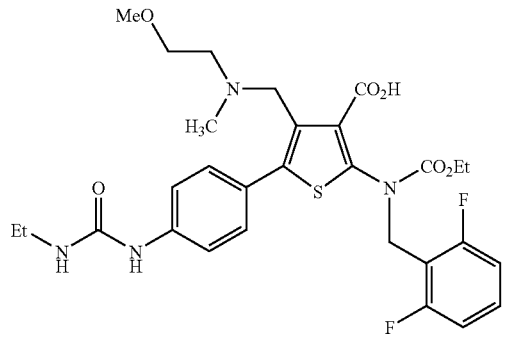

A 2 N sodium hydroxide solution (78.5 ml) was added to a solution of the compound of Reference Example 8 (19.9 g) in ethanol (472 ml) and the mixture was stirred at 60° C. for 5 hour. It was allowed to return to room temperature, followed by addition of 1 N hydrochloric acid (157 ml), and the solvent was distilled off. The obtained residue was dissolved in ethanol and toluene, and the solvent was distilled off again. Anhydrous ethanol (150 ml) was added to the residue, and the inorganic materials were filtered off. The residue obtained by concentrating and dried the filtrate to a solid, was finely divided in anhydrous ether, which was filtered and dried to give the title compound (18.2 g).

$^1$H-NMR (CDCl$_3$) δ: 1.14 (3H, t, J=7.2 Hz), 1.18 (3H, t, J=7.4 Hz), 2.55 (3H, s), 2.90 (2H, br), 3.18-3.39 (2H, m), 3.26 (3H, s), 3.54 (2H, br), 3.92-4.30 (4H, m), 5.02 (2H, s), 6.82 (2H, t, J=7.9 Hz), 6.92-7.10 (2H, m), 7.16-7.28 (1H, m), 7.50-7.71 (2H, m), 8.92 (1H, s), 9.27 (1H, s).

IR (KBr): 2982, 1715, 1595, 1543, 1472, 1406, 1314 cm$^{-1}$.

Reference Example 10

Preparation of 2-[N-(2,6-difluorobenzyl)-N-ethoxycarbonyl]amino-4-(N-methylaminomethyl)-5-(4-aminophenyl)thiophene-3-carboxylic acid ethyl ester

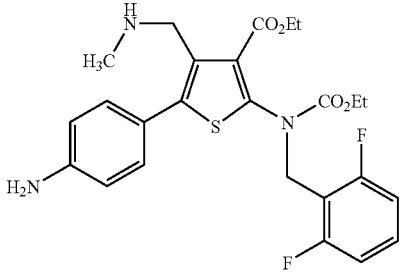

The similar reaction to that of Reference Example 7 was performed to obtain the title compound (9.65 g) as an oily matter from 4-(N-benzyl-N-methylaminomethyl)-2-[N-(2,6-difluorobenzyl)-N-ethoxycarbonyl]amino-5-(4-nitrophenyl)thiophene-3-carboxylic acid ethyl ester (14.0 g) (JP-A-2001-278884, WO00/56739), 2 N hydrochloride/diethyl ether solution (22.4 ml) and 50% hydrous-10% palladium/carbon (4.2 g).

$^1$H-NMR (CDCl$_3$) δ: 1.18 (3H, br), 1.32 (3H, t, J=7.0 Hz), 1.78 (1H, s), 2.32 (3H, s), 3.65 (2H, s), 3.78 (2H, s), 4.17-4.28 (4H, m), 4.95 (2H, s), 6.69 (2H, d, J=8.6 Hz), 6.83 (2H, t, J=7.9 Hz), 7.16-7.28 (3H, m).

IR (KBr): 2980, 1715, 1626, 1609, 1518, 1472, 1408, 1298, 1244 cm$^{-1}$.

Reference Example 11

Preparation of 4-[N-(2-ethoxyethyl)-N-methylaminomethyl]-2-[N-(2,6-difluorobenzyl)-N-ethoxycarbonyl]amino-5-(4-aminophenyl)thiophene-3-carboxylic acid ethyl ester

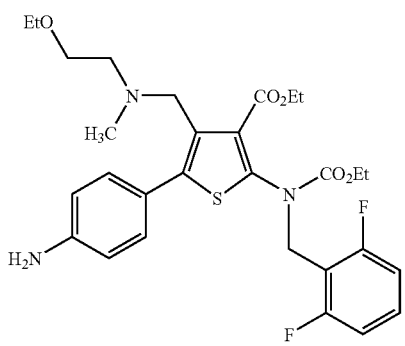

2-Ethoxyethyl chloride (1.02 g), N-ethyl diisopropylamine (2.01 ml) and potassium iodide (1.55 g) were added to a solution of the compound of Reference Example 10 (2.36 g) in DMF (46.8 ml) and the mixture was stirred at 70° C. for 24 hours. The reaction solution was partitioned between ethyl acetate and water, and the organic layer was washed with brine, and then was dried over magnesium sulfate. The residue obtained by distilling off the solvent, was subject to NH-silica gel (manufactured by Fuji Silysia Chemical Ltd.) chromatography to give the title compound (2.38 g) as an oily matter.

$^1$H-NMR (CDCl$_3$) δ: 1.15 (3H, t, J=7.2 Hz), 1.12-1.26 (3H, br), 1.30 (3H, t, J=7.5 Hz), 2.04 (3H, s), 2.40 (2H, t, J=6.4 Hz), 3.36 (2H, t, J=6.4 Hz), 3.41 (2H, q, J=7.0 Hz), 3.58 (2H, s), 3.78 (2H, s), 4.20 (2H, q, J=7.0 Hz), 4.10-4.21 (2H, m), 5.00 (2H, s), 6.66 (2H, d, J=8.4 Hz), 6.84 (2H, t, J=7.7 Hz), 7.17 (2H, d, J=8.4 Hz), 7.19-7.31 (1H, m).

IR (KBr): 1721, 1626, 1593, 1522, 1472, 1300 cm$^{-1}$.

Reference Example 12

Preparation of 2-[N-(2,6-difluorobenzyl)-N-ethoxycarbonyl]amino-4-[N-(2-ethoxyethyl)-N-methylaminomethyl]-5-[4-(ethylaminocarbonyl)aminophenyl]thiophene-3-carboxylic acid ethyl ester

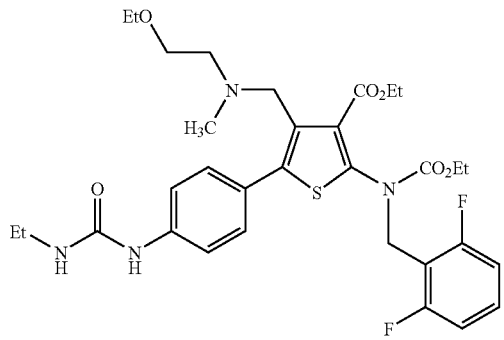

The similar reaction to that of Reference Example 8 was performed to obtain the title compound (1.83 g) as an oily matter from the compound of Reference Example 11 (2.2 g), pyridine (38 ml) and ethyl isocyanate (0.6 ml).

$^1$H-NMR (CDCl$_3$) δ: 1.13 (3H, t, J=7.5 Hz), 1.14 (3H, t, J=7.5 Hz), 1.24-1.32 (6H, m), 2.02 (3H, s), 2.39 (2H, t, J=6.3 Hz), 3.19-3.28 (2H, m), 3.30-3.44 (4H, m), 3.57 (2H, s), 4.11-4.24 (4H, m), 4.37 (1H, br), 5.00 (2H, s), 5.20 (1H, br), 6.84 (2H, t, J=8.0 Hz), 7.08 (1H, br), 7.19-7.35 (4H, m).

IR (KBr): 1715, 1593, 1539, 1472, 1379, 1308 cm$^{-1}$.

Reference Example 13

Preparation of ethyl 4-{[benzyl(methyl)amino]methyl}-2-[(2,6-difluorobenzyl)(ethoxycarbonyl)amino]-5-(4-{[(ethylamino)carbonyl]amino}phenyl)thiophene-3-carboxylate

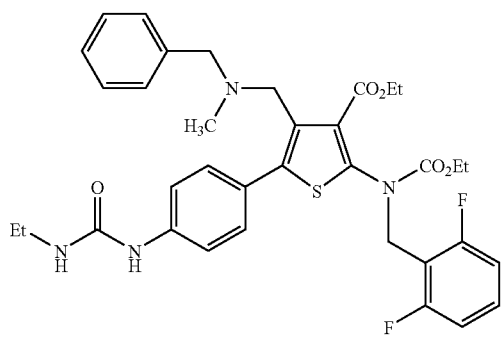

The similar reaction to that of Reference Example 8 was performed using 5-(4-aminophenyl)-4-(N-benzyl-N-methylaminomethyl)-2-[N-(2,6-difluorobenzyl)-N-ethoxycarbonyl]aminothiophene-3-carboxylic acid ethyl ester (JP-A-2001-278884, WO00/56739) (6.32 g, 10.64 mmol) to give the title compound (6.57 g, 93%) as colorless crystals.

$^1$H-NMR (CDCl$_3$) δ: 1.16 (3H, t, J=7.2 Hz), 1.29 (3H, t, J=7.2 Hz), 1.09-1.25 (3H, br), 1.89 (3H, s), 3.20 (2H, s), 3.24-3.37 (2H, m), 3.64 (2H, s), 4.21 (2H, q, J=7.2 Hz), 4.12-4.28 (2H, br), 4.88 (1H, br), 5.02 (2H, s), 6.63 (1H, br), 6.78 (2H, t, J=8.0 Hz), 7.07-7.40 (10H, m).

IR (KBr): 3331, 2980, 1721, 1661, 1593, 1541, 1472, 1406, 1310 cm$^{-1}$.

Reference Example 14

Preparation of N-(4-{5-{[benzyl(methyl)amino]methyl}-1-(2,6-difluorobenzyl)-3-[4-(2-methoxyethoxy)phenyl]-2,4-dioxo-1,2,3,4-tetrahydrothieno[2,3-d]pyrimidin-6-yl}phenyl)-N'-ethylurea

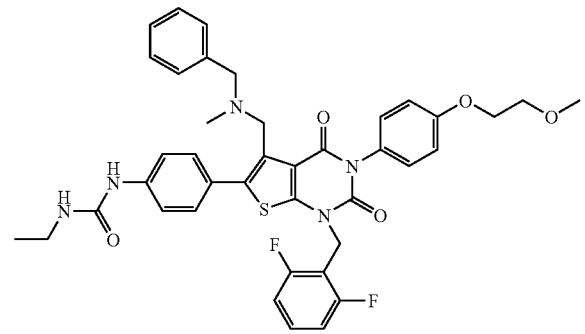

4-(2-Methoxyethoxy)aniline (8.72 g, 52.1 mmol) was dissolved in dichloromethane (60 ml), followed by dropwise addition of solution of dimethylaluminum chloride in hexane (0.98 M)(48.3 ml, 47.34 mmol) with ice-cooling and the mixture was stirred for at room temperature 1 hour. Then, a solution of the compound of Reference Example 13 (5.25 g, 7.89 mmol) in dichloromethane (50 ml) was added and the mixture was stirred at room temperature for 16 hours. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: ethyl acetate), and then was recrystallized from ethyl acetate/methanol to give the title compound (4.52 g, 77%) as colorless crystals.

$^1$H-NMR(CDCl$_3$) δ: 1.18 (3H, t, J=7.2 Hz), 2.05 (3H, s), 3.25-3.4 (2H, m), 3.45 (3H, s), 3.56 (2H, s), 3.7-3.8 (2H, m), 3.89 (2H, s), 4.1-4.2 (2H, m), 4.6-4.7(1H, m), 5.35 (2H, s), 6.32 (1H, s), 6.91 (2H, t, J=8.2 Hz), 7.05 (2H, d, J=9.0 Hz), 7.15-7.3 (3H, m), 7.36 (2H, d, J=8.6 Hz), 7.68 (2H, d, J=8.6 Hz).

IR (KBr): 1659, 1514, 1244, 1123, 1063, 1038, 928, 835 cm$^{-1}$.

mp 114-116° C.

Reference Example 15

Preparation of N-(4-{5-{[benzyl(methyl)amino]methyl}-1-(2,6-difluorobenzyl)-3-(4-fluorophenyl)-2,4-dioxo-1,2,3,4-tetrahydrothieno[2,3-d]pyrimidin-6-yl}phenyl)-N'-ethylurea

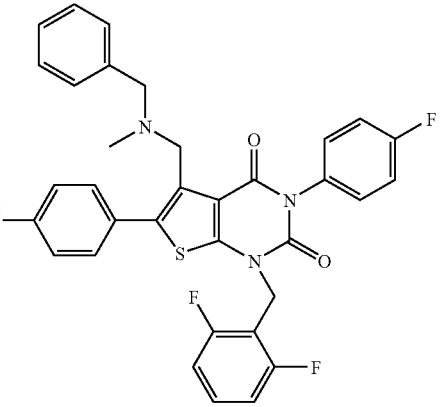

The similar reaction to that of Reference Example 14 was performed using the compound of Reference Example 13 (333 mg, 0.5 mmol) to give the title compound (162 mg, 48%) as colorless crystals.

$^1$H-NMR(CDCl$_3$) δ: 1.16 (3H, t, J=7.2 Hz), 2.04 (3H, s), 3.30 (2H, dq, J=5.5, 7.2 Hz), 3.55 (2H, s), 3.87 (2H, s), 4.81 (1H, t, J=5.5 Hz), 5.35 (2H, s), 6.58 (1H, s), 6.91 (2H, t, J=8.2 Hz), 7.15-7.30 (10H, m), 7.37 (2H, d, J=8.4 Hz), 7.65(2H, d, J=8.8 Hz).

IR (KBr): 3318, 1717, 1672, 1591, 1553, 1472, 1318, 1236 cm$^{-1}$.

Reference Example 16

Preparation of methyl 6-(bromomethyl)nicotinate

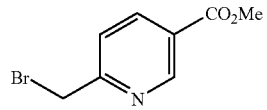

Methyl 6-methyl nicotinate (1.05 g, 10 mmol) was dissolved in ethyl acetate (50 ml), followed by addition of NBS (3.56 g, 20 mmol) and AIBN (329 mg, 2 mmol). After stirring at 80° C. for 3 hours, aqueous sodium bicarbonate was added and the mixture was extracted with ethyl acetate. The organic layer was washed with brine, dried over magnesium sulfate, and then concentrated under reduced pressure. The residue was purified by silica gel column chromatography (eluent: ethyl acetate/hexane; 4/1) to give the title compound (682 mg, 28%) as orange amorphous product.

$^1$H-NMR(CDCl$_3$) δ: 3.96 (3H, s), 4.58 (2H, s), 7.53 (1H, d, J=8.2 Hz), 8.30 (2H, dd, J=1.8, 8.2 Hz), 9.17 (1H, d, J=1.8 Hz).

Reference Example 17

Preparation of ethyl 2-[(2,6-difluorobenzyl)(ethoxy-carbonyl)amino]-5-(4-{[(ethylamino)carbonyl]amino}phenyl)-4-[(methylamino)methyl]thiophene-3-carboxylate

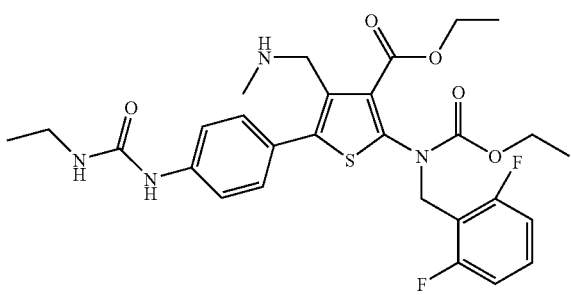

The similar reaction to that of Reference Example 7 was performed using the compound of Reference Example 13 (7.47 g, 11.2 mmol) to give the title compound (3.57 g, 55%) as yellow powder.

Reference Example 18

Preparation of ethyl 2-[(2,6-difluorobenzyl)(ethoxy-carbonyl)amino]-5-(4-{[(ethylamino)carbonyl]amino}phenyl)-4-{[methyl(pyridin-2-ylmethyl)amino]methyl}thiophene-3-carboxylate

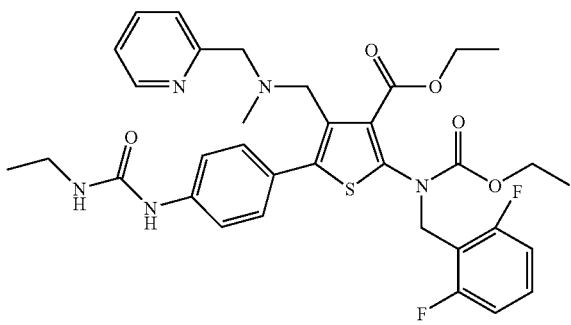

The similar reaction to that of Example 4 as described below was performed using the compound of Reference Example 17 (3.57 g, 6.21 mmol) and 2-chloromethylpyridine hydrochloride (1.53 g, 9.32 mmol) to give the title compound (4.68 g, DMF included) as a yellow oily matter.

Reference Example 19

Preparation of 2-[(2,6-difluorobenzyl)(ethoxycarbonyl)amino]-5-(4-{[(ethylamino)carbonyl]amino}phenyl)-4-{[methyl(pyridin-2-ylmethyl)amino]methyl}thiophene-3-carboxylic acid

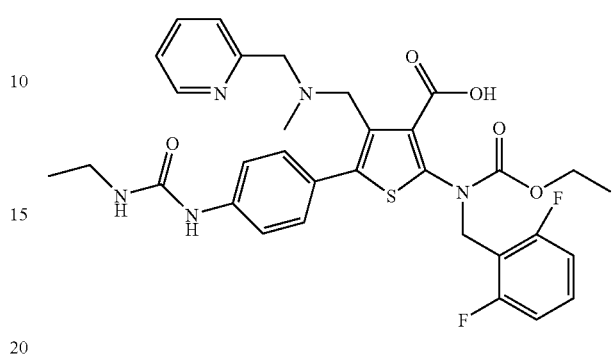

The similar reaction to that of Reference Example 9 was performed using the compound of Reference Example 18 (4.68 g, DMF included) and 2 N sodium hydroxide (8.75 ml, 17.5 mmol) to give the title compound (2.35 g, 59%, 2 steps) as light yellow powder.

$^1$H-NMR(CDCl$_3$) δ: 1.0-1.4 (6H, m), 2.36 (3H, s), 3.2-3.4 (2H, m), 3.7-4.3 (6H, m), 5.05 (2H, s), 6.45 (1H, s), 6.7-7.7 (11H, m), 8.45-8.5 (1H, m)

Reference Example 20

Preparation of ethyl 2-(1H-tetrazol-1-yl)propanate and ethyl 2-(2H-tetrazol-2-yl)propanate

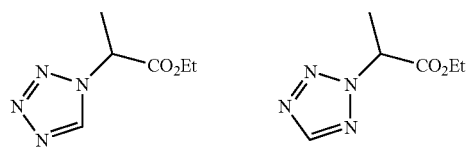

Tetrazole (2.80 g, 40 mmol) and ethyl 2-bromopropionate (5.71 ml, 44 mmol) were dissolved in acetonitrile (80 ml), followed by addition of potassium carbonate (8.29 g, 60 mmol). After stirring at room temperature for 4 days, saturated brine was added and the mixture was extracted twice with ethyl acetate. The organic layers were combined, dried over magnesium sulfate and then concentrated under reduced pressure to give the title compound (7.08 g, quant.) as a colorless oily matter.

$^1$H-NMR(CDCl$_3$) δ: 1.9-2.05 (6H, m), 3.7-3.85 (6H, m), 5.5-5.6 (1H, m), 5.65-5.75 (1H, m), 8.56 (1H, s), 8.81 (1H, s).

Reference Example 21

Preparation of 2-(1H-tetrazol-1-yl)propan-1-ol (1) and 2-(2H-tetrazol-2-yl)propan-1-ol (2)

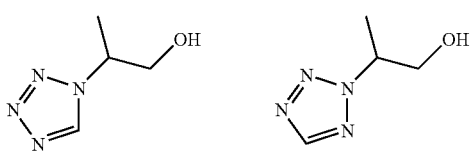

Lithium aluminum hydride (2.28 g, 60 mmol) was suspended in THF (60 ml), followed by dropwise addition of a solution of ethyl 2-(1H-tetrazol-1-yl)propanate and ethyl 2-(2H-tetrazol-2-yl)propanate (7.08 g, 40 mmol) in THF (60 ml) with ice-cooling. After stirring at 0° C. for 1 hour, 1 N sodium hydroxide (2.3 ml) and water (6.9 ml) were sequentially added dropwise. The mixture was filtered through Celite and the filtrate was concentrated. The residue was purified by silica gel column chromatography (eluent: ethyl acetate/methanol; 1/0 to 20/1) to give the title compound (1-yl product) (1.74 g, 34%) and the title compound (2-yl product) (1.29 g, 25%) as a colorless oily matter, respectively.

1-yl Product (1)
$^1$H-NMR(CDCl$_3$) δ: 1.68 (3H, d, J=7.0 Hz), 2.4-2.5 (1H, m), 3.9-4.1 (2H, m), 4.75-4.9 (1H, m), 8.70 (1H, s).

2-yl Product (2)
$^1$H-NMR(CDCl$_3$) δ: 1.67 (3H, d, J=7.0 Hz), 2.34 (1H, t, J=6.6 Hz), 4.0-4.2 (2H, m), 4.95-5.15 (1H, m), 8.54 (1H, s).

Reference Example 22

Preparation of ethyl 2-(1H-1,2,3-triazol-1-yl)propanate and ethyl 2-(2H-1,2,3-triazol-2-yl)propanate

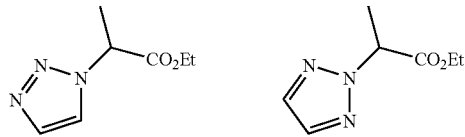

The similar reaction to that of Reference Example 20 was performed using 1,2,3-triazole (1.38 g, 20 mmol) and 2-bromopropionic acid ethyl (3.90 ml, 30 mmol) to give the title compound (3.43 g, quant., DMF included) as a colorless oily matter.
$^1$H-NMR(CDCl$_3$) δ: 1.2-1.35 (3H, m), 1.85 (1.5H, d, J=7.5 Hz), 1.91 (1.5H, d, J=7.5 Hz), 4.15-4.3 (2H, m), 5.42 (1H, q, J=7.5 Hz), 5.50 (1H, q, J=7.5 Hz), 7.66 (1H, s), 7.74 (1H, s).

Reference Example 23

Preparation of 2-(1H-1,2,3-triazol-1-yl)propan-1-ol (1) and 2-(2H-1,2,3-triazol-2-yl)propan-1-ol (2)

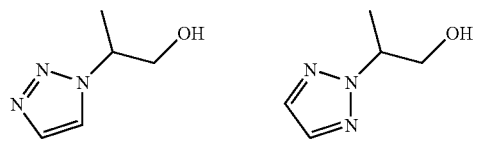

The similar reaction to that of Reference Example 21 was performed using ethyl 2-(1H-1,2,3-triazol-1-yl)propanate, ethyl 2-(2H-1,2,3-triazol-2-yl)propanate (3.43 g, DMF included) and lithium aluminum hydride (1.14 g, 30 mmol) to give the title compound (1-yl product) (1.03 g, 41%) and the title compound (2-yl product) (0.57 g, 22%) as a colorless oily matter, respectively.

1-yl Product (1)
$^1$H-NMR(CDCl$_3$) δ: 1.61 (3H, d, J=6.6 Hz), 2.59 (1H, t, J=6.6 Hz), 4.01 (2H, t, J=6.2 Hz), 4.65-4.85 (1H, m), 7.65 (1H, s), 7.71 (1H, s).

2-yl Product (2)
$^1$H-NMR(CDCl$_3$) δ: 1.59 (3H, d, J=6.6 Hz), 2.85 (1H, t, J=6.6 Hz), 4.01 (2H, t, J=6.6 Hz), 4.7-4.9 (1H, m), 7.64 (2H, s).

Reference Example 24

Preparation of 2-[N-(2,6-difluorobenzyl)-N-ethoxycarbonyl]amino-4-[N-(2-ethoxyethyl)-N-methylaminomethyl]-5-[4-(ethylaminocarbonyl)aminophenyl]thiophene-3-carboxylic acid

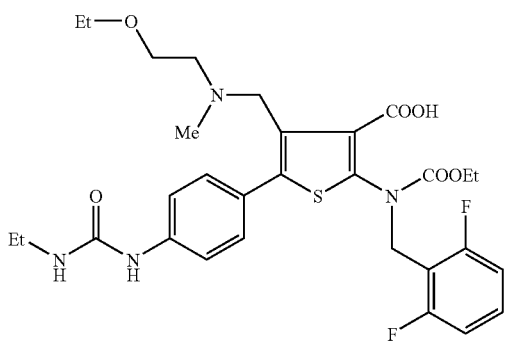

The similar reaction to that of Reference Example 9 was performed to obtain the title compound (9.89 g) from the compound of Reference Example 12 (10.96 g).
$^1$H-NMR (CDCl$_3$) δ: 1.12 (3H, t, J=7.2 Hz), 1.14 (3H, t, J=7.2 Hz), 1.18 (3H, t, J=7.4 Hz), 2.57 (3H, s), 2.62-3.10 (2H, br), 3.18-3.43 (4H, m), 3.58 (2H, brs), 4.01 (2H, brs), 4.09-4.24 (2H, m), 5.04 (2H, s), 6.81 (2H, t, J=7.6 Hz), 6.95-7.07 (2H, m), 7.19-7.27 (1H, m), 7.56-7.70 (2H, m), 9.12 (1H, s), 9.44 (1H, s).
IR (KBr): 1713, 1599, 1539, 1472, 1404, 1312 cm$^1$.

Example 1

Preparation of N-{4-[1-(2,6-difluorobenzyl)-5-{[methylamino]methyl}-2,4-dioxo-3-phenyl-1,2,3,4-tetrahydrothieno[2,3-d]pyrimidin-6-yl]phenyl)-N-ethylurea

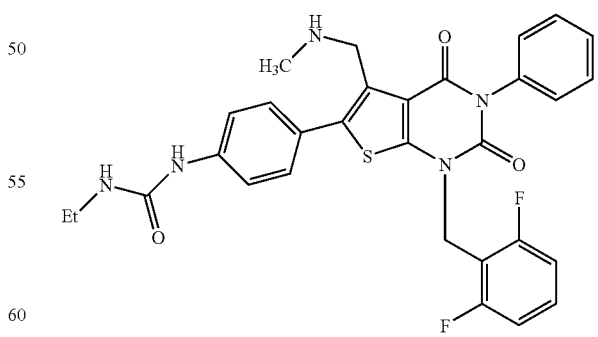

The similar reaction to that of Reference Example 7 was performed to obtain the title compound (791 mg) from N-{4-[5-[benzyl(methyl)amino]methyl}-1-(2,6-difluorobenzyl)-2,4-dioxo-3-phenyl-1,2,3,4-tetrahydrothieno[2,3-d]pyrimidin-6-yl]phenyl}-N-ethylurea (JP-A-2001-278884, WO00/

56739) (1.12 g) and 2 N hydrochloride/diethyl ether solution (0.76 ml) and 50% hydrous-10% palladium/carbon (336 mg).

¹H-NMR (CDCl₃) δ: 1.10 (3H, t, J=7.3 Hz), 2.34 (3H, s), 3.15-3.29 (2H, m), 3.78 (2H, s), 5.02 (1H, t, J=5.4 Hz), 5.36 (2H, s), 6.91 (2H, t, J=8.1 Hz), 7.10 (1H, s), 7.23-7.37 (8H, m), 7.41-7.60 (3H, m).

IR (KBr): 2975, 1713, 1669, 1593, 1534, 1472, 1316, 1236 cm⁻¹.

Elemental analysis for $C_{30}H_{27}N_5O_3SF_2 \cdot 1.0H_2O$

Calculated: C, 60.70; H, 4.92; N, 11.80. Found: C, 61.01; H, 5.03; N, 11.91.

Example 2

Preparation of N-[4-(1-(2,6-difluorobenzyl)-5-{[(2-methoxyethyl)amino]methyl}-2,4-dioxo-3-phenyl-1,2,3,4-tetrahydrothieno[2,3-d]pyrimidin-6-yl)phenyl]-N'-ethylurea

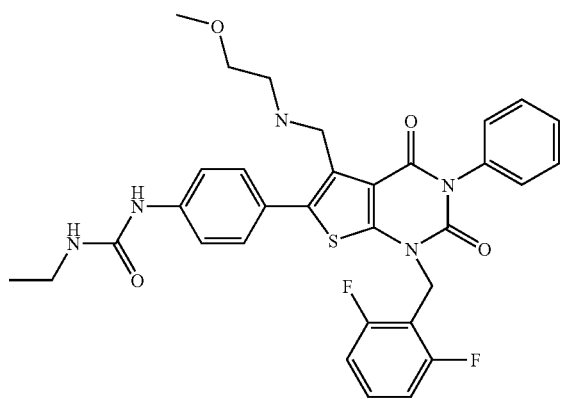

The compound of Reference Example 1 (1.60 g, 2 mmol) and 2-methoxyethylamine (0.74 g, 10 mmol) were dissolved in DMF (10 ml), followed by addition of N,N-diisopropylethylamine (0.52 ml, 3 mmol) and the mixture was stirred at 100° C. for 1 hour. Aqueous sodium bicarbonate was added to the reaction solution and the mixture was extracted with ethyl acetate. The organic layer was washed with brine, dried over magnesium sulfate, and then concentrated under reduced pressure. The residue was purified by silica gel column chromatography (eluent: ethyl acetate/methanol/triethylamine; 40/2/1), and then was recrystallized from dichloromethane/methanol to give the title compound (463 mg, 37%) as colorless crystals.

¹H-NMR(CDCl₃) δ: 1.11 (3H, t, J=7.2 Hz), 2.71 (2H, t, J=5.4 Hz), 3.15-3.25 (2H, m), 3.26 (3H, s), 3.40 (2H, t, J=5.4 Hz), 3.87 (2H, s), 5.15-5.25 (1H, m), 5.36 (2H, s), 6.85-6.9 (2H, m), 6.92 (2H, t, J=8.0 Hz), 7.25-7.6 (10H, m).

IR (KBr): 1717, 1667, 1472, 1236, 1034, 733 cm⁻¹.

Elemental analysis for $C_{32}H_{31}F_2N_5O_4S \cdot 0.2H_2O$

Calculated: C, 61.66; H, 5.08; N, 11.24. Found: C, 61.40; H, 4.98; N, 11.04.

mp 221-223° C.

Example 3

Preparation of N-[4-(1-(2,6-difluorobenzyl)-5-{[(2-methoxyethyl)amino]methyl}-2,4-dioxo-3-phenyl-1,2,3,4-tetrahydrothieno[2,3-d]pyrimidin-6-yl)phenyl]-N'-ethylurea

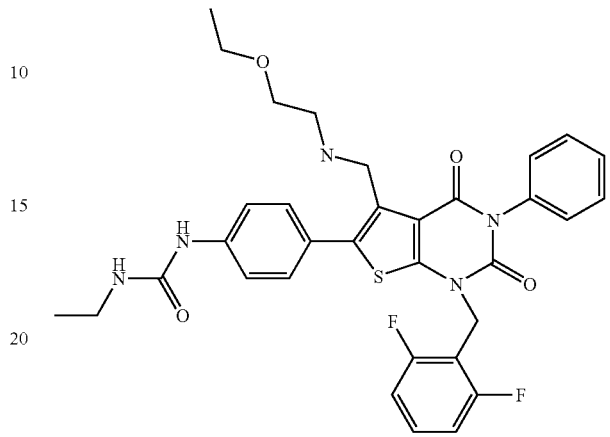

The similar reaction to that of Example 2 was performed using the compound of Reference Example 1 (1.60 g, 2 mmol) and 2-ethoxyethyl amine (1.78 g, 20 mmol) to give the title compound (396 mg, 31%) as colorless crystals.

¹H-NMR(CDCl₃) δ: 1.10 (6H, t, J=7.0 Hz), 2.65-2.75 (2H, m), 3.15-3.25 (2H, m), 3.42 (2H, q, J=7.0 Hz), 3.88 (2H, s), 5.29 (1H, t, J=5.4 Hz), 5.36 (2H, s), 6.92 (2H, t, J=8.0 Hz), 6.85-7.0 (2H, m), 7.2-7.35 (6H, m), 7.45-7.6 (3H, m).

IR (KBr): 1715, 1669, 1534, 1472, 1236, 1034, 733 cm⁻¹.

Elemental analysis for $C_{33}H_{33}F_2N_5O_4S$

Calculated: C, 62.55; H, 5.25; N, 11.05. Found: C, 62.27; H, 5.16; N, 11.06.

mp 211-213° C.

Example 4

Preparation of ethyl 3-[{[1-(2,6-difluorobenzyl)-6-(4-{[(ethylamino) carbonyl]amino}phenyl)-2,4-dioxo-3-phenyl-1,2,3,4-tetrahydrothieno[2,3-d]pyrimidin-5-yl]methyl}(methyl)amino]propanate

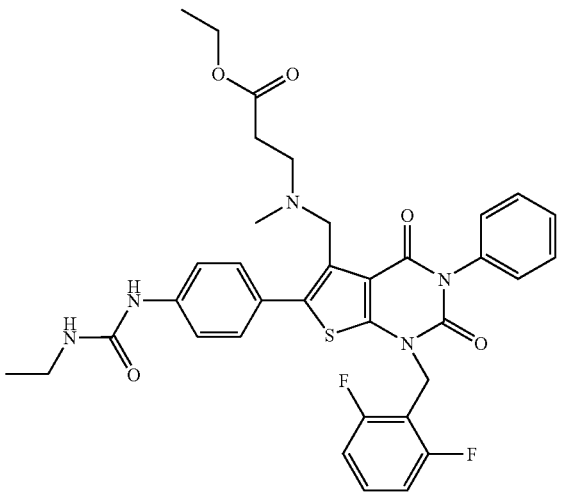

The compound of Example 1 (576 mg, 1 mmol) was dissolved in DMF (4 ml), followed by addition of N,N-diisopropylethylamine (0.52 ml, 1.5 mmol) and ethyl 3-bromopropionate (0.15 ml, 1.2 mmol) and the mixture was stirred at 50-60° C. for 16 hours.

Aqueous sodium bicarbonate was added and the mixture was extracted with ethyl acetate. The organic layer was washed with brine, dried over magnesium sulfate and then concentrated under reduced pressure. The residue was purified by silica gel column chromatography (eluent: ethyl acetate/methanol; 40/1), and further it was recrystallized from dichloromethane/methanol/diethyl ether to give the title compound (389 mg, 58%) as colorless crystals.

$^1$H-NMR(CDCl$_3$) δ: 1.14 (3H, t, J=7.0 Hz), 1.18 (3H, t, J=7.0 Hz), 2.13 (3H, s), 2.37 (2H, t, J=6.4 Hz), 2.75 (2H, t, J=6.4 Hz), 3.2-3.4 (2H, m), 3.78 (2H, s), 4.00 (2H, q, J=7.0 Hz), 4.7-4.8 (1H, s), 5.37 (2H, s), 6.36 (1H, s), 6.92 (2H, t, J=8.0 Hz), 7.2-7.6 (10H, m).

IR (KBr): 1717, 1669, 1532, 1472, 1236, 1034, 733 cm$^{-1}$.

Elemental analysis for C$_{35}$H$_{35}$F$_2$N$_5$O$_5$S.0.5H$_2$O

Calculated: C, 61.39; H, 5.30; N, 10.23. Found: C, 61.09; H, 5.10; N, 9.96.

mp 198-200° C.

Example 5

Preparation of ethyl[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]acetate

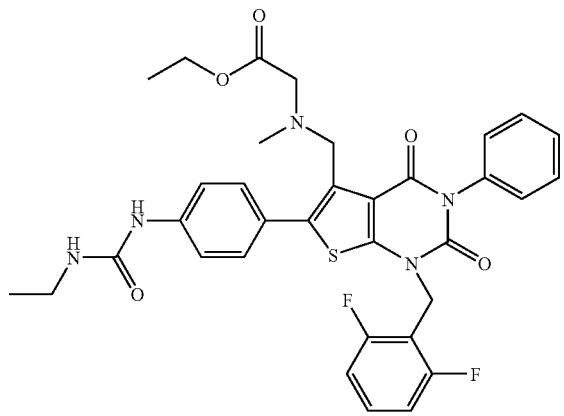

The similar reaction to that of Example 4 was performed using the compound of Example 1 (1.09 g, 1.8 mmol) and ethyl bromoacetate (0.24 ml, 2.16 mmol) to give the title compound (0.96 g, 81%) as colorless crystals.

$^1$H-NMR(CDCl$_3$) δ: 1.16 (3H, t, J=7.0 Hz), 1.17 (3H, t, J=7.2 Hz), 2.25 (3H, s), 3.2-3.4 (2H, m), 3.37 (2H, s), 3.98 (2H, q, J=7.0 Hz), 4.03 (2H, s), 4.7-4.8 (1H, m), 5.36 (2H, s), 6.44 (1H, s), 6.92 (2H, t, J=8.0 Hz), 7.25-7.55 (10H, m).

IR (KBr): 1713, 1674, 1472, 1460, 1316, 1236, 1036, 789, 735 cm$^{-1}$.

Elemental analysis for C$_{34}$H$_{33}$F$_2$N$_5$O$_5$S.0.2H$_2$O

Calculated: C, 61.38; H, 5.06; N, 10.53. Found: C, 61.18; H, 5.16; N, 10.51.

mp 208-209° C.

Example 6

Preparation of ethyl 4-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]butanate

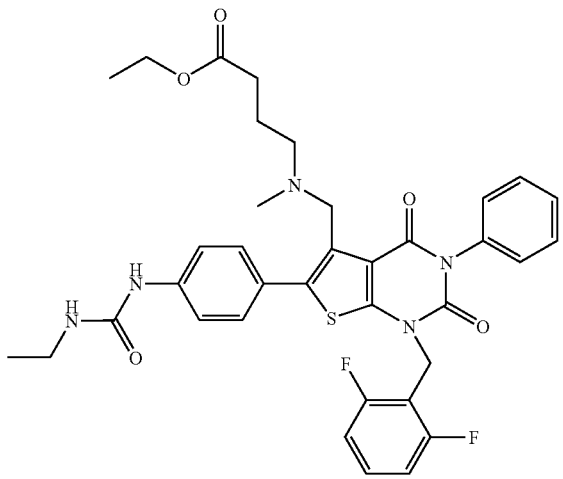

The similar reaction to that of Example 4 was performed using the compound of Example 1 (2.0 g, 3.47 mmol) and 4-bromo-n-ethyl butyrate (0.60 ml, 4.16 mmol) to give the title compound (1.82 g, 76%) as colorless crystals.

$^1$H-NMR(CDCl$_3$) δ: 1.18 (3H, t, J=7.2 Hz), 1.20 (3H, t, J=7.2 Hz), 1.55-1.75 (2H, m), 2.07 (3H, s), 2.18 (3H, t, J=7.4 Hz), 2.40 (2H, t, J=7.4 Hz), 3.2-3.4 (2H, m), 3.76 (2H, s), 4.05 (2H, q, J=7.2 Hz), 4.7-4.8 (1H, m), 5.37 (2H, s), 6.42 (1H, s), 6.92 (2H, t, J=8.2 Hz), 7.25-7.6 (10H, m).

IR (KBr): 1717, 1667, 1472, 1236, 1032, 735 cm$^{-1}$.

Elemental analysis for C$_{36}$H$_{37}$F$_2$N$_5$O$_5$S

Calculated: C, 62.69; H, 5.41; N, 10.15. Found: C, 62.29; H, 5.37; N, 10.15.

mp 203-204° C.

Example 7

Preparation of N-{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}-N-methyl-α-alanine

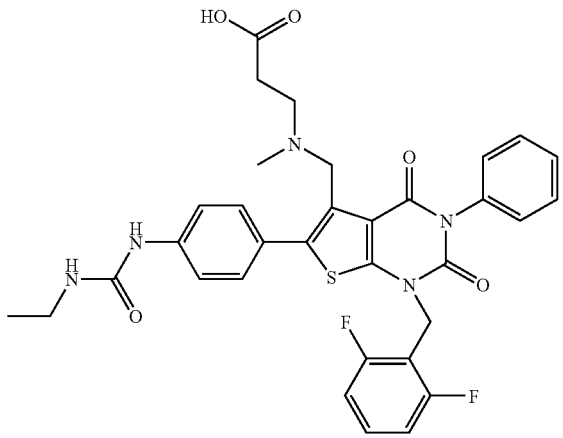

The compound of Example 4 (500 mg, 0.74 mmol) was dissolved in a mixed solution of ethanol (20 ml) and tetrahydrofuran (10 ml), followed by addition of 1 N aqueous sodium hydroxide solution (1 ml, 1 mmol) and the mixture was stirred at room temperature for 16 hours. 1 N hydrochloric acid (1 ml) was added with ice-cooling, and the precipitate was washed with water and ethyl acetate to give the title compound (144 mg, 30%) as brown powder.

$^1$H-NMR(CDCl$_3$+DMSO-d$_6$) δ: 1.16 (3H, t, J=7.4 Hz), 2.36 (3H, s), 2.3-2.4 (2H, m), 2.55-2.65 (2H, m), 3.2-3.3 (2H, m), 4.00 (2H, s), 5.34(2H, s), 5.85-5.95 (1H, m), 6.9-7.0 (2H, m), 7.2-7.6 (10H, m), 8.37 (1H, s).

IR (KBr): 1709, 1667, 1537, 1472, 1316, 1236, 1032 cm$^{-1}$.

Example 8

Preparation of [{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]acetic acid

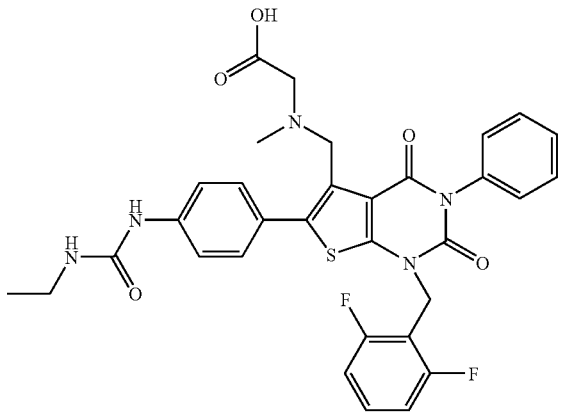

The similar reaction to that of Example 7 was performed using the compound of Example 5 (0.99 g, 1.5 mmol) and 1 N aqueous sodium hydroxide solution (2 ml, 2 mmol) to give the title compound (598 mg, 60%) as crude product of yellow powder, which was used in the next reaction.

Example 9

Preparation of 4-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]butanoic acid

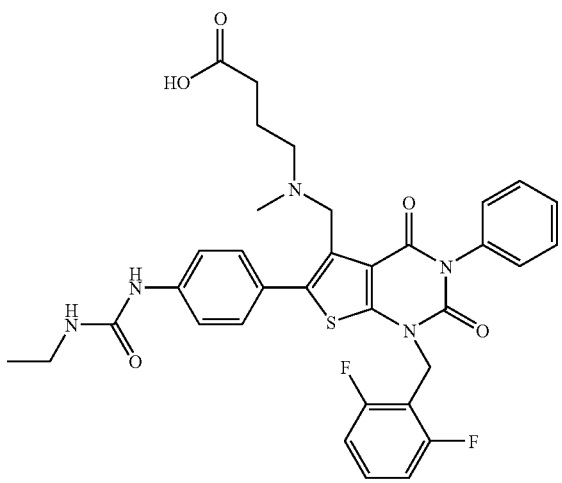

The similar reaction to that of Example 7 was performed using the compound of Example 6 (1.2 g, 1.74 mmol) and 1 N aqueous sodium hydroxide solution (2 ml, 2 mmol) to give the title compound (1.28 g, quant.) as yellow powder.

$^1$H-NMR (DMSO-d$_6$) δ: 1.06 (3H, t, J=7.0 Hz), 1.45-1.6 (2H, m), 2.00 (3H, s), 2.0-2.15 (2H, m), 2.2-2.35 (2H, m), 3.0-3.2 (2H, m), 3.68 (2H, s), 5.30(2H, s), 6.3-6.4 (1H, m), 7.05-7.55 (14H, m), 8.86 (1H, s).

Example 10

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N,N-dimethylpropanamide

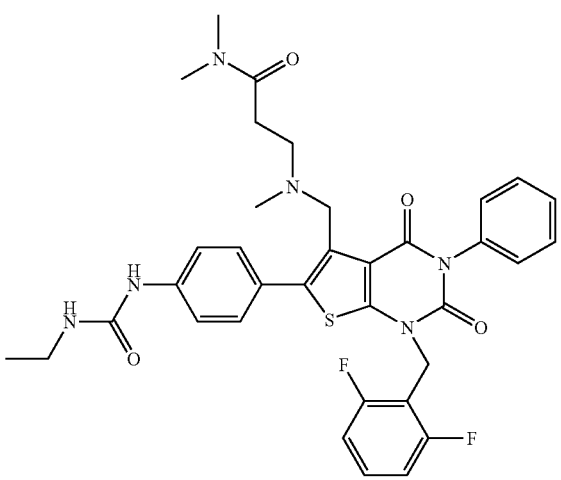

The compound of Example 7 (300 mg, 0.463 mmol) was dissolved in DMF (5 ml), followed by addition of a solution of 1-ethyl-3-(3-dimethylaminopropyl)-carbodiimide hydrochloride (142 mg, 0.741 mmol), 1-hydroxybenzotriazole (113 mg, 0.741 mmol), N,N-diisopropylethylamine (0.15 ml, 0.833 mmol) and dimethylamine in tetrahydrofuran (2 M) (0.46 ml, 0.926 mmol). After stirring at room temperature for 18 hours, aqueous sodium bicarbonate was added and the mixture was extracted with ethyl acetate. The organic layer was washed with brine, dried over magnesium sulfate, and then concentrated under reduced pressure. The residue was purified by silica gel column chromatography (eluent: ethyl acetate/methanol; 20/1), and then was recrystallized from dichloromethane/methanol to give the title compound (99 mg, 32%) as colorless crystals.

$^1$H-NMR(CDCl$_3$) δ: 1.14 (3H, t, J=7.2 Hz), 2.05 (3H, s), 2.4-2.5 (2H, m), 2.65-2.8 (2H, m), 2.86 (3H, s), 2.87 (3H, s), 3.2-3.35 (2H, m), 3.79 (2H, s), 5.1-5.25 (1H, m), 5.36 (2H, s), 6.91 (2H, t, J=8.0 Hz), 6.85-6.95 (1H, m), 7.1-7.55 (10H, m).

Example 11

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N,N-diethylpropanamide

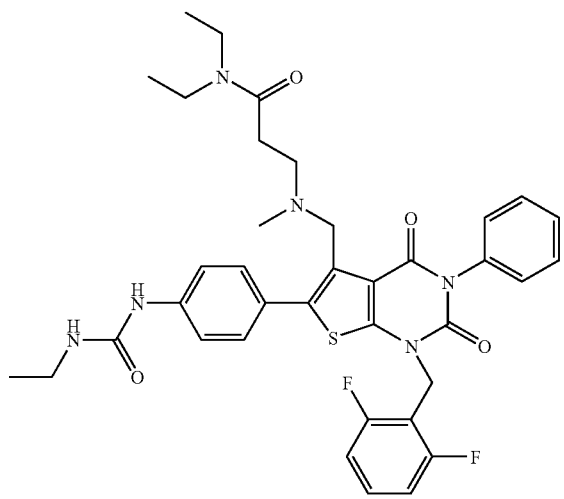

The similar reaction to that of Example 10 was performed using the compound of Example 7 (50 mg, 0.077 mmol) and diethylamine (11 mg, 0.154 mmol) to give the title compound (7.6 mg, 14%).

HPLC (220 nm) purity 91% (Retention Time: 2.66 min.)
MS (ESI+, m/e) 703 (M+1)

In addition, HPLC was measured under the following conditions.

Column: CAPCELLPAKCC18UG120, S-3 μm, 20×50 mm

Solvent: solvent A (0.1% trifluoroacetic acid-containing water), solvent B (0.1% trifluoroacetic acid-containing acetonitrile)

Gradient Cycle: 0.00 min. (solvent A/solvent B=90/10), 4.00 min. (solvent A/solvent B=5/95), 5.50 min. (solvent A/solvent B=5/95), 5.51 min. (solvent A/solvent B=90/10), 8.00 min. (solvent A/solvent B=90/10)

Flow rate: 0.5 ml/min.

IR (KBr): 1709, 1667, 1620, 1532, 1470, 1219, 1036, 793, 739 cm$^{-1}$.

Elemental analysis for $C_{35}H_{36}F_2N_6O_4S \cdot 0.5H_2O$
Calculated: C, 61.48; H, 5.45; N, 12.29. Found: C, 61.47; H, 5.23; N, 12.18.
mp 236-237° C.

Example 12

Preparation of N-{4-[1-(2,6-difluorobenzyl)-5-({methyl[3-oxo-3-(1-piperidyl)propyl]amino}methyl)-2,4-dioxo-3-phenyl-1,2,3,4-tetrahydrothieno[2,3-d]pyrimid-6-yl)phenyl]-N'-ethylurea

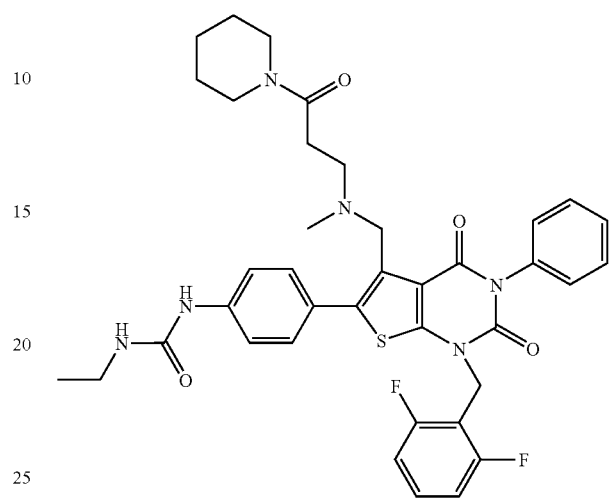

The similar reaction to that of Example 10 was performed using the compound of Example 7 (50 mg, 0.077 mmol) and piperidine (13 mg, 0.154 mmol) to give the title compound (4.0 mg, 7%).

HPLC (220 nm) purity 100% (Retention Time: 2.69 min.)
MS (ESI+, m/e) 715 (M+1)

Example 13

Preparation of N-{4-[1-(2,6-difluorobenzyl)-5-({methyl[3-(4-morpholinyl)-3-oxopropyl]amino}methyl)-2,4-dioxo-3-phenyl-1,2,3,4-tetrahydrothieno[2,3-d]pyrimid-6-yl]phenyl}-N'-ethylurea

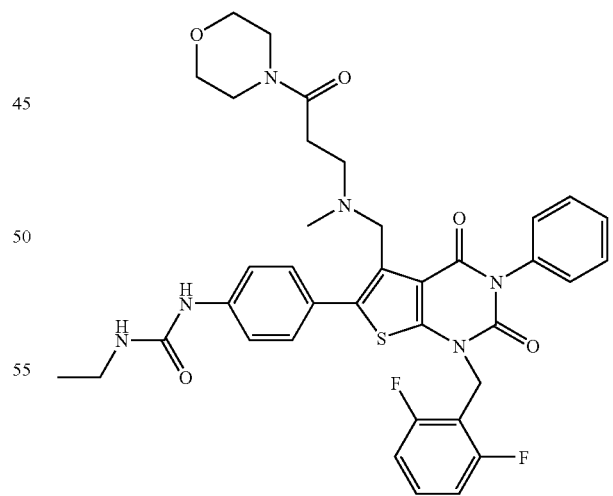

The similar reaction to that of Example 10 was performed using the compound of Example 7 (50 mg, 0.077 mmol) and morpholine (13 mg, 0.154 mmol) to give the title compound (17 mg, 31%) as colorless crystals.

HPLC (220 nm) purity 98% (Retention Time: 2.46 min.)
MS (ESI+, m/e) 717 (M+1)

Example 14

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}amino]-N-(2-methoxyethyl)-N-methyl-propanamide

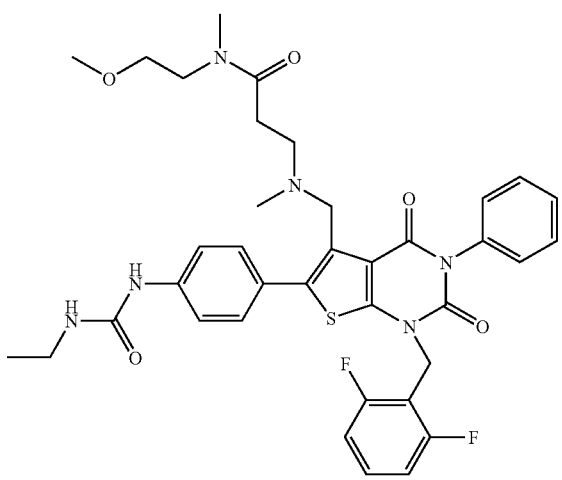

The similar reaction to that of Example 10 was performed using the compound of Example 7 (50 mg, 0.077 mmol) and N-(2-methoxyethyl)-N-methylamine (14 mg, 0.154 mmol) to give the title compound (17 mg, 31%).

HPLC (220 nm) purity 97% (Retention Time: 2.54 min.)
MS (ESI+, m/e) 719 (M+1)

Example 15

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N-methylpropanamide

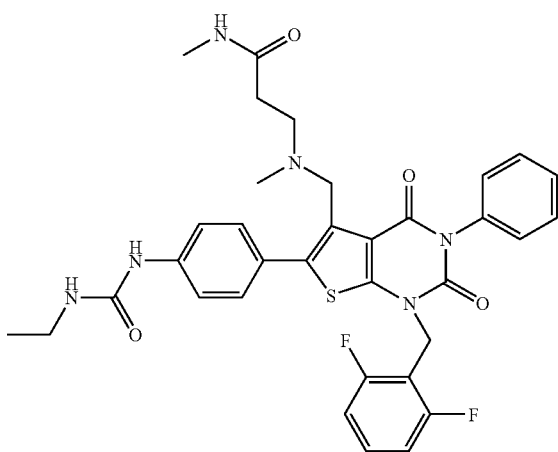

The similar reaction to that of Example 10 was performed using the compound of Example 7 (200 mg, 0.309 mmol) and a solution of methylamine in tetrahydrofuran (2 M) (1 ml, 2 mmol) to give the title compound (8 mg, 4%) as colorless crystals.

$^1$H-NMR(CDCl$_3$) δ: 1.17 (3H, t, J=7.2 Hz), 1.84 (3H, s), 2.2-2.3 (2H, m), 2.4-2.5 (5H, m), 3.2-3.4 (2H, m), 3.67 (2H, s), 5.05-5.15(1H, m), 5.37 (2H, s), 6.93 (2H, t, J=8.2 Hz), 7.1-7.6 (10H, m), 8.0-8.1 (1H, m).

IR (KBr): 1717, 1669, 1534, 1470, 1236, 1032, 735 cm$^{-1}$.

Example 16

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N-isopropylpropanamide

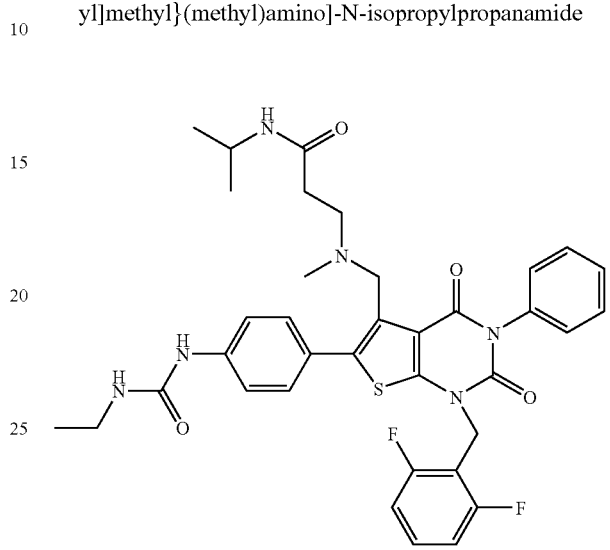

The similar reaction to that of Example 10 was performed using the compound of Example 7 (200 mg, 0.309 mol) and isopropylamine (0.53 ml, 6.18 mmol) to give the title compound (20 mg, 9%) as colorless crystals.

$^1$H-NMR(CDCl$_3$) δ: 0.89 (6H, t, J=6.6 Hz), 1.16 (3H, t, J=7.2 Hz), 2.06 (3H, s), 2.15-2.25 (2H, m), 2.35-2.45 (2H, m), 3.2-3.4 (2H, m), 3.75 (2H, s), 3.8-4.0 (1H, m), 5.2-5.3 (1H, m), 5.37 (2H, s), 6.91 (2H, t, J=8.2 Hz), 7.2-7.7 (11H, m).

IR (KBr): 1717, 1669, 1532, 1470, 1236, 1034, 731 cm$^{-1}$.
mp 213-215° C.

Example 17

Preparation of 2-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N,N-dimethylacetamide

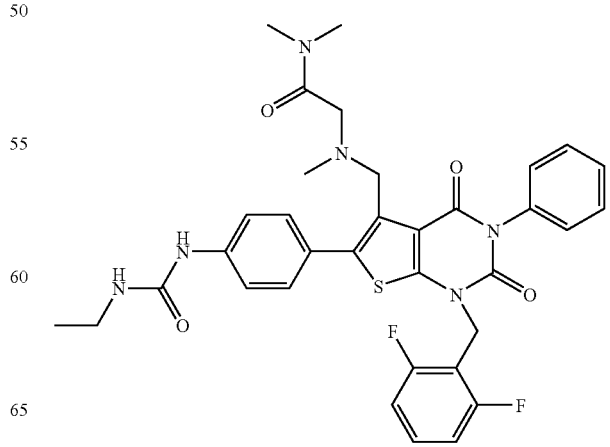

The similar reaction to that of Example 10 was performed using the compound of Example 8 (200 mg, 0.316 mmol) and a solution of dimethylamine in tetrahydrofuran (2 M) (1 ml, 2 mmol) to give the title compound (21 mg, 10%) as colorless crystals.

$^1$H-NMR(CDCl$_3$) δ: 1.12 (3H, t, J=7.4 Hz), 2.11 (3H, s), 2.81 (3H, s), 2.89 (3H, s), 3.2-3.35 (4H, m), 3.93 (2H, s), 5.25-5.35 (1H, m), 5.36 (2H, s), 6.92 (2H, t, J=8.0 Hz), 7.2-7.6 (10H, m).

IR (KBr): 1719, 1674, 1628, 1534, 1319, 1227, 1030 cm$^{-1}$.

mp 208-209° C.

Example 18

Preparation of 4-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N,N-dimethylbutane amide

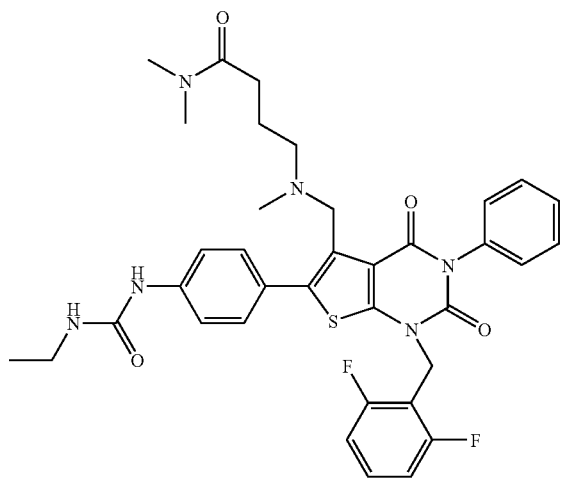

The similar reaction to that of Example 10 was performed using the compound of Example 9 (300 mg, 0.453 mmol) and a solution of dimethylamine in tetrahydrofuran (2 M) (0.45 ml, 0.906 mmol) to give the title compound (0.154 mg, 49%) as light yellow crystals.

$^1$H-NMR(CDCl$_3$) δ: 1.15 (3H, t, J=7.4 Hz), 1.6-1.75 (2H, m), 1.98 (3H, s), 2.15-2.3 (2H, m), 2.3-2.5 (2H, m), 2.84 (3H, s), 2.88 (3H, s), 3.2-3.4 (2H, m), 3.74 (2H, s), 5.2-5.3 (1H, m), 5.36 (2H, s), 6.91 (2H, t, J=8.0 Hz), 7.2-7.6 (10H, m).

IR (KBr): 1717, 1663, 1626, 1470, 1233, 1030, 741 cm$^{-1}$.

Elemental analysis for C$_{36}$H$_{38}$F$_2$N$_6$O$_4$S.0.5H$_2$O

Calculated: C, 61.97; H, 5.63; N, 12.04. Found: C, 61.89; H, 5.63; N, 12.13.

mp 191-193° C.

Example 19

Preparation of N-{2-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]ethyl}acetamide

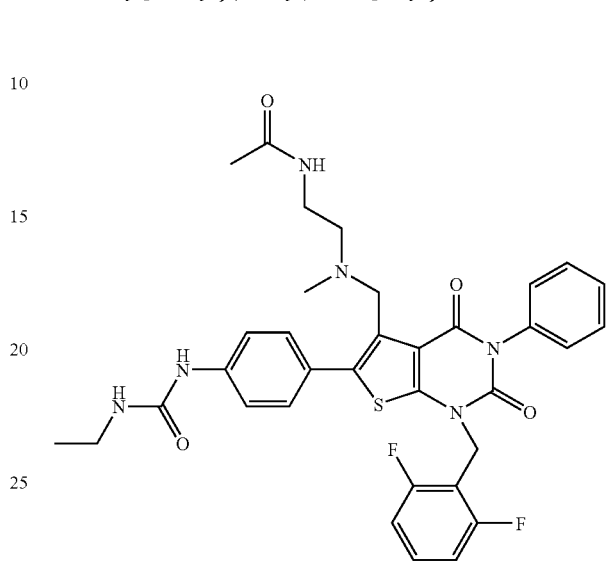

N-2-hydroxyethylacetamide (516 mg, 5 mmol) was dissolved in tetrahydrofuran (10 ml), followed by addition of triethylamine (0.69 ml, 5 mmol) and methanesulfonyl chloride (0.39 ml, 5 mmol) and the mixture was stirred at room temperature for 30 minutes.

Aqueous sodium bicarbonate was added and the mixture was extracted with ethyl acetate. The aqueous layer was salted out and then extracted with ethyl acetate. The organic layers were combined, dried over magnesium sulfate, and then concentrated under reduced pressure to give mesylate. A solution of the obtained mesylate, the compound of Example 1 (288 mg, 0.5 mmol), N,N-diisopropylethylamine (0.17 ml, 1 mmol) and potassium iodide (0.83 g, 5 mmol) in DMF (4 ml) was stirred at 50 to 60° C. for 3 days, followed by addition of aqueous sodium bicarbonate, and then the mixture was extracted with ethyl acetate. The organic layer was washed with brine, dried over magnesium sulfate, and then concentrated under reduced pressure. The residue was purified by silica gel column chromatography (eluent: ethyl acetate/methanol; 10/1), and then was recrystallized from dichloromethane/methanol/diethyl ether to give the title compound (123 mg, 37%) as colorless crystals.

$^1$H-NMR(CDCl$_3$) δ: 1.15 (3H, t, J=7.2 Hz), 1.53 (3H, s), 1.58 (3H, s), 2.3-2.4 (2H, m), 3.05-3.2 (2H, m), 3.2-3.4 (2H, m), 3.62 (2H, s), 5.2-5.3 (1H, m), 5.37 (2H, s), 6.93 (2H, t, J=8.0 Hz), 7.15-7.6 (10H, m).

IR (KBr): 1717, 1655, 1535, 1468, 1236, 1032, 735 cm$^{-1}$.

Elemental analysis for C$_{34}$H$_{34}$F$_2$N$_6$O$_4$S.2.0H$_2$O

Calculated: C, 58.61; H, 5.50; N, 12.06. Found: C, 58.43; H, 5.21; N, 11.97.

mp 185-186° C.

Example 20

Preparation of N-{4-[1-(2,6-difluorobenzyl)-5-({methyl[2-(2-oxo-1-pyrrolidinyl)ethyl]amino}methyl)-2,4-dioxo-3-phenyl-1,2,3,4-tetrahydrothieno[2,3-d]pyrimidin-6-yl]phenyl}-N'-ethylurea

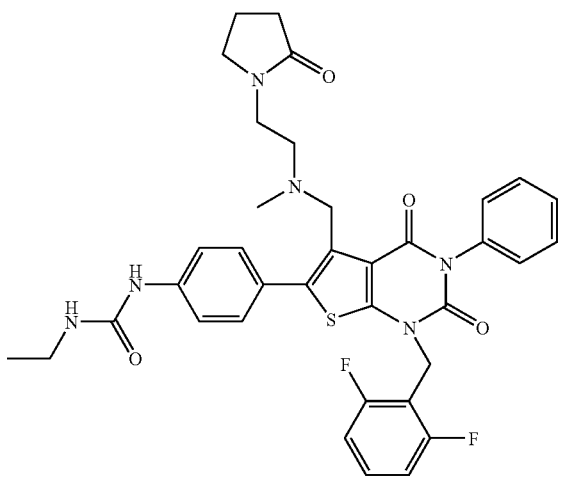

The similar reaction to that of Example 19 was performed using the compound of Example 1 (288 mg, 0.5 mmol) and 1-(2-hydroxyethyl)-2-pyrrolidone (0.65 g, 5 mmol) to give the title compound (85 mg, 25%) as colorless crystals.

$^1$H-NMR(CDCl$_3$) δ: 1.15 (3H, t, J=7.2 Hz), 1.7-1.9 (2H, m), 2.12 (3H, s), 2.15-2.3 (2H, m), 2.45-2.6 (2H, m), 3.15-3.35 (6H, m), 3.76 (2H, s), 5.1-5.2 (1H, m), 5.37 (2H, s), 6.91 (2H, t, J=8.0 Hz), 7.1-7.55 (10H, m).

IR (KBr): 1717, 1667, 1534, 1470, 1236, 1032, 737 cm$^{-1}$.

Elemental analysis for C$_{36}$H$_{36}$F$_2$N$_6$O$_4$S.1.0H$_2$O

Calculated: C, 61.35; H, 5.43; N, 11.92. Found: C, 61.11; H, 5.23; N, 11.70.

mp 140-142° C.

Example 21

Preparation of N-{4-[1-(2,6-difluorobenzyl)-5-({methyl[2-(2-oxo-1-pyrrolidinyl)propyl]amino}methyl)-2,4-dioxo-3-phenyl-1,2,3,4-tetrahydrothieno[2,3-d]pyrimidin-6-yl]phenyl}-N'-ethylurea

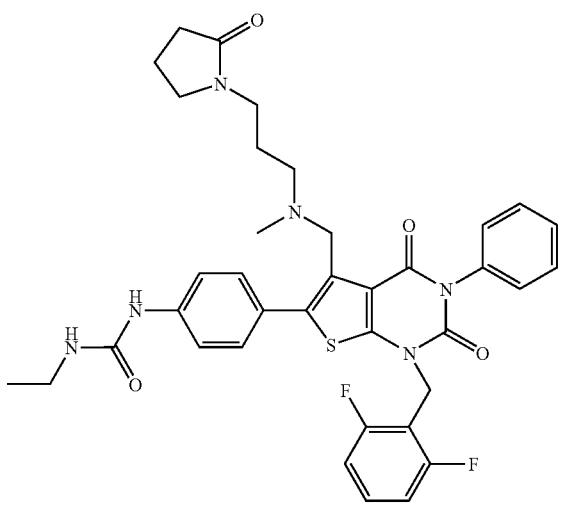

The similar reaction to that of Example 19 was performed using the compound of Example 1 (288 mg, 0.5 mmol) and 1-(3-hydroxypropyl)-2-pyrrolidone (716 mg, 5 mmol) to give the title compound (205 mg, 59%) as colorless crystals.

$^1$H-NMR(CDCl$_3$) δ: 1.15 (3H, t, J=7.2 Hz), 1.8-2.0 (2H, m), 2.02 (3H, s), 2.25-2.4 (4H, m), 3.1-3.4 (6H, m), 3.73 (2H, s), 5.2-5.3 (1H, m), 5.36 (2H, s), 6.91 (2H, t, J=8.2 Hz), 7.2-7.6 (10H, m).

IR (KBr): 1713, 1672, 1532, 1460, 1318, 1238, 1034, 735 cm$^{-1}$.

Elemental analysis for C$_{37}$H$_{38}$F$_2$N$_6$O$_4$S.1.2H$_2$O

Calculated: C, 61.52; H, 5.64; N, 11.63. Found: C, 61.17; H, 5.25; N, 11.56.

mp 193-195° C.

Example 22

Preparation of N-{2-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]ethyl}methanesulfonamide

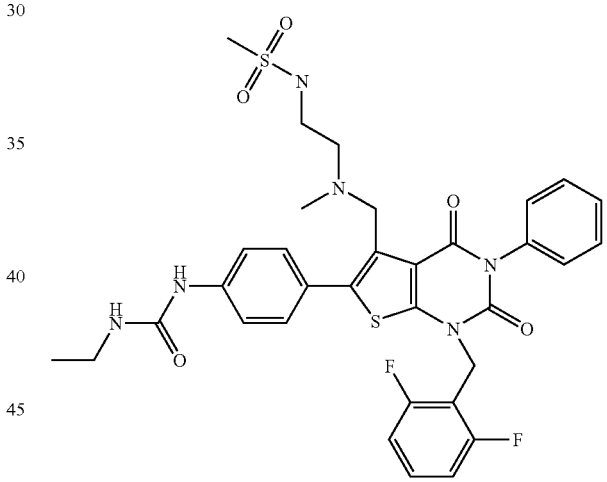

The similar reaction to that of Example 19 was performed using the compound of Example 1 (288 mg, 0.5 mmol) and 2-aminoethanol (153 mg, 2.5 mmol) to give the title compound (267 mg, 77%) as colorless crystals.

$^1$H-NMR(CDCl$_3$) δ: 1.18 (3H, t, J=7.2 Hz), 1.83 (3H, s), 2.45-2.55 (2H, m), 2.54 (3H, s), 3.05-3.15 (2H, m), 3.25-3.35 (2H, m), 3.67 (2H, s), 4.85-4.9 (1H, m), 5.25-5.35 (1H, brm), 5.36 (2H, s), 6.68 (1H, s), 6.93 (2H, t, J=8.1 Hz), 7.2-7.6 (10H, m).

IR (KBr): 1717, 1667, 1470, 1316, 1236, 1148, 1032 cm$^{-1}$.

Elemental analysis for C$_{33}$H$_{34}$F$_2$N$_6$O$_5$S$_2$.1.0H$_2$O

Calculated: C, 55.45; H, 5.08; N, 11.76. Found: C, 55.42; H, 5.14; N, 11.66.

mp 186-188° C.

Example 23

Preparation of N-{2-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]ethyl}-N-methylmethanesulfonamide

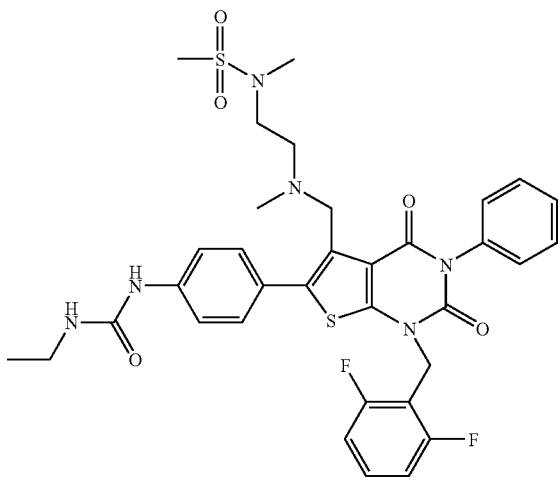

The similar reaction to that of Example 19 was performed using the compound of Example 1 (2.90 g, 5.04 mmol) and 2-methylamino ethanol (1.88 g, 25 mmol) to give the title compound (3.04 g, 85%) as colorless crystals.

¹H-NMR(CDCl₃) δ: 1.18 (3H, t, J=7.2 Hz), 2.12 (3H, s), 2.54 (3H, t, J=6.2 Hz), 2.71 (6H, s), 3.1-3.2 (2H, m), 3.2-3.4 (2H, m), 3.81 (2H, s), 4.75-4.85 (1H, m), 5.37 (2H, s), 6.53 (1H, s), 6.92 (2H, t, J=8.0 Hz), 7.2-7.6 (10H, m).

IR (KBr): 1713, 1674, 1535, 1460, 1325, 1238, 1138, 1036, 976, 789 cm⁻¹.

Elemental analysis for $C_{34}H_{36}F_2N_6O_5S_2$

Calculated: C, 57.45; H, 5.10; N, 11.82. Found: C, 57.09; H, 5.23; N, 11.59.

mp 216-218° C.

Example 24

Preparation of N-{4-[1-(2,6-difluorobenzyl)-5-({methyl[2-(2-oxo-1,3-oxazolin-3-yl)ethyl]amino}methyl)-2,4-dioxo-3-phenyl-1,2,3,4-tetrahydrothieno[2,3-d]pyrimidin-6-yl]phenyl}-N'-ethylurea

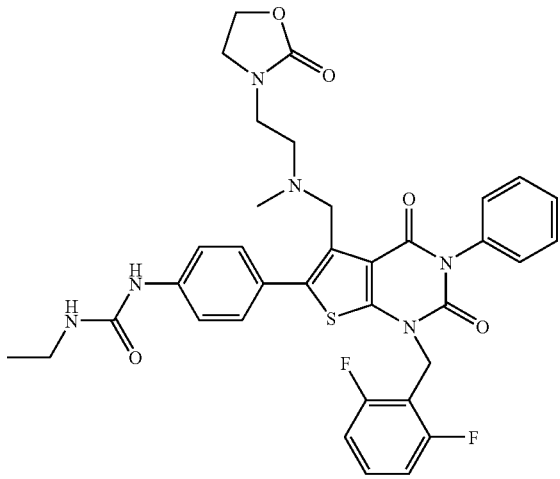

2-oxo-1,3-oxazoline (1.74 g, 10 mmol) was dissolved in DMF (15 ml), followed by addition of 65% oily sodium hydride (0.40 g, 11 mmol) with ice-cooling and the mixture was stirred at room temperature for 1 hour. Then, 1-bromo-2-chloroethane (1.66 ml, 20 mmol) was added with ice-cooling and the mixture was stirred at room temperature for 3 days. Aqueous sodium bicarbonate was added and the mixture was extracted with ethyl acetate. The organic layers were combined, dried over magnesium sulfate, and then concentrated under reduced pressure to give halide. A solution of the obtained halide, the compound of Example 1 (200 mg, 0.347 mmol), N,N-diisopropylethylamine (0.12 ml, 0.694 mmol) and potassium iodide (115 mg, 0.694 mmol) in DMF (4 ml) was stirred at 50 to 60° C. for 16 hours, followed by addition of aqueous sodium bicarbonate, and then the mixture was extracted with ethyl acetate. The organic layer was washed with brine, dried over magnesium sulfate, and then concentrated under reduced pressure. The residue was purified by silica gel column chromatography (eluent: ethyl acetate), and then was recrystallized from dichloromethane/methanol/diethyl ether to give the title compound (41 mg, 17%) as colorless crystals.

¹H-NMR(CDCl₃) δ: 1.15 (3H, t, J=7.4 Hz), 2.09 (3H, s), 2.45-2.6 (2H, m), 3.2-3.45 (6H, m), 3.78 (2H, s), 4.0-4.15 (2H, m), 5.1-5.2 (1H, m), 5.36 (2H, s), 6.92 (2H, t, J=8.4 Hz), 7.04 (1H, s), 7.2-7.6 (10H, m).

IR (KBr): 1717, 1671, 1535, 1468, 1236, 1034, 737 cm⁻¹.

Elemental analysis for $C_{35}H_{34}F_2N_6O_5S \cdot 1.0H_2O$

Calculated: C, 59.48; H, 5.13; N, 11.89. Found: C, 59.50; H, 4.89; N, 12.02.

mp 153-155° C.

Example 25

Preparation of N-{4-[5-{[{2-[benzyl(methyl)amino]ethyl}(methyl)amino]methyl}-1-(2,6-difluorobenzyl)-2,4-dioxo-3-phenyl-1,2,3,4-tetrahydrothieno[2,3-d]pyrimidin-6-yl]phenyl}-N'-ethylurea

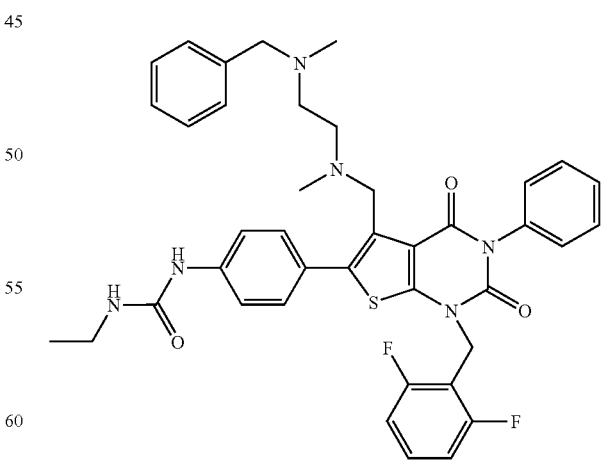

The similar reaction to that of Example 24 was performed using the compound of Example 1 (1.15 g, 2 mmol) and N-methyl-N-benzylamine (1.21 g, 10 mmol) to give the title compound (939 mg, 65%) as light yellow crystals.

¹H-NMR(CDCl₃) δ: 1.16 (3H, t, J=7.2 Hz), 2.08 (3H, s), 2.11 (3H, s), 2.35-2.5 (2H, m), 2.5-2.65 (2H, m), 3.2-3.4 (2H, m), 3.41 (2H, s), 3.81 (2H, s), 4.65-4.75 (1H, m), 5.35 (2H, s), 6.35-6.45 (1H, m), 6.91 (2H, t, J=8.2), 7.2-7.6 (15H, m).

IR (KBr): 1717, 1667, 1532, 1470, 1236, 1032, 735 cm⁻¹.

Elemental analysis for $C_{40}H_{40}F_2N_6O_3S \cdot 0.6H_2O$

Calculated: C, 65.48; H, 5.66; N, 11.45. Found: C, 65.18; H, 5.58; N, 11.49.

mp 151-153° C.

Example 26

Preparation of N-{4-[1-(2,6-difluorobenzyl)-5-({methyl[2-(methylamino)ethyl]amino}methyl)-2,4-dioxo-3-phenyl-1,2,3,4-tetrahydrothieno[2,3-d]pyrimidin-6-yl)phenyl}-N'-ethylurea

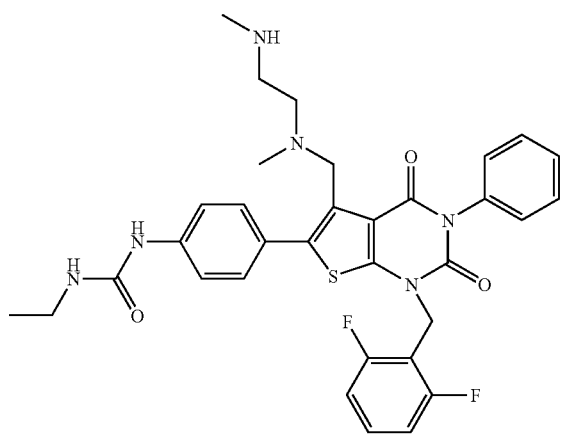

The compound of Example 25 (900 mg, 1.2 mmol) was dissolved in methanol (30 ml), followed by addition of 1 N hydrochloric acid (2.5 ml, 2.5 mmol) and 10% hydrous palladium carbon (300 mg) and the mixture was stirred at room temperature for 3 hours under hydrogen atmosphere. Palladium carbon was filtered off, and then the mixture was neutralized by adding 1 N aqueous sodium hydroxide solution (2.5 ml). It was concentrated under reduced pressure, followed by addition of aqueous sodium bicarbonate and the mixture was extracted with ethyl acetate. The organic layer was washed with brine, dried over magnesium sulfate and then concentrated under reduced pressure. The residue was purified by silica gel column chromatography (eluent: ethyl acetate/methanol; 10/1), and then was recrystallized from dichloromethane/methanol/diethyl ether to give the title compound (453 mg, 49%) as colorless crystals.

¹H-NMR(CDCl₃) δ: 1.17 (3H, t, J=7.2 Hz), 2.02 (3H, s), 2.25 (3H, s), 2.4-2.6 (4H, m), 3.2-3.4 (2H, m), 3.76 (2H, s), 4.9-5.0 (1H, m), 5.36 (2H, s), 6.65-6.75 (1H, m), 6.92 (2H, t, J=8.2 Hz), 7.2-7.6 (10H, m).

IR (KBr): 1713, 1672, 1534, 1472, 1458, 1316, 1238, 1034, 789 cm⁻¹.

Elemental analysis for $C_{33}H_{34}F_2N_6O_3S \cdot 0.2H_2O$

Calculated: C, 62.29; H, 5.45; N, 13.21. Found: C, 62.01; H, 5.43; N, 13.15.

mp 192-193° C.

Example 27

Preparation of N-{2-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]ethyl}-N-methylacetamide

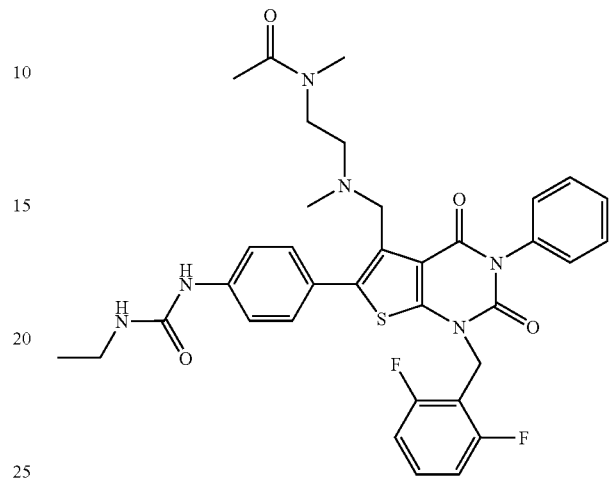

The compound of Example 26 (200 mg, 0.316 mmol) was dissolved in THF (8 ml), followed by addition of triethylamine (0.066 ml, 0.474 mmol) and acetic acid anhydride (0.036 ml, 0.379 mmol) and the mixture was at room temperature for 2 hours. Aqueous sodium bicarbonate was added and the mixture was extracted with ethyl acetate. The organic layer was washed with brine, dried over magnesium sulfate and then concentrated under reduced pressure. The residue was recrystallized from dichloromethane/methanol/diethyl ether to give the title compound (163 mg, 76%) as colorless crystals.

¹H-NMR(CDCl₃) δ: 1.15 (1.5H, t, J=7.2 Hz), 1.16 (1.5H, t, J=7.2 Hz), 1.94 (1.5H, s), 2.00 (1.5H, s), 2.13 (1.5H, s), 2.18 (1.5H, s), 2.5-2.6 (2H, m), 2.75 (1.5H, s), 2.83 (1.5H, s), 3.2-3.4 (4H, m), 3.78 (1H, s), 3.82 (1H, s), 5.2-5.3(1H, m), 5.37 (2H, s), 6.91 (2H, t, J=8.0 Hz), 7.1-7.2 (1H, m), 7.2-7.6 (10H, m).

IR (KBr): 1713, 1674, 1535, 1460, 1316, 1238, 1036, 787, 735 cm⁻¹.

Elemental analysis for $C_{35}H_{36}F_2N_6O_4S \cdot 0.8H_2O$

Calculated: C, 61.00; H, 5.50; N, 12.19. Found: C, 60.71; H, 5.20; N, 12.09.

mp 180-181° C.

Example 28

Preparation of N-(4-{1-(2,6-difluorobenzyl)-3-[4-(2-methoxyethoxy)phenyl]-5-[(methylamino)methyl]-2,4-dioxo-1,2,3,4-tetrahydrothieno[2,3-d]pyrimidin-6-yl}phenyl)-N'-ethylurea

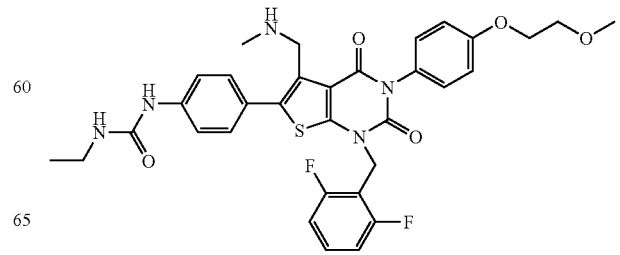

The compound of Reference Example 14 (2.0 g, 2.70 mmol) was dissolved in methanol (50 ml), followed by addition of 1 N hydrochloric acid (6 ml) and 10% hydrous palladium carbon (0.75 g) and the mixture was stirred at room temperature for 4 hours under hydrogen atmosphere. Palladium carbon was filtered off and the mixture was neutralized by adding 1 N aqueous sodium hydroxide solution (6 ml) to the filtrate. It was concentrated under reduced pressure, followed by addition of aqueous sodium bicarbonate and the mixture was extracted with ethyl acetate. The organic layer was washed with brine, dried over magnesium sulfate and then concentrated under reduced pressure. The precipitate was washed with diethyl ether to give the title compound (1.50 g, 86%) as colorless crystals.

$^1$H-NMR(CDCl$_3$) δ: 1.45 (3H, t, J=7.2 Hz), 2.34 (3H, s), 3.2-3.4 (2H, m), 3.46 (3H, s), 3.7-3.8 (4H, m), 4.16 (2H, t, J=4.8 Hz), 4.8-4.9 (1H, m), 5.36 (2H, s), 6.82 (1H, s), 6.91 (2H, t, J=8.2 Hz), 7.05 (2H, d, J=9.0 Hz), 7.17 (2H, d, J=9.0 Hz), 7.25-7.4 (5H, m).

IR (KBr): 1713, 1665, 1472, 1254, 1034, 791 cm$^{-1}$.

Elemental analysis for C$_{33}$H$_{33}$F$_2$N$_5$O$_5$S.0.2H$_2$O

Calculated: C, 60.67; H, 5.15; N, 10.72. Found: C, 60.42; H, 5.14; N, 10.67.

mp 203-205° C.

Example 29

Preparation of N-(4-(1-(2,6-difluorobenzyl)-3-(4-fluorophenyl)-5-[(methylamino)methyl]-2,4-dioxo-1,2,3,4-tetrahydrothieno[2,3-d]pyrimidin-6-yl}phenyl)-N'-ethylurea

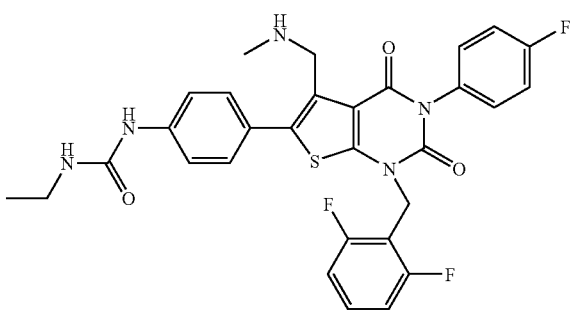

The similar reaction to that of Example 28 was performed using the compound of Reference Example 15 (2.1 g, 3.07 mmol) to give the title compound (1.43 g, 78%) as colorless crystals.

$^1$H-NMR(CDCl$_3$) δ: 1.1-1.2 (3H, m), 2.35 (3H, s), 3.25-3.35 (2H, m), 3.76 (2H, s), 4.7-4.8 (1H, m), 5.36 (2H, s), 6.55-6.6 (1H, m), 6.85-7.0 (2H, m), 7.15-7.45 (10H, m).

IR (KBr): 1721, 1663, 1472, 1238, 1034, 839, 762 cm$^{-1}$.

mp 220-221° C.

Example 30

Preparation of 3-[{[1-(2,6-difluorobenzyl)-6-(4-{[(ethylaminocarbonyl)amino]phenyl}-3-(4-fluorophenyl)-2,4-dioxo-1,2,3,4-tetrahydrothieno[2,3-d]pyrimidin-5-yl)methyl](methyl)amino}-N-methylpropanamide

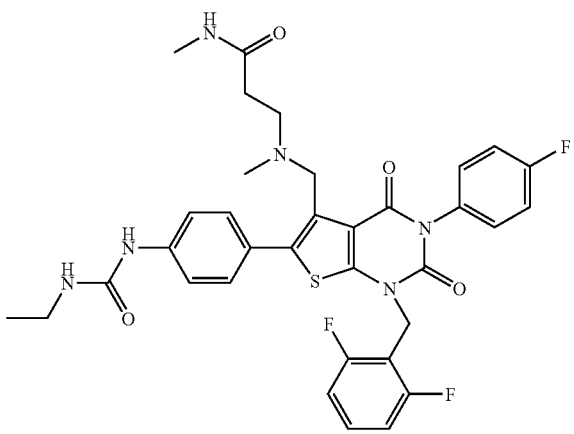

The similar reaction to that of Example 4 was performed using the compound of Example 29 (200 mg, 0.337 mmol) and 3-bromo-N-methylpropanamide (84 mg, 0.506 mmol) to give the title compound (116 mg, 51%) as colorless crystals.

$^1$H-NMR(CDCl$_3$) δ: 1.16 (3H, t, J=7.2 Hz), 1.85 (3H, s), 2.2-2.3 (2H, m), 2.35-2.5 (2H, m), 2.45 (2H, d, J=4.4 Hz), 3.2-3.4 (2H, m), 3.67 (2H, s), 5.2-5.3 (1H, m), 5.36 (2H, s), 6.92 (2H, t, J=8.0 Hz), 7.15-7.5 (9H, m), 8.0-8.1 (1H, m).

IR (KBr): 1721, 1667, 1474, 1236, 1036, 837, 762 cm$^{-1}$.

Elemental analysis for C$_{34}$H$_{33}$F$_3$N$_6$O$_4$S.0.5H$_2$O

Calculated: C, 59.38; H, 4.98; N, 12.22. Found: C, 59.39; H, 4.91; N, 12.15.

mp 237-239° C.

Example 31

Preparation of 3-[({1-2,6-(difluorobenzyl)-6-(4-{[(ethylaminocarbonyl)amino]phenyl}-3-[4-(2-methoxyethoxy)phenyl]-2,4-dioxo-1,2,3,4-tetrahydrothieno[2,3-d]pyrimidin-5-yl)methyl)(methyl)amino)-N-methylpropanamide

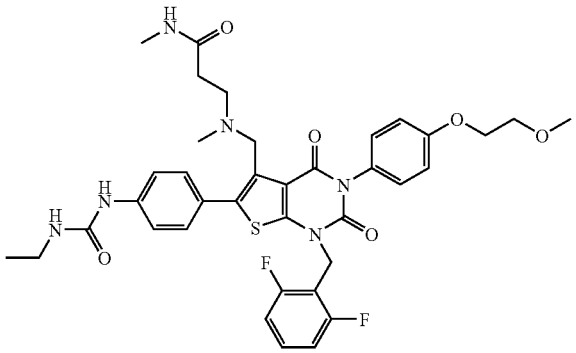

The similar reaction to that of Example 4 was performed using the compound of Example 28 (200 mg, 0.308 mmol) and 3-bromo-N-methylpropanamide (77 mg, 0.462 mmol) to give the title compound (168 mg, 74%) as colorless crystals.

$^1$H-NMR(CDCl$_3$) δ: 1.15 (3H, t, J=7.4 Hz), 1.81 (3H, s), 2.2-2.5 (7H, m), 3.2-3.4 (2H, m), 3.46 (3H, s), 3.66 (2H, s), 3.77 (2H, t, J=4.8 Hz), 4.16 (2H, t, J=4.8 Hz), 5.2-5.3 (1H, m), 5.36 (2H, s), 6.91 (2H, t, J=8.2 Hz), 7.05 (2H, d, J=8.8 Hz), 7.1-7.5 (5H, m), 7.41 (2H, d, J=8.8 Hz), 7.59 (1H, s), 8.05-8.15 (1H, m).

IR (KBr): 1715, 1667, 1470, 1238, 1032, 764 cm$^{-1}$.

Elemental analysis for C$_{37}$H$_{40}$F$_2$N$_6$O$_6$S.0.5H$_2$O

Calculated: C, 59.75; H, 5.56; N, 11.30. Found: C, 59.52; H, 5.45; N, 11.26.

mp 163-165° C.

Example 32

Preparation of 3-[{[1-(2,6-difluorobenzyl)-6-(4-{[(ethylaminocarbonyl)amino]phenyl}-3-(4-fluorophenyl)-2,4-dioxo-1,2,3,4-tetrahydrothieno[2,3-d]pyrimidin-5-yl)methyl](methyl)amino}-N,N-dimethylpropanamide

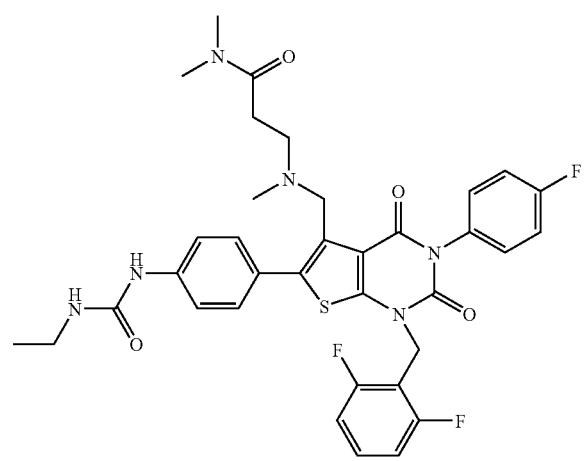

The similar reaction to that of Example 4 was performed using the compound of Example 29 (200 mg, 0.300 mmol) and 3-bromo-N-methylpropanamide (77 mg, 0.462 mmol) to give the title compound (50 mg, 24%) as colorless crystals.

$^1$H-NMR(CDCl$_3$) δ: 1.14 (3H, t, J=7.2 Hz), 2.05 (3H, s), 2.4-2.5 (2H, m), 2.7-2.8 (2H, m), 2.87 (3H, s), 2.89 (2H, s), 3.2-3.4 (2H, m), 3.77 (2H, s), 5.2-5.3 (1H, m), 5.35 (2H, s), 6.91 (2H, t, J=8.2 Hz), 7.1-7.45 (9H, m).

IR (KBr): 1719, 1669, 1626, 1472, 1236, 1032, 764 cm$^1$.

Elemental analysis for C$_{35}$H$_{35}$F$_3$N$_6$O$_4$S.0.5H$_2$O

Calculated: C, 59.90; H, 5.17; N, 11.98. Found: C, 59.60; H, 4.95; N, 11.86.

mp 210-212° C.

Example 33

Preparation of N-{4-[1-(2,6-difluorobenzyl)-3-(4-fluorophenyl)-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea

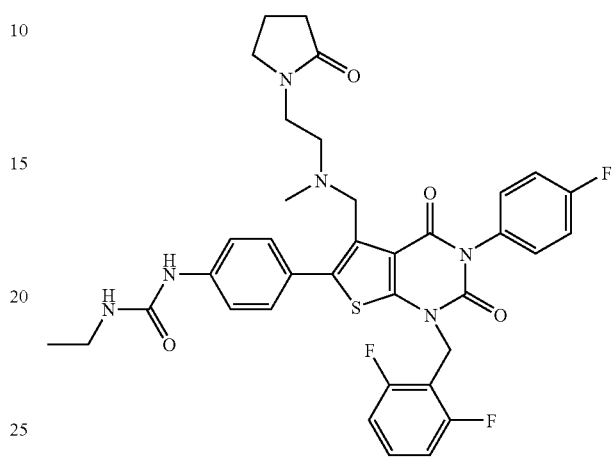

The similar reaction to that of Example 19 was performed using the compound of Example 29 (297 mg, 0.5 mmol) and 1-(2-hydroxyethyl)-2-pyrrolidone (0.65 g, 5 mmol) to give the title compound (179 mg, 50%) as colorless crystals.

$^1$H-NMR(CDCl$_3$) δ: 1.15 (3H, t, J=7.2 Hz), 1.7-1.9 (2H, m), 2.12 (3H, s), 2.23 (2H, t, J=8.0 Hz), 2.5-2.6 (2H, m), 3.15-3.4 (6H, m), 3.75 (2H, s), 5.2-5.3 (1H, m), 5.36 (2H, s), 6.91 (2H, t, J=8.2 Hz), 7.1-7.3 (5H, m), 7.39 (2H, d, J=8.6 Hz), 7.48 (2H, d, J=8.6 Hz).

IR (KBr): 1721, 1665, 1464, 1236, 1036, 837, 762 cm$^{-1}$.

Elemental analysis for C$_{36}$H$_{35}$F$_3$N$_6$O$_4$S.0.5H$_2$O

Calculated: C, 60.58; H, 5.08; N, 11.77. Found: C, 60.67; H, 4.87; N, 11.83.

mp 204-206° C.

Example 34

Preparation of N-{4-[1-(2,6-difluorobenzyl)-3-[4-(2-methoxyethoxy)phenyl]-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea

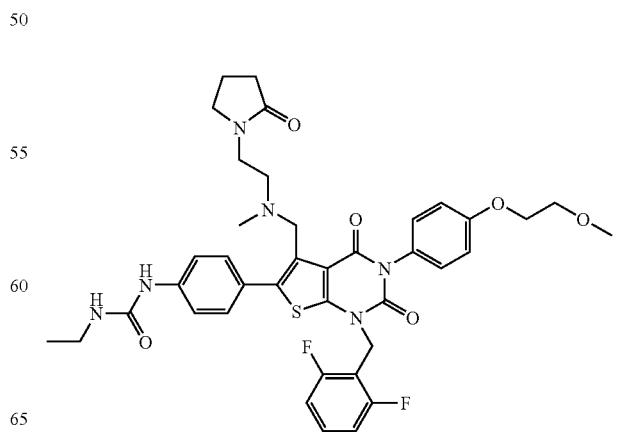

The similar reaction to that of Example 19 was performed using the compound of Example 28 (325 mg, 0.5 mmol) and 1-(2-hydroxyethyl)-2-pyrrolidone (0.65 g, 5 mmol) to give the title compound (302 mg, 79%) as colorless crystals.

$^1$H-NMR(CDCl$_3$) δ: 1.15 (3H, t, J=7.2 Hz), 1.7-1.9 (2H, m), 2.12 (3H, s), 2.23 (2H, t, J=7.8 Hz), 2.5-2.6 (2H, m), 3.15-3.35 (6H, m), 3.46 (3H, s), 3.7-3.8 (4H, m), 4.15 (2H, t, J=4.8 Hz), 5.15-5.25 (1H, m), 5.36 (2H, s), 6.90 (2H, t, J=8.2 Hz), 7.03 (2H, d, J=9.0 Hz), 7.16 (2H, d, J=9.0 Hz), 7.25-7.35 (2H, m), 7.39 (2H, d, J=8.4 Hz), 7.48 (2H, d, J=4.8 Hz).

IR (KBr): 1717, 1665, 1534, 1470, 1238, 1032 cm$^{-1}$.

Elemental analysis for C$_{39}$H$_{42}$F$_2$N$_6$O$_6$S·0.5H$_2$O

Calculated: C, 60.85; H, 5.63; N, 10.92. Found: C, 60.58; H, 5.60; N, 10.80.

mp 175-177° C.

Example 35

Preparation of N-{4-[1-(2,6-difluorobenzyl)-3-(4-fluorophenyl)-5-({methyl[2-(2-oxo-1,3-oxazolidin-3-yl)methyl]amino}methyl)-2,4-dioxo-1,2,3,4-tetrahydrothieno[2,3-d]pyrimidin-6-yl]phenyl}-N'-ethylurea

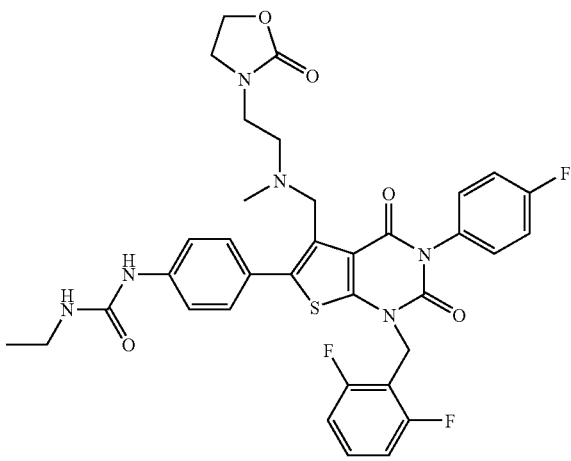

The similar reaction to that of Example 24 was performed using the compound of Example 29 (200 mg, 0.34 mmol) and 2-oxo-1,3-oxazoline (0.87 g, 10 mmol) to give the title compound (37 mg, 15%) as colorless crystals.

$^1$H-NMR(CDCl$_3$) δ: 1.17 (3H, t, J=7.2 Hz), 2.10 (3H, s), 2.5-2.6 (2H, m), 3.2-3.45 (6H, m), 3.78 (2H, s), 4.0-4.15 (2H, m), 5.0-5.1 (1H, m), 5.36 (2H, s), 6.8-6.9 (1H, m), 6.92 (2H, t, J=8.2 Hz), 7.1-7.35 (5H, m), 7.40 (2H, d, J=8.8 Hz), 7.48 (2H, d, J=8.8 Hz).

IR (KBr): 1721, 1665, 1472, 1236, 1036, 762 cm$^{-1}$.

mp 193-195° C.

Example 36

Preparation of N-(4-[1-(2,6-difluorobenzyl)-3-(4-fluorophenyl)-5-({methyl[(1-methyl-2-oxo-3-pyrrolidinyl)methyl]amino}methyl)-2,4-dioxo-1,2,3,4-tetrahydrothieno[2,3-d]pyrimidin-6-yl]phenyl}-N'-ethylurea

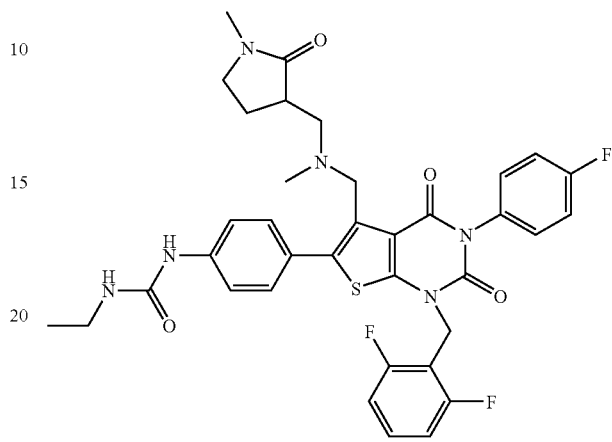

The similar reaction to that of Example 19 was performed using the compound of Example 29 (237 mg, 0.4 mmol) and 3-(hydroxymethyl)-1-methylpyrrolidin-2-one (0.52 g, 4 mmol) to give the title compound (88 mg, 31%) as colorless crystals.

$^1$H-NMR(CDCl$_3$) δ: 1.15 (3H, t, J=7.4 Hz), 1.7-1.9 (1H, m), 1.95 (3H, s), 2.0-2.2 (1H, m), 2.4-2.8 (3H, m), 2.79 (3H, s), 3.2-3.4 (4H, m), 3.77 (2H, s), 5.15-5.25 (1H, m), 5.25-5.45 (2H, m), 6.92 (2H, t, J=8.2 Hz), 7.15-7.45 (10H, m).

IR (KBr): 1723, 1665, 1474, 1236, 1036, 837, 762 cm$^{-1}$.

Elemental analysis for C$_{36}$H$_{35}$F$_3$N$_6$O$_4$S·0.5H$_2$O

Calculated: C, 60.58; H, 5.08; N, 11.77. Found: C, 60.34; H, 4.99; N, 11.69.

mp 233-234° C.

Example 37

Preparation of N-{2-[{[1-(2,6-difluorobenzyl)-6-(4-{[(ethylamino)carbonyl]amino}phenyl)-3-(4-fluorophenyl)-2,4-dioxo-1,2,3,4-tetrahydrothieno[2,3-d]pyrimidin-5-yl]methyl}(methyl)amino]ethyl}-N-methylsulfonamide

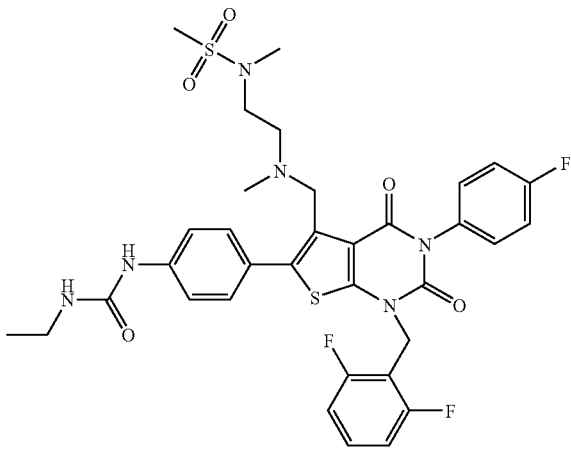

The similar reaction to that of Example 19 was performed using the compound of Example 29 (250 mg, 0.42 mmol) and 2-methylamino ethanol (158 mg, 2.1 mmol) to give the title compound (133 mg, 44%) as colorless crystals.

$^1$H-NMR(CDCl$_3$) δ: 1.18 (3H, t, J=7.2 Hz), 2.13 (3H, s), 2.5-2.6 (2H, m), 2.706 (3H, s), 2.713 (3H, s), 3.1-3.2 (2H, m), 3.2-3.4 (2H, m), 3.80 (2H, s), 4.7-4.8 (1H, m), 5.36 (2H, s), 6.47 (1H, s), 6.92 (2H, t, J=7.8 Hz), 7.15-7.35 (5H, m), 7.39 (2H, d, J=8.6 Hz), 7.48 (2H, d, J=8.6 Hz).

IR (KBr): 1723, 1663, 1474, 1333, 1236, 1144, 1034, 762 cm$^{-1}$.

Elemental analysis for C$_{34}$H$_{35}$F$_3$N$_6$O$_5$S$_2$

Calculated: C, 56.03; H, 4.84; N, 11.53. Found: C, 55.74; H, 4.76; N, 11.46.

mp 228-230° C.

Example 38

Preparation of N-{2-[({1-2,6-(difluorobenzyl)-6-(4-{[(ethylamino)carbonyl]amino}phenyl)-3-[4-(2-methoxyethoxy)phenyl]-2,4-dioxo-1,2,3,4-tetrahydrothieno[2,3-d]pyrimidin-5-yl)methyl)(methyl)amino)ethyl)-N-methylsulfonamide

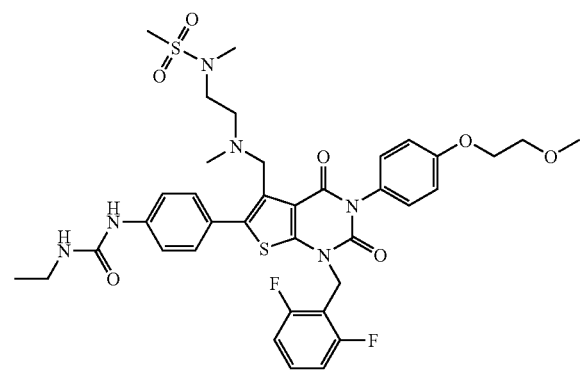

The similar reaction to that of Example 19 was performed using the compound of Example 28 (250 mg, 0.385 mmol) and 2-methylamino ethanol (158 mg, 2.1 mmol) to give the title compound (218 mg, 72%) as colorless crystals.

$^1$H-NMR(CDCl$_3$) δ: 1.18 (3H, t, J=7.2 Hz), 2.12 (3H, s), 2.5-2.6 (2H, m), 2.70 (6H, s), 3.1-3.2 (2H, m), 3.2-3.4 (2H, m), 3.45 (3H, s), 3.7-3.85 (4H, m), 4.1-4.2 (2H, m), 4.7-4.8 (1H, m), 5.36 (2H, s), 6.46 (1H, s), 6.91 (2H, t, J=8.2 Hz), 7.03 (2H, d, J=9.0 Hz), 7.16 (2H, d, J=9.0 Hz), 7.25-7.35 (1H, m), 7.38 (2H, d, J=8.6 Hz), 7.48 (2H, d, J=8.6 Hz).

IR (KBr): 1717, 1663, 1472, 1331, 1238, 1032, 762 cm$^{-1}$.

Elemental analysis for C$_{37}$H$_{42}$F$_2$N$_6$O$_7$S$_2$·0.1H$_2$O

Calculated: C, 56.49; H, 5.41; N, 10.68. Found: C, 56.21; H, 5.35; N, 10.68.

mp 197-199° C.

Example 39

Preparation of 2-[4-(1-(2,6-difluorobenzyl)-6-(4-{[(ethylamino)carbonyl]amino}phenyl)-5-{[(2-ethoxyethyl)(methyl)amino]methyl}-2,4-dioxo-1,4-dihydrothieno[2,3-d]pyrimidin-3(2H)-yl)phenyl]-N,N-dimethylacetamide

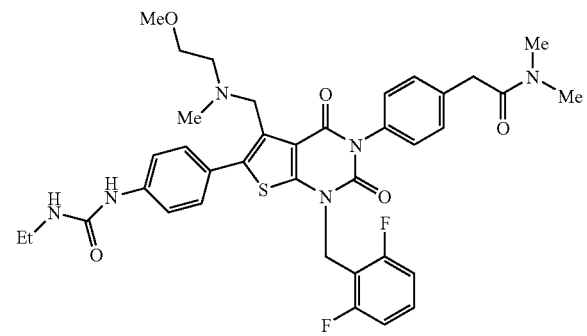

N-ethyl diisopropylamine (323 µl) was added to a solution of the compound of Reference Example 9 (454 mg), 1-ethyl-3-(3-dimethylaminopropyl)-carbodiimide hydrochloride (288 mg), 1-hydroxybenzotriazole (230 mg) and 4-aminophenyl-N,N-dimethylacetamide (268 mg) in DMF (7.5 ml) with ice-cooling and the mixture was allowed to return to room temperature slowly and was stirred for 24 hours. Thereafter, the reaction solution was partitioned between ethyl acetate and water. The organic layer was washed with water and saturated brine sequentially, and dried over anhydrous sodium sulfate. The residue obtained by distilling off the solvent under reduced pressure, was purified by aminopropyl silica gel (manufactured by Fuji Silysia Chemical Ltd.) chromatography to give the crude amide product (384 mg), which was then dissolved in ethanol (24.5 ml), followed by addition of sodium ethoxide (66.5 mg) and the mixture was stirred at room temperature for 3 hours. The precipitated crystals were filtered, washed and dried to give the title compound (117 mg).

$^1$H-NMR (CDCl$_3$) δ: 1.15 (3H, t, J=7.1 Hz), 2.08 (3H, s), 2.57 (2H, t, J=5.8 Hz), 2.98 (3H, s), 3.04 (3H, s), 3.22 (3H, s), 3.21-3.34 (2H, m), 3.36 (2H, t, J=5.8 Hz), 3.78 (4H, s), 5.14 (1H, t, J=5.5 Hz), 5.33 (2H, s), 6.90 (2H, t, J=8.1 Hz), 6.99 (1H, s), 7.23 (2H, d, J=8.4 Hz), 7.21-7.29 (1H, m), 7.34 (2H, d, J=8.4 Hz), 7.41 (2H, d, J=8.4 Hz), 7.50 (2H, d, J=8.4 Hz).

IR (KBr): 1715, 1671, 1593, 1534, 1464, 1318, 1236 cm$^{-1}$.

Elemental analysis for C$_{37}$H$_{40}$N$_6$O$_5$SF$_2$·0.5H$_2$O

Calculated: C, 61.06; H, 5.68; N, 11.55. Found: C, 60.94; H, 5.48; N, 11.57.

Example 40

Production of 2-[4-(2,6-1-(difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenyl)-N-ethylacetamide

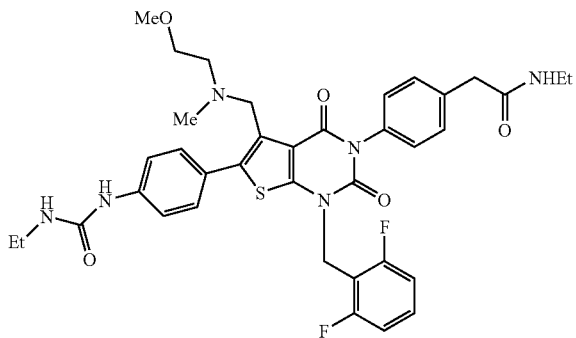

The similar reaction to that of Example 39 was performed to obtain the crude amide product (330 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-aminophenyl-N-ethylacetamide (268 mg) and N-ethyl diisopropylamine (323 μl), and then ethanol (20.5 ml) and sodium ethoxide (55 mg) were used to give the title compound (268 mg).

$^1$H-NMR (CDCl$_3$+CD$_3$OD) δ: 1.09 (3H, t, J=7.2 Hz), 1.17 (3H, t, J=7.4 Hz), 2.09 (3H, s), 2.59 (2H, t, J=5.8 Hz), 3.19-3.33 (4H, m), 3.25 (3H, s), 3.40 (2H, t, J=5.8 Hz), 3.64 (2H, s), 3.82 (2H, s), 5.37 (2H, s), 6.93 (2H, t, J=8.2 Hz), 7.27 (2H, d, J=8.4 Hz), 7.24-7.33 (1H, m), 7.40 (2H, d, J=8.4 Hz), 7.44 (4H, s).

IR (KBr): 1721, 1667, 1628, 1532, 1470 cm$^{-1}$.

Elemental analysis for C$_{37}$H$_{40}$N$_6$O$_5$SF$_2$.0.25H$_2$O

Calculated: C, 61.44; H, 5.64; N, 11.62. Found: C, 61.49; H, 5.52; N, 11.68.

Example 41

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenyl]-N-methylacetamide

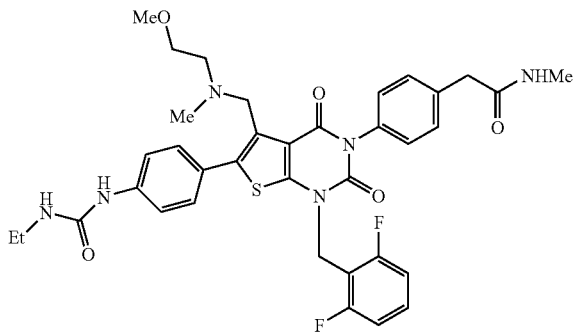

The similar reaction to that of Example 39 was performed to obtain the crude amide product (387 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-aminophenyl-N-methylacetamide (246 mg) and N-ethyl diisopropylamine (323 μl), and then ethanol (8.5 ml) and sodium methoxide (64 mg) were used to give the title compound (264 mg).

$^1$H-NMR (CDCl$_3$+CD$_3$OD) δ: 1.16 (3H, t, J=7.2 Hz), 2.08 (3H, s), 2.58 (2H, t, J=5.8 Hz), 2.73 (3H, s), 3.23-3.30 (2H, m), 3.25 (3H, s), 3.40 (2H, t, J=5.8 Hz), 3.65 (2H, s), 3.81 (2H, s), 5.37 (2H, s), 6.94 (2H, t, J=8.1 Hz), 7.27 (2H, d, J=8.4 Hz), 7.27-7.35 (1H, m), 7.40 (2H, d, J=8.4 Hz), 7.44 (4H, s).

IR (KBr): 1717, 1669, 1593, 1553, 1532, 1470, 1318, 1236 cm$^{-1}$.

Elemental analysis for C$_{36}$H$_{38}$N$_6$O$_5$SF$_2$.0.5H$_2$O

Calculated: C, 60.58; H, 5.51; N, 11.77. Found: C, 60.31; H, 5.51; N, 11.88.

Example 42

Preparation of N-[4-(1-(2,6-difluorobenzyl)-5-{[(2-methoxyethyl)(methyl)amino]methyl}-2,4-dioxo-3-(4-[2-oxo-2-(1-pyrrolidinyl)ethoxy]phenyl}-1,2,3,4-tetrahydrothieno[2,3-d]pyrimidin-6-yl)phenyl]-N'-ethylurea

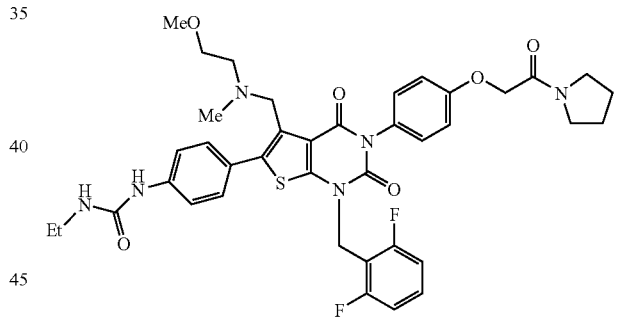

The similar reaction to that of Example 39 was performed to obtain the crude amide product (501 mg) from the compound obtained in Reference Example 9 (454 mg), diethyl phosphorocyanidate (152 μl) and 4-aminophenoxypyrrolidinyl acetamide (330 mg), and then ethanol (29 ml) and sodium ethoxide (80 mg) were used to give the title compound (331 mg).

$^1$H-NMR (DMSO-d$_6$) δ: 1.05 (3H, t, J=7.2 Hz), 1.74-1.83 (2H, m), 1.87-1.93 (2H, m), 2.05 (3H, s), 2.47 (2H, t, J=5.7 Hz) 3.07-3.15 (2H, m), 3.15 (3H, s), 3.28-3.37 (4H, m), 3.49 (2H, t, J=5.7 Hz), 3.70 (2H, s), 4.77 (2H, s), 5.28 (2H, s), 6.20 (1H, t, J=5.6 Hz), 6.99 (2H, t, J=9.0 Hz), 7.10-7.16 (4H, m), 7.40-7.54 (5H, m), 8.67 (1H, s).

IR (KBr): 1717, 1665, 1595, 1531, 1462, 1300, 1229 cm$^{-1}$.

Elemental analysis for C$_{39}$H$_{42}$N$_6$O$_6$SF$_2$.0.5H$_2$O

Calculated: C, 60.84; H, 5.63; N, 10.92. Found: C, 60.96; H, 5.36; N, 10.74.

Example 43

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenoxy]-N-ethylacetamide

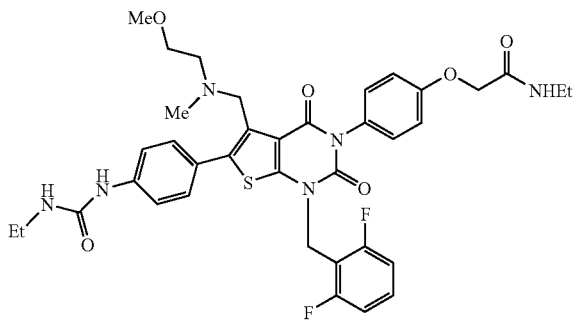

The similar reaction to that of Example 39 was performed to obtain the crude amide product (493 mg) from the compound obtained in Reference Example 9 (454 mg), diethyl phosphorocyanidate (152 μl) and 4-aminophenoxy-N-ethylacetamide (292 mg), and then ethanol (30 ml) and sodium ethoxide (82 mg) were used to give the title compound (356 mg).

$^1$H-NMR (DMSO-$d_6$) δ: 1.06 (3H, t, J=6.9 Hz), 1.07 (3H, t, J=7.2 Hz), 2.05 (3H, s), 2.48 (2H, t, J=6.0 Hz), 3.07-3.23 (4H, m), 3.15 (3H, s), 3.30 (2H, t, J=6.0 Hz), 3.70 (2H, s), 4.51 (2H, s), 5.28 (2H, s), 6.20 (1H, t, J=5.4 Hz), 7.04 (2H, d, J=8.7 Hz), 7.10-7.17 (4H, m), 7.41-7.54 (5H, m), 8.16 (1H, t, J=5.1 Hz), 8.66 (1H, s).

IR (KBr): 1717, 1669, 1595, 1532, 1470, 1314, 1236 cm$^{-1}$.

Elemental analysis for $C_{37}H_{40}N_6O_6SF_2 \cdot 0.5H_2O$

Calculated: C, 59.75; H, 5.56; N, 11.30. Found: C, 59.73; H, 5.27; N, 11.17.

Example 44

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenoxy]-N-methylacetamide

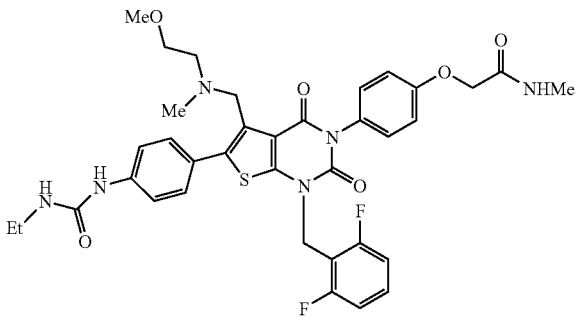

The similar reaction to that of Example 39 was performed to obtain the crude amide product (447 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-aminophenyl-N-ethylacetamide (270 mg) and N-ethyl diisopropylamine (323 μl), and then ethanol (27 ml) and sodium ethoxide (74 mg) were used to give the title compound (339 mg).

$^1$H-NMR (DMSO-$d_6$) δ: 1.06 (3H, t, J=7.1 Hz), 2.05 (3H, s), 2.48 (2H, t, J=6.0 Hz), 2.68 (3H, d, J=1.8 Hz), 3.07-3.15 (2H, m), 3.15 (3H, s), 3.30 (2H, t, J=6.0 Hz), 3.70 (2H, s), 4.52 (2H, s), 5.28 (2H, s), 6.20 (1H, t, J=5.6 Hz), 7.05 (2H, d, J=8.7 Hz), 7.10-7.18 (4H, m), 7.41-7.54 (5H, m), 8.10 (1H, q, J=1.8 Hz), 8.67 (1H, s).

IR (KBr): 1717, 1667, 1595, 1532, 1472, 1298, 1236 cm$^{-1}$.

Elemental analysis for $C_{36}H_{38}N_6O_6SF_2 \cdot H_2O$

Calculated: C, 58.53; H, 5.46; N, 11.38. Found: C, 58.56; H, 5.45; N, 11.44.

Example 45

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenoxy]-N,N-dimethylacetamide

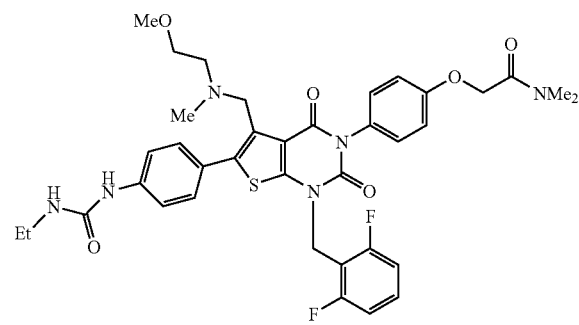

The similar reaction to that of Example 39 was performed to obtain the crude amide product (511 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-aminophenoxy-N-methylacetamide (270 mg) and N-ethyl diisopropylamine (323 μl), and then ethanol (30 ml) and sodium ethoxide (82 mg) were used to give the title compound (375 mg).

$^1$H-NMR (DMSO-$d_6$) δ: 1.06 (3H, t, J=7.2 Hz), 2.05 (3H, s), 2.48 (2H, t, J=6.0 Hz), 2.87 (3H, s), 3.03 (3H, s), 3.07-3.14 (2H, m), 3.15 (3H, s), 3.31 (2H, t, J=6.0 Hz), 3.70 (2H, s), 4.86 (2H, s), 5.28 (2H, s), 6.19 (1H, t, J=5.4 Hz), 6.99 (2H, d, J=9.0 Hz), 7.11-7.16 (4H, m), 7.40-7.54 (5H, m), 8.65 (1H, s).

IR (KBr): 1721, 1669, 1593, 1532, 1470, 1314, 1236 cm$^{-1}$.

Elemental analysis for $C_{37}H_{40}N_6O_6SF_2 \cdot 0.5H_2O$

Calculated: C, 59.75; H, 5.56; N, 11.30. Found: C, 59.90; H, 5.79; N, 11.53.

Example 46

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)phenoxy]acetamide

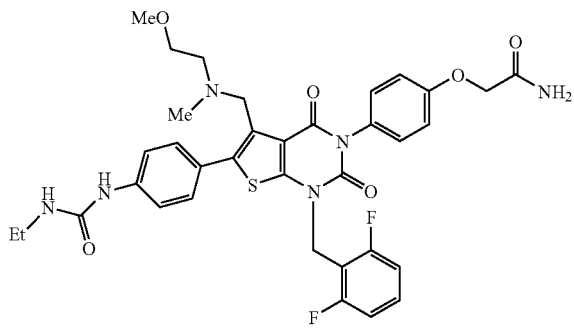

The similar reaction to that of Example 39 was performed to obtain the crude amide product (397 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-aminophenoxy acetamide (250 mg) and N-ethyl diisopropylamine (323 μl), and then ethanol (25 ml) and sodium ethoxide (68 mg) were used to give the title compound (298 mg).

$^1$H-NMR (DMSO-$d_6$) δ: 1.06 (3H, t, J=7.2 Hz), 2.05 (3H, s), 2.48 (2H, t, J=6.0 Hz), 3.07-3.15 (2H, m), 3.15 (3H, s), 3.31 (2H, t, J=5.7 Hz), 3.70 (2H, s), 4.48 (2H, s), 5.29 (2H, s), 6.19 (1H, t, J=5.5 Hz), 7.04 (2H, d, J=9.3 Hz), 7.13 (2H, t, J=8.7 Hz), 7.15 (2H, d, J=9.0 Hz), 7.40-7.59 (7H, m), 8.66 (1H, s).

IR (KBr): 1715, 1669, 1593, 1539, 1472, 1296, 1236 cm$^{-1}$.

Elemental analysis for $C_{35}H_{36}N_6O_6SF_2 \cdot 0.5H_2O$

Calculated: C, 58.73; H, 5.21; N, 11.74. Found: C, 58.98; H, 5.13; N, 11.80.

Example 47

Preparation of 2-[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)]benzamide

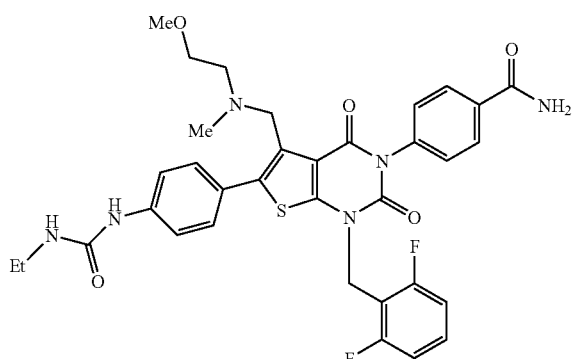

The similar reaction to that of Example 39 was performed to obtain the crude amide product (216 mg) from the compound obtained in Reference Example 9 (390 mg), 1-ethyl-3-(3-dimethylaminopropyl)-carbodiimide hydrochloride (246 mg), 1-hydroxybenzotriazole (196 mg), 4-amino benzamide (174 mg) and N-ethyl diisopropylamine (207 μl), and then ethanol (9 ml) and sodium ethoxide (25 mg) were used to give the title compound (72 mg).

$^1$H-NMR (DMSO-$d_6$) δ: 1.06 (3H, t, J=7.1 Hz), 2.05 (3H, s), 2.48 (2H, t, J=6.0 Hz), 3.07-3.16 (2H, m), 3.15 (3H, s), 3.31 (2H, t, J=6.0 Hz), 3.70 (2H, s), 5.29 (2H, s), 6.19 (1H, t, J=5.4 Hz), 7.13 (2H, t, J=8.4 Hz), 7.33 (2H, d, J=8.4 Hz), 7.43-7.54 (6H, m), 7.97 (2H, d, J=8.4 Hz), 8.07 (1H, s), 8.65 (1H, s).

IR (KBr): 1717, 1669, 1601, 1532, 1472, 1385, 1319 cm$^{-1}$.

Elemental analysis for $C_{34}H_{34}N_6O_5SF_2 \cdot 0.5H_2O$

Calculated: C, 59.55; H, 5.14; N, 12.26. Found: C, 59.74; H, 5.42; N, 12.55.

Example 48

Preparation of methyl[4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)benzoate

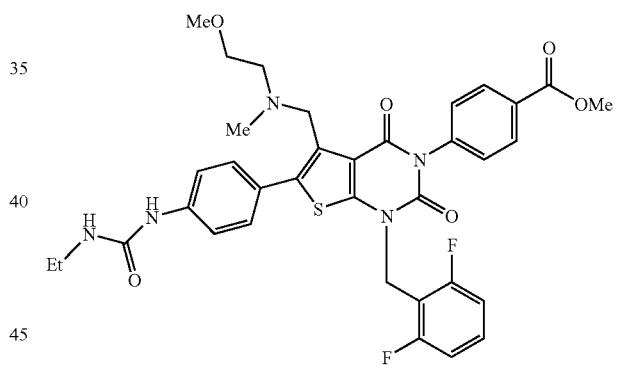

The similar reaction to that of Example 39 was performed to obtain the crude amide product (2.92 g) from the compound obtained in Reference Example 9 (5.45 g), 1-ethyl-3-(3-dimethylaminopropyl)-carbodiimide hydrochloride (2.59 g), 1-hydroxybenzotriazole (2.07 g), methyl 4-amino benzoate (2.04 g) and N-ethyl diisopropylamine (2.91 ml) and then methanol (198 ml) and sodium methoxide (427 mg) were used to give the title compound (2.30 g).

$^1$H-NMR (CDCl$_3$) δ: 1.16 (3H, t, J=7.1 Hz), 2.11 (3H, s), 2.60 (2H, t, J=5.7 Hz), 3.24 (3H, s), 3.22-3.32 (2H, m), 3.40 (2H, t, J=5.7 Hz), 3.80 (2H, s), 3.93 (3H, s), 4.82 (1H, t, J=5.9 Hz), 5.35 (2H, s), 6.58 (1H, s), 6.92 (2H, t, J=8.1 Hz), 7.24-7.39 (5H, m), 7.52 (2H, d, J=8.4 Hz), 8.17 (2H, d, J=8.4 Hz).

IR (KBr): 2978, 1717, 1674, 1593, 1532, 1464, 1281 cm$^{-1}$.

Elemental analysis for $C_{35}H_{35}N_5O_6SF_2 \cdot H_2O$

Calculated: C, 59.23; H, 5.25; N, 9.87. Found: C, 59.38; H, 5.30; N, 9.86.

Example 49

Preparation of ethyl[4-(1-(2,6-difluorobenzyl))-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl]benzoate

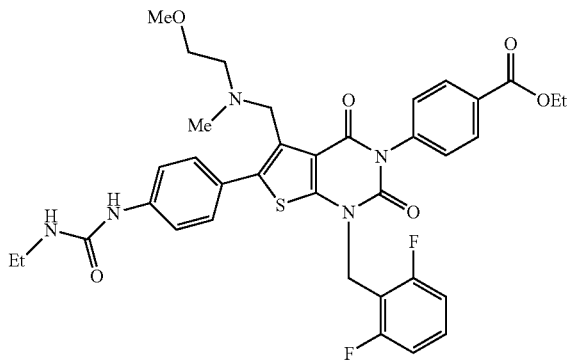

The similar reaction to that of Example 39 was performed to obtain the crude amide product (1.76 g) from the compound obtained in Reference Example 9 (6.05 g), 1-ethyl-3-(3-dimethylaminopropyl)-carbodiimide hydrochloride (2.3 g), 1-hydroxybenzotriazole (1.84 g), ethyl 4-amino benzoate (1.98 g) and N-ethyl diisopropylamine (2.07 ml) and then said product (0.74 g), ethanol (49 ml) and sodium ethoxide (134 mg) were used to give the title compound (0.294 g).

$^1$H-NMR (CDCl$_3$) δ: 1.17 (3H, t, J=7.4 Hz), 1.39 (3H, t, J=7.1 Hz), 2.11 (3H, s), 2.62 (2H, t, J=5.9 Hz), 3.25 (3H, s), 3.24-3.35 (2H, m), 3.41 (2H, t, J=5.9 Hz), 3.81 (2H, s), 4.40 (2H, q, J=7.1 Hz), 4.74 (1H, t, J=6.0 Hz), 5.36 (2H, s), 6.45 (1H, s), 6.93 (2H, t, J=8.2 Hz), 7.26-7.39 (5H, m), 7.54 (2H, d, J=8.4 Hz), 8.18 (2H, d, J=8.4 Hz).

IR (KBr): 1713, 1669, 1595, 1535, 1464, 1277 cm$^{-1}$.

Elemental analysis for C$_{36}$H$_{37}$N$_5$O$_6$SF$_2$.0.5H$_2$O

Calculated: C, 60.49; H, 5.36; N, 9.80. Found: C, 60.69; H, 5.29; N, 9.72.

Example 50

Preparation of N-[4-(1-(2,6-difluorobenzyl)-3-(4-hydroxy-3-methylphenyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

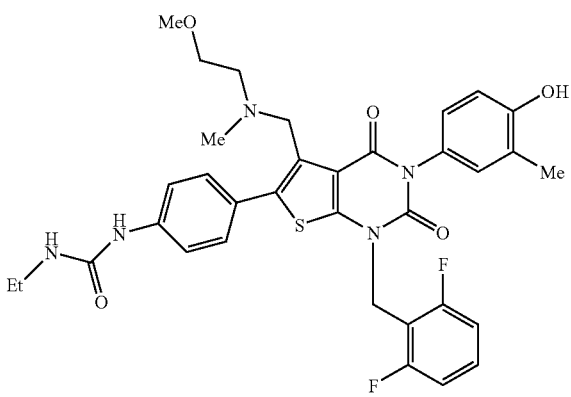

The similar reaction to that of Example 39 was performed to obtain the crude amide product (230 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-hydroxy-3-methylaniline-hydrogen bromide salt (306 mg) and N-ethyl diisopropylamine (484 µl) and then methanol (20 ml) and sodium ethoxide (40.2 mg) were used to give the title compound (130 mg).

$^1$H-NMR (CDCl$_3$) δ: 1.16 (3H, t, J=7.1 Hz), 2.11 (3H, s), 2.60 (2H, t, J=5.7 Hz), 3.24 (3H, s), 3.22-3.32 (2H, m), 3.40 (2H, t, J=5.7 Hz), 3.80 (2H, s), 3.93 (3H, s), 4.82 (1H, t, J=5.9 Hz), 5.35 (2H, s), 6.58 (1H, s), 6.92 (2H, t, J=8.1 Hz), 7.24-7.39 (5H, m), 7.52 (2H, d, J=8.4 Hz), 8.17 (2H, d, J=8.4 Hz).

IR (KBr): 2978, 1717, 1674, 1593, 1532, 1464, 1281 cm$^{-1}$.

Elemental analysis for C$_{34}$H$_{35}$N$_5$O$_5$SF$_2$.0.75H$_2$O

Calculated: C, 60.30; H, 5.43; N, 10.34. Found: C, 60.32; H, 5.53; N, 10.20.

Example 51

Preparation of N-[4-(1-(2,6-difluorobenzyl)-5-{[(2-methoxyethyl)(methyl)amino]methyl}-3-[4-methoxy-3-(methoxymethyl)phenyl]-2,4-dioxo-1,2,3,4-tetrahydrothieno[2,3-d]pyrimidin-6-yl)phenyl]-N'-ethylurea

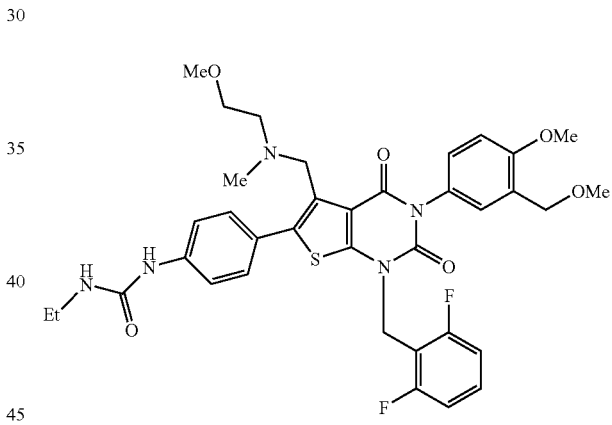

The similar reaction to that of Example 39 was performed to obtain the crude amide product (352 mg) from the compound obtained in Reference Example 9 (454 mg), 1-ethyl-3-(3-dimethylaminopropyl)-carbodiimide hydrochloride (288 mg), 1-hydroxybenzotriazole (230 mg), 4-methoxy-3-methoxymethyl aniline (251 mg) and N-ethyl diisopropylamine (323 µl), and then ethanol (22 ml) and sodium ethoxide (59.3 mg) were used to give the title compound (230 mg).

$^1$H-NMR (CDCl$_3$) δ: 1.14 (3H, t, J=7.0 Hz), 2.12 (3H, s), 2.62 (2H, t, J=5.7 Hz), 3.25 (3H, s), 3.21-3.34 (2H, m), 3.41 (3H, s), 3.40 (2H, t, J=5.7 Hz), 3.83 (5H, s), 4.50 (2H, s), 4.88 (1H, t, J=5.4 Hz), 5.35 (2H, s), 6.66 (1H, s), 6.89-6.96 (3H, m), 7.16 (1H, dd, J=2.4 Hz, 8.7 Hz), 7.24-7.28 (2H, m), 7.35 (2H, d, J=8.4 Hz), 7.53 (2H, d, J=8.4 Hz).

IR (KBr): 1713, 1671, 1593, 1534, 1464, 1314 cm$^{-1}$.

Elemental analysis for C$_{36}$H$_{39}$N$_5$O$_6$SF$_2$.0.5H$_2$O

Calculated: C, 60.32; H, 5.62; N, 9.77. Found: C, 60.58; H, 5.46; N, 9.86.

Example 52

Preparation of N-[4-(1-(2,6-difluorobenzyl)-3-[4-(1-hydroxy-1-methylethyl)phenyl]-5-({[(2-methoxyethyl)(methyl)amino]methyl}-2,4-dioxo-1,2,3,4-tetrahydrothieno[2,3-d]pyrimidin-6-yl)phenyl]-N'-ethylurea

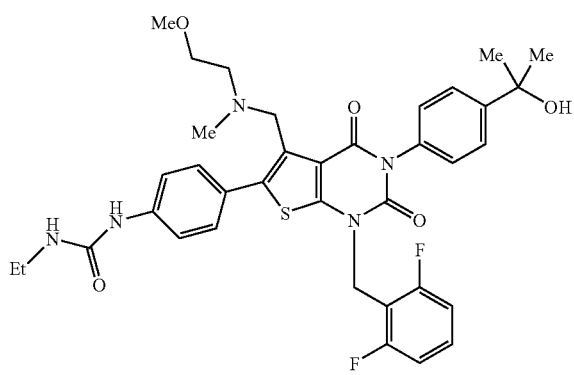

The similar reaction to that of Example 39 was performed to obtain the crude amide product (217 mg) from the compound obtained in Reference Example 9 (318 mg), 1-ethyl-3-(3-dimethylaminopropyl)carbodiimide hydrochloride (202 mg), 1-hydroxybenzotriazole (161 mg), 4-(1-hydroxy-1-methylethyl)aniline (160 mg) and N-ethyl diisopropylamine (288 μl), and then ethanol (12 ml) and sodium ethoxide (32.7 mg) were used to give the title compound (46 mg).

Elemental analysis for $C_{36}H_{39}N_5O_5SF_2 \cdot 0.75H_2O$

Calculated: C, 61.31; H, 5.79; N, 9.93. Found: C, 61.18; H, 5.56; N, 9.88.

$^1$H-NMR (CDCl$_3$) δ: 1.15 (3H, t, J=7.2 Hz), 1.58 (6H, s), 1.96 (1H, s), 2.13 (3H, s), 2.62 (2H, t, J=5.8 Hz), 3.25 (3H, s), 3.22-3.31 (2H, m), 3.40 (2H, t, J=5.8 Hz), 3.82 (2H, s), 4.85 (1H, t, J=5.4 Hz), 5.36 (2H, s), 6.65 (1H, s), 6.92 (2H, t, J=8.1 Hz), 7.24 (2H, dd, J=8.4 Hz), 7.25-7.31 (1H, m), 7.35 (2H, d, J=8.4 Hz), 7.53 (2H, d, J=8.4 Hz), 7.60 (2H, d, J=8.4 Hz).

IR (KBr): 3335, 2975, 1715, 1669, 1593, 1537, 1470, 1316 cm$^{-1}$.

Example 53

Preparation of N-[4-(1-(2,6-difluorobenzyl)-5-{[(2-methoxyethyl)(methyl)amino]methyl}-3-(6-methoxy-3-pyridinyl)-2,4-dioxo-1,2,3,4-tetrahydrothieno[2,3-d]pyrimidin-6-yl)phenyl]-N'-ethylurea

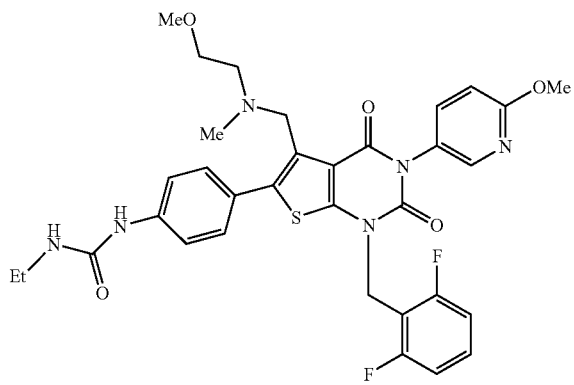

The similar reaction to that of Example 39 was performed to obtain the crude amide product (450 mg) from the compound obtained in Reference Example 9 (454 mg), diethyl phosphorocyanidate (164 mg), 5-amino-2-methoxypyridine (186 mg) and N-ethyl diisopropylamine (2259 μl), and then ethanol (29.5 ml) and sodium ethoxide (80 mg) were used to give the title compound (265 mg).

$^1$H-NMR (CDCl$_3$) δ: 1.16 (3H, t, J=7.2 Hz), 2.11 (3H, s), 2.62 (2H, t, J=5.6 Hz), 3.25 (3H, s), 3.23-3.34 (2H, m), 3.41 (2H, t, J=5.6 Hz), 3.81 (2H, s), 3.96 (3H, s), 4.86 (1H, t, J=5.5 Hz), 5.35 (2H, s), 6.62 (1H, s), 6.83-6.96 (3H, m), 7.23-7.31 (1H, m), 7.37 (2H, d, J=8.4 Hz), 7.47-7.54 (3H, m), 8.09 (1H, d, J=2.6 Hz).

IR (KBr): 1717, 1672, 1593, 1532, 1464, 1387, 1283 cm$^{-1}$.

Elemental analysis for $C_{33}H_{34}N_6O_5SF_2 \cdot 0.25H_2O$

Calculated: C, 59.23; H, 5.20; N, 12.56. Found: C, 59.18; H, 5.12; N, 12.48.

Example 54

Preparation of N-[4-(1-(2,6-difluorobenzyl)-5-{[(2-methoxyethyl)(methyl)amino]methyl}-2,4-dioxo-3-(2-oxo-1,2-dihydro-4-pyrimidinyl)-1,2,3,4-tetrahydrothieno[2,3-d]pyrimidin-6-yl)phenyl]-N'-ethylurea

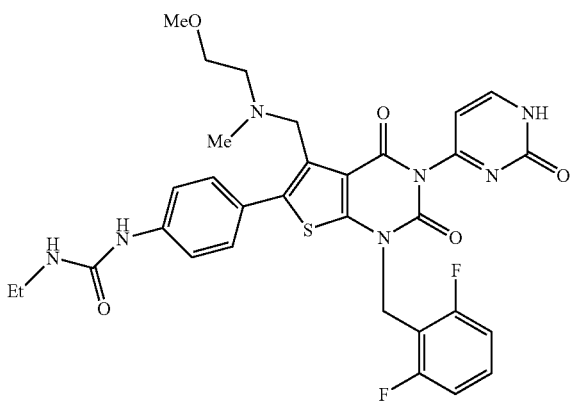

The similar reaction to that of Example 39 was performed to obtain the crude amide product (64 mg) from the compound obtained in Reference Example 9 (454 mg), diethyl phosphorocyanidate (164 mg), cytosine (167 mg) and N-ethyl diisopropylamine (2259 μl), and then ethanol (3.9 ml) and sodium ethoxide (10.5 mg) were used to give the title compound (24 mg).

$^1$H-NMR (DMSO-d$_6$+D$_2$O) δ: 1.07 (3H, t, J=7.2 Hz), 2.14 (3H, brs), 2.53 (2H, brs), 3.08-3.13 (2H, m), 3.16 (3H, s), 3.38 (2H, brs), 3.71 (2H, s), 5.29 (2H, s), 6.55 (1H, d, J=6.6 Hz), 7.14 (2H, t, J=8.2 Hz), 7.40-7.60 (5H, m), 8.18 (1H, d, J=6.6 Hz).

IR (KBr): 1717, 1674, 1593, 1537, 1470, 1441, 1318, 1236 cm$^{-1}$.

Elemental analysis for $C_{31}H_{31}N_7O_5SF_2 \cdot 1.75H_2O$

Calculated: C, 54.50; H, 5.09; N, 14.35. Found: C, 54.49; H, 5.03; N, 14.60.

Example 55

Preparation of N-[4-(3-cyclohexyl-1-(2,6-difluorobenzyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

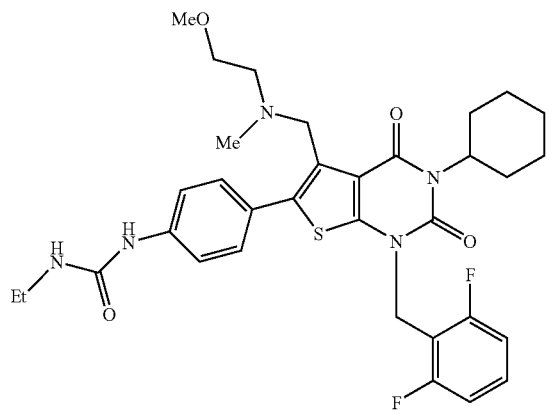

The similar reaction to that of Example 39 was performed to obtain the crude amide product (354 mg) from the compound obtained in Reference Example 9 (363 mg), 1-ethyl-3-(3-dimethylaminopropyl)-carbodiimide hydrochloride (173 mg), 1-hydroxybenzotriazole (138 mg), cyclohexylamine (99 mg), and N-ethyl diisopropylamine (155 µl), and then methanol (20 ml) and sodium methoxide (222 mg) were used to give the title compound (173 mg).

$^1$H-NMR (CDCl$_3$) δ: 1.16 (3H, t, J=7.4 Hz), 1.21-1.54 (4H, m), 1.60-1.93 (4H, m), 2.14 (3H, s), 2.36-2.60 (2H, m), 2.65 (2H, t, J=5.8 Hz), 3.23-3.37 (2H, m), 3.30 (3H, s), 3.45 (2H, t, J=5.8 Hz), 3.84 (2H, s), 4.83 (1H, t, J=6.2 Hz), 4.86-5.00 (1H, m), 5.29 (2H, s), 6.53 (1H, s), 6.90 (2H, t, J=8.3 Hz), 7.21-7.28 (1H, m), 7.35 (2H, d, J=8.4 Hz), 7.51 (2H, d, J=8.4 Hz).

IR (KBr): 1705, 1661, 1593, 1537, 1470, 1314, 1236 cm$^{-1}$.

Elemental analysis for C$_{33}$H$_{39}$N$_5$O$_4$SF$_2$.0.5H$_2$O

Calculated: C, 61.09; H, 6.21; N, 10.79. Found: C, 61.34; H, 6.27; N, 10.97.

Example 56

Preparation of N-[4-(1-(2,6-difluorobenzyl)-5-{[(2-methoxyethyl)(methyl)amino]methyl}-2,4-dioxo-3-(1-piperidinyl)-1,2,3,4-tetrahydrothieno[2,3-d]pyrimidin-6-yl)phenyl]-N'-ethylurea

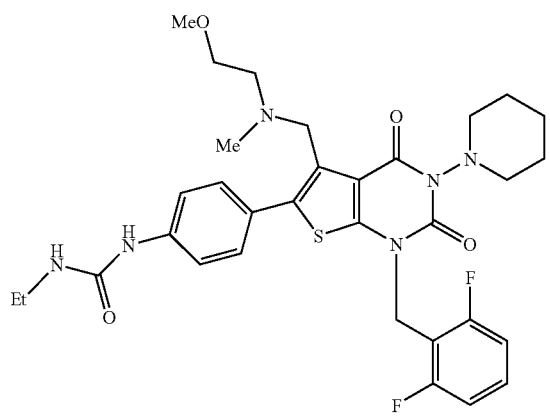

The similar reaction to that of Example 39 was performed to obtain the crude amide product (174 mg) from the compound obtained in Reference Example 9 (363 mg), 1-ethyl-3-(3-dimethylaminopropyl)-carbodiimide hydrochloride (173 mg), 1-hydroxybenzotriazole (138 mg), 1-aminopiperidine (100 mg) and N-ethyl diisopropylamine (155 µl), and then methanol (11 ml) and sodium methoxide (119 mg) were used to give the title compound (100 mg).

$^1$H-NMR (CDCl$_3$) δ: 1.15 (3H, t, J=7.2 Hz), 1.30-1.60 (2H, m), 1.62-1.84 (4H, m), 2.14 (3H, s), 2.65 (2H, t, J=5.9 Hz), 3.20-3.33 (4H, m), 3.28 (3H, s), 3.34-3.42 (2H, m), 3.43 (2H, t, J=5.9 Hz), 3.84 (2H, s), 4.97 (1H, t, J=5.5 Hz), 5.30 (2H, s), 6.79 (1H, s), 6.89 (2H, t, J=8.2 Hz), 7.21-7.32 (1H, m), 7.36 (2H, d, J=8.4 Hz), 7.51 (2H, d, J=8.4 Hz).

IR (KBr): 1715, 1678, 1593, 1537, 1462, 1314, 1236 cm$^{-1}$.

Elemental analysis for C$_{32}$H$_{38}$N$_6$O$_4$SF$_2$.0.5H$_2$O

Calculated: C, 59.15; H, 6.05; N, 12.93. Found: C, 59.41; H, 5.94; N, 12.91.

Example 57

Preparation of N-[4-(1-(2,6-difluorobenzyl)-5-{[(2-methoxyethyl)(methyl)amino]methyl}-3-(4-morpholinyl)-2,4-dioxo-1,2,3,4-tetrahydrothieno[2,3-d]pyrimidin-6-yl)phenyl]-N'-ethylurea

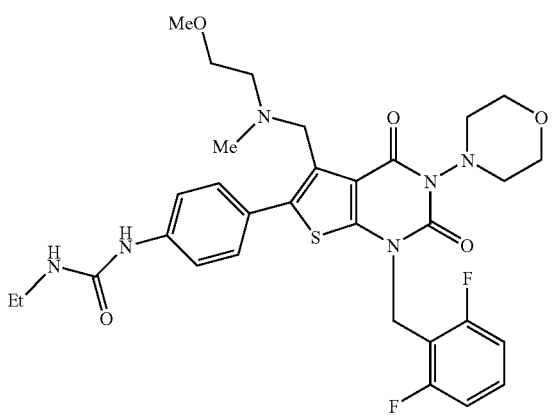

The similar reaction to that of Example 39 was performed to obtain the crude amide product (136 mg) from the compound obtained in Reference Example 9 (363 mg), 1-ethyl-3-(3-dimethylaminopropyl)carbodiimide hydrochloride (173 mg), 1-hydroxybenzotriazole (138 mg), 1-aminopiperidine (102 mg) and N-ethyl diisopropylamine (155 µl), and then methanol (9 ml) and sodium methoxide (97 mg) were used to give the title compound (64 mg).

$^1$H-NMR (CDCl$_3$) δ: 1.16 (3H, t, J=7.3 Hz), 2.13 (3H, s), 2.65 (2H, t, J=5.7 Hz), 3.23-3.60 (4H, m), 3.29 (3H, s), 3.43 (2H, t, J=5.7 Hz), 3.45-3.60 (2H, m), 3.83 (2H, s), 3.80-3.93 (4H, m), 4.89 (1H, t, J=5.5 Hz), 5.30 (2H, s), 6.68 (1H, s), 6.90 (2H, t, J=8.1 Hz), 7.22-7.30 (1H, m), 7.37 (2H, d, J=8.4 Hz), 7.49 (2H, d, J=8.4 Hz).

IR (KBr): 1715, 1678, 1593, 1532, 1470, 1314, 1236 cm$^{-1}$.

Elemental analysis for C$_{31}$H$_{36}$N$_6$O$_5$SF$_2$.0.25H$_2$O

Calculated: C, 57.53; H, 5.68; N, 12.98. Found: C, 57.59; H, 5.82; N, 12.99.

Example 58

Preparation of N-[4-(1-(2,6-difluorobenzyl)-3-(4-fluorophenyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

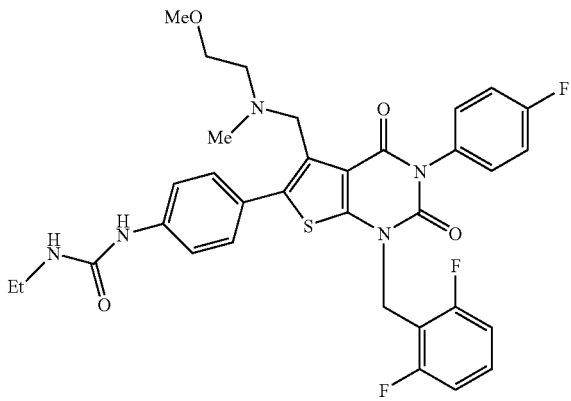

The similar reaction to that of Example 39 was performed to obtain the crude amide product (311 mg) from the compound obtained in Reference Example 9 (605 mg), 1-ethyl-3-(3-dimethylaminopropyl)carbodiimide hydrochloride (230 mg), 1-hydroxybenzotriazole (184 mg), 4-fluoroaniline (134 mg), N-ethyl diisopropylamine (215 μl), and then methanol (27 ml) and sodium methoxide (286 mg) were used to give the title compound (311 mg).

$^1$H-NMR (CDCl$_3$) δ: 1.16 (3H, t, J=7.4 Hz), 2.12 (3H, s), 2.62 (2H, t, J=5.8 Hz), 3.25 (3H, s), 3.25-3.34 (2H, m), 3.41 (2H, t, J=5.8 Hz), 3.81 (2H, s), 4.78 (1H, brs), 5.35 (2H, s), 6.50 (1H, s), 6.92 (2H, t, J=8.0 Hz), 7.15-7.34 (5H, m), 7.37 (2H, d, J=8.4 Hz), 7.64 (2H, d, J=8.4 Hz).

IR (KBr): 1715, 1674, 1593, 1532, 1470, 1316, 1236 cm$^{-1}$.

Elemental analysis for C$_{33}$H$_{32}$N$_5$O$_4$SF$_3$·0.25H$_2$O

Calculated: C, 60.40; H, 4.99; N, 10.67. Found: C, 60.39; H, 4.82; N, 10.58.

Example 59

Preparation of N-[4-(1-(2,6-difluorobenzyl)-3-(2,4-difluorophenyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

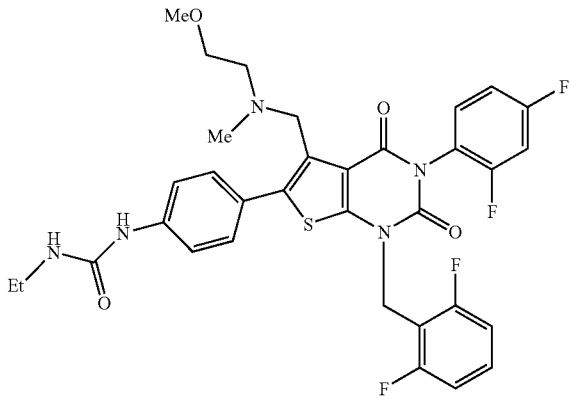

The similar reaction to that of Example 39 was performed to obtain the crude amide product (246 mg) from the compound obtained in Reference Example 9 (400 mg), 1-ethyl-3-(3-dimethylaminopropyl)carbodiimide hydrochloride (190 mg), 1-hydroxybenzotriazole (153 mg), 2,4-difluoroaniline (128 mg), N-ethyl diisopropylamine (190 μl), and then methanol (16.8 ml) and sodium methoxide (181 mg) were used to give the title compound (162 mg).

$^1$H-NMR (CDCl$_3$) δ: 1.15 (3H, t, J=7.4 Hz), 2.13 (3H, s), 2.62 (2H, t, J=5.7 Hz), 3.26 (3H, s), 3.24-3.34 (2H, m), 3.41 (2H, t, J=5.7 Hz), 3.73 (1H, d, J=12.3 Hz), 3.89 (1H, d, J=12.3 Hz), 4.86 (1H, t, J=5.1 Hz), 5.36 (2H, d, J=3.9 Hz), 6.61 (1H, s), 6.92 (2H, t, J=8.1 Hz), 6.99 (2H, d, J=8.1 Hz), 7.28-7.34 (2H, m), 7.44 (2H, d, J=8.7 Hz), 7.53 (2H, d, J=8.7 Hz).

IR (KBr): 1721, 1682, 1593, 1532, 1470, 1316, 1277 cm$^{-1}$.

Elemental analysis for C$_{33}$H$_{31}$N$_5$O$_4$SF$_4$

Calculated: C, 59.18; H, 4.67; N, 10.46. Found: C, 59.12; H, 4.57; N, 10.50.

Example 60

Preparation of N-[4-(1-(2,6-difluorobenzyl)-3-(3,5-difluorophenyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

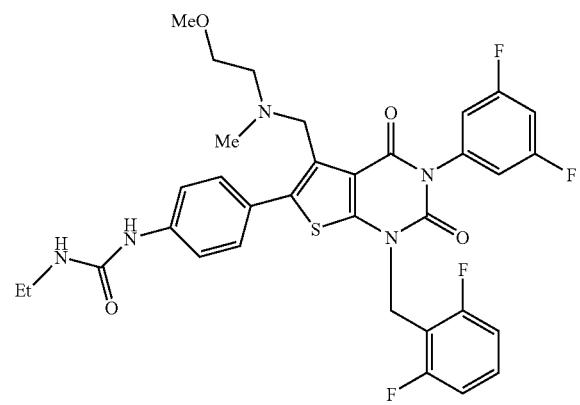

The similar reaction to that of Example 39 was performed to obtain the crude amide product (58 mg) from the compound obtained in Reference Example 9 (400 mg), 1-ethyl-3-(3-dimethylaminopropyl)carbodiimide hydrochloride (190 mg), 1-hydroxybenzotriazole (153 mg), 3,5-difluoroaniline (128 mg) and N-ethyl diisopropylamine (190 μl), and then methanol (0.8 ml) and sodium methoxide (43 mg) were used to give the title compound (33 mg).

$^1$H-NMR (CDCl$_3$) δ: 1.18 (3H, t, J=7.3 Hz), 2.11 (3H, s), 2.63 (2H, t, J=5.6 Hz), 3.27 (3H, s), 3.26-3.35 (2H, m), 3.42 (2H, t, J=5.6 Hz), 3.80 (2H, s), 4.68 (1H, t, J=6.6 Hz), 5.35 (2H, s), 6.37 (1H, s), 6.85-6.97 (5H, m), 7.25-7.32 (1H, m), 7.38 (2H, d, J=8.4 Hz), 7.54 (2H, d, J=8.4 Hz).

IR (KBr): 1719, 1672, 1640, 1607, 1566, 1472, 1302 cm$^{-1}$.

Elemental analysis for C$_{33}$H$_{31}$N$_5$O$_4$SF$_4$

Calculated: C, 59.18; H, 4.67; N, 10.46. Found: C, 58.93; H, 4.64; N, 10.31.

Example 61

Preparation of 4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)-N-isopropyl benzamide

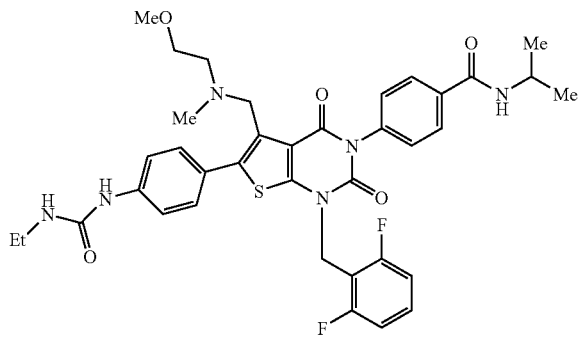

Isopropylamine (85.1 mg) and N-ethyl diisopropylamine (155 mg) were dissolved in methylene chloride (3 ml), followed by addition of a 1 M solution of dimethylaluminum chloride in hexane (1.23 ml) with ice-cooling and the mixture was stirred for 30 minutes. Then, a solution of the compound of Example 48 (139 mg) in dichloromethane (3 ml) was added and the mixture was allowed to return to room temperature slowly and was stirred for 19 hours. The reaction solution was partitioned between chloroform and saturated aqueous sodium bicarbonate. The organic layer was dried over anhydrous sodium sulfate and the solvent was distilled off under reduced pressure to give the residue, which was purified by aminopropyl silica gel (manufactured by Fuji Silysia Chemical Ltd.) chromatography. The eluate was recrystallized from dichloromethane/methanol to give the title compound (62 mg).

$^1$H-NMR (CDCl$_3$+CD$_3$OD) δ: 1.17 (3H, t, J=7.4 Hz), 1.28 (6H, d, J=6.6 Hz), 2.07 (3H, s), 2.57 (2H, t, J=5.9 Hz), 3.24 (3H, s), 3.23-3.32 (2H, m), 3.40 (2H, t, J=5.9 Hz), 3.81 (2H, s), 4.23-4.30 (1H, m), 5.37 (2H, s), 6.94 (2H, t, J=7.8 Hz), 7.28-7.34 (1H, m), 7.36 (2H, d, J=8.7 Hz), 7.43 (4H, s), 7.78 (2H, d, J=8.7 Hz)

IR (KBr): 1721, 1667, 1597, 1537, 1472, 1323, 1238 cm$^{-1}$.

Elemental analysis for C$_{37}$H$_{40}$N$_6$O$_5$SF$_2$.0.5H$_2$O

Calculated: C, 61.06; H, 5.68; N, 11.55. Found: C, 60.78; H, 5.57; N, 11.50.

Example 62

Preparation of N-cyclopropyl-4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl) benzamide

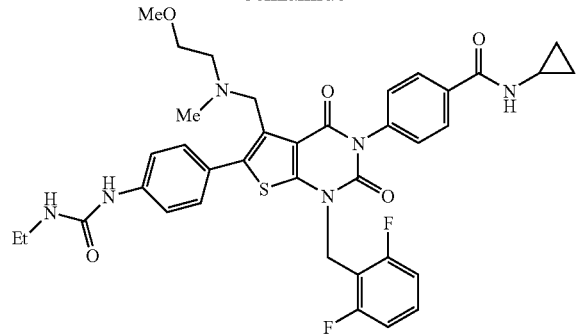

The similar reaction to that of Example 61 was performed using cyclopropylamine (83 mg), N-ethyl diisopropylamine (155 mg), a 1 M solution of dimethylaluminum chloride in hexane (1.23 ml) and the compound of Example 48 (139 mg) to give the title compound (88 mg).

$^1$H-NMR (CDCl$_3$+CD$_3$OD) δ: 0.61-0.64 (2H, m), 1.17 (3H, t, J=7.4 Hz), 2.06 (3H, s), 2.56 (2H, t, J=5.9 Hz), 2.90-2.94 (1H, m), 3.23 (3H, s), 3.28-3.33 (2H, m), 3.38 (2H, t, J=5.9 Hz), 3.79 (2H, s), 5.35 (2H, s), 6.93 (2H, t, J=8.1 Hz), 7.27-7.32 (1H, m), 7.34 (2H, d, J=8.7 Hz), 7.41-7.45 (4H, m), 7.86 (2H, d, J=8.7 Hz).

IR (KBr): 1717, 1669, 1597, 1532, 1472, 1318, 1236 cm$^{-1}$.

Elemental analysis for C$_{37}$H$_{38}$N$_6$O$_5$SF$_2$.0.5H$_2$O

Calculated: C, 61.23; H, 5.42; N, 11.58. Found: C, 60.22; H, 5.30; N, 11.62.

Example 63

Preparation of 4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)-N-methylbenzamide

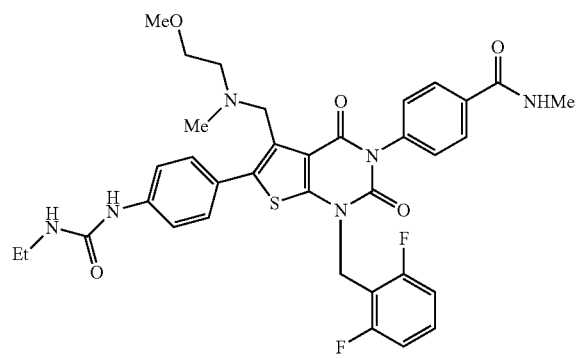

The similar reaction to that of Example 61 was performed using a 2 M methylamine/tetrahydrofuran solution (0.72 ml), N-ethyl diisopropylamine (155 mg), a 1 M solution of dimethylaluminum chloride in hexane (1.23 ml) and the compound of Example 48 (139 mg) to give the title compound (58 mg).

$^1$H-NMR (CDCl$_3$+CD$_3$OD) δ: 1.16 (3H, t, J=7.2 Hz), 2.07 (3H, s) 2.57 (2H, t, J=5.7 Hz), 2.99 (3H, d, J=4.8 Hz), 3.23 (3H, s), 3.24-3.32 (2H, m), 3.39 (2H, t, J=5.7 Hz), 3.80 (2H, s), 5.36 (2H, s), 5.54 (1H, t, J=5.4 Hz), 6.93 (2H, t, J=8.3 Hz), 7.23 (1H, q, J=4.8 Hz), 7.30-7.34 (2H, m), 7.35 (2H, d, J=8.4 Hz), 7.42 (4H, s), 7.89 (2H, d, J=8.4 Hz).

IR (KBr): 1717, 1669, 1595, 1552, 1472, 1318, 1236 cm$^{-1}$.

Elemental analysis for C$_{35}$H$_{36}$N$_6$O$_5$SF$_2$.H$_2$O

Calculated: C, 59.31; H, 5.40; N, 11.86. Found: C, 59.55; H, 5.30; N, 12.06.

Example 64

Preparation of 4-(1-(2,6-difluorobenzyl)-6-(4-{[(ethylamino)carbonyl]amino}phenyl)-5-{[(2-methoxyethyl)(methyl)amino]methyl}-2,4-dioxo-1,4-dihydrothieno[2,3-d]pyrimidin-3(2H)-yl)-N,N-dimethylbenzamide

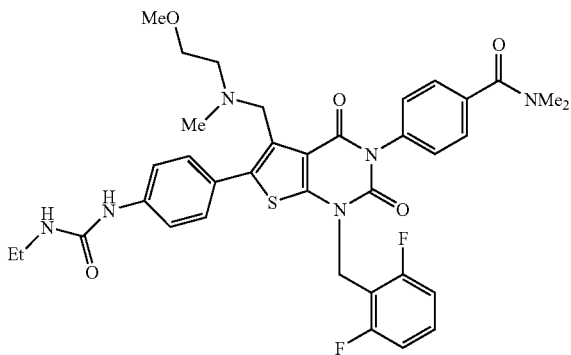

The similar reaction to that of Example 61 was performed using a 2 M dimethylamine/tetrahydrofuran solution (0.72 ml), N-ethyl diisopropylamine (155 mg), a 1 M solution of dimethylaluminum chloride in hexane (1.23 ml) and the compound of Example 48 (139 mg) to give the title compound (119 mg).

$^1$H-NMR (CDCl$_3$) δ: 1.20 (3H, t, J=7.2 Hz), 1.90 (3H, s), 2.34 (2H, t, J=5.8 Hz), 3.10 (6H, s), 3.16 (2H, t, J=5.8 Hz), 3.18 (3H, s), 3.26-3.39 (2H, m), 3.78 (2H, s), 5.35 (2H, s), 5.77 (1H, t, J=4.9 Hz), 6.91 (2H, t, J=8.3 Hz), 7.05 (2H, d, J=8.4 Hz), 7.22-7.34 (1H, m), 7.37 (4H, d, J=8.4 Hz), 7.58 (2H, d, J=8.4 Hz), 7.91 (1H, s).

IR (KBr): 1717, 1672, 1597, 1537, 1462, 1319, 1231 cm$^{-1}$.

Elemental analysis for C$_{36}$H$_{38}$N$_6$O$_5$SF$_2$.0.5H$_2$O

Calculated: C, 60.58; H, 5.51; N, 11.77. Found: C, 60.82; H, 5.44; N, 11.85.

Example 65

Preparation of N-{4-[1-(2,6-difluorobenzyl)-5-{[(2-methoxyethyl)(methyl)amino]methyl}-3-(4-methoxy-3-methylphenyl)-2,4-dioxo-1,2,3,4-tetrahydrothieno[2,3-d]pyrimidin-6-yl]phenyl}-N'-ethylurea

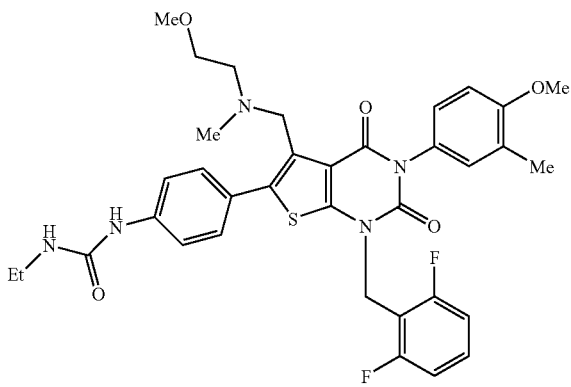

4-methoxy-3-methylaniline (959 mg) was dissolved in dichloromethane (11.3 ml), followed by addition of a 1 M solution of dimethylaluminum chloride in hexane (5.75 ml) with ice-cooling and the mixture was stirred for 30 minutes. Then, a solution of the compound of Reference Example 8 (597 mg) in dichloromethane (5 ml) was added and the mixture was allowed to return to room temperature slowly and was stirred for 21 hour.

The reaction solution was partitioned between chloroform and saturated aqueous sodium bicarbonate. The organic layer was dried over anhydrous sodium sulfate and the solvent was distilled off under reduced pressure to give the residue, which was purified by aminopropyl silica gel (manufactured by Fuji Silysia Chemical Ltd.) chromatography to give the title compound (129 mg) as crystalline powder.

$^1$H-NMR (CDCl$_3$) δ: 1.14 (3H, t, J=7.1 Hz), 2.12 (3H, s), 2.21 (3H, s), 2.61 (2H, t, J=5.9 Hz), 3.25 (3H, s), 3.21-3.34 (2H, m), 3.40 (2H, t, J=5.9 Hz), 3.83 (2H+3H, s), 4.90 (1H, t, J=6.0 Hz), 5.35 (2H, s), 6.71 (1H, s), 6.91 (2H, t, J=7.7 Hz), 6.88-7.10 (3H, m), 7.24-7.30 (1H, m), 7.35 (2H, d, J=8.4 Hz), 7.52 (2H, d, J=8.4 Hz).

IR (KBr): 2971, 1713, 1669, 1593, 1532, 1470, 1314, 1256 cm$^{-1}$.

Elemental analysis for C$_{35}$H$_{37}$N$_5$O$_5$SF$_2$.0.5H$_2$O

Calculated: C, 61.21; H, 5.58; N, 10.20. Found: C, 61.22; H, 5.60; N, 10.23.

Example 66

Preparation of N-[4-(1-(2,6-difluorobenzyl)-3-(3,5-didimethylphenyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

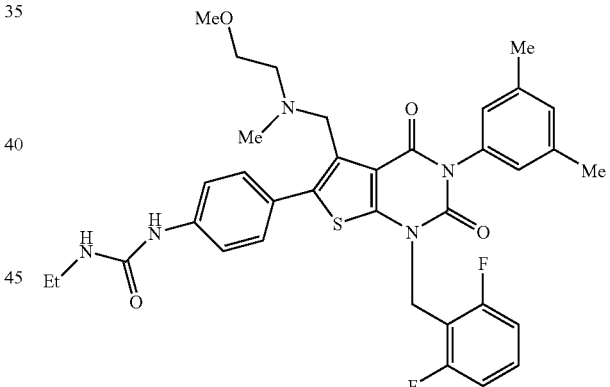

The similar reaction to that of Example 65 was performed using 3,5-dimethylaniline (665 mg), a 1 M solution of dimethylaluminum chloride in hexane (5.09 ml) and the compound of Reference Example 8 (526 mg) to give the title compound (323 mg).

$^1$H-NMR (CDCl$_3$) δ: 1.15 (3H, t, J=7.3 Hz), 2.13 (3H, s), 2.33 (6H, s), 2.63 (2H, t, J=5.9 Hz), 3.26 (3H, s), 3.21-3.35 (2H, m), 3.41 (2H, t, J=5.9 Hz), 3.83 (2H, s), 4.81 (1H, t, J=4.9 Hz), 5.35 (2H, s), 6.56 (1H, s), 6.88 (2H, s), 6.92 (2H, t, J=8.0 Hz), 7.03 (1H, s), 7.22-7.36 (1H, m), 7.35 (2H, d, J=8.4 Hz), 7.55 (2H, d, J=8.4 Hz).

IR (KBr): 2973, 1715, 1672, 1593, 1537, 1470, 1316, 1236 cm$^{-1}$.

Elemental analysis for C$_{35}$H$_{37}$N$_5$O$_4$SF$_2$.0.25H$_2$O

Calculated: C, 63.10; H, 5.67; N, 10.51. Found: C, 63.18; H, 5.58; N, 10.53.

Example 67

Preparation of N-[4-(1-(2,6-difluorobenzyl)-5-([(2-ethoxyethyl)(methyl)amino]methyl)-3-(4-fluorophenyl)-2,4-dioxo-1,2,3,4-tetrahydrothieno[2,3-d]pyrimidin-6-yl)phenyl]-N'-ethylurea

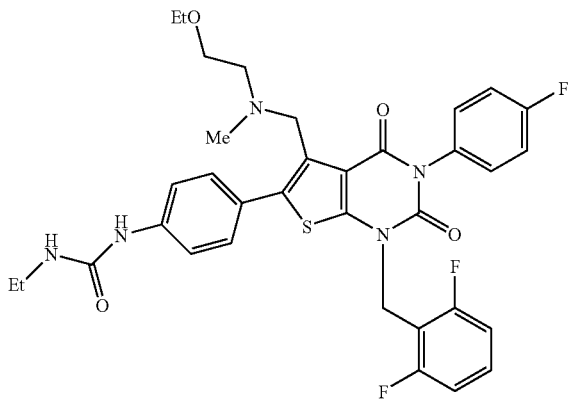

The similar reaction to that of Example 65 was performed using 4-fluoroaniline (306 mg), a 1 M solution of dimethylaluminum chloride in hexane (2.55 ml) and the compound of Reference Example 12 (324 mg) to give the title compound (105 mg).

$^1$H-NMR (CDCl$_3$) δ: 1.11 (3H, t, J=6.9 Hz), 1.16 (3H, t, J=6.9 Hz), 2.13 (3H, s), 2.63 (2H, t, J=6.0 Hz), 3.26-3.35 (2H, m), 3.40 (2H, q, J=6.9 Hz), 3.45 (2H, t, J=6.0 Hz), 3.81 (2H, s), 4.78 (1H, t, J=5.3 Hz), 5.35 (2H, s), 6.49 (1H, s), 6.92 (2H, t, J=8.1 Hz), 7.15-7.31 (5H, m), 7.36 (2H, d, J=8.7 Hz), 7.55 (2H, d, J=8.7 Hz).

IR (KBr): 1715, 1674, 1593, 1532, 1470, 1236 cm$^{-1}$.

Elemental analysis for C$_{34}$H$_{34}$N$_5$O$_4$SF$_3$

Calculated: C, 61.34; H, 5.15; N, 10.52. Found: C, 61.22; H, 5.15; N, 10.61.

Example 68

Preparation of N-[4-(1-(2,6-difluorobenzyl)-3-(2,6-difluorophenyl)-5-{[(2-methoxyethyl)(methyl)amino]methyl]-2,4-dioxo-1,2,3,4-tetrahydrothieno[2,3-d]pyrimidin-6-yl)phenyl]-N'-ethylurea

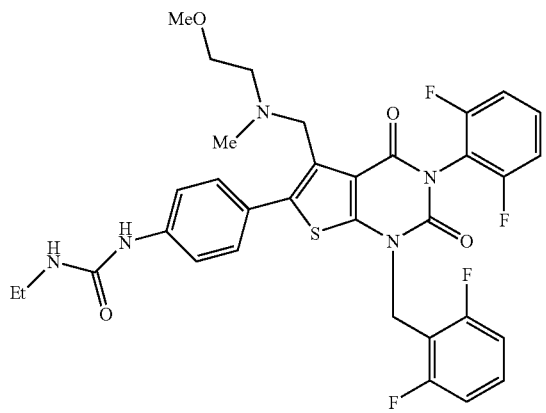

The similar reaction to that of Example 65 was performed using 2,6-difluoro aniline (674 mg), a 1 M solution of dimethylaluminum chloride in hexane (4.84 ml) and the compound of Reference Example 8 (502 mg) to give the title compound (172 mg).

$^1$H-NMR (CDCl$_3$) δ: 1.16 (3H, t, J=7.4 Hz), 2.16 (3H, s), 2.62 (2H, t, J=5.7 Hz), 3.26 (3H, s), 3.25-3.34 (2H, m), 3.41 (2H, t, J=5.7 Hz), 3.83 (2H, s), 4.82 (1H, brs), 5.40 (2H, s), 6.55 (1H, brs), 6.93 (2H, t, J=8.1 Hz), 7.05 (2H, t, J=8.0 Hz), 7.28-7.45 (2H, m), 7.36 (2H, d, J=8.4 Hz), 7.57 (2H, d, J=8.4 Hz).

IR (KBr): 2976, 1723, 1682, 1601, 1534, 1472, 1316, 1238 cm$^{-1}$.

Elemental analysis for C$_{33}$H$_{31}$N$_5$O$_4$SF$_4$.0.5H$_2$O

Calculated: C, 58.40; H, 4.75; N, 10.32. Found: C, 58.15; H, 4.86; N, 10.27.

Example 69

Preparation of N-[4-(1-(2,6-difluorobenzyl)-5-([(2-methoxyethyl)(methyl)amino]methyl}-2,4-dioxo-3-(2,4,6-trifluoro phenyl)-1,2,3,4-tetrahydrothieno[2,3-d]pyrimidin-6-yl)phenyl]-N'-ethylurea

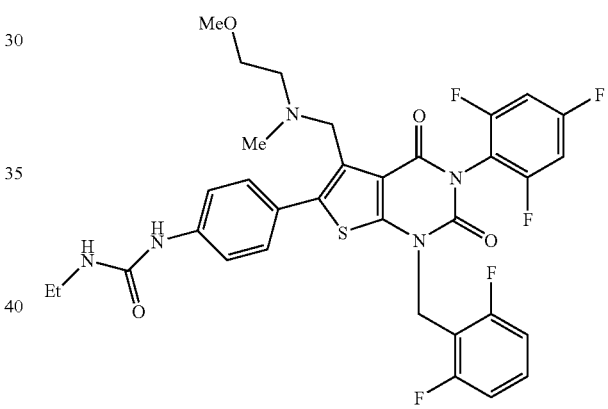

The similar reaction to that of Example 65 was performed using 2,4,6-trifluoroaniline (599 mg), a 1 M solution of dimethylaluminum chloride in hexane (3.78 ml) and the compound of Reference Example 8 (391 mg) to give the title compound (158 mg).

$^1$H-NMR (CDCl$_3$) δ: 1.16 (3H, t, J=7.2 Hz), 2.15 (3H, s), 2.61 (2H, t, J=5.9 Hz), 3.26 (3H, s), 3.23-3.33 (2H, m), 3.41 (2H, t, J=5.9 Hz), 3.82 (2H, s), 4.81 (1H, t, J=5.4 Hz), 5.39 (2H, s), 6.54 (1H, s), 6.82 (2H, t, J=7.8 Hz), 6.93 (2H, t, J=8.1 Hz), 7.24-7.34 (1H, m), 7.36 (2H, d, J=8.8 Hz), 7.56 (2H, d, J=8.6 Hz).

IR (KBr): 2976, 1725, 1684, 1593, 1532, 1470, 1318, 1236 cm$^{-1}$.

Elemental analysis for C$_{33}$H$_{30}$N$_5$O$_4$SF$_5$.0.5H$_2$O

Calculated: C, 56.89; H, 4.48; N, 10.05. Found: C, 56.92; H, 4.57; N, 10.06.

Example 70

Preparation of N-{4-[1-(2,6-difluorobenzyl)-3-(3-fluoro-4-methoxyphenyl)-5-{[(2-methoxyethyl)(methyl)amino]methyl}-2,4-dioxo-1,2,3,4-tetrahydrothieno[2,3-d]pyrimidin-6-yl]phenyl}-N'-ethylurea

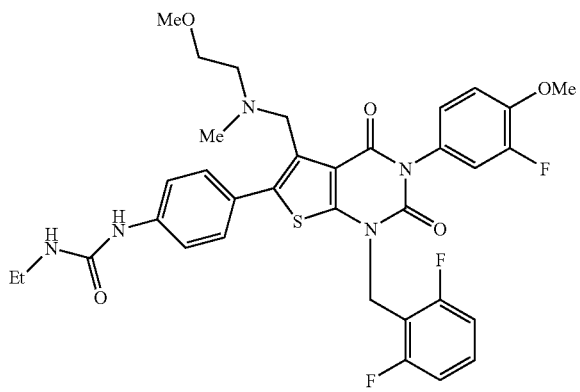

The similar reaction to that of Example 65 was performed using 4-fluoro-3-methoxyaniline (589 mg), a 1 M solution of dimethylaluminum chloride in hexane (3.87 ml) and the compound of Reference Example 8 (400 mg) to give the title compound (248 mg).

$^1$H-NMR (CDCl$_3$) δ: 1.17 (3H, t, J=7.2 Hz), 2.12 (3H, s), 2.62 (2H, t, J=5.9 Hz), 3.26 (3H, s), 3.27-3.35 (2H, m), 3.41 (2H, t, J=5.9 Hz), 3.81 (2H, s), 3.91 (3H, s), 4.77 (1H, t, J=5.4 Hz), 5.34 (2H, s), 6.49 (1H, s), 6.92 (2H, t, J=8.3 Hz), 7.00-7.08 (3H, m), 7.26-7.33 (1H, m), 7.36 (2H, d, J=8.7 Hz), 7.54 (2H, d, J=8.7 Hz).

IR (KBr): 2976, 1715, 1669, 1593, 1520, 1464, 1310, 1273 cm$^{-1}$.

Elemental analysis for C$_{34}$H$_{34}$N$_5$O$_5$SF$_3$·0.5H$_2$O
Calculated: C, 59.12; H, 5.12; N, 10.14. Found: C, 59.39; H, 5.15; N, 10.16.

Example 71

Preparation of N-{4-[1-(2,6-difluorobenzyl)-3-(4-fluoro-3-methylphenyl)-5-{[(2-methoxyethyl)(methyl)amino]methyl}-2,4-dioxo-1,2,3,4-tetrahydrothieno[2,3-d]pyrimidin-6-yl]phenyl}-N'-ethylurea

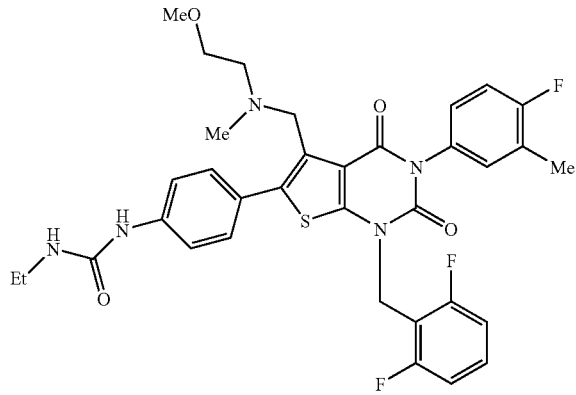

The similar reaction to that of Example 65 was performed using 3-methyl-4-fluoroaniline (540 mg), a 1 M solution of dimethylaluminum chloride in hexane (4.0 ml) and the compound of Reference Example 8 (414 mg) to give the title compound (303 mg).

$^1$H-NMR (CDCl$_3$) δ: 1.17 (3H, t, J=7.4 Hz), 2.13 (3H, s), 2.29 (3H, s), 2.62 (2H, t, J=5.7 Hz), 3.26 (3H, s), 3.26-3.35 (2H, m), 3.41 (2H, t, J=5.7 Hz), 3.81 (2H, s), 4.74 (1H, t, J=5.6 Hz), 5.35 (2H, s), 6.44 (1H, s), 6.92 (2H, t, J=8.3 Hz), 7.02-7.15 (3H, m), 7.26-7.34 (1H, m), 7.36 (2H, d, J=8.4 Hz), 7.55 (2H, d, J=8.4 Hz).

IR (KBr): 2924, 1715, 1669, 1593, 1532, 1470, 1316, 1236 cm$^{-1}$.

Elemental analysis for C$_{34}$H$_{34}$N$_5$O$_4$SF$_3$·0.75H$_2$O
Calculated: C, 60.12; H, 5.27; N, 10.31. Found: C, 60.13; H, 5.09; N, 10.51.

Example 72

Preparation of N-{4-[1-(2,6-difluorobenzyl)-3-(3-fluoro-4-methylphenyl)-5-{[(2-methoxyethyl)(methyl)amino]methyl}-2,4-dioxo-1,2,3,4-tetrahydrothieno[2,3-d]pyrimidin-6-yl]phenyl}-N'-ethylurea

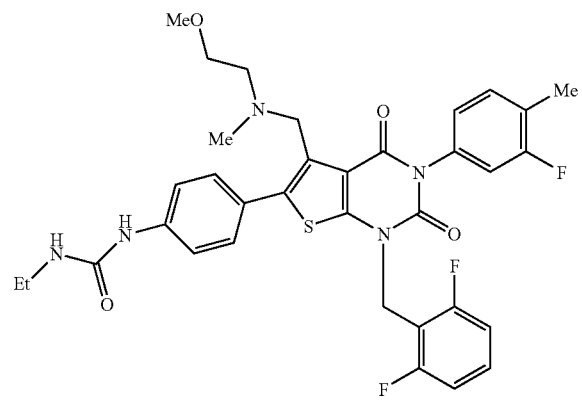

The similar reaction to that of Example 65 was performed using 4-methyl-3-fluoroaniline (535 mg), a 1 M solution of dimethylaluminum chloride in hexane (3.96 ml) and the compound of Reference Example 8 (410 mg) to give the title compound (248 mg).

$^1$H-NMR (CDCl$_3$) δ: 1.17 (3H, t, J=7.2 Hz), 2.12 (3H, s), 2.30 (3H, s), 2.62 (2H, t, J=5.9 Hz), 3.26 (3H, s), 3.26-3.35 (2H, m), 3.41 (2H, t, J=5.9 Hz), 3.81 (2H, s), 4.75 (1H, t, J=5.4 Hz), 5.35 (2H, s), 6.47 (1H, s), 6.92 (2H, t, J=8.4 Hz), 6.95-6.99 (2H, m), 7.26-7.33 (2H, m), 7.36 (2H, d, J=8.7 Hz), 7.54 (2H, d, J=8.7 Hz).

IR (KBr): 2976, 1715, 1669, 1593, 1532, 1470, 1316, 1236 cm$^{-1}$.

Elemental analysis for C$_{34}$H$_{34}$N$_5$O$_4$SF$_3$·0.5H$_2$O
Calculated: C, 60.52; H, 5.23; N, 10.38. Found: C, 60.79; H, 5.37; N, 10.45.

Example 73

Preparation of N-[4-(3-cyclopropyl-1-(2,6-difluorobenzyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

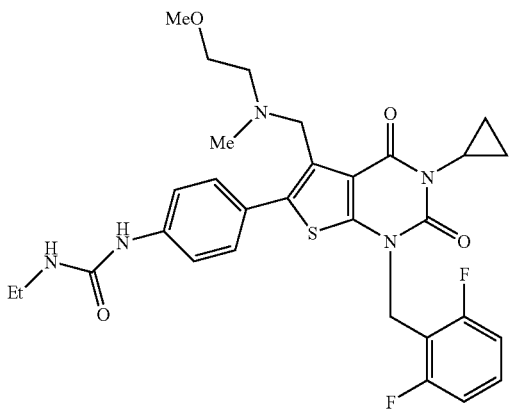

The similar reaction to that of Example 39 was performed to obtain the crude amide product (96 mg) from the compound obtained in Reference Example 9 (242 mg), 1-ethyl-3-(3-dimethylaminopropyl)carbodiimide hydrochloride (115 mg), 1-hydroxybenzotriazole (92 mg), cyclopropylamine (38 mg) and N-ethyl diisopropylamine (104 μl), and then methanol (7.5 ml) and sodium methoxide (80 mg) were used to give the title compound (58 mg).

$^1$H-NMR (CDCl$_3$) δ: 0.77-0.89 (2H, m), 1.17 (3H, t, J=7.4 Hz), 1.15-1.26 (2H, m), 2.15 (3H, s), 2.67 (2H, t, J=6.1 Hz), 2.73-2.80 (1H, m), 3.24-3.38 (2H, m), 3.30 (3H, s), 3.45 (2H, t, J=6.1 Hz), 3.84 (2H, s), 4.74 (1H, t, J=5.5 Hz), 5.31 (2H, s), 6.43 (1H, s), 6.90 (2H, t, J=8.1 Hz), 7.25-7.33 (1H, m), 7.35 (2H, d, J=8.8 Hz), 7.53 (2H, d, J=8.8 Hz).

IR (KBr): 2975, 1713, 1672, 1593, 1534, 1472, 1316, 1236 cm$^{-1}$.

Elemental analysis for C$_{30}$H$_{33}$N$_5$O$_4$SF$_2$

Calculated: C, 60.29; H, 5.57; N, 11.72. Found: C, 60.23; H, 5.38; N, 11.84.

Example 74

Preparation of N-[4-(3-cyclopentyl-1-(2,6-difluorobenzyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

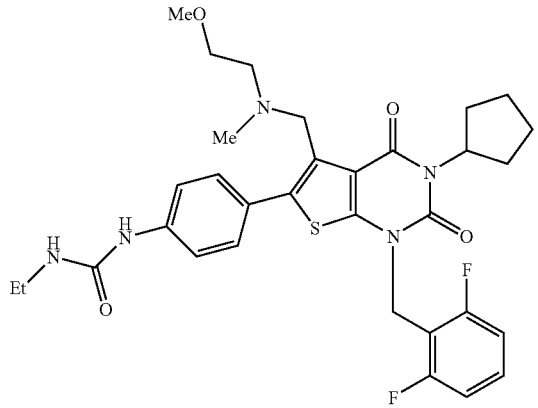

The similar reaction to that of Example 39 was performed to obtain the crude amide product (114 mg) from the compound obtained in Reference Example 9 (242 mg), 1-ethyl-3-(3-dimethylaminopropyl)carbodiimide hydrochloride (115 mg), 1-hydroxybenzotriazole (92 mg), cyclopentylamine (56 mg) and N-ethyl diisopropylamine (104 μμl) and then methanol (8.5 ml) and sodium methoxide (91 mg) were used to give the title compound (59 mg).

$^1$H-NMR (CDCl$_3$) δ: 1.16 (3H, t, J=7.2 Hz), 1.50-1.69 (2H, m), 1.77-2.05 (4H, m), 2.11 (3H, s), 2.07-2.26 (2H, m), 2.65 (2H, t, J=5.9 Hz), 3.23-3.37 (2H, m), 3.30 (3H, s), 3.46 (2H, t, J=5.9 Hz), 3.84 (2H, s), 4.84 (1H, t, J=5.5 Hz), 5.31 (2H, s), 5.38-5.55 (1H, m), 6.56 (1H, s), 6.89 (2H, t, J=8.2 Hz), 7.20-7.34 (1H, m), 7.35 (2H, d, J=8.8 Hz), 7.48 (2H, d, J=8.8 Hz).

IR (KBr): 1705, 1661, 1593, 1537, 1470, 1316, 1236 cm$^{-1}$.

Elemental analysis for C$_{32}$H$_{37}$N$_5$O$_4$SF$_2$

Calculated: C, 61.42; H, 5.96; N, 11.19. Found: C, 61.12; H, 5.91; N, 11.12.

Example 75

Preparation of N-[4-(1-(2,6-difluorobenzyl)-3-hexahydro cyclopenta[c]pyrrol-2(1H)-yl-5-{[(2-methoxyethyl)(methyl)aminomethyl]-2,4-dioxo-1,2,3,4-tetrahydrothieno[2,3-d]pyrimidin-6-yl}phenyl)-N'-ethylurea

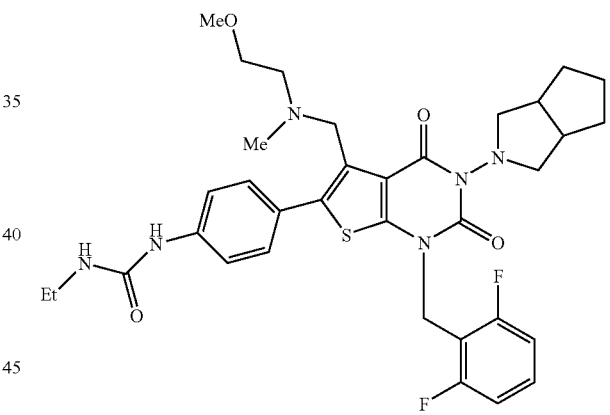

3-amino-3-azabicyclo[3.3.0]octane-hydrochloride (678 mg) was suspended in dichloromethane (7.6 ml), followed by addition of triethylamine (639 μl) and the mixture was stirred for 20 minutes. Thereafter, a 1 M dimethylaluminum chloride/hexane solution (3.87 ml) was added while stirring with ice-cooling for 20 minutes and the mixture was allowed to return to room temperature for 30 minutes and then ice-cooled again. Then, a solution of the compound of Reference Example 8 (400 mg) in dichloromethane (4 ml) was added and the mixture was stirred at room temperature for 19 hours. The reaction solution was partitioned between chloroform and saturated aqueous sodium bicarbonate, and the organic layer was dried over anhydride magnesium sulfate. The residue, after distilling off the solvent under reduced pressure, was dissolved in methanol (6.3 ml), followed by addition of sodium methoxide (324 mg) and the mixture was stirred at room temperature for 13 hours. The reaction solution was partitioned between ethyl acetate and water, the organic layer was washed with saturated brine and dried over anhydride magnesium sulfate, and then the solvent was distilled off under reduced pressure. The obtained residue was purified by chromatography of aminopropyl silica gel (manufactured by Fuji Silysia Chemical Ltd.), and it was recrystallized from ethyl acetate-diethyl ether to give the title compound (168 mg).

$^1$H-NMR (CDCl$_3$) δ: 1.15 (3H, t, J=7.3 Hz), 1.50-1.92 (6H, m), 2.11 (3H, s), 2.65 (2H, t, J=6.2 Hz), 2.64-2.78 (2H, brs), 3.16-3.36 (2H, m), 3.28 (3H, s), 3.45 (2H, t, J=6.2 Hz), 3.41-3.53 (2H, m), 3.84 (2H, s), 5.03 (1H, t, J=5.5 Hz), 5.31 (2H, s), 6.90 (2H, t, J=8.6 Hz), 6.91 (1H, s), 7.21-7.33 (1H, m), 7.37 (2H, d, J=8.4 Hz), 7.47 (2H, d, J=8.4 Hz).

IR (KBr): 1715, 1674, 1593, 1537, 1462, 1314, 1236 cm$^{-1}$.

Elemental analysis for C$_{34}$H$_{40}$N$_6$O$_4$SF$_2$

Calculated: C, 61.24; H, 6.05; N, 12.60. Found: C, 61.08; H, 6.15; N, 12.37.

Example 76

Preparation of N-[4-(3-(1-azepanyl)-1-(2,6-difluorobenzyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

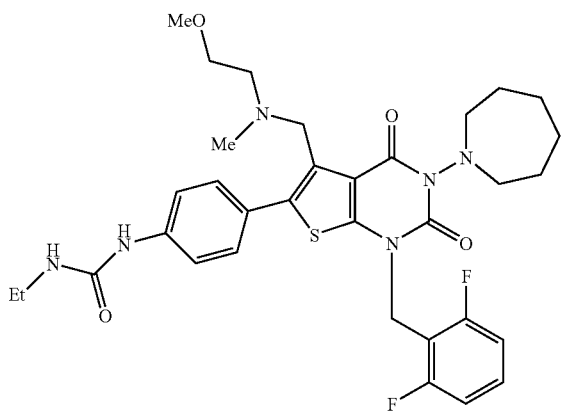

The similar reaction to that of Example 75 was performed using 1-amino homo piperidine (470 mg), a 1 M dimethylaluminum chloride/hexane solution (3.81 ml), the compound of Reference Example 8 (394 mg) and sodium methoxide (324 mg) to give the title compound (232 mg).

$^1$H-NMR (CDCl$_3$) δ: 1.16 (3H, t, J=7.1 Hz), 1.63-1.85 (8H, m), 2.14 (3H, s), 2.66 (2H, t, J=5.8 Hz), 3.21-3.36 (6H, m), 3.29 (3H, s), 3.44 (2H, t, J=5.8 Hz), 3.84 (2H, s), 4.87 (1H, t, J=5.5 Hz), 5.32 (2H, s), 6.60 (1H, s), 6.89 (2H, t, J=8.3 Hz), 7.21-7.32 (1H, m), 7.35 (2H, d, J=8.4 Hz), 7.52 (2H, d, J=8.4 Hz).

IR (KBr): 1719, 1676, 1593, 1534, 1460, 1315, 1236 cm$^{-1}$.

Elemental analysis for C$_{33}$H$_{40}$N$_6$O$_4$SF$_2$.0.25H$_2$O

Calculated: C, 60.12; H, 6.19; N, 12.75. Found: C, 60.01; H, 6.12; N, 12.68.

Example 77

Preparation of N-{4-[1-(2,6-difluorobenzyl)-5-{[(2-methoxyethyl)(methyl)amino]methyl}-2,4-dioxo-3-(1-pyrrolidinyl)-1,2,3,4-tetrahydrothieno[2,3-d]pyrimidin-6-yl]phenyl}-N'-ethylurea

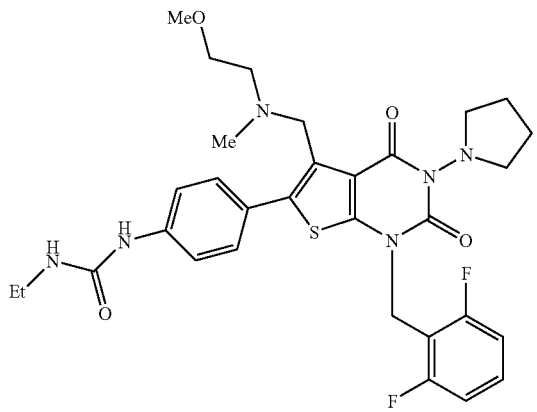

The similar reaction to that of Example 75 was performed using 1-amino pyrrolidine (583 mg), a 1 M dimethylaluminum chloride/hexane solution (4.41 ml), the compound of Reference Example 8 (455 mg) and sodium methoxide (324 mg) to give the title compound (230 mg).

$^1$H-NMR (CDCl$_3$) δ: 1.15 (3H, t, J=7.2 Hz), 2.00 (4H, t, J=6.6 Hz), 2.12 (3H, s), 2.67 (2H, t, J=5.9 Hz), 3.26-3.36 (6H, m), 3.28 (3H, s), 3.45 (2H, t, J=5.9 Hz), 3.85 (2H, s), 5.08 (1H, brs), 5.32 (2H, s), 6.90 (2H, t, J=8.0 Hz), 6.84-6.95 (1H, brs), 7.22-7.33 (1H, m), 7.37 (2H, d, J=8.6 Hz), 7.47 (2H, d, J=8.6 Hz).

IR (KBr): 1715, 1676, 1593, 1534, 1462, 1316, 1236 cm$^{-1}$.

Elemental analysis for C$_{31}$H$_{36}$N$_6$O$_4$SF$_2$.0.5H$_2$O

Calculated: C, 58.57; H, 5.87; N, 13.22. Found: C, 58.51; H, 5.63; N, 13.06.

Example 78

Preparation of N-{4-[1-(2,6-difluorobenzyl)-5-{[(2-methoxyethyl)(methyl)amino]methyl}-2,4-dioxo-3-(1H-pyrrol-1-yl)-1,2,3,4-tetrahydrothieno[2,3-d]pyrimidin-6-yl]phenyl}-N'-ethylurea

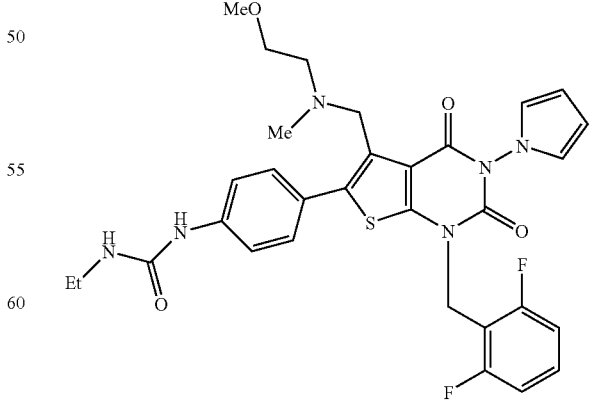

The similar reaction to that of Example 75 was performed using 1-aminopyrrole (403 mg), a 1 M dimethylaluminum chloride/hexane solution (4.55 ml) and the compound of Reference Example 8 (471 mg) to give the title compound (230 mg).

$^1$H-NMR (CDCl$_3$) δ: 1.17 (3H, t, J=7.3 Hz), 2.11 (3H, s), 2.62 (2H, t, J=5.9 Hz), 3.24-3.34 (2H, m), 3.26 (3H, s), 3.41 (2H, t, J=5.9 Hz), 3.80 (2H, s), 4.79 (1H, t, J=5.5 Hz), 5.35 (2H, s), 6.34 (2H, t, J=2.4 Hz), 6.54 (1H, s), 6.72 (1H, t, J=2.4 Hz), 6.93 (2H, t, J=8.2 Hz), 7.24-7.32 (1H, m), 7.38 (2H, d, J=8.4 Hz), 7.50 (2H, d, J=8.4 Hz).

IR (KBr): 1734, 1699, 1593, 1530, 1470, 1316, 1236 cm$^{-1}$.

Elemental analysis for C$_{31}$H$_{32}$N$_6$O$_4$SF$_2$.0.25H$_2$O

Calculated: C, 59.37; H, 5.22; N, 13.40. Found: C, 59.41; H, 5.09; N, 13.52.

Example 79

Preparation of N-[4-(1-(2,6-difluorobenzyl)-5-{[(2-ethoxyethyl)(methyl)amino]methyl}-2,4-dioxo-3-(1-piperidinyl)-1,2,3,4-tetrahydrothieno[2,3-d]pyrimidin-6-yl)phenyl]-N'-ethylurea

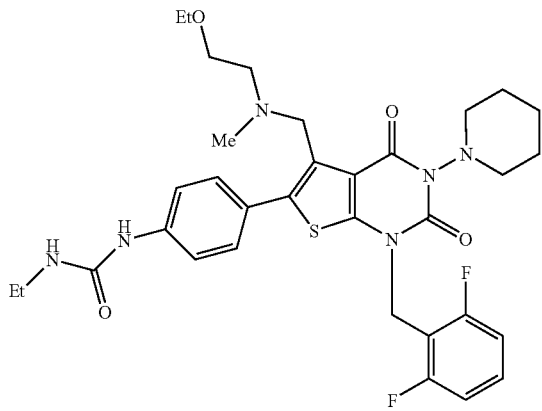

The similar reaction to that of Example 75 was performed using 1-aminopiperidine (397 mg), a 1 M dimethylaluminum chloride/hexane solution (3.67 ml), the compound of Reference Example 12 (391 mg) and sodium methoxide (324 mg) to give the title compound (130 mg).

$^1$H-NMR (CDCl$_3$) δ: 1.13 (3H, t, J=7.0 Hz), 1.15 (3H, t, J=7.4 Hz), 1.36-1.57 (2H, m), 1.64-1.84 (4H, m), 2.14 (3H, s), 2.66 (2H, t, J=6.0 Hz), 3.20-3.50 (10H, m), 3.84 (2H, s), 5.03 (1H, t, J=5.3 Hz), 5.30 (2H, s), 6.90 (2H, t, J=8.3 Hz), 6.88 (1H, s), 7.21-7.33 (1H, m), 7.36 (2H, d, J=8.8 Hz), 7.51 (2H, d, J=8.8 Hz).

IR (KBr): 1717, 1678, 1593, 1534, 1462, 1315, 1236 cm$^{-1}$.

Elemental analysis for C$_{33}$H$_{40}$N$_6$O$_4$SF$_2$

Calculated: C, 60.53; H, 6.16; N, 12.84. Found: C, 60.27; H, 6.11; N, 12.80.

Example 80

Preparation of N-[4-(1-(2,6-difluorobenzyl)-5-{[(2-ethoxyethyl)(methyl)amino]methyl}-2,4-dioxo-3-phenyl-1,2,3,4-tetrahydrothieno[2,3-d]pyrimidin-6-yl)phenyl]-N'-ethylurea

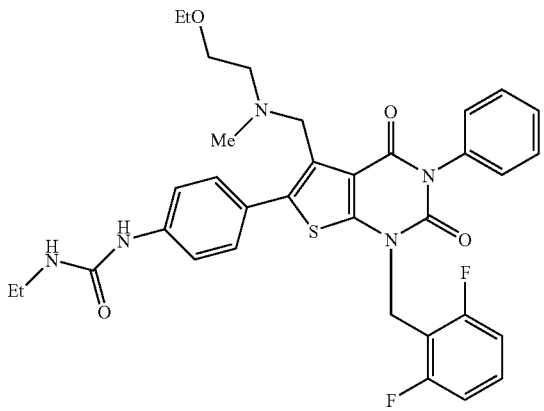

The compound of Example 1 (288 mg), potassium iodide (104 mg), N-ethyl diisopropylamine (294 µl) and 2-ethoxyethyl chloride (176 µl) were suspended in DMF (5 ml) and the mixture was stirred at 60° C. for 23 hours. The reaction solution was partitioned between ethyl acetate and water, the organic layer was washed with saturated brine and dried over anhydride magnesium sulfate, and then the solvent was distilled off under reduced pressure. The obtained residue was purified by aminopropyl silica gel (manufactured by Fuji Silysia Chemical Ltd.) chromatography and recrystallized with ethyl acetate to give the title compound (196 mg).

$^1$H-NMR (CDCl$_3$) δ: 1.11 (3H, t, J=6.9 Hz), 1.12 (3H, t, J=7.2 Hz), 2.12 (3H, s), 2.62 (2H, t, J=5.8 Hz), 3.20-3.29 (2H, m), 3.38 (2H, q, J=6.9 Hz), 3.44 (2H, t, J=5.8 Hz), 3.83 (2H, s), 5.00 (1H, t, J=5.6 Hz), 5.35 (2H, s), 6.84 (1H, s), 6.91 (2H, t, J=8.1 Hz), 7.25-7.29 (3H, m), 7.35 (2H, d, J=8.7 Hz), 7.39-7.53 (5H, m).

IR (KBr): 2975, 1715, 1669, 1593, 1539, 1464, 1318, 1236 cm$^{-1}$.

Elemental analysis for C$_{34}$H$_{35}$N$_5$O$_4$SF$_2$

Calculated: C, 63.04; H, 5.45; N, 10.81. Found: C, 62.98; H, 5.37; N, 10.68.

Example 81

Preparation of N-[4-(1-(2,6-difluorobenzyl)-5-{[(2-methoxyethyl)(methyl)amino]methyl}-2,4-dioxo-3-phenyl-1,2,3,4-tetrahydrothieno[2,3-d]pyrimidin-6-yl)phenyl]-N'-ethylurea

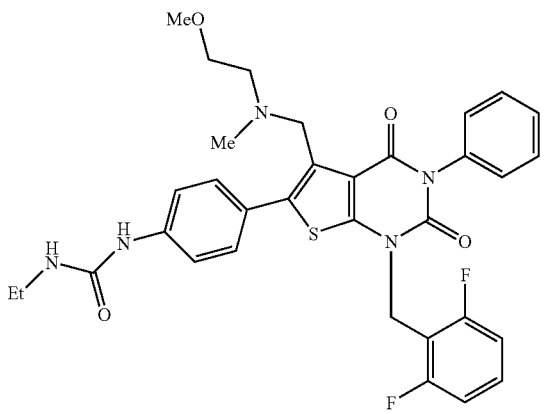

The similar reaction to that of Example 80 was performed using the compound of Example 1 (23.48 g), potassium iodide (20.31 g), N-ethyl diisopropylamine (21.3 ml) and 2-methoxyethyl chloride (14.93 ml) to give the title compound (18.76 g).

$^1$H-NMR (CDCl$_3$) δ: 1.17 (3H, t, J=7.1 Hz), 2.13 (3H, s), 2.63 (2H, t, J=5.8 Hz), 3.26 (3H, s), 3.28 (2H, q, J=7.1 Hz), 3.41 (2H, t, J=5.8 Hz), 3.82 (2H, s), 4.72 (1H, t, J=5.8 Hz), 5.36 (2H, s), 6.43 (1H, s), 6.92 (2H, t, J=8.2 Hz), 7.26-7.51 (5H, m), 7.36 (2H, d, J=8.8 Hz), 7.56 (2H, d, J=8.8 Hz).

IR (KBr): 3333, 1715, 1669, 1593, 1537, 1470, 1316, 1236 cm$^{-1}$.

Elemental analysis for C$_{33}$H$_{33}$N$_5$O$_4$SF$_2$

Calculated: C, 62.55; H, 5.25; N, 11.05. Found: C, 62.44; H, 5.17; N, 11.00.

Example 82

Preparation of N-{4-[1-(2,6-difluorobenzyl)-5-{[(2-methoxyethyl)(methyl)amino]methyl)-2,4-dioxo-3-(6-oxo-1,6-dihydro-3-pyridinyl)-1,2,3,4-tetrahydrothieno[2,3-d]pyrimidin-6-yl]phenyl}-N'-ethylurea

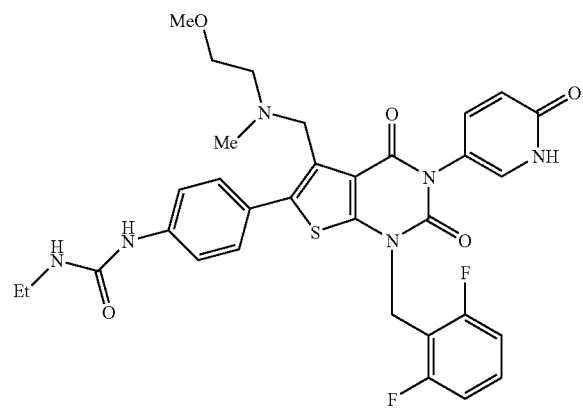

The similar reaction to that of Example 39 was performed to obtain the crude amide product (288 mg) from the compound of Reference Example 9 (454 mg), diethyl phosphorocyanidate (245 mg), 5-amino-2(1H)-pyridinone (172 mg) and N-ethyl diisopropylamine (259 μl), and then ethanol (19.5 ml) and sodium ethoxide (53 mg) were used to give the title compound (206 mg).

$^1$H-NMR (DMSO-d$_6$) δ: 1.06 (3H, t, J=7.2 Hz), 2.06 (3H, s), 2.49 (2H, t, J=6.0 Hz), 3.07-3.16 (2H, m), 3.16 (3H, s), 3.32 (2H, t, J=6.0 Hz), 3.71 (2H, s), 5.26 (2H, s), 6.18 (1H, t, J=5.4 Hz), 6.39 (1H, d, J=9.6 Hz), 7.12 (2H, t, J=8.4 Hz), 7.31 (1H, dd, J=1.2 Hz, 8.4 Hz), 7.44-7.53 (6H, m), 8.64 (1H, s), 11.79 (1H, s).

IR (KBr): 1717, 1669, 1626, 1593, 1532, 1462, 1235 cm$^{-1}$.

Elemental analysis for C$_{32}$H$_{32}$N$_6$O$_5$SF$_2$·0.5H$_2$O

Calculated: C, 58.26; H, 5.04; N, 12.74. Found: C, 58.20; H, 5.13; N, 12.73.

Example 83

Preparation of N-{4-[1-(2,6-difluorobenzyl)-5-{[(2-methoxyethyl)(methyl)amino]methyl}-2,4-dioxo-3-(1-methyl-6-oxo-1,6-dihydro-3-pyridinyl)-1,2,3,4-tetrahydrothieno[2,3-d]pyrimidin-6-yl]phenyl)-N'-ethylurea

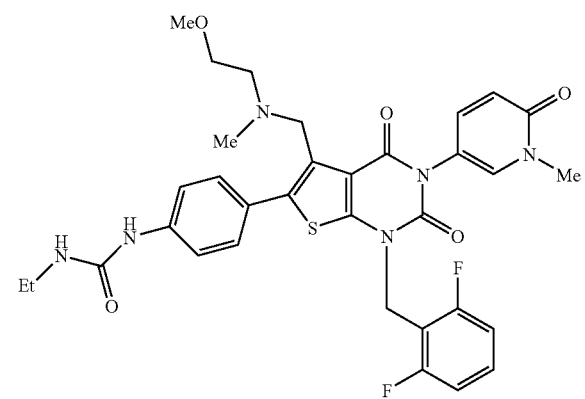

The similar reaction to that of Example 39 was performed to obtain the crude amide product (433 mg) from the compound of Reference Example 9 (454 mg), diethyl phosphorocyanidate (245 mg), 1-methyl-5-amino-2(1H)-pyridinone (186 mg) and N-ethyl diisopropylamine (259 μl), and then ethanol (29.5 ml) and sodium ethoxide (80 mg) were used to give the title compound (283 mg).

$^1$H-NMR (CDCl$_3$) δ: 1.18 (3H, t, J=7.2 Hz), 2.11 (3H, s), 2.62 (2H, t, J=5.8 Hz), 3.26 (3H, s), 3.27-3.36 (2H, m), 3.42 (2H, t, J=5.8 Hz), 3.57 (3H, s), 3.79 (2H, s), 5.01 (1H, brs), 5.32 (2H, s), 6.66 (1H, d, J=9.6 Hz), 6.93 (2H, t, J=8.4 Hz), 6.86-6.98 (1H, brs), 7.24-7.32 (2H, m), 7.34-7.43 (3H, m), 7.49 (2H, d, J=8.7 Hz).

IR (KBr): 1715, 1674, 1593, 1537, 1470, 1316, 1236 cm$^{-1}$.

Elemental analysis for C$_{33}$H$_{34}$N$_6$O$_5$SF$_2$·0.25H$_2$O

Calculated: C, 59.23; H, 5.20; N, 12.56. Found: C, 59.21; H, 4.99; N, 12.49.

Example 84

Preparation of N-(4-{1-(2,6-difluorobenzyl)-5-[(methyl([(2S)-1-(methylsulfonyl)pyrrolidinyl]methyl}amino)methyl]-2,4-dioxo-3-phenyl-1,2,3,4-tetrahydrothieno[2,3-d]pyrimidin-6-yl)-N'-ethylurea

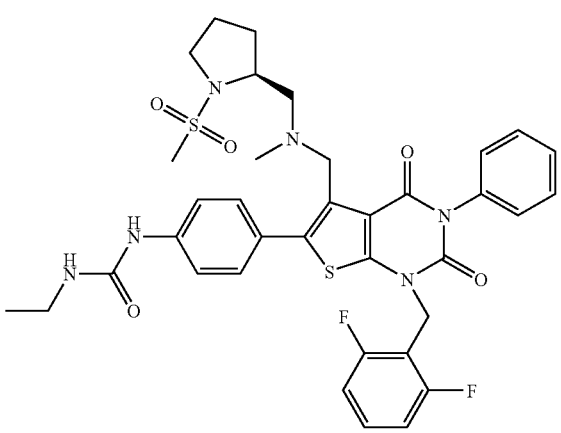

The similar reaction to that of Example 19 was performed using the compound of Example 1 (403 mg, 0.7 mmol) and (L)-prolinol (0.35 g, 3.5 mmol) to give the title compound (325 mg, 63%) as colorless crystals.

$^1$H-NMR (CDCl$_3$) δ: 1.17 (3H, t, J=7.4 Hz), 1.7-1.8 (4H, m), 2.07(3H, s), 2.2-2.6 (2H, m), 2.73 (3H, s), 3.15-3.4 (4H, m), 3.65-3.9 (3H, m), 4.7-4.8 (1H, m), 5.37 (2H, s), 6.51 (1H, s), 6.92 (2H, t, J=8.2 Hz), 7.2-7.6 (10H, m).

IR (KBr): 1723, 1671, 1472, 1335, 1142, 1030, 735 cm$^{-1}$.

Elemental analysis for C$_{36}$H$_{38}$F$_2$N$_6$O$_5$S$_2$.0.5H$_2$O

Calculated: C, 57.97; H, 5.27; N, 11.27. Found: C, 57.99; H, 5.03; N, 11.39.

mp 189-191° C.

Example 85

Preparation of N-(4-{1-(2,6-difluorobenzyl)-5-[(methyl][(2R)-1-(methylsulfonyl)pyrrolidinyl] methyl}amino)methyl]-2,4-dioxo-3-phenyl-1,2,3,4-tetrahydrothieno[2,3-d]pyrimidin-6-yl)-N'-ethylurea

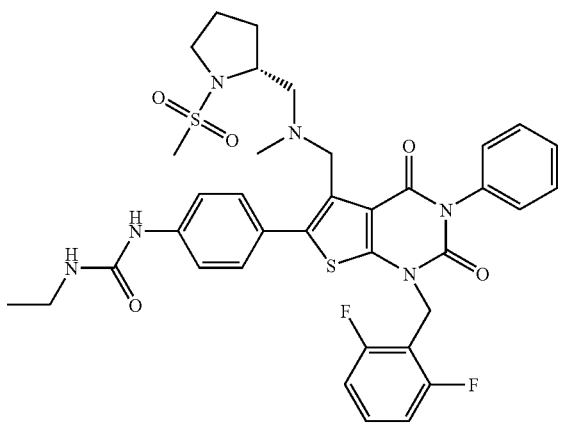

The similar reaction to that of Example 19 was performed using the compound of Example 1 (403 mg, 0.7 mmol) and (R)-prolinol (0.35 g, 3.5 mmol) to give the title compound (312 mg, 60%) as colorless crystals.

$^1$H-NMR(CDCl$_3$) δ: 1.18 (3H, t, J=7.2 Hz), 1.7-1.8 (4H, m), 2.07(3H, s), 2.2-2.6 (2H, m), 2.73 (3H, s), 3.15-3.4 (4H, m), 3.65-3.9 (3H, m), 4.7-4.8 (1H, m), 5.37 (2H, s), 6.50 (1H, s), 6.92 (2H, t, J=8.2 Hz), 7.2-7.6 (10H, m).

IR (KBr): 1717, 1671, 1470, 1335, 1144, 1030, 735 cm$^{-1}$.

Elemental analysis for C$_{36}$H$_{38}$F$_2$N$_6$O$_5$S$_2$.0.5H$_2$O

Calculated: C, 57.97; H, 5.27; N, 11.27. Found: C, 58.06; H, 5.28; N, 11.43.

mp 189-190° C.

Example 86

Preparation of N-[4-(1-(2,6-difluorobenzyl)-5-([[2-(1,1-dioxo-2-isothiazolidinyl)ethyl](methyl)amino] methyl}-2,4-dioxo-3-phenyl-1,2,3,4-tetrahydrothieno[2,3-d]pyrimidin-6-yl)phenyl]-N'-ethylurea

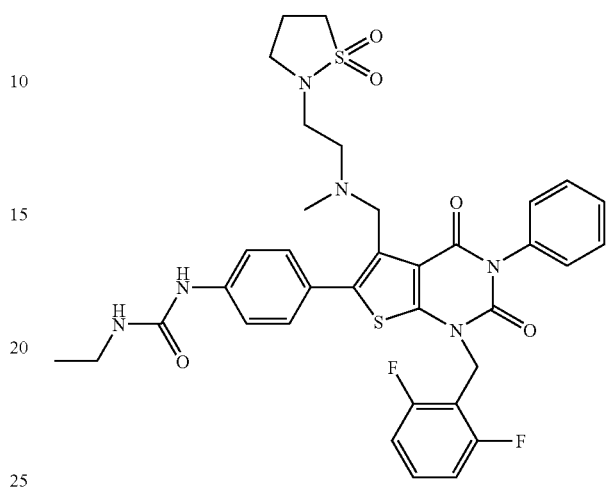

The similar reaction to that of Example 4 was performed using the compound of Example 1 (461 mg, 0.8 mmol) and 2-(1,1-dioxideisothiazolin-2-yl)ethyl methanesulfonate (0.71 g, 2.92 mmol) to give the title compound (552 mg, 85%) as colorless crystals.

$^1$H-NMR(CDCl$_3$) δ: 1.18 (3H, t, J=7.2 Hz), 2.11(3H, s), 2.1-2.25 (2H, m), 2.62 (2H, t, J=6.0 Hz), 2.95-3.1 (4H, m), 3.13 (3H, t, J=6.8 Hz), 3.2-3.4 (2H, m), 3.79 (2H, s), 4.8-4.9 (1H, m), 5.37 (2H, s), 6.59 (1H, s), 6.93 (2H, t, J=8.2), 7.2-7.6 (10H, m).

IR (KBr): 1713, 1674, 1460, 1316, 1236, 1138, 1036, 735 cm$^{-1}$.

Elemental analysis for C$_{35}$H$_{36}$F$_2$N$_6$O$_5$S$_2$

Calculated: C, 58.16; H, 5.02; N, 11.63. Found: C, 57.89; H, 4.98; N, 11.63.

mp 210-211° C.

Example 87

Preparation of N-(4-{1-(2,6-difluorobenzyl)-3-(4-fluorophenyl)-5-[(methyl{[(2S)-1-(methylsulfonyl) pyrrolidinyl]methyl}amino)methyl]-2,4-dioxo-1,2,3, 4-tetrahydrothieno[2,3-d]pyrimidin-6-yl}phenyl)-N'-ethylurea

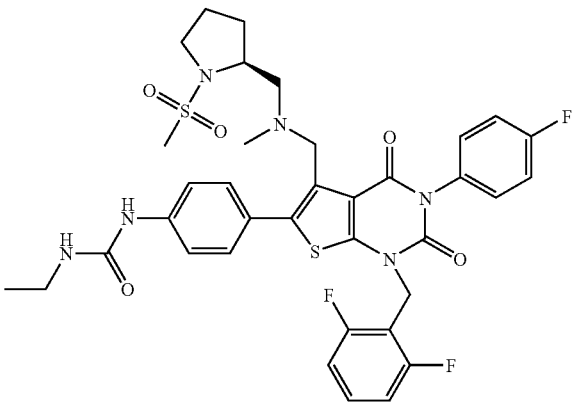

The similar reaction to that of Example 19 was performed using the compound of Example 29 (350 mg, 0.59 mmol) to give the title compound (216 mg, 48%) as colorless crystals.

$^1$H-NMR(CDCl$_3$) δ: 1.18 (3H, t, J=7.2 Hz), 1.7-1.85 (4H, m), 2.07 (3H, s), 2.2-2.4 (1H, m), 2.5-2.65 (1H, m), 2.73 (3H, s), 3.2-3.4 (4H, m), 3.65-3.8 (1H, m), 3.72 (1H, d, J=12.8 Hz), 3.87 (1H, d, J=12.8 Hz), 4.7-4.8 (1H, m), 5.36 (2H, s), 6.54 (1H, s), 6.92 (2H, t, J=8.0 Hz), 7.1-7.5 (9H, m).

IR (KBr): 1721, 1671, 1472, 1335, 1236, 1144, 1030 cm$^{-1}$.

Elemental analysis for C$_{36}$H$_{37}$F$_3$N$_6$O$_5$S$_2$·1.0H$_2$O

Calculated: C, 55.95; H, 5.09; N, 10.87. Found: C, 55.75; H, 4.82; N, 10.95.

Example 88

Preparation of N-(4-{1-(2,6-difluorobenzyl)-3-[4-(2-methoxyethoxy)phenyl]-5-[(methyl{[(2S)-1-(methylsulfonyl)pyrrolidinyl]methyl}amino)methyl]-2,4-dioxo-1,2,3,4-tetrahydrothieno[2,3-d]pyrimidin-6-yl}phenyl)-N'-ethylurea

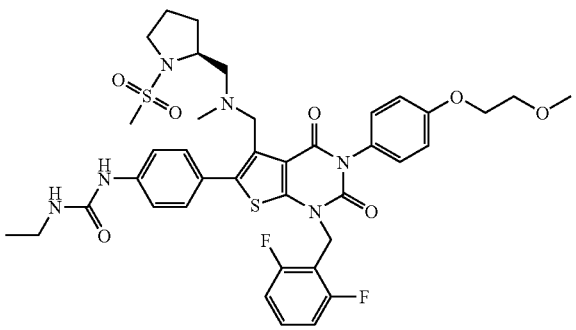

The similar reaction to that of Example 19 was performed using the compound of Example 28 (350 mg, 0.54 mmol) to give the title compound (158 mg, 36%) as colorless crystals.

$^1$H-NMR(CDCl$_3$) δ: 1.18 (3H, t, J=7.2 Hz), 1.7-1.85 (4H, m), 2.05 (3H, s), 2.2-2.4 (1H, m), 2.5-2.6 (1H, m), 3.2-3.4 (4H, m), 3.46 (3H, s), 3.7-3.9 (5H, m), 4.1-4.2 (2H, m), 4.7-4.8 (1H, m), 5.36 (2H, s), 6.49 (1H, s), 6.91 (2H, t, J=8.0 Hz), 7.03 (2H, d, J=9.0 Hz), 7.16 (2H, d, J=9.0 Hz), 7.2-7.5 (5H, m).

IR (KBr): 1719, 1667, 1470, 1333, 1250, 1144, 1030, 789 cm$^{-1}$.

Elemental analysis for C$_{39}$H$_{44}$F$_2$N$_6$O$_7$S$_2$·0.5H$_2$O

Calculated: C, 57.13; H, 5.53; N, 10.25. Found: C, 56.88; H, 5.67; N, 10.00.

Example 89

Preparation of N-{4-[1-(2,6-difluorobenzyl)-5-{[(2-methoxyethyl)(methyl)amino]methyl}-2,4-dioxo-3-(2-pyridinyl)-1,2,3,4-tetrahydrothieno[2,3-d]pyrimidin-6-yl]phenyl}-N'-ethylurea

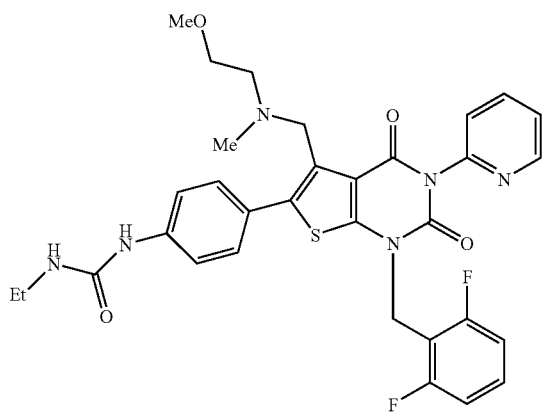

The similar reaction to that of Example 39 was performed to obtain the crude amide product (361 mg) from the compound of Reference Example 9 (454 mg), diethyl phosphorocyanidate (245 mg), 2-aminopyridine (142 mg) and N-ethyl diisopropylamine (259 μl), and then ethanol (24.7 ml) and sodium ethoxide (67 mg) were used to give the title compound (198 mg).

$^1$H-NMR (CDCl$_3$) δ: 1.14 (3H, t, J=7.4 Hz), 2.12 (3H, s), 2.61 (2H, t, J=5.9 Hz), 3.25 (3H, s), 3.25-3.31 (2H, m), 3.40 (2H, t, J=5.9 Hz), 3.80 (2H, br), 4.87 (1H, t, J=5.6 Hz), 5.20 (2H, br), 6.90 (1H, s), 6.91 (2H, t, J=8.1 Hz), 7.25-7.44 (2H, m), 7.35 (2H, d, J=8.7 Hz), 7.48 (2H, d, J=8.7 Hz), 7.91 (1H, dt, J=1.8 Hz, 8.1 Hz), 8.68-8.70 (1H, m).

IR (KBr): 1717, 1672, 1593, 1532, 1460, 1318, 1236 cm$^{-1}$.

Elemental analysis for C$_{32}$H$_{32}$N$_6$O$_4$SF$_2$·0.5H$_2$O

Calculated: C, 59.71; H, 5.17; N, 13.06. Found: C, 59.95; H, 5.18; N, 12.99.

Example 90

Preparation of N-[4-(1-(2,6-difluorobenzyl)-5-{[(2-propoxy ethyl)(methyl)amino]methyl}-2,4-dioxo-3-phenyl-1,2,3,4-tetrahydrothieno[2,3-d]pyrimidin-6-yl)phenyl]-N'-ethylurea

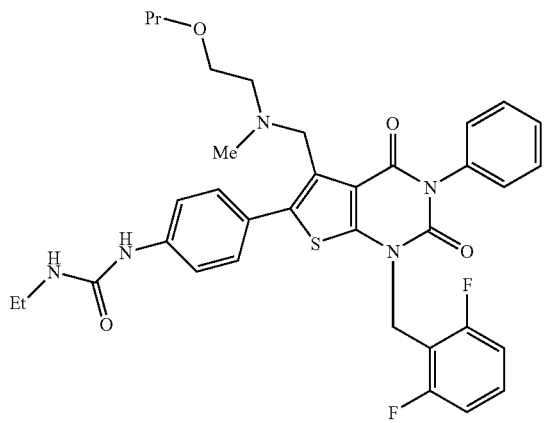

The compound of Example 1 (172 mg), potassium iodide (50 mg), N-ethyl diisopropylamine (294 μl) and 2-propoxy ethyl chloride (111 mg) were suspended in DMF (3 ml) and the mixture was stirred at 75° C. for 24 hours. The reaction solution was partitioned between ethyl acetate and water, the organic layer was washed with saturated brine and dried over anhydride magnesium sulfate, and then the solvent was distilled off under reduced pressure. The obtained residue was purified by aminopropyl silica gel (manufactured by Fuji Silysia Chemical Ltd.) chromatography and recrystallized with dichloromethane-methanol to give the title compound (112 mg).

$^1$H-NMR (CDCl$_3$) δ: 0.83 (3H, t, J=7.3 Hz), 1.13 (3H, t, J=7.2 Hz), 1.40-1.58 (2H, m), 2.13 (3H, s), 2.63 (2H, t, J=6.0 Hz), 3.20-3.33 (4H, m), 3.44 (2H, t, J=6.0 Hz), 3.82 (2H, s), 4.93 (1H, t, J=5.5 Hz), 5.36 (2H, s), 6.74 (1H, s), 6.92 (2H, t, J=8.2 Hz), 7.23-7.37 (5H, m), 7.41-7.54 (5H, m).

IR (KBr): 2965, 1715, 1674, 1593, 1537, 1470, 1318 cm$^{-1}$.

Elemental analysis for $C_{35}H_{37}N_5O_4SF_2 \cdot 0.5H_2O$

Calculated: C, 62.67; H, 5.71; N, 10.44. Found: C, 62.96; H, 5.73; N, 10.41.

Example 91

Preparation of N-{4-[5-{[cyclohexyl(methyl)amino]methyl}-1-(2,6-difluorobenzyl)-2,4-dioxo-3-phenyl-1,2,3,4-tetrahydrothieno[2,3-d]pyrimidin-6-yl]phenyl}-N'-ethylurea

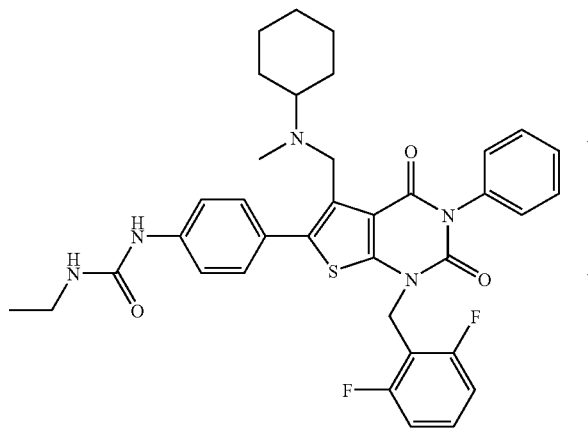

The similar reaction to that of Example 2 was performed using the compound of Reference Example 1 (0.40 g, 0.5 mmol) and N-methylcyclohexyl amine (0.11 g, 1.0 mmol) to give the title compound (150 mg, 45%) as colorless crystals.

$^1$H-NMR(CDCl$_3$) δ: 1.06 (3H, t, J=7.0 Hz), 2.05 (3H, s), 1.20-1.40 (6H, m), 1.50-1.70 (4H, m), 2.05-2.15 (1H, m), 3.24 (2H, q, J=7.0 Hz), 3.82 (2H, s), 5.20 (1H, t, J=5.4 Hz), 5.35 (2H, s), 6.94 (2H, t, J=8.0 Hz), 7.25-7.35 (6H, m), 7.45-7.60 (4H, m).

Elemental analysis for $C_{36}H_{37}F_2N_5O_3S$

Calculated: C, 65.73; H, 5.67; N, 10.65. Found: C, 65.98; H, 5.72; N, 10.42.

mp 210-212° C.

Example 92

Preparation of N-[4-(1-(2,6-difluorobenzyl)-5-{[isopropyl(methyl)amino]methyl}-2,4-dioxo-3-phenyl-1,2,3,4-tetrahydrothieno[2,3-d]pyrimidin-6-yl)phenyl]-N'-ethylurea

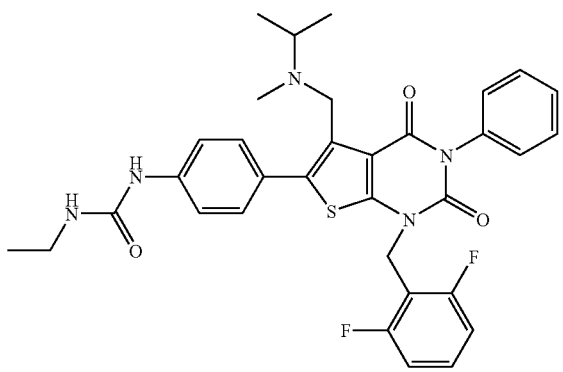

The similar reaction to that of Example 2 was performed using the compound of Reference Example 1 (0.40 g, 0.5 mmol) and N-methylisopropylamine (0.07 g, 1.0 mmol) to give the title compound (130 mg, 41%) as colorless crystals.

$^1$H-NMR(CDCl$_3$) δ: 1.02 (3H, t, J=7.0 Hz), 1.03 (6H, d, J=7.0 Hz), 2.60-2.75 (1H, m), 3.254 (2H, q, J=7.0 Hz), 3.83 (2H, s), 5.26 (1H, t, J=5.4 Hz), 5.36 (2H, s), 6.98 (2H, t, J=8.0 Hz), 7.25-7.35 (6H, m), 7.45-7.60 (4H, m).

Elemental analysis for $C_{33}H_{33}F_2N_5O_3S$

Calculated: C, 64.16; H, 5.38; N, 11.34. Found: C, 64.32; H, 5.51; N, 11.20.

mp 208-210° C.

Example 93

Preparation of N-{4-[5-{[cyclopentyl(methyl)amino]methyl}-1-(2,6-difluorobenzyl)-2,4-dioxo-3-phenyl-1,2,3,4-tetrahydrothieno[2,3-d]pyrimidin-6-yl]phenyl}-N'-ethylurea

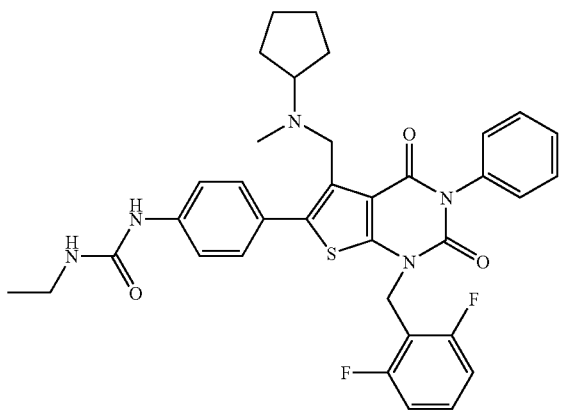

The similar reaction to that of Example 2 was performed using the compound of Reference Example 1 (0.40 g, 0.5 mmol) and N-methylcyclopentylamine (0.10 g, 1.0 mmol) to give the title compound (110 mg, 40%) as colorless crystals.

$^1$H-NMR(CDCl$_3$) δ: 1.02 (3H, t, J=7.0 Hz), 1.20-1.50 (4H, m), 1.50-1.70 (4H, m), 2.10 (3H, s), 2.05-2.15 (1H, m), 3.26 (2H, q, J=7.0 Hz), 3.84 (2H, s), 5.30 (1H, t, J=5.4 Hz), 5.35 (2H, s), 6.99 (2H, t, J=8.0 Hz), 7.25-7.35 (6H, m), 7.45-7.60 (4H, m).

Elemental analysis for C$_{35}$H$_{35}$F$_2$N$_5$O$_3$S

Calculated: C, 65.30; H, 5.48; N, 10.88. Found: C, 65.35; H, 5.28; N, 11.06.

mp 210-213° C.

Example 94

Preparation of N-{4-[1-(2,6-difluorobenzyl)-5-({methyl[3-oxo-3-(1-pyrrolidinyl)propyl]amino}methyl)-2,4-dioxo-3-phenyl-1,2,3,4-tetrahydrothieno[2,3-d]pyrimidin-6-yl]phenyl}-N'-ethylurea

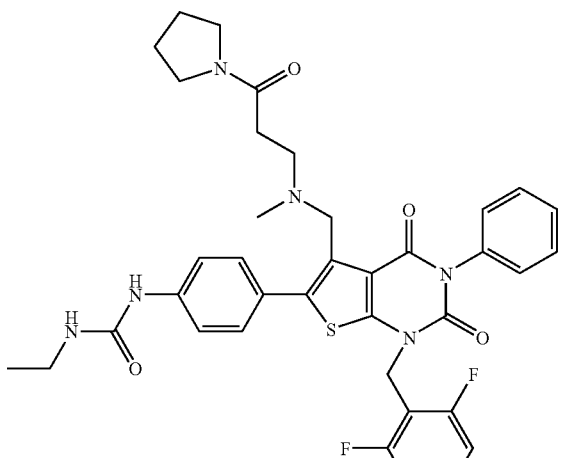

The similar reaction to that of Example 19 was performed using the compound of Example 1 (288 mg, 0.5 mmol) and 1-(3-bromo propanoyl)pyrrolidone (0.21 g, 1.0 mmol) to give the title compound (300 mg, 86%) as colorless crystals.

$^1$H-NMR(CDCl$_3$) δ: 1.10 (3H, t, J=7.2), 1.75-1.95 (4H, m), 2.10 (3H, s), 2.60-2.70 (4H, m), 2.90-3.10(2H, m), 3.26 (2H, q, J=7.2 Hz), 3.45-3.65 (2H, m), 3.82 (2H, s), 5.25 (1H, t, J=5.4 Hz), 5.36 (2H, s), 6.96 (2H, t, J=8.0), 6.85-6.95 (1H, m), 7.10-7.55 (10H, m).

Elemental analysis for C$_{37}$H$_{38}$F$_2$N$_6$O$_4$S

Calculated: C, 63.41; H, 5.47; N, 11.99. Found: C, 63.66; H, 5.22; N, 12.26.

mp 240-244° C.

Example 95

Preparation of 3-[{[1-(2,6-difluorobenzyl)-6-(4-{[(ethylamino)carbonyl]amino}phenyl)-2,4-dioxo-3-phenyl-1,2,3,4-tetrahydrothieno[2,3-d]pyrimidin-5-yl]methyl}(methyl)amino]-N-(2-methoxyethyl)propanamide

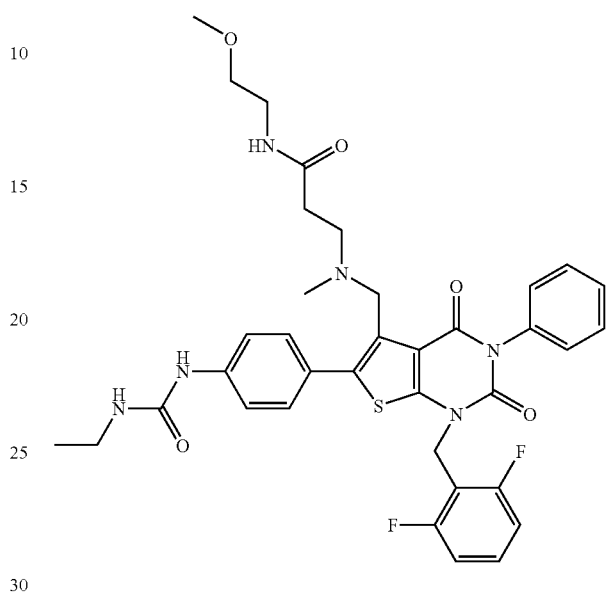

The similar reaction to that of Example 19 was performed using the compound of Example 1 (288 mg, 0.5 mmol) and 1-(3-bromo propanoyl)-3-methoxyethylamine (0.21 g, 1.0 mmol) to give the title compound (300 mg, 85%) as colorless crystals.

$^1$H-NMR(CDCl$_3$) δ: 1.10 (3H, t, J=7.2 Hz), 2.10 (3H, s), 2.65-2.75 (4H, m), 3.25 (2H, q, J=7.2 Hz), 3.30 (3H, s), 3.30-3.37 (2H, m), 3.38-3.50 (2H, m), 3.80 (2H, s), 5.30 (1H, t, J=5.4 Hz), 5.36 (2H, s), 6.98 (2H, t, J=8.0 Hz), 6.85-6.95 (1H, m), 7.10-7.60 (10H, m).

Elemental analysis for C$_{36}$H$_{38}$F$_2$N$_6$O$_5$S

Calculated: C, 61.35; H, 5.43; N, 11.92. Found: C, 64.60; H, 5.54; N, 11.76.

mp 240-244° C.

Example 96

Preparation of N-[4-(3-(4-nitrophenyl)-1-(2,6-difluorobenzyl)-5-{[2-methoxyethyl(methyl)amino]methyl}-2,4-dioxo-1,2,3,4-tetrahydrothieno[2,3-d]pyrimidin-6-yl)phenyl]-N'-ethylurea

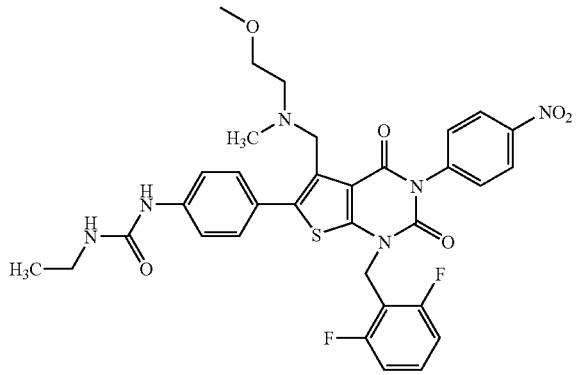

4-nitroaniline (2.21 g, 16 mmol) was dissolved in dichloromethane (50 ml), followed by dropwise addition of a solution of dimethylaluminum chloride in hexane (0.98 M) (16.3 ml, 16.0 mmol) with ice-cooling and the mixture was stirred at room temperature for 1 hour. Then, the compound of Reference Example 8 (1.21 g, 2.0 mmol) was added and the mixture was stirred at room temperature for 16 hours. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: ethyl acetate) to give the title compound (1.00 g, 92%) as colorless amorphous matter.

$^1$H-NMR(CDCl$_3$) δ: 1.18 (3H, t, J=7.0 Hz), 2.15 (3H, s), 2.64 (2H, t, J=6.0 Hz), 3.25 (3H, s), 3.30 (2H, q, J=7.2 Hz), 3.40 (2H, t, J=6.0 Hz), 3.83 (2H, s), 4.6-4.7 (1H, m), 5.35 (2H, s), 6.34 (1H, s), 6.91 (2H, t, J=8.2 Hz), 7.25-7.40 (9H, m).

Example 97

Preparation of N-[4-(3-(4-aminophenyl)-1-(2,6-difluorobenzyl)-5-{[2-methoxyethyl(methyl)amino]methyl}-2,4-dioxo-1,2,3,4-tetrahydrothieno[2,3-d]pyrimidin-6-yl)phenyl]-N'-ethylurea

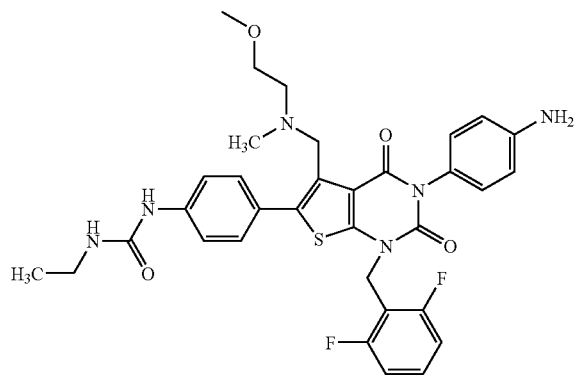

2 N-hydrochloride/diethyl ether solution (20 ml) and 50% hydrous-10% palladium/carbon (1.00 g) were added to a solution of the compound of Example 96 (1.00 g) in ethanol (200 ml) and the mixture was stirred thoroughly under hydrogen atmosphere for 1 hour. The filtrate except a catalyst was neutralized with aqueous sodium bicarbonate, and then the solvent was distilled off. The obtained residue was partitioned between ethyl acetate and water, and then the organic layer was washed with saturated brine and dried over anhydride magnesium sulfate. The residue obtained by distilling off the solvent under the reduced pressure, was subject to NH-silica gel (manufactured by Fuji Silysia Chemical Ltd.) chromatography, and was recrystallized from methanol to give the title compound (0.80 g, 62%).

$^1$H-NMR(CDCl$_3$) δ: 1.18 (3H, t, J=7.0 Hz), 2.14 (3H, s), 2.64 (2H, t, J=6.0 Hz), 3.26 (3H, s), 3.30 (2H, q, J=7.2 Hz), 3.41 (2H, t, J=6.0 Hz), 3.77 (2H, s), 3.83 (2H, s), 4.6-4.7 (1H, m), 5.35 (2H, s), 6.3-6.4 (1H, m), 6.76 (2H, d, J=8.4 Hz), 6.91 (2H, t, J=8.0 Hz), 7.05 (2H, d, J=8.4 Hz), 7.2-7.3 (1H, m), 7.35 (2H, d, J=8.1 Hz), 7.56 (2H, d, J=8.1 Hz).

Elemental analysis for C$_{33}$H$_{34}$F$_2$N$_6$O$_4$S

Calculated: C, 61.10; H, 5.28; N, 12.95. Found: C, 61.23; H, 5.33; N, 13.06.

mp 205-207° C.

Example 98

Preparation of N-[4-(3-(4-acetoaminophenyl)-1-(2,6-difluorobenzyl)-5-{[2-methoxyethyl(methyl)amino]methyl}-2,4-dioxo-1,2,3,4-tetrahydrothieno[2,3-d]pyrimidin-6-yl)phenyl]-N'-ethylurea

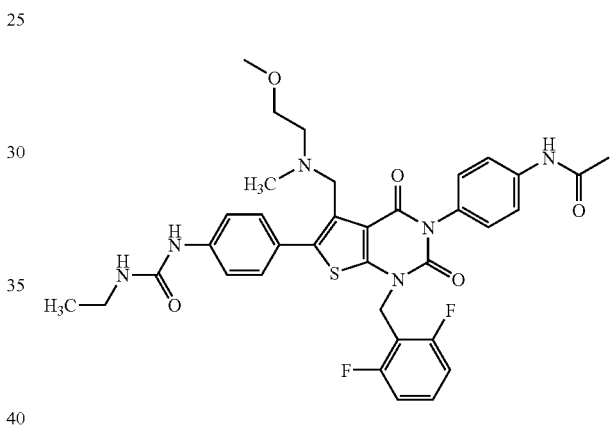

Acetic acid anhydride (50 mg) was added dropwise to a solution of the compound of Example 97 (0.10 g) in pyridine (1.00 ml) and the mixture was stirred at room temperature for 18 hours. After distilling off the solvent under reduced pressure, the obtained residue was partitioned between ethyl acetate and water, and the organic layer was washed with saturated brine and then dried over anhydride magnesium sulfate. The residue obtained by distilling off the solvent under the reduced pressure, was subject to NH-silica gel (manufactured by Fuji Silysia Chemical Ltd.) chromatography, and was recrystallized from methanol to give the title compound (0.08 g, 77%).

$^1$H-NMR(CDCl$_3$) δ: 1.16 (3H, t, J=7.0 Hz), 2.10 (3H, s), 2.17 (3H, s), 2.61 (2H, t, J=6.0 Hz), 3.25 (3H, s), 3.30 (2H, q, J=7.2 Hz), 3.40 (2H, t, J=6.0 Hz), 3.81 (2H, s), 5.35 (2H, s), 5.6-5.7 (1H, m), 6.92 (2H, t, J=8.0 Hz), 7.19 (2H, d, J=9.0 Hz), 7.3-7.4 (1H, m), 7.46 (4H, s), 7.72 (2H, d, J=8.1 Hz), 8.74 (1H, s).

Elemental analysis for C$_{35}$H$_{36}$F$_2$N$_6$O$_5$S

Calculated: C, 60.86; H, 5.25; N, 12.17. Found: C, 61.03; H, 5.38; N, 12.02.

mp 218-220° C.

Example 99

Preparation of N-[4-(3-(4-{(ethylamino)carbonylamino}phenyl)-1-(2,6-difluorobenzyl)-5-{[2-methoxyethyl(methyl)amino]methyl}-2,4-dioxo-1,2,3,4-tetrahydrothieno[2,3-d]pyrimidin-6-yl)phenyl]-N'-ethylurea

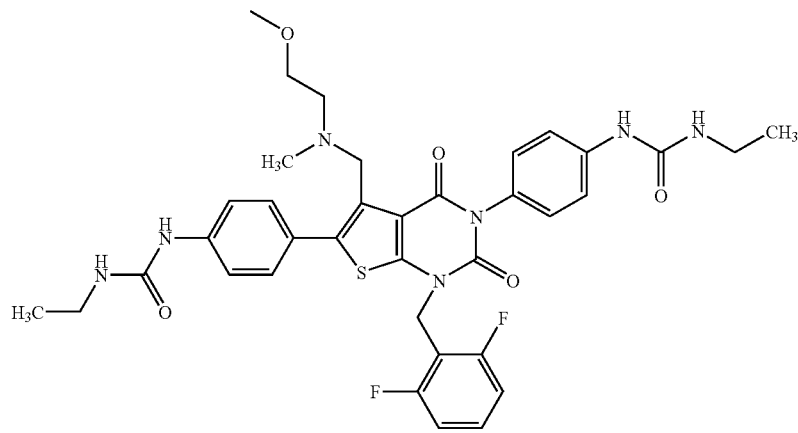

Ethyl isothianate (36 mg) was added dropwise to a solution of the compound of Example 97 (0.10 g) in pyridine (1.00 ml) and the mixture was stirred at room temperature for 18 hours. After distilling off the solvent under reduced pressure, the obtained residue was partitioned between ethyl acetate and water, and the organic layer was washed with saturated brine and then dried over anhydride magnesium sulfate. The residue obtained by distilling off the solvent under the reduced pressure was recrystallized from methanol to give the title compound (0.06 g, 56%).

$^1$H-NMR(CDCl$_3$) δ: 1.15 (3H, t, J=7.0 Hz), 1.16 (3H, t, J=7.0 Hz), 2.10 (3H, s), 2.61 (2H, t, J=6.0 Hz), 3.25 (3H, s), 3.27 (2H, q, J=7.2 Hz), 3.28 (2H, q, J=7.2 Hz), 3.40 (2H, t, J=6.0 Hz), 3.81 (2H, s), 5.34 (2H, s), 5.5-5.6 (1H, m), 5.6-5.7 (1H, m), 6.92 (2H, t, J=8.0 Hz), 7.13 (2H, d, J=9.0 Hz), 7.2-7.3 (1H, m), 7.45 (4H, s), 7.52 (2H, d, J=9.0 Hz), 7.85 (1H, s), 7.98 (1H, s).

Elemental analysis for C$_{36}$H$_{39}$F$_2$N$_7$O$_5$S

Calculated: C, 60.07; H, 5.46; N, 13.62. Found: C, 59.94; H, 5.48; N, 13.68.

mp 236-239° C.

Example 100

Preparation of 3-[({1-2,6-(difluorobenzyl)-6-(4-{[(ethylamino)carbonyl]amino}phenyl)-3-[4-(2-methoxyethoxy)phenyl]-2,4-dioxo-1,2,3,4-tetrahydrothieno[2,3-d]pyrimidin-5-yl)methyl)(methyl)amino)-N,N-dimethylpropanamide

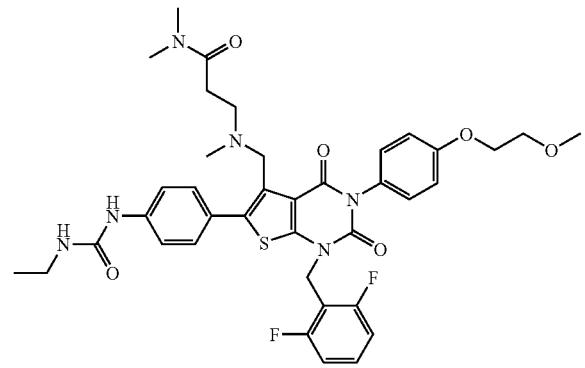

The similar reaction to that of Example 4 was performed using the compound of Example 28 (974 mg, 1.5 mmol) and 3-bromo-N,N-dimethylpropanamide (360 mg, 2.0 mmol) to give the title compound (760 mg, 68%) as colorless crystals.

$^1$H-NMR(CDCl$_3$) δ: 1.15 (3H, t, J=7.4 Hz), 2.07 (3H, s), 2.17 (3H, s), 2.46 (2H, t, J=6.0 Hz), 2.76 (2H, t, J=6.0 Hz), 2.86 (3H, s), 2.89 (3H, s), 3.29 (2H, q, J=7.2 Hz), 3.46 (3H, s), 3.7-3.8 (4H, m), 4.1-4.2 (2H, m), 4.8-5.2 (1H, br), 5.35 (2H, s), 6.91 (2H, t, J=8.4 Hz), 7.04 (2H, d, J=9.0 Hz), 7.18 (2H, d, J=9.0 Hz), 7.25-7.45 (5H, m).

Elemental analysis for C$_{38}$H$_{42}$F$_2$N$_6$O$_6$S

Calculated: C, 60.95; H, 5.65; N, 11.22. Found: C, 61.08; H, 5.54; N, 11.05.

mp 215-218° C.

Example 101

Preparation of N-[4-(3-[3,4-bis(2-methoxyethoxy)phenyl]-1-(2,6-difluorobenzyl)-5-{[(2-methoxyethyl)(methyl)amino]methyl}-2,4-dioxo-1,2,3,4-tetrahydrothieno[2,3-d]pyrimidin-6-yl)phenyl]-N'-ethylurea

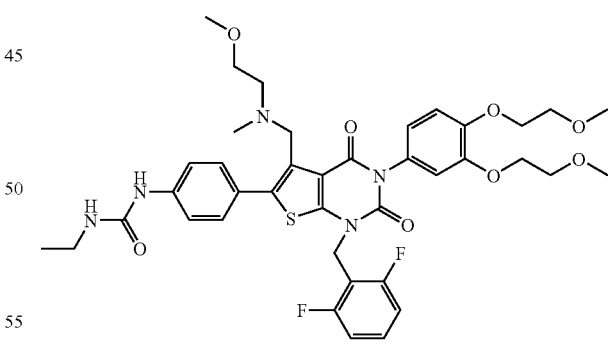

3,4-bis(2-methoxyethoxy)aniline (3.62 g, 15.0 mmol) was dissolved in dichloromethane (20 ml), followed by dropwise addition of a solution of dimethylaluminum chloride in hexane (0.98 M) (15.3 ml, 15.0 mmol) with ice-cooling and the mixture was stirred at room temperature for 1 hour. Then, the compound of Reference Example 8 (1.21 g, 2.0 mmol) was added and the mixture was stirred at room temperature for 16 hours. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: ethyl acetate), and then was recrystallized from methanol to give the title compound (0.75 g, 48%) as colorless crystals.

$^1$H-NMR(CDCl$_3$) δ: 1.16 (3H, t, J=7.4 Hz), 2.12 (3H, s), 2.62 (2H, t, J=6.0 Hz), 3.25 (3H, s), 3.29 (2H, q, J=7.2 Hz), 3.35-3.45 (8H, s), 3.70-3.80 (4H, m), 3.82 (2H, s), 4.10-4.20 (4H, m), 4.7-4.9 (1H, br), 5.34 (2H, s), 6.5-6.7 (1H, br), 6.80-6.90 (2H, m), 6.94 (2H, t, J=8.4 Hz), 7.01 (1H, d, J=9.0 Hz), 7.26-7.36 (1H, m), 7.35 (2H, d, J=8.7 Hz), 7.52 (2H, d, J=8.7 Hz).

Elemental analysis for C$_{39}$H$_{45}$F$_2$N$_5$O$_8$S.0.5H$_2$O

Calculated: C, 59.23; H, 5.86; N, 8.86. Found: C, 59.32; H, 5.89; N, 8.82.

mp 206-208° C.

Example 102

Preparation of N-[4-(3-[4-((benzyloxy)phenyl)-1-(2,6-difluorobenzyl)-5-{[2-methoxyethyl(methyl)amino]methyl}-2,4-dioxo-1,2,3,4-tetrahydrothieno[2,3-d]pyrimidin-6-yl]phenyl)-N'-ethylurea

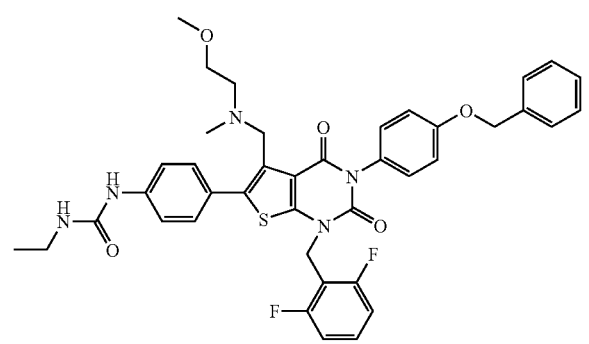

4-benzyloxyaniline (3.78 g, 16.0 mmol) was dissolved in dichloromethane (60 ml), followed by dropwise addition of a solution of dimethylaluminum chloride in hexane (0.98 M) (16.4 ml, 16.0 mmol) with ice-cooling and the mixture was stirred at room temperature for 1 hour. Then, the compound of Reference Example 8 (1.21 g, 2.0 mmol) was added and the mixture was stirred at room temperature for 16 hours. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: chloroform-methanol), and then was recrystallized from methanol to give the title compound (1.42 g, 96%) as colorless crystals.

$^1$H-NMR(CDCl$_3$) δ: 1.18 (3H, t, J=7.2 Hz), 2.14 (3H, s), 2.63 (2H, t, J=5.7 Hz), 3.26 (3H, s), 3.31 (2H, q, J=7.2 Hz), 3.41 (2H, t, J=5.7 Hz), 3.82 (2H, s), 4.6-4.7 (1H, m), 5.08 (2H, s), 5.35 (2H, s), 6.3-6.4 (1H, m), 6.91 (2H, t, J=8.1 Hz), 7.07 (2H, d, J=6.6 Hz), 7.19 (2H, d, J=6.6 Hz), 7.26-7.45 (10H, m), 7.57 (2H, d, J=8.4 Hz).

Elemental analysis for C$_{40}$H$_{39}$F$_2$N$_5$O$_5$S

Calculated: C, 64.94; H, 5.31; N, 9.47. Found: C, 64.77; H, 5.03; N, 9.38.

mp 223-225° C.

Example 103

Preparation of N-[4-(1-(2,6-difluorobenzyl)-3-(4-hydroxyphenyl)-5-{[({[2-methoxyethyl(methyl)amino]methyl}-2,4-dioxo-1,2,3,4-tetrahydrothieno[2,3-d]pyrimidin-6-yl)phenyl]-N'-ethylurea

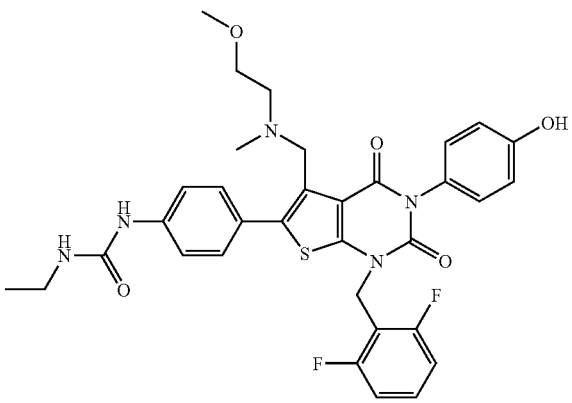

A 2 N hydrochloride/diethyl ether solution (1 ml) and 50% hydrous-10% palladium/carbon (1.00 g) were added to a solution of the compound of Example 102 (1.04 g) in ethanol (200 ml) and the mixture was stirred thoroughly under hydrogen atmosphere for 1 hour. The filtrate except a catalyst was neutralized with aqueous sodium bicarbonate, and the precipitate was filtered. It was washed with diethyl ether and dried under reduced pressure to give the title compound of white powder (0.88 g, 97%).

$^1$H-NMR(CDCl$_3$) δ: 1.18 (3H, t, J=7.2 Hz), 2.15 (3H, s), 2.64 (2H, t, J=5.7 Hz), 3.25 (3H, s), 3.30 (2H, q, J=7.2 Hz), 3.42 (2H, t, J=5.7 Hz), 3.80 (2H, s), 4.2-4.3 (1H, m), 5.36 (2H, s), 6.3-6.4 (1H, m), 6.95 (2H, t, J=8.1 Hz), 7.10 (2H, d, J=6.6 Hz), 7.19 (2H, d, J=6.6 Hz), 7.25-7.40 (5H, m), 7.58 (2H, d, J=8.4 Hz).

Elemental analysis for C$_{33}$H$_{33}$F$_2$N$_5$O$_5$S

Calculated: C, 61.00; H, 5.12; N, 10.78. Found: C, 60.86; H, 5.26; N, 10.62.

mp 260-265° C.

Example 104

Preparation of N-[4-(1-(2,6-difluorobenzyl)-3-[4-(2-methoxyethoxy)phenyl]-5-{[(2-methoxyethyl(methyl)amino)methyl]-2,4-dioxo-1,2,3,4-tetrahydrothieno[2,3-d]pyrimidin-6-yl}phenyl)-N'-ethylurea

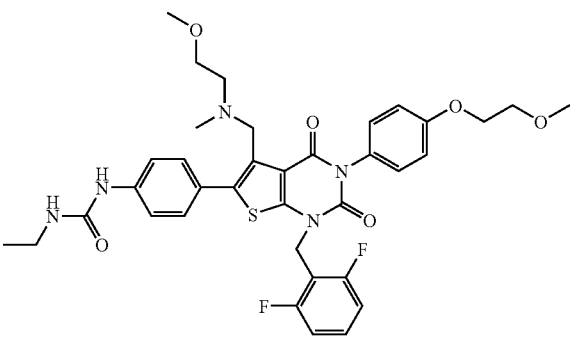

A suspension of the compound of Example 103 (0.13 g, 0.2 mmol), bromoethyl methyl ether (70 mg, 0.5 mmol) and cesium carbonate (0.16 g, 0.5 mmol) in DMF (2 ml) was stirred at 80° C. for 5 hours. The reaction solution was partitioned between ethyl acetate and water, and then the organic layer was separated, dried over magnesium sulfate and then concentrated under reduced pressure. The residue was purified by silica gel column chromatography (eluent: chloroform-methanol), and was recrystallized from ethyl acetate/methanol to give the title compound (0.12 g, 85%) as colorless crystals.

$^1$H-NMR(CDCl$_3$) δ: 1.19 (3H, t, J=7.2 Hz), 2.14 (3H, s), 2.64 (2H, t, J=5.7 Hz), 3.26 (3H, s), 3.32 (2H, q, J=7.2 Hz), 3.41 (2H, t, J=5.7 Hz), 3.45 (3H, s), 3.76 (2H, q, J=4.5 Hz), 3.83 (2H, s), 4.15 (2H, q, J=4.5 Hz), 4.6-4.7 (1H, m), 5.36 (2H, s), 6.2-6.3 (1H, m), 6.92 (2H, t, J=7.8 Hz), 7.03 (2H, d, J=6.6 Hz), 7.18 (2H, d, J=6.6 Hz), 7.26-7.35 (1H, m), 7.36 (2H, d, J=8.7 Hz), 7.56 (2H, d, J=8.7 Hz).

Elemental analysis for C$_{36}$H$_{39}$F$_2$N$_5$O$_6$S

Calculated: C, 61.09; H, 5.55; N, 9.89. Found: C, 61.23; H, 5.62; N, 10.11.

mp 215-218° C.

Example 105

Preparation of N-[4-(3-[3,4-bis(2-methoxyethoxy)phenyl]-1-(2,6-difluorobenzyl)-5-{[(2-methoxyethyl(methyl)amino)methyl]-2,4-dioxo-1,2,3,4-tetrahydrothieno[2,3-d]pyrimidin-6-yl}phenyl)-N'-ethylurea

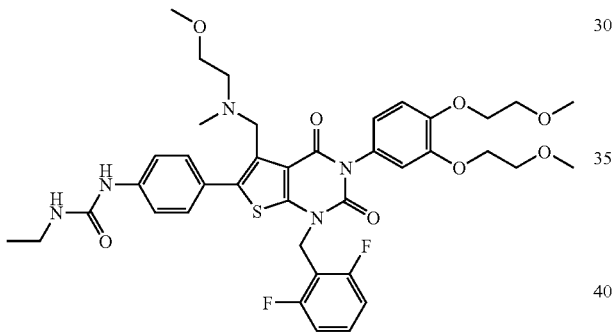

3,4-bis(2-methoxyethoxy)aniline (3.62 g, 15.0 mmol) was dissolved in dichloromethane (60 ml), followed by dropwise addition of a solution of dimethylaluminum chloride in hexane (0.98 M) (15.3 ml, 15.0 mmol) with ice-cooling and the mixture was stirred at room temperature for 1 hour. Then, the compound of Reference Example 8 (1.21 g, 2.0 mmol) was added and the mixture was stirred at room temperature for 16 hours. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: chloroform-methanol), and then was recrystallized from methanol to give the title compound (0.75 g, 48%) as colorless crystals.

$^1$H-NMR(CDCl$_3$) δ: 1.16 (3H, t, J=7.2 Hz), 2.12 (3H, s), 2.62 (2H, t, J=5.7 Hz), 3.25 (3H, s), 3.29 (2H, q, J=7.2 Hz), 3.38-3.44 (4H, m), 3.45 (3H, s), 3.76 (4H, q, J=4.5 Hz), 3.82 (2H, s), 4.17 (4H, q, J=4.5 Hz), 4.7-4.8 (1H, m), 5.34 (2H, s), 6.6-6.7 (1H, m), 6.82-6.85 (2H, m), 6.91 (2H, t, J=7.8 Hz), 7.00 (1H, d, J=6.9 Hz), 7.26-7.35 (1H, m), 7.36 (2H, d, J=8.7 Hz), 7.53 (2H, d, J=8.7 Hz).

Elemental analysis for C$_{39}$H$_{45}$F$_2$N$_5$O$_8$S.0.5H$_2$O

Calculated: C, 59.23; H, 5.86; N, 8.86. Found: C, 59.32; H, 5.89; N, 8.82.

mp 222-225° C.

Example 106

Preparation of N-{2-[4-(1-(2,6-difluorobenzyl)-6-(4-{[(ethylamino)carbonyl]amino}phenyl)-5-{[(2-methoxyethyl(methyl)amino)methyl]-2,4-dioxo-1,2,3,4-tetrahydrothieno[2,3-d]pyrimidin-3(2H)-yl}phenoxy)ethyl]methanesulfonamide

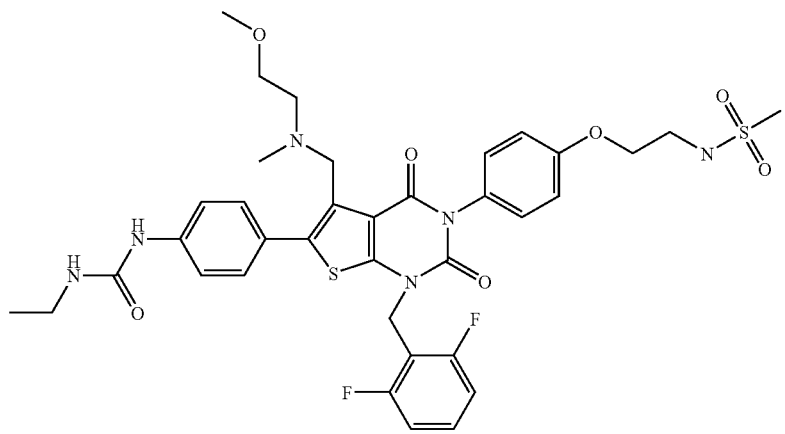

A suspension of the compound of Example 103 (0.33 g, 0.5 mmol), N-mesyl-2-bromoethylamine (0.12 g, 0.6 mmol) and cesium carbonate (0.16 g, 0.5 mmol) in DMF (5 ml) was stirred at room temperature for 16 hours. The reaction solution was partitioned between ethyl acetate and water, and the organic layer was separated, dried over magnesium sulfate and then concentrated under reduced pressure. The residue was purified by silica gel column chromatography (eluent: chloroform-methanol), and was recrystallized from methanol-ether to give the title compound (0.32 g, 83%) as colorless crystals.

$^1$H-NMR(CDCl$_3$) δ: 1.18 (3H, t, J=7.2 Hz), 2.14 (3H, s), 2.64 (2H, t, J=5.7 Hz), 2.96 (3H, s), 3.32 (2H, q, J=7.2 Hz), 3.41 (2H, t, J=5.7 Hz), 3.45 (3H, s), 3.76 (2H, q, J=4.5 Hz), 3.83 (2H, s), 4.15 (2H, q, J=4.5 Hz), 4.6-4.7 (1H, m), 5.35 (2H, s), 6.2-6.3 (1H, m), 6.98 (2H, t, J=7.8 Hz), 7.03 (2H, d, J=6.6 Hz), 7.18 (2H, d, J=6.6 Hz), 7.26-7.34 (1H, m), 7.38 (2H, d, J=8.7 Hz), 7.58 (2H, d, J=8.7 Hz).

Elemental analysis for C$_{36}$H$_{40}$F$_2$N$_6$O$_7$S$_2$

Calculated: C, 56.09; H, 5.23; N, 10.90. Found: C, 55.96; H, 5.38; N, 10.83.

mp 232-235° C.

Example 107

Preparation of 2-[4-(1-(2,6-difluorobenzyl)-6-(4-{[(ethylamino)carbonyl]amino}phenyl)-5-([(2-methoxyethyl(methyl)amino)methyl]-2,4-dioxo-1,2,3,4-tetrahydrothieno[2,3-d]pyrimidin-3(2H)-yl}phenoxy)ethyl acetate

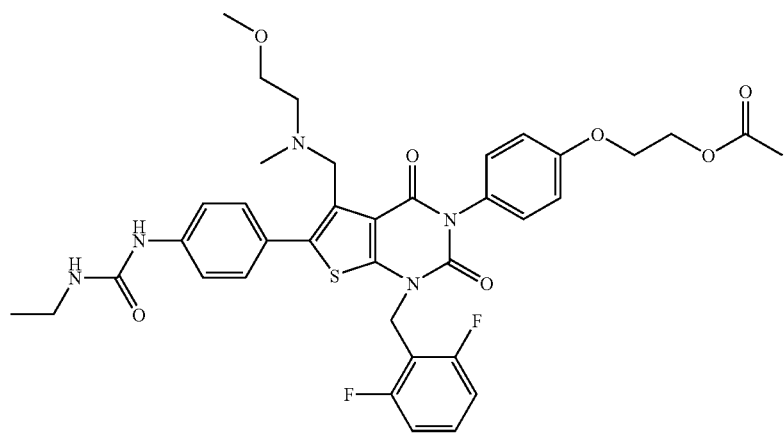

A suspension of the compound of Example 103 (0.33 g, 0.5 mol), 2-bromoethyl acetate (0.10 g, 0.6 mmol) and cesium carbonate (0.16 g, 0.5 mmol) in DMF (5 ml) was stirred at room temperature for 5 hours. The reaction solution was partitioned between ethyl acetate and water, and the organic layer was separated, dried over magnesium sulfate, and concentrated under reduced pressure. The residue was purified by silica gel column chromatography (eluent: chloroform-methanol), and then was recrystallized from methanol to give the title compound (0.35 g, 95%) as colorless crystals.

$^1$H-NMR(CDCl$_3$) δ: 1.16 (3H, t, J=7.2 Hz), 2.09 (3H, s), 2.15 (3H, s), 2.64 (2H, t, J=5.7 Hz), 3.32 (2H, q, J=7.2 Hz), 3.40 (2H, t, J=5.7 Hz), 3.45 (3H, s), 3.56 (2H, q, J=4.5 Hz), 3.83 (2H, s), 4.15 (2H, q, J=4.5 Hz), 4.6-4.7 (1H, m), 5.36 (2H, s), 6.2-6.3 (1H, m), 6.92 (2H, t, J=7.8 Hz), 7.03 (2H, d, J=6.6 Hz), 7.18 (2H, d, J=6.6 Hz), 7.26-7.35 (1H, m), 7.36 (2H, d, J=8.7 Hz), 7.56 (2H, d, J=8.7 Hz).

Elemental analysis for C$_{37}$H$_{39}$F$_2$N$_5$O$_7$S

Calculated: C, 60.40; H, 5.34; N, 9.52. Found: C, 60.33; H, 5.46; N, 9.43.

mp 212-215° C.

Example 108

Preparation of N-[4-(1-(2,6-difluorobenzyl)-3-[4-(2-2,6-difluorobenzylethoxy)phenyl]-5-([({[2-methoxyethyl(methyl)amino]methyl)-2,4-dioxo-1,2,3,4-tetrahydrothieno[2,3-d]pyrimidin-6-yl)phenyl]-N'-ethylurea

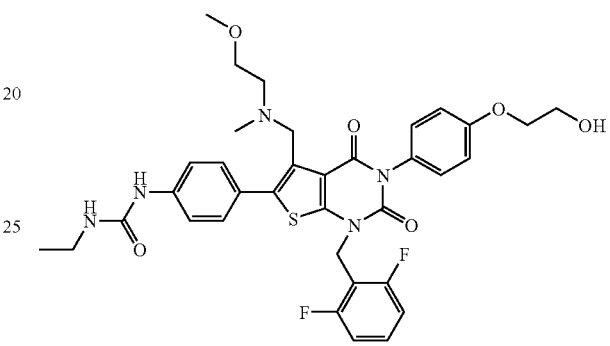

A 1 N potassium hydroxide solution (1.0 ml) was added to a solution of the compound of Example 107 (0.25 g) in ethanol (5 ml) and the mixture was stirred at room temperature for 6 hours.

The reaction solution was partitioned between ethyl acetate and water, and the organic layer was separated, dried over magnesium sulfate, and concentrated under reduced pressure. The residue was purified by silica gel column chromatography (eluent: chloroform-methanol), and then was recrystallized from methanol to give the title compound (0.20 g, 85%) as colorless crystals.

$^1$H-NMR(CDCl$_3$) δ: 1.16 (3H, t, J=7.2 Hz), 2.15 (3H, s), 2.64 (2H, t, J=5.7 Hz), 3.32 (2H, q, J=7.2 Hz), 3.42 (2H, t, J=5.7 Hz), 3.45 (3H, s), 3.55 (2H, q, J=4.5 Hz), 3.85 (2H, s), 3.95 (2H, q, J=4.5 Hz), 4.6-4.7 (1H, m), 5.36 (2H, s), 6.2-6.3

(1H, m), 6.92 (2H, t, J=7.8 Hz), 7.06 (2H, d, J=6.6 Hz), 7.19 (2H, d, J=6.6 Hz), 7.25-7.35 (1H, m), 7.38 (2H, d, J=8.7 Hz)), 7.54 (2H, d, J=8.7 Hz).

Elemental analysis for $C_{35}H_{37}F_2N_5O_6S$

Calculated: C, 60.59; H, 5.38; N, 10.09. Found: C, 60.65; H, 5.49; N, 10.20.

mp 236-238° C.

Example 109

Preparation of N-[4-(1-(2,6-difluorobenzyl)-5-{[[2-(2-methoxyethoxy)ethyl](methyl)amino]methyl}-2,4-dioxo-3 phenyl-1,2,3,4-tetrahydrothieno[2,3-d]pyrimidin-6-yl)phenyl]-N'-ethylurea

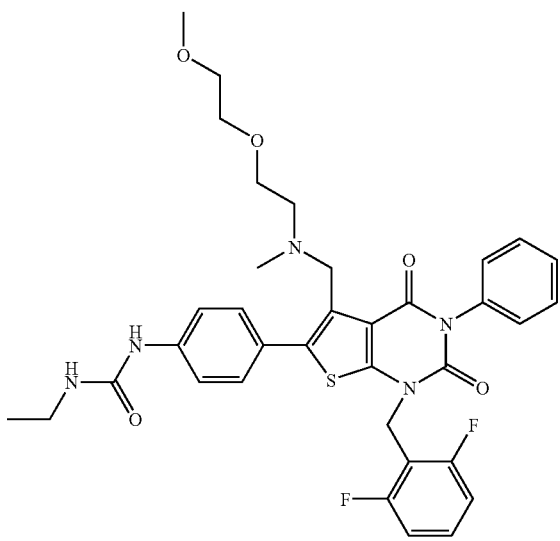

The similar reaction to that of Example 19 was performed using the compound of Example 1 (575 mg, 1.0 mmol) and 1-bromo-2-(2-methoxyethoxy)ethane (0.37 g, 2.0 mmol) to give the title compound (480 mg, 68%) as colorless crystals.

$^1$H-NMR(CDCl$_3$) δ: 1.15 (3H, t, J=7.0 Hz), 2.23 (3H, s), 2.64 (2H, d, J=4.4 Hz), 3.28 (2H, q, J=7.2 Hz), 3.75-3.90 (7H, m), 4.84 (1H, t, J=4.4 Hz), 4.92 (1H, t, J=4.4 Hz), 5.36 (2H, s), 6.63 (1H, s), 6.92 (2H, t, J=8.2 Hz), 7.2-7.6 (10H, m).

Elemental analysis for $C_{35}H_{37}F_2N_5O_5S$

Calculated: C, 62.02; H, 5.50; N, 10.33. Found: C, 62.14; H, 5.36; N, 10.56.

mp 228-231° C.

Example 110

Preparation of N-[4-(1-(2,6-difluorobenzyl)-[(2-(2-propoxy)ethyl(methyl)amino}methyl]-2,4-dioxo-3 phenyl-1,2,3,4-tetrahydrothieno[2,3-d]pyrimidin-6-yl)phenyl]-N'-ethylurea

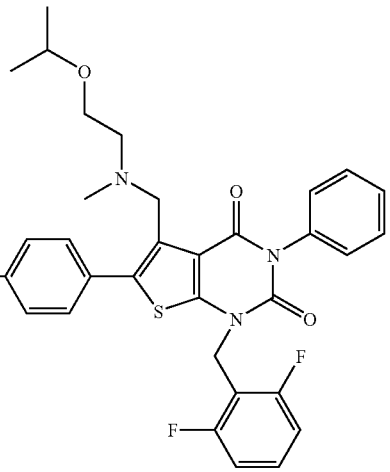

The similar reaction to that of Example 19 was performed using the compound of Example 1 (575 mg, 1.0 mmol) and 2-isopropyloxyethylmethanesulfonate (0.36 g, 2.0 mmol) to give the title compound (450 mg, 68%) as colorless crystals.

$^1$H-NMR(CDCl$_3$) δ: 1.06 (6H, d, J=6.2 Hz), 1.15 (3H, t, J=7.0 Hz), 2.15 (3H, s), 2.63 (2H, t, J=5.8 Hz), 3.28 (2H, q, J=7.2 Hz), 3.43 (2H, t, J=5.8 Hz), 3.42-3.54 (1H, m), 3.84 (2H, s), 4.914 (1H, t, J=4.4 Hz), 5.36 (2H, s), 6.68 (1H, s), 6.92 (2H, t, J=8.0 Hz), 7.2-7.6 (10H, m).

Elemental analysis for $C_{35}H_{37}F_2N_5O_4S$

Calculated: C, 63.52; H, 5.64; N, 10.58. Found: C, 63.30; H, 5.55; N, 10.48.

mp 224-224° C.

Example 111

Preparation of N-[4-(1-(2,6-difluorobenzyl)-5-[{[2-(2-ethoxy)ethoxy]ethyl(methyl)amino}methyl]-2,4-dioxo-3-phenyl-1,2,3,4-tetrahydrothieno[2,3-d]pyrimidin-6-yl)phenyl]-N'-ethylurea

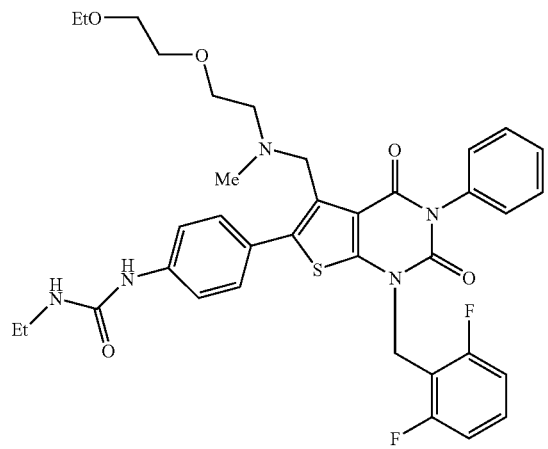

The similar reaction to that of Example 19 was performed using the compound of Example 1 (575 mg, 1.0 mmol) and 1-bromo-2-(2-ethoxy ethoxy)ethane (0.39 g, 2.0 mmol) to give the title compound (400 mg, 56%) as colorless crystals.

$^1$H-NMR(CDCl$_3$) δ: 1.05 (3H, t, J=6.0 Hz), 1.15 (3H, t, J=7.0 Hz), 2.64 (2H, d, J=4.4 Hz), 3.28 (2H, q, J=7.2 Hz), 3.42 (2H, q, J=6.0 Hz), 3.75-3.90 (7H, m), 4.84 (1H, t, J=4.4 Hz), 4.92 (1H, t, J=4.4 Hz), 5.36 (2H, s), 6.63 (1H, s), 6.92 (2H, t, J=8.2 Hz), 7.2-7.6 (10H, m).

Elemental analysis for C$_{36}$H$_{39}$F$_2$N$_5$O$_5$S

Calculated: C, 62.50; H, 5.49; N, 10.12. Found: C, 62.63; H, 5.43; N, 10.22.

mp 230-233° C.

Example 112

Preparation of N-[4-(1-(2,6-difluorobenzyl)-5-{[(2-methoxyethyl)(methyl)amino]methyl}-2,4-dioxo-3-phenyl-1,2,3,4-tetrahydrothieno[2,3-d]pyrimidin-6-yl)phenyl]-N'-ethylurea 1 hydrochloride

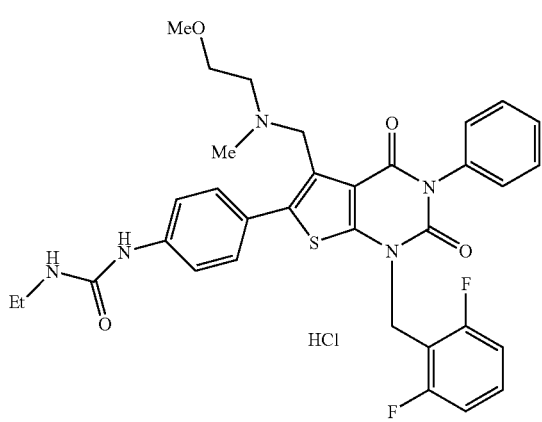

12% methanolic hydrochloride (2.65 g) was added to a solution of the compound of Example 81 (2.80 g) in dichloromethane (14 ml) with ice-cooling and stirring, the mixture was stirred for 15 minutes and then the solvent was distilled off. The obtained residue was finely dissolved in anhydrous diethyl ether, and the crystalline powder was filtered and dried to give the title compound (2.92 g).

$^1$H-NMR (CDCl$_3$) δ: 1.10 (3H, t, J=7.1 Hz), 2.67 (3H, s), 3.10-3.30 (4H, m), 3.22 (3H, s), 3.60 (2H, s), 4.47 (2H, br), 5.30 (2H, s), 6.45 (1H, t, J=5.3 Hz), 6.91 (2H, t, J=8.1 Hz), 7.09 (2H, d, J=8.8 Hz), 7.24-7.58 (5H, m), 7.66 (2H, d, J=8.8 Hz), 9.44 (1H, s).

IR (KBr): 3303, 1713, 1667, 1593, 1539, 1472, 1318, 1235 cm$^{-1}$.

Elemental analysis for C$_{33}$H$_{33}$N$_5$O$_4$SF$_2$.HCl.H$_2$O

Calculated: C, 57.59; H, 5.27; N, 10.18. Found: C, 57.66; H, 5.40; N, 10.31.

Example 113

Preparation of N-(4-(1-(2,6-difluorobenzyl)-5-((methyl(2-pyridylmethyl)amino)methyl)-2,4-dioxo-3-phenyl-1,2,3,4-tetrahydrothieno[2,3-d]pyrimidin-6-yl)-N'-ethylurea

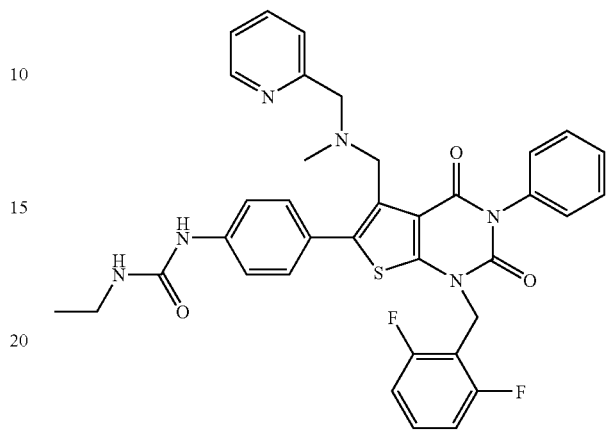

The similar reaction to that of Example 4 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (350 mg, 0.608 mmol) and 2-chloromethylpyridine hydrochloride (199 mg, 1.2 mmol) to give the title compound (294 mg, 73%) as colorless crystals.

$^1$H-NMR(CDCl$_3$) δ: 1.16 (3H, t, J=7.2 Hz), 2.09 (3H, s), 3.2-3.4 (2H, m), 3.70(2H, s), 3.98 (2H, s), 4.75-4.85 (1H, m), 5.35 (2H, s), 6.61 (1H, s), 6.91 (2H, t, J=8.2 Hz), 7.0-7.1 (1H, m), 7.2-7.6 (12H, m), 8.42 (1H, d, J=4.4 Hz).

IR (KBr): 1715, 1676, 1530, 1458, 1314, 1238, 1036, 735 cm$^{-1}$.

Elemental analysis for C$_{36}$H$_{32}$F$_2$N$_6$O$_3$S.0.5H$_2$O

Calculated: C, 63.99; H, 4.92; N, 12.44. Found: C, 63.77; H, 5.01; N, 12.53.

mp 203-204° C.

Example 114

Preparation of N-[4-(1-(2,6-difluorobenzyl)-3-(4-fluorophenyl)-5-{[methyl(2-pyridylmethyl)amino]methyl}-2,4-dioxo-1,2,3,4-tetrahydrothieno[2,3-d]pyrimidin-6-yl)-N'-ethylurea

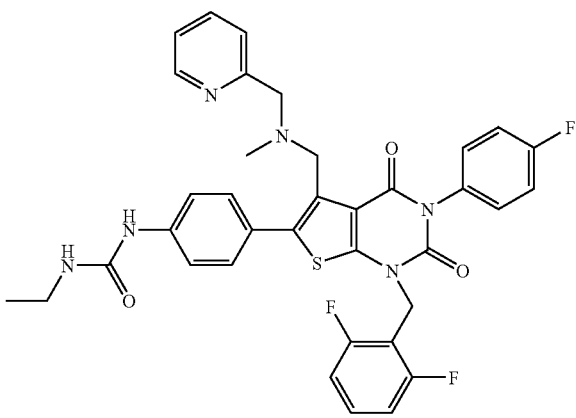

The similar reaction to that of Example 4 was performed using N-(4-{1-(2,6-difluorobenzyl)-3-(4-fluorophenyl)-5-[(methylamino)methyl]-2,4-dioxo-1,2,3,4-tetrahydrothieno[2,3-d]pyrimidin-6-yl}phenyl)-N'-ethylurea (350 mg, 0.590 mmol) and 2-chloromethylpyridine hydrochloride (193 mg, 1.18 mmol) to give the title compound (292 mg, 72%) as colorless crystals.

$^1$H-NMR(CDCl$_3$) δ: 1.16 (3H, t, J=7.2 Hz), 2.09 (3H, s), 3.2-3.4 (2H, m), 3.70 (2H, s), 3.96 (2H, s), 4.75-4.85 (1H, m), 5.34 (2H, s), 6.63 (1H, s), 6.91 (2H, t, J=8.2 Hz), 7.0-7.6 (12H, m), 8.43 (1H, d, J=4.8 Hz).

IR (KBr): 1721, 1667, 1635, 1472, 1236, 1034, 766 cm$^{-1}$.
Elemental analysis for C$_{36}$H$_{31}$F$_3$N$_6$O$_3$S Calculated: C, 63.15; H, 4.56; N, 12.27. Found: C, 63.34; H, 4.53; N, 12.47.
mp 243-244° C.

Example 115

Preparation of N-(4-(1-(2,6-difluorobenzyl)-5-[((((6-(hydroxymethyl)-2-pyridyl)methyl)(methyl)amino)methyl)-2,4-dioxo-3-phenyl-1,2,3,4-tetrahydrothieno[2,3-d]pyrimidin-6-yl)-N'-ethylurea

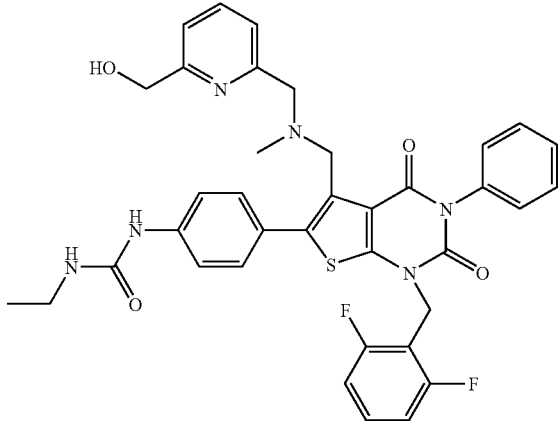

The similar reaction to that of Example 4 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (200 mg, 0.347 mmol) and 6-bromomethyl-2-pyridinemethanol (0.14 g, 0.694 mmol) to give the title compound (190 mg, 79%) as colorless crystals.

$^1$H-NMR(CDCl$_3$) δ: 1.17 (3H, t, J=7.2 Hz), 2.13 (3H, s), 3.2-3.4 (2H, m), 3.71 (2H, s), 3.96 (2H, s), 4.2-4.4 (1H, br), 4.68 (2H, s), 4.9-5.0 (1H, m), 5.36 (2H, s), 6.66 (1H, s), 6.92 (2H, t, J=8.0 Hz), 7.0-7.6 (13H, m).

IR (KBr): 1713, 1674, 1530, 1458, 1314, 1238, 1036, 789, 735 cm$^{-1}$.

Elemental analysis for C$_{37}$H$_{34}$F$_2$N$_6$O$_4$S·1.0H$_2$O

Calculated: C, 62.17; H, 5.08; N, 11.76. Found: C, 62.19; H, 4.98; N, 11.78.

Example 116

Preparation of methyl 6-(((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl)(methyl)amino)methyl)nicotinate

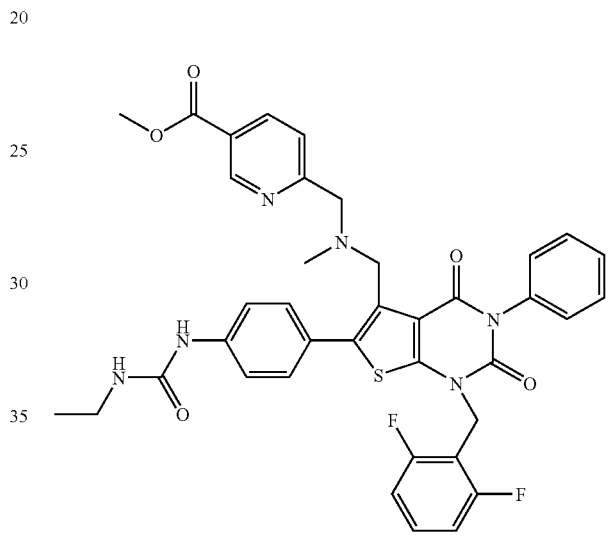

The similar reaction to that of Example 4 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (748 mg, 1.3 mmol) and methyl 6-(bromomethyl)nicotinate (0.49 g, 2.13 mmol) to give the title compound (559 mg, 59%) as colorless crystals.

$^1$H-NMR(CDCl$_3$) δ: 1.19 (3H, t, J=7.2 Hz), 2.09 (3H, s), 3.2-3.4 (2H, m), 3.75 (2H, s), 3.93 (3H, s), 3.98 (2H, s), 4.65-4.75 (1H, m), 5.35 (2H, s), 6.44 (1H, s), 6.91 (2H, t, J=8.2 Hz), 7.2-7.6 (11H, m), 8.11 (1H, dd, J=2.2, 8.0 Hz), 9.0-9.05 (1H, m).

IR (KBr): 1730, 1715, 1674, 1458, 1314, 1291, 1238, 1121, 1036, 735 cm$^{-1}$.

Elemental analysis for C$_{38}$H$_{34}$F$_2$N$_6$O$_5$S

Calculated: C, 62.97; H, 4.73; N, 11.60. Found: C, 62.71; H, 4.47; N, 11.51.

Example 117

Preparation of 6-((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl)(methyl)amino)methyl)-N-methylnicotinamide

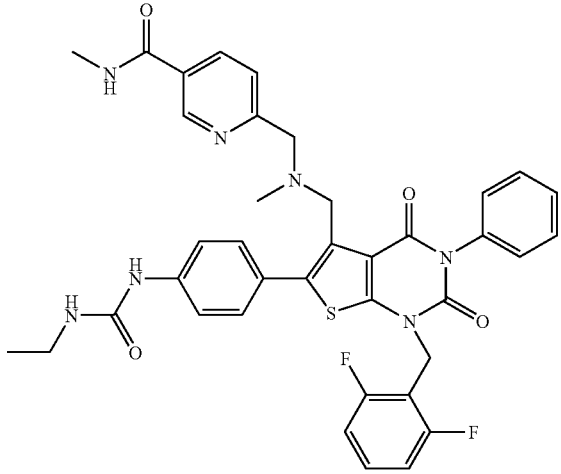

Ethyl diisopropylamine (0.48 ml, 2.76 mmol) and a solution of dimethylaluminum chloride in hexane (0.98 M)(1.69 ml, 1.656 mmol) were added dropwise to a solution of methylamine (a 2 M THF solution)(1.38 ml, 2.76 mmol) in dichloromethane (4 ml) with ice-cooling and the mixture was stirred at room temperature for 30 minutes. Then, a solution of methyl 6-((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl)(methyl)amino)methyl)nicotinate (200 mg, 0.276 mmol) in dichloromethane (14 ml) was added and the mixture was stirred at room temperature for 2 days. Aqueous sodium bicarbonate was added and the mixture was extracted with chloroform. The organic layer was washed with brine, dried over magnesium sulfate and then concentrated under reduced pressure. The residue was purified by silica gel column chromatography (eluent: ethyl acetate/methanol; 40/1), and then was recrystallized from dichloromethane/methanol to give the title compound (99 mg, 50%) as colorless crystals.

$^1$H-NMR(CDCl$_3$) δ: 1.18 (3H, t, J=7.2 Hz), 2.25 (3H, s), 3.01 (3H, d, t=4.6 Hz), 3.2-3.4 (2H, m), 3.68 (2H, s), 3.89 (2H, s), 5.05-5.15 (1H, m), 5.34 (2H, s), 6.91 (2H, t, J=7.8), 6.9-7.0 (1H, m), 7.05-7.15 (2H, m), 7.2-7.6 (10H, m), 7.85-7.95 (1H, m), 8.8-8.85 (1H, m).

IR (KBr): 1717, 1671, 1472, 1240, 1032, 735 cm$^{-1}$.

Elemental analysis for C$_{38}$H$_{35}$F$_2$N$_7$O$_4$S.0.5H$_2$O

Calculated: C, 62.28; H, 4.95; N, 13.38. Found: C, 62.32; H, 4.77; N, 13.26.

Example 118

Preparation of ethyl 6-((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl)(methyl)amino)methyl)-2-pyridine carboxylate

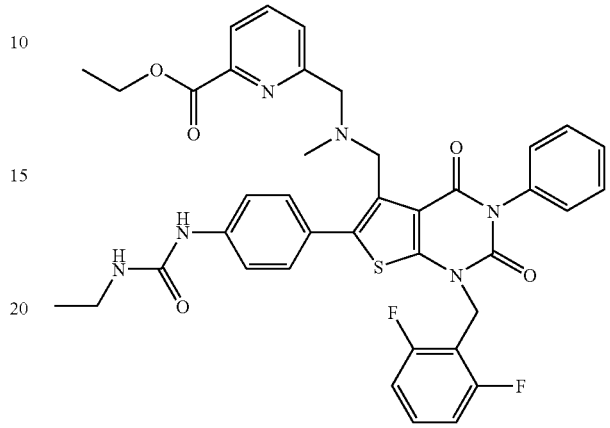

The similar reaction to that of Example 4 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (576 mg, 1 mmol) and ethyl 6-bromomethyl-2-pyridine carboxylate (399 mg, 2.2 mmol) to give the title compound (605 mg, 82%) as colorless crystals.

$^1$H-NMR(CDCl$_3$) δ: 1.15 (3H, t, J=7.2 Hz), 1.39 (3H, t, J=7.2 Hz), 2.03 (3H, s), 3.2-3.4 (2H, m), 3.77 (2H, s), 3.97 (2H, s), 4.42 (2H, q, J=7.2 Hz), 4.85-4.95 (1H, m), 5.34 (2H, s), 6.81 (1H, s), 6.91 (2H, t, J=8.2 Hz), 7.2-7.6 (11H, m), 7.67 (1H, t, J=7.2 Hz), 7.90 (1H, d, J=7.2 Hz).

IR (KBr): 1717, 1671, 1593, 1532, 1468, 1318, 1236, 1032, 762 cm$^{-1}$.

Elemental analysis for C$_{39}$H$_{36}$F$_2$N$_6$O$_5$S

Calculated: C, 63.40; H, 4.91; N, 11.38. Found: C, 63.23; H, 4.90; N, 11.21.

Example 119

Preparation of 6-((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl)(methyl)amino)methyl)-N-methyl-2-pyridine carboxamide

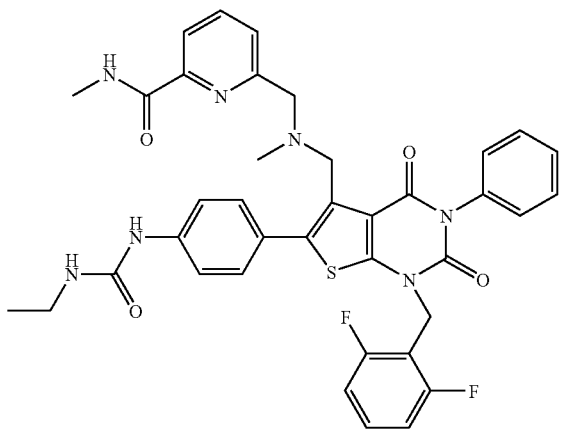

The similar reaction to that of Example 117 was performed using methylamine (a 2 M THF solution) (2.03 ml, 4.06 mmol) and ethyl 6-((((1-(2,6-difluorobenzyl)-6-(4-(((ethylaminocarbonyl)amino)phenyl)-2,4-dioxo-3-phenyl-1,2,3,4-tetrahydrothieno[2,3-d]pyrimidin-5-yl)methyl) (methyl) amino)methyl)-2-pyridine carboxylate (300 mg, 0.406 mmol) to give the title compound (191 mg, 65%) as colorless crystals.

$^1$H-NMR(CDCl$_3$) δ: 1.19 (3H, t, J=7.2 Hz), 2.14 (3H, s), 2.95 (3H, d, J=5.2 Hz), 3.2-3.4 (2H, m), 3.72 (2H, s), 3.97 (2H, s), 4.95-5.0 (1H, m), 5.36 (2H, s), 6.84 (1H, s), 6.92 (2H, t, J=8.2 Hz), 7.25-7.6 (11H, m), 7.66 (1H, t, J=7.4 Hz), 7.95 (1H, d, J=7.4 Hz), 8.05-8.15 (1H, m).

IR (KBr): 1721, 1661, 1534, 1472, 1236, 1032, 737 cm$^{-1}$.

Elemental analysis for C$_{38}$H$_{35}$F$_2$N$_7$O$_4$S.1.4H$_2$O

Calculated: C, 60.93; H, 5.09; N, 13.09. Found: C, 61.24; H, 5.20; N, 12.81.

Example 120

Preparation of N-(4-(1-(2,6-difluorobenzyl)-5-(((2-(1H-imidazol-1-yl)ethyl)(methyl)amino)methyl)-2,4-dioxo-3-phenyl-1,2,3,4-tetrahydrothieno[2,3-d]pyrimidin-6-yl)phenyl)-N'-ethylurea

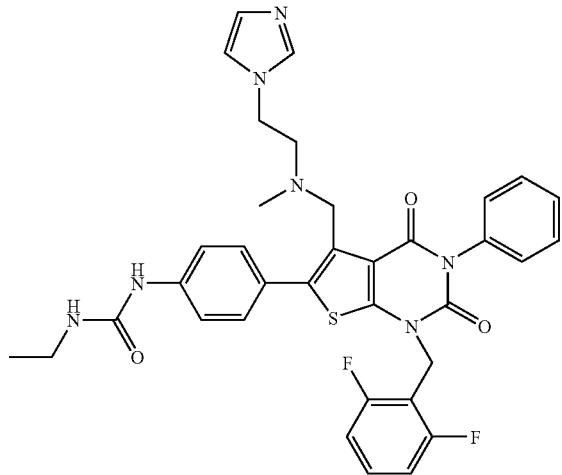

N-(4-(1-(2,6-difluorobenzyl)-5-(((2-hydroxyethyl)(methyl)amino)methyl)-2,4-dioxo-3-phenyl-1,2,3,4-tetrahydrothieno[2,3-d]pyrimidin-6-yl)phenyl)-N'-ethylurea (135 mg, 0.218 mmol) was dissolved in tetrahydrofuran (30 ml), followed by addition of triethylamine (0.18 ml, 1.308 mmol) and methanesulfonyl chloride (0.070 ml, 0.872 mmol) and the mixture was stirred at room temperature for 1 hour. Aqueous sodium bicarbonate was added and the mixture was extracted with ethyl acetate. The aqueous layer was salted out and then extracted with ethyl acetate. The organic layers were combined, dried over magnesium sulfate, and then concentrated under reduced pressure, to give mesylate. A solution of the obtained mesylate, imidazole (148 mg, 2.18 mmol), potassium carbonate (60 mg, 0.436 mmol) in DMF (4 ml) was stirred at room temperature for 16 hours, followed by addition of water, and the mixture was extracted with ethyl acetate. The organic layer was washed with brine, dried over magnesium sulfate, and then concentrated under reduced pressure. The residue was purified by silica gel column chromatography (eluent: ethyl acetate/methanol; 40/1), and further it was recrystallized from dichloromethane/methanol/diethyl ether to give the title compound (33 mg, 22%) as colorless crystals.

$^1$H-NMR(CDCl$_3$) δ: 1.16 (3H, t, J=7.2 Hz), 2.19 (3H, s), 2.65-2.75 (2H, m), 3.2-3.4 (2H, m), 3.80 (2H, s), 3.85-4.0 (2H, m), 5.25-5.35 (1H, m), 5.37 (2H, s), 6.81 (1H, s), 6.85-7.0 (3H, m), 7.2-7.6 (12H, m).

Example 121

Preparation of N-(4-(1-(2,6-difluorobenzyl)-5-(((2-(2-(2-hydroxyethyl)-1H-imidazol-1-yl)ethyl)(methyl)amino)methyl)-2,4-dioxo-3-phenyl-1,2,3,4-tetrahydrothieno[2,3-d]pyrimidin-6-yl)phenyl)-N'-ethylurea

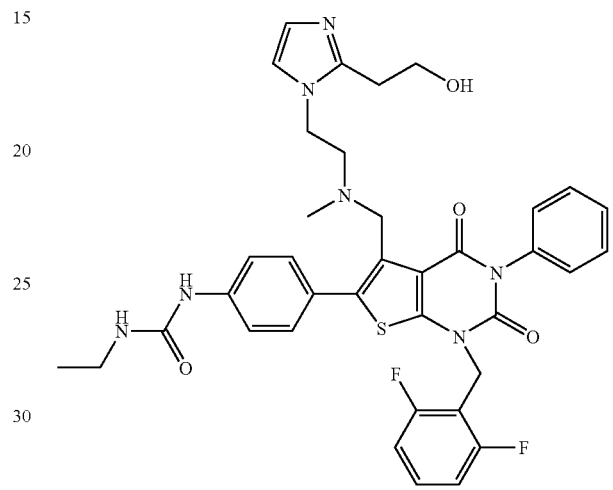

The similar reaction to that of Example 120 was performed using N-(4-(1-(2,6-difluorobenzyl)-5-(((2-hydroxyethyl)(methyl)amino)methyl)-2,4-dioxo-3-phenyl-1,2,3,4-tetrahydrothieno[2,3-d]pyrimidin-6-yl)phenyl)-N'-ethylurea (135 mg, 0.218 mmol) and 2-(2-hydroxyethyl)imidazole (122 mg, 1.09 mmol) to give the title compound (23 mg, 15%) as colorless crystals.

$^1$H-NMR(CDCl$_3$) δ: 1.18 (3H, t, J=7.2 Hz), 2.22 (3H, s), 2.6-2.75 (4H, m), 3.2-3.4 (2H, m), 3.75 (2H, s), 3.7-3.85 (2H, m), 3.9-4.0 (2H, m), 4.95-5.05 (1H, m), 5.37 (2H, s), 6.75 (1H, s), 6.82 (1H, s), 6.93 (2H, t, J=8.2 Hz), 7.1-7.6 (11H, m).

Example 122

Preparation of 2-(4-(1-(2,6-difluorobenzyl)-6-(4-(((ethylaminocarbonyl)amino)phenyl)-5-((methyl(2-pyridylmethyl)amino)methyl)-2,4-dioxo-1,4-dihydrothieno[2,3-d]pyrimidin-3(2H)-yl)phenoxy)-N-methylacetamide

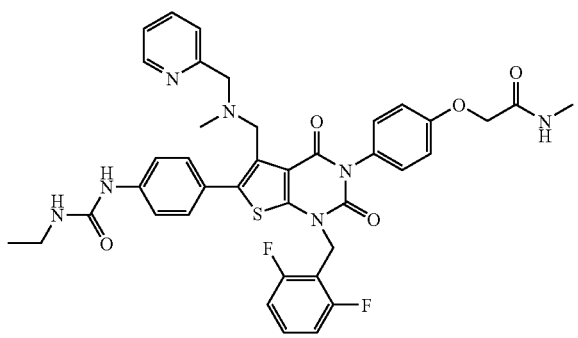

Ethyl diisopropylamine (0.14 ml, 0.8 mmol) and diethyl phosphorocyanidate (0.11 ml, 0.75 mmol) were added to a solution of the compound of Reference Example 19 (319 mg, 0.5 mmol) and 4-aminophenoxy-N-methylacetamide (135 mg, 0.75 mmol) in DMF (4 ml) and the mixture was stirred at room temperature for 3 days. Aqueous sodium bicarbonate was added, the mixture was extracted with ethyl acetate, and the organic layer was washed with brine. After drying over magnesium sulfate, it was concentrated under reduced pressure and was purified by silica gel column chromatography (eluent: ethyl acetate/methanol; 20/1) to give amide. The obtained amide was dissolved in methanol (8 ml), followed by addition of sodium methoxide (189 mg, 3.5 mmol). After stirring at room temperature for 2 hours, it was concentrated, neutralized by adding 1 N hydrochloric acid, and extracted with ethyl acetate. The organic layer was washed with brine, dried over magnesium sulfate, and then concentrated under reduced pressure. The residue was purified by silica gel column chromatography (eluent: ethyl acetate/methanol; 20/1), and then was recrystallized from dichloromethane/methanol/diethyl ether to give the title compound (122 mg, 46%) as colorless crystals.

$^1$H-NMR(CDCl$_3$) δ: 1.16 (3H, t, J=7.2 Hz), 2.09 (3H, s), 2.92 (3H, d, J=4.8 Hz), 3.2-3.4 (2H, m), 3.70 (2H, s), 3.96 (2H, s), 4.54 (2H, s), 4.8-4.9 (1H, m), 5.34 (2H, s), 6.5-6.7 (2H, m), 6.91 (2H, t, J=8.0 Hz), 7.0-7.6 (11H, m), 8.4-8.5 (1H, m).

IR (KBr): 1719, 1669, 1472, 1236, 1032, 764 cm$^{-1}$.

Elemental analysis for C$_{39}$H$_{37}$F$_2$N$_7$O$_5$S.1.0H$_2$O

Calculated: C, 60.69; H, 5.09; N, 12.70. Found: C, 60.89; H, 5.00; N, 12.78.

Example 123

Preparation of 2-(4-(1-(2,6-difluorobenzyl)-6-(4-(((ethylaminocarbonyl)amino)phenyl)-5-((methyl(2-pyridylmethyl)amino)methyl)-2,4-dioxo-1,4-dihydrothieno[2,3-d]pyrimidin-3(2H)-yl)phenyl)-N-ethylacetamide

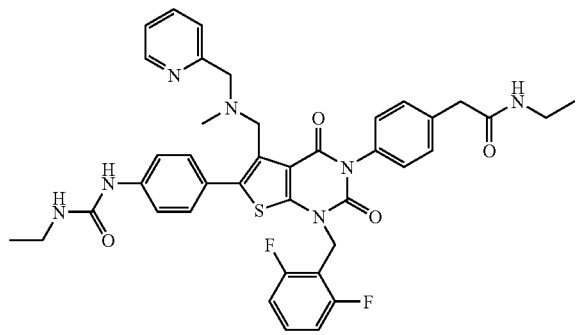

The similar reaction to that of Example 122 was performed using the compound of Reference Example 19 (319 mg, 0.5 mmol) and 4-aminophenoxy-N-methylacetamide (134 mg, 0.75 mmol) to give the title compound (43 mg, 14%) as colorless crystals.

$^1$H-NMR(CDCl$_3$) δ: 1.05-1.3 (6H, m), 2.10 (3H, s), 3.2-3.4 (4H, m), 3.64 (2H, s), 3.71 (2H, s), 3.97 (2H, s), 4.75-4.85 (1H, m), 5.34 (2H, s), 5.5-5.6 (1H, m), 6.61 (1H, s), 6.92 (2H, t, J=8.0 Hz), 7.0-7.5 (10H, m), 7.55 (2H, d, J=8.2 Hz), 8.4-8.5 (1H, m).

IR (KBr): 1713, 1671, 1555, 1470, 1238, 1032, 762 cm$^{-1}$.

Elemental analysis for C$_{40}$H$_{39}$F$_2$N$_7$O$_4$S.1.0H$_2$O

Calculated: C, 62.41; H, 5.37; N, 12.74. Found: C, 62.54; H, 5.13; N, 12.84.

Example 124

Preparation of N-(4-(1-(2,6-difluorobenzyl)-3-(4-hydroxycyclohexyl)-5-((methyl(2-pyridylmethyl)amino)methyl)-2,4-dioxo-1,4-dihydrothieno[2,3-d]pyrimidin-6-yl)phenyl)-N'-ethylurea

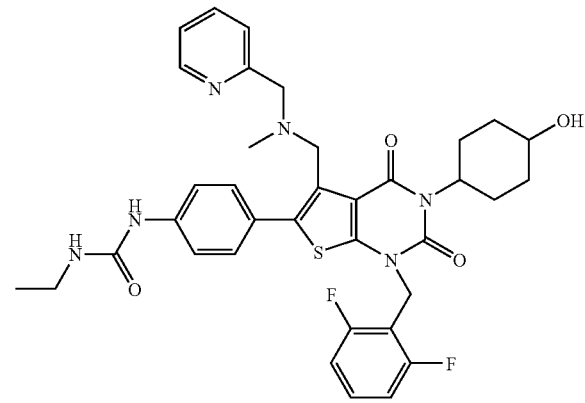

The similar reaction to that of Example 122 was performed using the compound of Reference Example 19 (319 mg, 0.5 mmol) and trans-4-aminocyclohexanol (86 mg, 0.75 mmol) to give the title compound (82 mg, 29%) as colorless crystals.

$^1$H-NMR(CDCl$_3$) δ: 1.17 (3H, t, J=7.2 Hz), 1.4-1.8 (4H, m), 2.0-2.2 (2H, m), 2.13 (3H, s), 2.55-2.75 (2H, m), 3.2-3.4 (2H, m), 3.7-3.8 (1H, m), 3.73 (2H, s), 3.99 (2H, s), 4.75-4.85 (1H, m), 4.9-5.05 (1H, m), 5.28 (2H, s), 6.5-6.6 (1H, m), 6.9 (2H, t, J=8.8 Hz), 7.0-7.6 (8H, m), 8.4-8.5 (1H, m).

IR (KBr): 1707, 1659, 1472, 1314, 1236, 1067, 1032, 781 cm$^{-1}$.

Elemental analysis for C$_{36}$H$_{38}$F$_2$N$_6$O$_4$S.0.6H$_2$O

Calculated: C, 61.81; H, 5.65; N, 12.01. Found: C, 61.54; H, 5.76; N, 11.92.

Example 125

Preparation of N-(4-(1-(2,6-difluorobenzyl)-5-((methyl(2-(2H-tetrazol-2-yl)ethyl)amino)methyl)-2,4-dioxo-3-phenyl-1,2,3,4-tetrahydrothieno[2,3-d]pyrimidin-6-yl)phenyl)-N'-ethylurea (1)

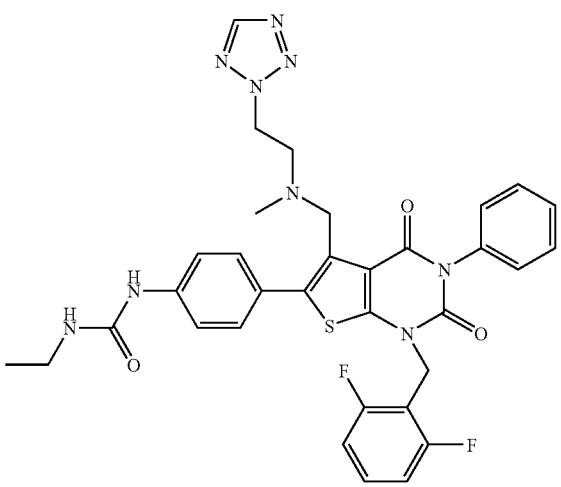

123

Preparation of N-(4-(1-(2,6-difluorobenzyl)-5-((methyl(2-(1H-tetrazol-1-yl)ethyl)amino)methyl)-2,4-dioxo-3-phenyl-1,2,3,4-tetrahydrothieno[2,3-d]pyrimidin-6-yl)phenyl)-N'-ethylurea (2)

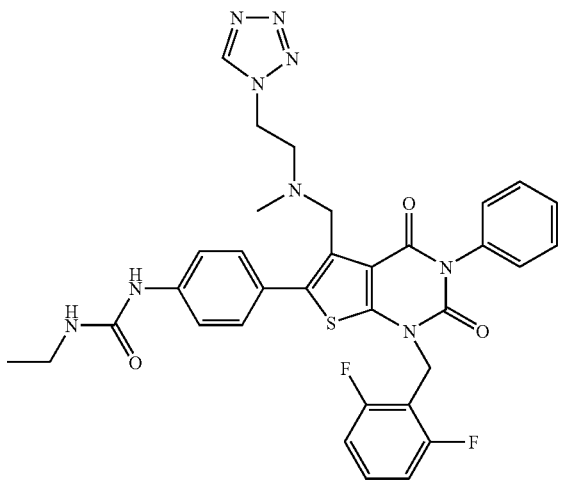

Potassium carbonate (2.075 g, 15 mmol) was added to a solution of tetrazole (0.70 g, 20 mmol) and 1-bromo-2-chloroethane (1.25 ml, 15 mmol) in DMF (5 ml) and the mixture was stirred at room temperature for 16 hours. Saturated brine was added and the mixture was extracted twice with ethyl acetate. The organic layers were combined, dried over magnesium sulfate, and then concentrated under reduced pressure to give halide (2.115 g, DMF included). The similar reaction to that of Example 4 was performed using the obtained halide and N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (576 mg, 1 mmol) to give the title compounds 2-yl product (104 mg, 16%) and 1-yl product (379 mg, 56%) as colorless crystals, respectively.

2-yl Product (1)

$^1$H-NMR(CDCl$_3$) δ: 1.19 (3H, t, J=7.2 Hz), 2.24 (3H, s), 3.03 (2H, t, J=6.3 Hz), 3.3-3.4 (2H, m), 3.77 (2H, s), 4.64 (2H, t, J=6.3 Hz), 4.75-4.85 (1H, m), 5.37 (2H, s), 6.48 (1H, s), 6.92 (2H, t, J=8.0 Hz), 6.85-6.95 (1H, m), 7.15-7.55 (9H, m), 8.28 (1H, s).

IR (KBr): 1713, 1667, 1470, 1236, 1034, 735 cm$^{-1}$.

Elemental analysis for C$_{33}$H$_{31}$F$_2$N$_9$O$_3$S.0.5H$_2$O

Calculated: C, 58.23; H, 4.74; N, 18.52. Found: C, 58.06; H, 4.64; N, 18.33.

1-yl Product (2)

$^1$H-NMR(CDCl$_3$) δ: 1.19 (3H, t, J=7.2 Hz), 2.04 (3H, s), 2.73 (2H, t, J=5.4 Hz), 3.25-3.4 (2H, m), 3.78 (2H, s), 4.43 (2H, t, J=5.4 Hz), 4.95-5.05 (1H, m), 5.36 (2H, s), 6.73 (1H, s), 6.90 (2H, t, J=8.2 Hz), 6.85-6.95 (1H, m), 7.2-7.6 (9H, m), 8.54(1H, s).

IR (KBr): 1711, 1667, 1534, 1470, 1236, 1034, 735 cm$^{-1}$.

Elemental analysis for C$_{33}$H$_{31}$F$_2$N$_9$O$_3$S.0.5H$_2$O

Calculated: C, 58.23; H, 4.74; N, 18.52. Found: C, 58.16; H, 4.68; N, 18.31.

124

Example 126

Preparation of N-(4-(1-(2,6-difluorobenzyl)-3-(2-hydroxyethyl)-5-((methyl(2-pyridylmethyl)amino)methyl)-2,4-dioxo-1,2,3,4-tetrahydrothieno[2,3-d]pyrimidin-6-yl)phenyl)-N'-ethylurea

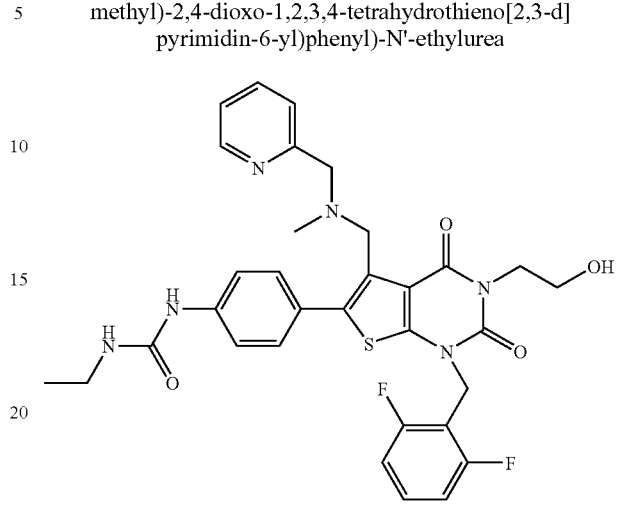

The similar reaction to that of Example 122 was performed using the compound of Reference Example 19 (350 mg, 0.55 mmol) and 2-aminoethanol (0.10 ml, 1.65 mmol) to give the title compound (23 mg, 7%) as colorless crystals.

$^1$H-NMR(CDCl$_3$) δ: 1.19 (3H, t, J=7.4 Hz), 2.21 (3H, s), 3.2-3.4 (2H, m), 3.77 (2H, s), 3.98 (2H, s), 3.9-4.1(2H, m), 4.35-4.45 (2H, m), 4.8-4.9 (1H, m), 5.25 (2H, s), 6.65-6.7 (1H, m), 6.90 (2H, t, J=7.8 Hz), 6.95-7.1 (1H, m), 7.2-7.6 (7H, m), 8.35-8.4 (1H, m).

Example 127

Preparation of N-(4-(1-(2,6-difluorobenzyl)-3-(3-hydroxypropyl)-5-((methyl(2-pyridylmethyl)amino)methyl)-2,4-dioxo-1,2,3,4-tetrahydrothieno[2,3-d]pyrimidin-6-yl)phenyl)-N'-ethylurea

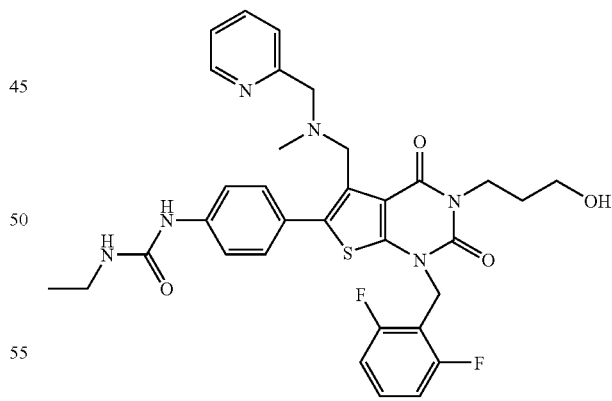

The similar reaction to that of Example 122 was performed using the compound of Reference Example 19 (350 mg, 0.55 mmol) and 3-aminopropanol (0.13 ml, 1.65 mmol) to give the title compound (15 mg, 4%) as colorless crystals.

$^1$H-NMR(CDCl$_3$) δ: 1.19 (3H, t, J=7.2 Hz), 1.85-2.05 (2H, m), 2.12 (3H, s), 3.25-3.4 (2H, m), 3.5-3.65 (2H, m), 3.72 (2H, s), 3.98 (2H, s), 4.2-4.3(2H, m), 4.7-4.8 (1H, m), 5.34 (2H, s), 6.45-6.55 (1H, m), 6.91 (2H, t, J=8.2 Hz), 7.0-7.1 (1H, m), 7.2-7.6 (7H, m), 8.4-8.5 (1H, m).

Example 128

Preparation of N-(4-(1-(2,6-difluorobenzyl)-3-(4-fluorophenyl)-5-((methyl(2-(2H-1,2,3-triazol-2-yl)ethyl)amino)methyl)-2,4-dioxo-1,2,3,4-tetrahydrothieno[2,3-d]pyrimidin-6-yl)phenyl)-N'-ethylurea (1)

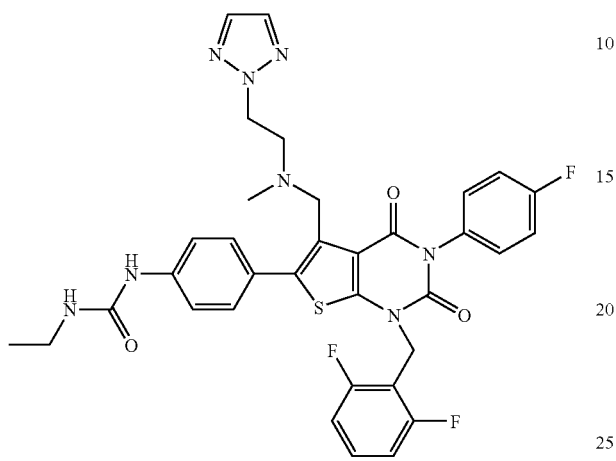

Preparation of N-(4-(1-(2,6-difluorobenzyl)-3-(4-fluorophenyl)-5-((methyl(2-(1H-1,2,3-triazol-1-yl)ethyl)amino)methyl)-2,4-dioxo-1,2,3,4-tetrahydrothieno[2,3-d]pyrimidin-6-yl)phenyl)-N'-ethylurea (2)

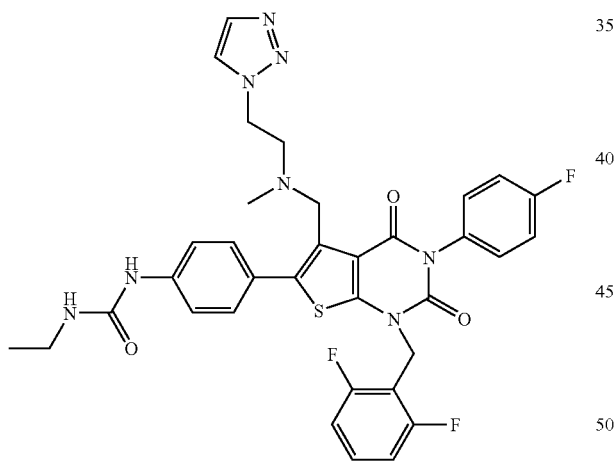

The similar reaction to that of Example 125 was performed using N-(4-{1-(2,6-difluorobenzyl)-3-(4-fluorophenyl)-5-[(methylamino)methyl]-2,4-dioxo-1,2,3,4-tetrahydrothieno[2,3-d]pyrimidin-6-yl}phenyl)-N'-ethylurea (594 mg, 1 mmol) and 1,2,3-triazole (0.69 g, 10 mmol) to give the title compounds 2-yl product (97 mg, 14%) and 1-yl product (381 mg, 56%) as colorless crystals, respectively.

2-yl Product (1)
$^1$H-NMR(CDCl$_3$) δ: 1.19 (3H, t, J=7.2 Hz), 2.22 (3H, s), 2.98 (2H, t, J=6.4 Hz), 3.25-3.45 (2H, m), 3.77 (2H, s), 4.44 (2H, t, J=6.4 Hz), 4.6-4.7 (1H, m), 5.36 (2H, s), 6.30 (1H, s), 6.93 (2H, t, J=8.2 Hz), 7.1-7.5 (11H, m).
Elemental analysis for C$_{34}$H$_{31}$F$_3$N$_8$O$_3$S.0.5H$_2$O
Calculated: C, 58.53; H, 4.62; N, 16.06. Found: C, 58.40; H, 4.51; N, 15.90.

1-yl Product (2)
$^1$H-NMR(CDCl$_3$) δ: 1.19 (3H, t, J=7.2 Hz), 2.16 (3H, s), 2.82 (2H, t, J=5.8 Hz), 3.2-3.4 (2H, m), 3.78 (2H, s), 4.40 (2H, t, J=5.8 Hz), 5.0-5.1 (1H, m), 5.36 (2H, s), 6.88 (1H, s), 6.92 (2H, t, J=8.2 Hz), 7.15-7.4 (9H, m), 7.50 (1H, s), 7.55 (1H, s).
Elemental analysis for C$_{34}$H$_{31}$F$_3$N$_8$O$_3$S.0.5H$_2$O
Calculated: C, 58.53; H, 4.62; N, 16.06. Found: C, 58.34; H, 4.58; N, 15.91.

Example 129

Preparation of N-(4-(1-(2,6-difluorobenzyl)-3-(4-fluorophenyl)-5-((methyl(2-(2H-tetrazol-2-yl)ethyl)amino)methyl)-2,4-dioxo-1,2,3,4-tetrahydrothieno[2,3-d]pyrimidin-6-yl)phenyl)-N'-ethylurea (1)

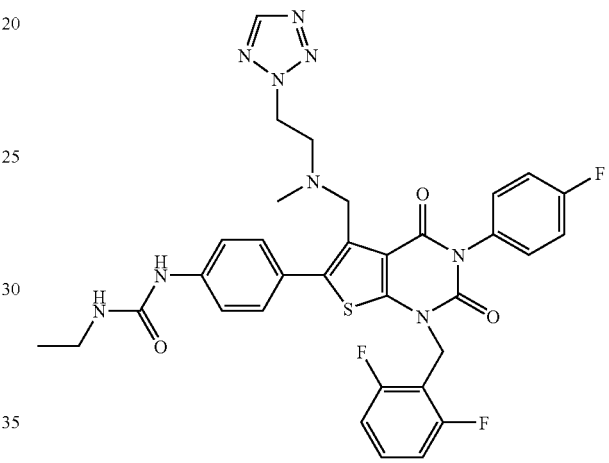

Preparation of N-(4-(1-(2,6-difluorobenzyl)-3-(4-fluorophenyl)-5-((methyl(2-(1H-tetrazol-1-yl)ethyl)amino)methyl)-2,4-dioxo-1,2,3,4-tetrahydrothieno[2,3-d]pyrimidin-6-yl)phenyl)-N'-ethylurea (2)

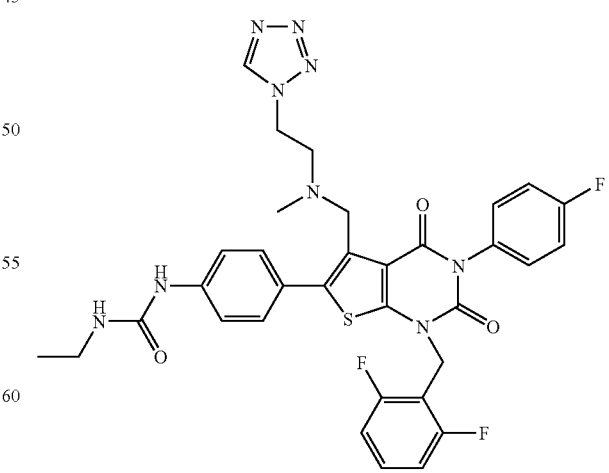

The similar reaction to that of Example 125 was performed using N-(4-{1-(2,6-difluorobenzyl)-3-(4-fluorophenyl)-5-[(methylamino)methyl]-2,4-dioxo-1,2,3,4-tetrahydrothieno

[2,3-d]pyrimidin-6-yl}phenyl)-N'-ethylurea (594 mg, 1 mmol) and tetrazole (0.70 g, 10 mmol) to give the title compounds 2-yl product (100 mg, 14%) and 1-yl product (324 mg, 47%) as colorless crystals, respectively.

2-yl Product (1)

$^1$H-NMR(CDCl$_3$) δ: 1.19 (3H, t, J=7.4 Hz), 2.24 (3H, s), 3.01 (2H, t, J=6.2 Hz), 3.25-3.45 (2H, m), 3.77 (2H, s), 4.63 (2H, t, J=6.2 Hz), 4.7-4.8 (1H, m), 5.36 (2H, s), 6.42 (1H, s), 6.93 (2H, t, J=7.8 Hz), 7.1-7.4 (9H, m), 8.29 (1H, s).

Elemental analysis for C$_{33}$H$_{30}$F$_3$N$_9$O$_3$S.0.5H$_2$O

Calculated: C, 56.73; H, 4.47; N, 18.04. Found: C, 56.99; H, 4.32; N, 17.93.

1-yl Product (2)

$^1$H-NMR(CDCl$_3$) δ: 1.20 (3H, t, J=7.4 Hz), 2.08 (3H, s), 2.65-2.75 (2H, m), 3.25-3.45 (2H, m), 3.77 (2H, s), 4.35-4.45 (2H, m), 4.9-5.0 (1H, m), 5.36 (2H, s), 6.64 (1H, s), 6.91 (2H, t, J=8.2 Hz), 7.15-7.4 (9H, m), 8.53 (1H, s).

Elemental analysis for C$_{33}$H$_{30}$F$_3$N$_9$O$_3$S

Calculated: C, 57.47; H, 4.38; N, 18.28. Found: C, 57.20; H, 4.29; N, 18.13.

Example 130

Preparation of N-(4-(1-(2,6-difluorobenzyl)-5-((methyl(2-(1H-1,2,3-triazol-1-yl)propyl)amino)methyl)-2,4-dioxo-3-phenyl-1,2,3,4-tetrahydrothieno[2,3-d]pyrimidin-6-yl)phenyl)-N'-ethylurea

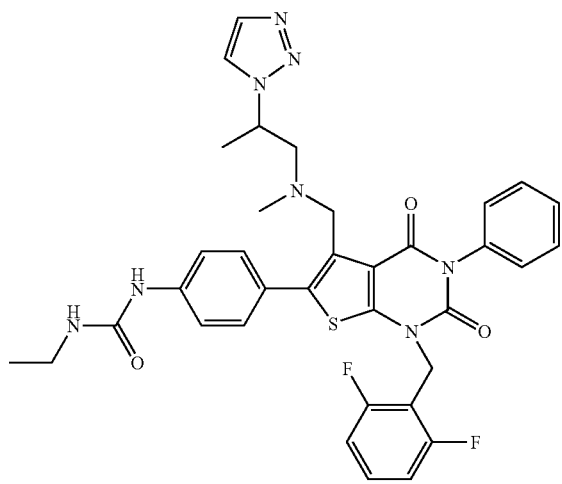

The similar reaction to that of Example 19 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (200 mg, 0.347 mmol) and the compound of Reference Example 23 (0.515 g, 4.05 mmol) to give the title compound (38 mg, 16%) as light yellow crystals.

$^1$H-NMR(CDCl$_3$) δ: 1.18 (3H, t, J=7.0 Hz), 1.43 (3H, d, J=6.2 Hz), 2.03 (3H, s), 2.55-2.8 (1H, m), 2.85-3.05 (1H, m), 3.2-3.4 (2H, m), 3.65-3.85 (2H, m), 4.7-4.85 (1H, m), 5.05-5.15 (1H, m), 5.37 (2H, s), 6.85-7.0 (3H, m), 7.2-7.6 (12H, m).

Example 131

Preparation of N-(4-(1-(2,6-difluorobenzyl)-3-(4-fluorophenyl)-5-((methyl(2-(1H-1,2,3-triazol-1-yl)propyl)amino)methyl)-2,4-dioxo-1,2,3,4-tetrahydrothieno[2,3-d]pyrimidin-6-yl)phenyl)-N'-ethylurea

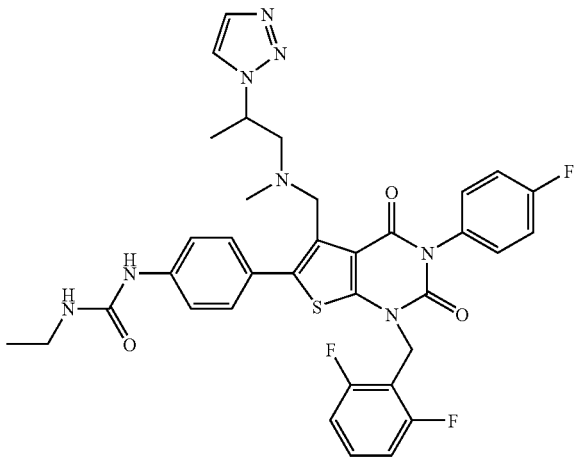

The similar reaction to that of Example 19 was performed using N-(4-{1-(2,6-difluorobenzyl)-3-(4-fluorophenyl)-5-[(methylamino)methyl]-2,4-dioxo-1,2,3,4-tetrahydrothieno[2,3-d]pyrimidin-6-yl}phenyl)-N'-ethylurea (110 mg, 0.185 mmol) and the compound of Reference Example 23 (0.515 g, 4.05 mmol) to give the title compound (12 mg, 9%) as colorless crystals.

$^1$H-NMR(CDCl$_3$) δ: 1.20 (3H, t, J=7.2 Hz), 1.43 (3H, d, J=6.6 Hz), 2.07 (3H, s), 2.5-2.7 (1H, m), 2.85-3.05 (1H, m), 3.2-3.4 (2H, m), 3.65-3.85 (2H, m), 4.7-4.85 (1H, m), 4.9-5.0 (1H, m), 5.36 (2H, s), 6.68 (1H, s), 6.92 (2H, t, J=7.8 Hz), 7.1-7.45 (10H, m), 7.52 (1H, s).

Example 132

Preparation of N-(4-(1-(2,6-difluorobenzyl)-5-((methyl(2-(1H-tetrazol-1-yl)propyl)amino)methyl)-2,4-dioxo-3-phenyl-1,2,3,4-tetrahydrothieno[2,3-d]pyrimidin-6-yl)phenyl)-N'-ethylurea

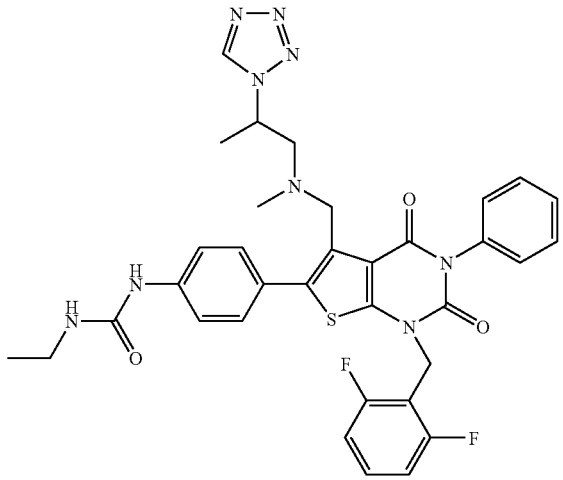

The similar reaction to that of Example 19 was performed using N-(4-{1-(2,6-difluorobenzyl)-3-phenyl-5-[(methylamino)methyl]-2,4-dioxo-1,2,3,4-tetrahydrothieno[2,3-d]pyrimidin-6-yl}phenyl)-N'-ethylurea (150 mg, 0.261 mmol) and the compound of Reference Example 21 (0.435 g, 3.385 mmol) to give the title compound (44 mg, 25%) as light yellow crystals.

$^1$H-NMR(CDCl$_3$) δ: 1.20 (3H, t, J=7.2 Hz), 1.46 (3H, d, J=6.6 Hz), 2.45-2.55 (1H, m), 2.85-2.95 (1H, m), 3.25-3.4 (2H, m), 3.59 (1H, d, J=12.0 Hz), 4.75-4.85 (1H, m), 4.91 (1H, t, J=5.4 Hz), 5.29 (1H, d, J=15.7 Hz), 5.43 (1H, d, J=15.7 Hz), 6.60 (1H, s), 6.90 (2H, t, J=8.1 Hz), 7.2-7.6 (10H, m), 8.50 (1H, s).

Example 133

Preparation of N-(4-(1-(2,6-difluorobenzyl)-5-(((2-methoxyethyl)(methyl)amino)methyl)-3-(2-methoxy-3-pyridinyl)-2,4-dioxo-1,2,3,4-tetrahydrothieno[2,3-d]pyrimidin-6-yl)phenyl)-N'-ethylurea

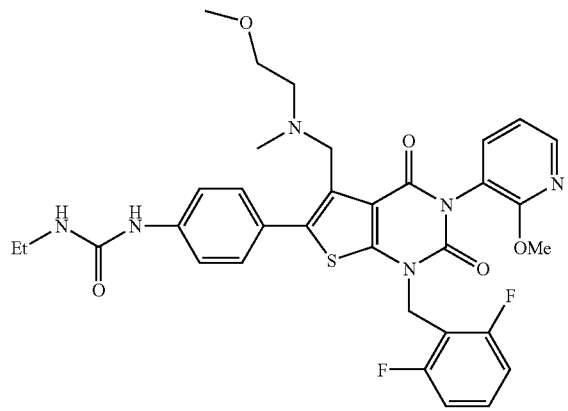

Diethyl phosphorocyanidate (289 mg) and N-ethyl diisopropylamine (336 µl) were added to a solution of the compound obtained in Reference Example 9 (560 mg) and 2-methoxy-3-aminopyridine (220 mg) in DMF (8.8 ml) with ice-cooling, the mixture was allowed to return to room temperature slowly and was stirred for 13 hours, and then the reaction solution was partitioned between ethyl acetate and water. The organic layer was washed with water and saturated brine sequentially, and was dried over anhydrous sodium sulfate. The residue obtained by distilling off the solvent under reduced pressure, was purified by aminopropyl silica gel (manufactured by Fuji Silysia Chemical Ltd.) chromatography to give the crude amide product (546 mg), which was then dissolved in ethanol (29 ml), followed by addition of a 28% solution of sodium methoxide in methanol (280 mg) and the mixture was stirred at room temperature for 1.5 hours. After neutralizing it with 1 N-hydrochloric acid (1.45 ml), the solvent was distilled off and the residue was partitioned between ethyl acetate and water. The organic layer was washed with water and saturated brine sequentially, and was dried over anhydrous sodium sulfate. The residue obtained by distilling off the solvent under reduced pressure, was purified by silica gel chromatography (Merck Co.; 45 g; eluent: 4% methanol-containing chloroform→5% (5% ammonia-containing methanol)-containing chloroform to give the title compound (370 mg) as colorless powder.

Elemental analysis for $C_{33}H_{34}N_6O_5SF_2 \cdot 0.5H_2O$

Calculated: C, 58.83; H, 5.24; N, 12.47. Found: C, 59.09; H, 5.22; N, 12.62.

$^1$H-NMR (CDCl$_3$) δ: 1.07 (3H, t, J=7.1 Hz), 2.12 (3H, s), 2.60 (2H, t, J=5.7 Hz), 3.22 (3H, s), 3.39 (2H, t, J=5.7 Hz), 3.71 (1H, d, J=12.0 Hz), 3.91 (3H, s), 3.92 (1H, d, J=12.0 Hz), 5.25-5.46 (3H, m), 6.91 (2H, t, J=8.0 Hz), 6.98-7.01 (1H, m), 7.22-7.48 (6H, m), 7.56 (1H, d, J=7.4 Hz), 8.20 (1H, d, J=5.2 Hz).

IR (KBr): 1715, 1674, 1597, 1537, 1472, 1314 cm$^{-1}$.

Example 134

Preparation of N-(4-(1-(2,6-difluorobenzyl)-5-(((2-methoxyethyl)(methyl)amino)methyl)-2,4-dioxo-3-(2-pyridinylmethyl)-1,2,3,4-tetrahydrothieno[2,3-d]pyrimidin-6-yl)phenyl)-N'-ethylurea

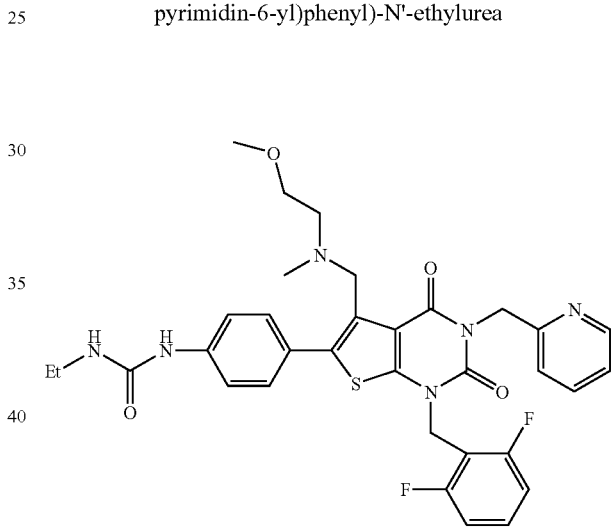

The similar reaction to that of Example 133 was performed to obtain the crude amide product (180 mg) from the compound obtained in Reference Example 9 (303 mg), diethyl phosphorocyanidate (152 µl), N-ethyl diisopropylamine (190 µl) and 2-aminomethylpyridine (109 mg), and then ethanol (12.5 ml) and a 28% solution of sodium methoxide in methanol (97 mg) were used to give the title compound (95 mg) as colorless powder.

Elemental analysis for $C_{33}H_{34}N_6O_4SF_2 \cdot 0.5H_2O$

Calculated: C, 60.26; H, 5.36; N, 12.78. Found: C, 60.28; H, 5.37; N, 12.60.

$^1$H-NMR (CDCl$_3$) δ: 1.10 (3H, t, J=7.2 Hz), 1.98 (3H, s), 2.53 (2H, t, J=5.9 Hz), 3.22 (3H, s), 3.21-3.31 (2H, m), 3.37 (2H, t, J=5.9 Hz), 3.73 (2H, s), 5.03 (1H, t, J=5.4 Hz), 5.12 (2H, s), 5.41 (2H, s), 6.90 (2H, t, J=8.1 Hz), 7.08 (2H, d, J=8.4 Hz), 7.20-7.32 (4H, m), 7.42 (1H, d, J=7.8 Hz), 7.74 (1H, dt, J=1.8 Hz, 7.8 Hz), 8.33 (1H, s), 8.51 (1H, d, J=3.9 Hz).

IR (KBr): 1707, 1667, 1593, 1537, 1472, 1316, 1236 cm$^{-1}$.

Example 135

Preparation of N-(4-(1-(2,6-difluorobenzyl)-5-(((2-methoxyethyl)(methyl)amino)methyl)-2,4-dioxo-3-(3-pyridinylmethyl)-1,2,3,4-tetrahydrothieno[2,3-d]pyrimidin-6-yl)phenyl)-N'-ethylurea

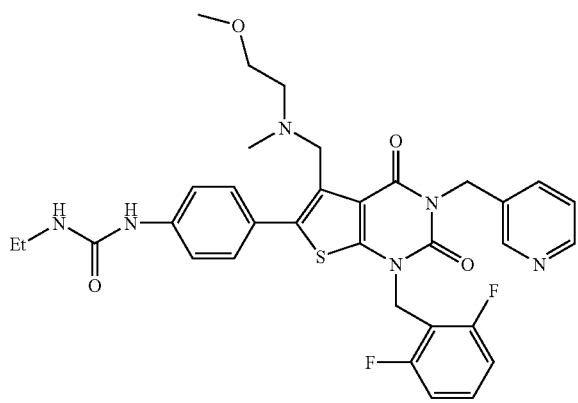

The similar reaction to that of Example 133 was performed to obtain the crude amide product (205 mg) from the compound of Reference Example 9 (303 mg), diethyl phosphorocyanidate (152 µl), N-ethyl diisopropylamine (190 µl) and 3-aminomethylpyridine (109 mg), and then ethanol (14.4 ml) and a 28% solution of sodium methoxide in methanol (111 mg) were used to give the title compound (134 mg) as colorless powder.

Elemental analysis for $C_{33}H_{34}N_6O_4SF_2 \cdot 0.5H_2O$

Calculated: C, 60.26; H, 5.36; N, 12.78. Found: C, 60.32; H, 5.51; N, 12.67.

$^1$H-NMR (CDCl$_3$) δ: 1.16 (3H, t, J=7.2 Hz), 2.10 (3H, s), 2.63 (2H, t, J=5.9 Hz), 3.28 (3H, s), 3.25-3.34 (2H, m), 3.44 (2H, t, J=5.9 Hz), 3.82 (2H, s), 4.92 (1H, t, J=5.6 Hz), 5.25 (2H, s), 5.32 (2H, s), 6.71 (1H, s), 6.87 (2H, t, J=8.1 Hz), 7.21-7.29 (2H, m), 7.33 (2H, d, J=8.7 Hz), 7.44 (2H, d, J=8.7 Hz), 7.83 (1H, dt, J=1.8 Hz, 7.8 Hz), 8.50 (1H, dd, J=1.8 Hz, 4.8 Hz), 8.76 (1H, d, J=1.8 Hz)

IR (KBr): 1705, 1661, 1593, 1537, 1472, 1318, 1236 cm$^{-1}$.

Example 136

Preparation of N-(4-(1-(2,6-difluorobenzyl)-5-(((2-methoxyethyl)(methyl)amino)methyl)-2,4-dioxo-3-(4-pyridinylmethyl)-1,2,3,4-tetrahydrothieno[2,3-d]pyrimidin-6-yl)phenyl)-N'-ethylurea

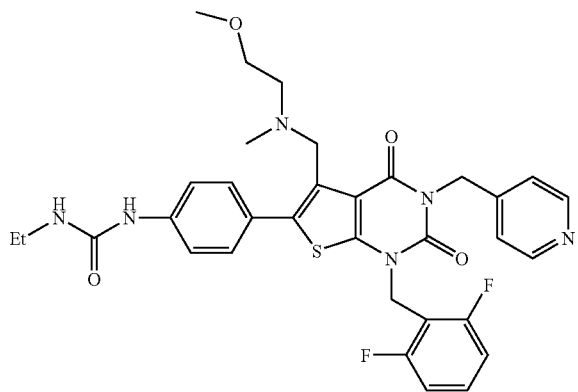

The similar reaction to that of Example 133 was performed to obtain the crude amide product (189 mg) from the compound obtained in Reference Example 9 (303 mg), diethyl phosphorocyanidate (152 µl), N-ethyl diisopropylamine (190 µl) and 4-aminomethylpyridine (109 mg), and then ethanol (13 ml) and a 28% solution of sodium methoxide in methanol (101 mg) were used to give the title compound (70 mg) as colorless powder.

Elemental analysis for $C_{33}H_{34}N_6O_4SF_2$

Calculated: C, 61.10; H, 5.28; N, 12.95. Found: C, 61.05; H, 5.32; N, 12.79.

$^1$H-NMR (CDCl$_3$) δ: 1.16 (3H, t, J=7.2 Hz), 2.11 (3H, s), 2.62 (2H, t, J=5.7 Hz), 3.27 (3H, s), 3.21-3.34 (2H, m), 3.43 (2H, t, J=5.7 Hz), 3.82 (2H, s), 4.88 (1H, t, J=5.6 Hz), 5.24 (2H, s), 5.34 (2H, s), 6.73 (1H, s), 6.89 (2H, t, J=8.1 Hz), 7.23-7.31 (3H, m), 7.36 (2H, d, J=8.7 Hz), 7.47 (2H, d, J=8.7 Hz), 8.53 (2H, dd, J=1.5 Hz, 4.5 Hz).

IR (KBr): 1707, 1667, 1595, 1534, 1472, 1316, 1236 cm$^{-1}$.

Example 137

Preparation of N-[4-(1-(2,6-difluorobenzyl)-5-{[(2-ethoxyethyl)(methyl)amino]methyl}-2,4-dioxo-3-(2-pyridyl)-1,2,3,4-tetrahydrothieno[2,3-d]pyrimidin-6-yl)phenyl]-N'-ethylurea

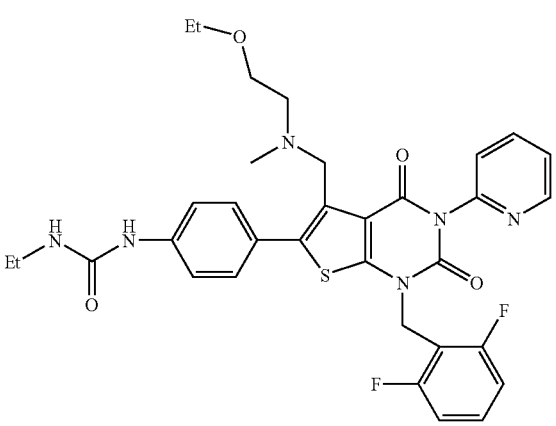

The similar reaction to that of Example 133 was performed to obtain the crude amide product (5.20 g) from the compound obtained in Reference Example 24 (7.42 g), diethyl phosphorocyanidate (6.52 g), N-ethyl diisopropylamine (6.46 g) and 2-aminopyrimidine (1.90 g), and then methanol (50 ml) and sodium methoxide (4.05 g) were used to give the title compound (2.05 g) as colorless powder.

Elemental analysis for $C_{33}H_{34}N_6O_4SF_2$

Calculated: C, 61.10; H, 5.28; N, 12.95. Found: C, 60.85; H, 5.42; N, 12.91.

$^1$H-NMR (CDCl$_3$) δ: 1.10 (6H, t, J=7.1 Hz), 2.11 (3H, s), 2.61 (2H, t, J=6.0 Hz), 3.20-3.29 (2H, m), 3.37 (2H, q, J=7.1 Hz), 3.43 (2H, t, J=6.0 Hz), 3.77 (2H, brs), 5.13 (1H, t, J=5.4 Hz), 5.37 (2H, brs), 6.90 (2H, t, J=8.0 Hz), 7.24-7.44 (8H, m), 7.90 (1H, dt, J=2.1 Hz, 7.8 Hz), 8.65-8.68 (1H, m).

IR (KBr): 1717, 1672, 1593, 1532, 1460 cm$^{-1}$.

Example 138

Preparation of N-(4-(1-(2,6-difluorobenzyl)-3-(5-fluoro-2-pyridinyl)-5-(((2-methoxyethyl)(methyl)amino)methyl)-2,4-dioxo-1,2,3,4-tetrahydrothieno[2,3-d]pyrimidin-6-yl)phenyl)-N'-ethylurea

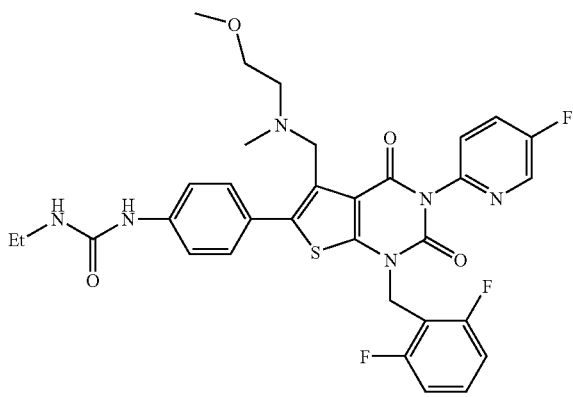

The similar reaction to that of Example 133 was performed to obtain the crude amide product (218 mg) from the compound obtained in Reference Example 9 (303 mg), diethyl phosphorocyanidate (152 µl), N-ethyl diisopropylamine (190 µl) and 2-amino-5-fluoropyridine (113 mg), and then ethanol (12.5 ml) and a 28% solution of sodium methoxide in methanol (116 mg) were used to give the title compound (159 mg) as colorless powder.

Elemental analysis for $C_{32}H_{31}N_6O_4SF_3$

Calculated: C, 58.89; H, 4.79; N, 12.88. Found: C, 58.59; H, 4.83; N, 12.71.

$^1$H-NMR (CDCl$_3$) δ: 1.14 (3H, t, J=7.2 Hz), 2.11 (3H, s), 2.60 (2H, t, J=5.9 Hz), 3.24 (3H, s), 3.23-3.32 (2H, m), 3.40 (2H, t, J=5.9 Hz), 3.79 (2H, brs), 4.91 (1H, t, J=5.6 Hz), 5.28 (2H, brs), 6.76 (1H, s), 6.90 (2H, t, J=8.1 Hz), 7.24-7.39 (4H, m), 7.50 (2H, d, J=8.7 Hz), 7.55-7.61 (1H, m), 8.50 (1H, d, J=3.0 Hz).

IR (KBr): 1715, 1674, 1593, 1532, 1462 cm$^{-1}$.

Example 139

Preparation of N-(4-(3-(5-chloro-2-pyridinyl)-1-(2,6-difluorobenzyl)-5-(((2-methoxyethyl)(methyl)amino)methyl)-2,4-dioxo-1,2,3,4-tetrahydrothieno[2,3-d]pyrimidin-6-yl)phenyl)-N'-ethylurea

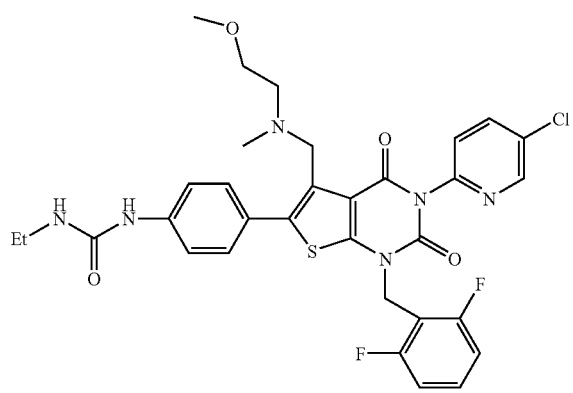

The similar reaction to that of Example 133 was performed to obtain the crude amide product (256 mg) from the compound obtained in Reference Example 9 (363 mg), diethyl phosphorocyanidate (182 µl), N-ethyl diisopropylamine (228 µl) and 2-amino-5-chloropyridine (155 mg), and then ethanol (17.8 ml) and a 28% solution of sodium methoxide in methanol (138 mg) were used to give the title compound (119 mg) as colorless powder.

Elemental analysis for $C_{32}H_{31}N_6O_4SClF_2 \cdot 0.75H_2O$

Calculated: C, 56.30; H, 4.80; N, 12.31. Found: C, 56.25; H, 4.67; N, 12.13.

$^1$H-NMR (CDCl$_3$) δ: 1.13 (3H, t, J=7.2 Hz), 2.11 (3H, s), 2.59 (2H, t, J=5.7 Hz), 3.24 (3H, s), 3.22-3.31 (2H, m), 3.39 (2H, t, J=5.7 Hz), 3.77 (2H, brs), 5.02 (1H, t, J=5.4 Hz), 5.28 (2H, brs), 6.90 (2H, t, J=8.3 Hz), 6.91 (1H, s), 7.25-7.37 (4H, m), 7.48 (2H, d, J=8.7 Hz), 7.83 (1H, dd, J=2.7 Hz, 8.4 Hz), 8.59 (1H, d, J=2.7 Hz).

IR (KBr): 2975, 1717, 1674, 1593, 1532, 1456 cm$^{-1}$.

Example 140

Preparation of N-(4-(3-(5-bromo-2-pyridinyl)-1-(2,6-difluorobenzyl)-5-(((2-methoxyethyl)(methyl)amino)methyl)-2,4-dioxo-1,2,3,4-tetrahydrothieno[2,3-d]pyrimidin-6-yl)phenyl)-N'-ethylurea

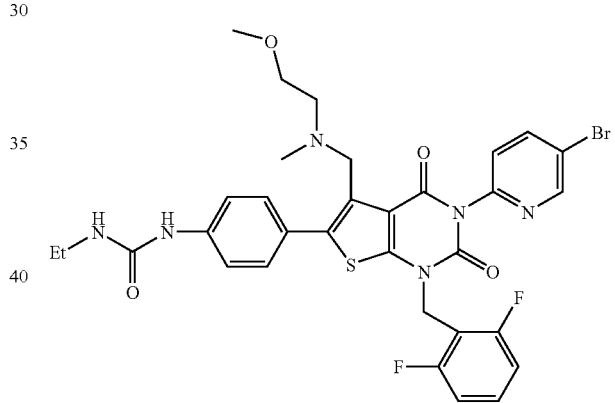

The similar reaction to that of Example 133 was performed to obtain the crude amide product (230 mg) from the compound obtained in Reference Example 9 (363 mg), diethyl phosphorocyanidate (182 µl), N-ethyl diisopropylamine (228 µl) and 2-amino-5-bromopyridine (208 mg), and then ethanol (15 ml) and a 28% solution of sodium methoxide in methanol (116 mg) were used to give the title compound (84 mg) as colorless powder.

Elemental analysis for $C_{32}H_{31}N_6O_4SBrF_2 \cdot 0.5H_2O$

Calculated: C, 53.19; H, 4.46; N, 11.63. Found: C, 53.33; H, 4.53; N, 11.62.

$^1$H-NMR (CDCl$_3$) δ: 1.10 (3H, t, J=7.2 Hz), 2.10 (3H, s), 2.59 (2H, t, J=5.9 Hz), 3.23 (3H, s), 3.19-3.28 (2H, m), 3.39 (2H, t, J=5.9 Hz), 3.77 (2H, brs), 5.22 (1H, t, J=5.6 Hz), 5.27 (2H, brs), 6.90 (2H, t, J=8.1 Hz), 7.18 (1H, s), 7.23-7.34 (1H, m), 7.29 (1H, d, J=8.4 Hz), 7.35 (2H, d, J=8.4 Hz), 7.45 (2H, d, J=8.4 Hz), 7.97 (1H, dd, J=2.4 Hz, 8.4 Hz), 8.69 (1H, d, J=2.4 Hz).

IR (KBr): 2976, 1717, 1674, 1593, 1532, 1456 cm$^{-1}$.

Example 141

Preparation of N-[4-(1-(2,6-difluorobenzyl)-5-{[(2-methoxyethyl)(methyl)amino]methyl}-2,4-dioxo-3-(5-methyl-2-pyridyl)-1,2,3,4-tetrahydrothieno[2,3-d]pyrimidin-6-yl)phenyl]-N'-ethylurea

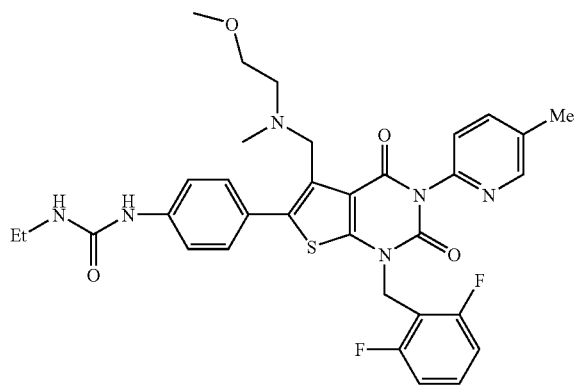

The similar reaction to that of Example 133 was performed to obtain the crude amide product (275 mg) from the compound obtained in Reference Example 9 (363 mg), diethyl phosphorocyanidate (182 μl), N-ethyl diisopropylamine (228 μl) and 2-amino-5-methylpyridine (130 mg), and then ethanol (19.8 ml) and a 28% solution of sodium methoxide in methanol (153 mg) were used to give the title compound (196 mg) as colorless powder.

Elemental analysis for $C_{33}H_{34}N_6O_4SF_2 \cdot 0.75H_2O$

Calculated: C, 59.85; H, 5.40; N, 12.69. Found: C, 59.79; H, 5.20; N, 12.51.

$^1$H-NMR (CDCl$_3$) δ: 1.08 (3H, t, J=7.1 Hz), 2.09 (3H, s), 2.39 (3H, s), 2.58 (2H, t, J=5.7 Hz), 3.22 (3H, s), 3.17-3.26 (2H, m), 3.38 (2H, t, J=5.7 Hz), 3.67 (1H, brs), 3.85 (1H, brs), 5.09 (1H, brs), 5.31 (1H, t, J=5.4 Hz), 5.37 (1H, brs), 6.88 (2H, t, J=8.1 Hz), 7.22-7.31 (1H, m), 7.28 (1H, d, J=8.1 Hz), 7.33 (2H, d, J=8.7 Hz), 7.38 (2H, d, J=8.7 Hz), 7.55 (1H, s), 7.69 (1H, dd, J=2.4 Hz, 8.1 Hz), 8.46 (1H, d, J=2.4 Hz).

IR (KBr): 2976, 1715, 1669, 1593, 1532, 1462 cm$^{-1}$.

Example 142

Preparation of N-[4-(1-(2,6-difluorobenzyl)-5-{[(2-methoxyethyl)(methyl)amino]methyl}-2,4-dioxo-3-(6-methyl-2-pyridyl)-1,2,3,4-tetrahydrothieno[2,3-d]pyrimidin-6-yl)phenyl]-N'-ethylurea

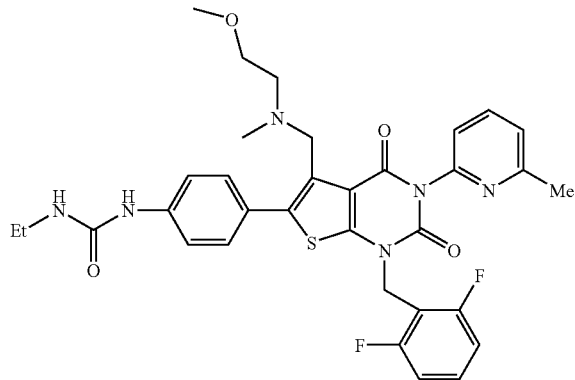

The similar reaction to that of Example 133 was performed to obtain the crude amide product (275 mg) from the compound obtained in Reference Example 9 (363 mg), diethyl phosphorocyanidate (182 μl), N-ethyl diisopropylamine (228 μl) and 2-amino-6-methylpyridine (130 mg), and then ethanol (19.8 ml) and a 28% solution of sodium methoxide in methanol (153 mg) were used to give the title compound (195 mg) as colorless powder.

Elemental analysis for $C_{33}H_{34}N_6O_4SF_2 \cdot H_2O$

Calculated: C, 59.45; H, 5.44; N, 12.60. Found: C, 59.41; H, 5.25; N, 12.49.

$^1$H-NMR (CDCl$_3$) δ: 1.09 (3H, t, J=7.2 Hz), 2.08 (3H, s), 2.59 (2H, t, J=6.0 Hz), 2.61 (3H, s), 3.23 (3H, s), 3.18-3.27 (2H, m), 3.38 (2H, t, J=6.0 Hz), 3.62 (1H, d, J=12.3 Hz), 3.92 (1H, d, J=12.3 Hz), 4.93 (1H, d, J=15.6 Hz), 5.17 (1H, t, J=5.6 Hz), 5.46 (1H, d, J=15.6 Hz), 6.89 (2H, t, J=8.4 Hz), 7.21 (1H, d, J=7.8 Hz), 7.26 (1H, d, J=7.8 Hz), 7.27-7.38 (5H, m), 7.62 (1H, s), 7.79 (1H, t, J=7.8 Hz).

IR (KBr): 2975, 1715, 1672, 1601, 1532, 1456 cm$^{-1}$.

Example 143

Preparation of N-(4-(1-(2,6-difluorobenzyl)-5-(((2-ethoxyethyl)(methyl)amino)methyl)-3-(2-pyrimidinyl)-2,4-dioxo-1,2,3,4-tetrahydrothieno[2,3-d]pyrimidin-6-yl)phenyl)-N'-ethylurea

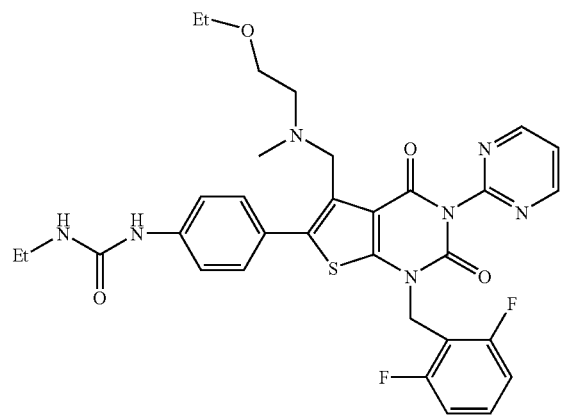

The similar reaction to that of Example 133 was performed to obtain the crude amide product (87 mg) from the compound obtained in Reference Example 24 (372 mg), diethyl phosphorocyanidate (228 μl), N-ethyl diisopropylamine (310 μl) and 2-aminopyrimidine (143 mg), and then methanol (6 ml) and a 28% solution of sodium methoxide in methanol (46 mg) were used to give the title compound (47 mg) as colorless powder.

Elemental analysis for $C_{32}H_{33}N_7O_4SF_2 \cdot H_2O$

Calculated: C, 57.56; H, 5.28; N, 14.68. Found: C, 57.66; H, 5.26; N, 14.28.

$^1$H-NMR (CDCl$_3$) δ: 1.11 (3H, t, J=6.9 Hz), 1.13 (3H, t, J=6.9 Hz), 2.16 (3H, s), 2.60 (2H, t, J=6.2 Hz), 3.21-3.30 (2H, m), 3.38 (2H, q, J=6.9 Hz), 3.44 (2H, t, J=6.2 Hz), 3.79 (2H, s), 5.09 (1H, t, J=5.6 Hz), 5.32 (2H, s), 6.90 (2H, t, J=8.1 Hz), 6.98 (1H, s), 7.24-7.31 (1H, m), 7.36 (2H, d, J=8.7 Hz), 7.41 (1H, t, J=4.8 Hz), 7.54 (2H, d, J=8.7 Hz), 8.91 (2H, d, J=4.8 Hz).

IR (KBr): 2975, 1717, 1674, 1593, 1532, 1472, 1406 cm$^{-1}$.

Example 144

Preparation of N-(4-(1-(2,6-difluorobenzyl)-5-(((2-ethoxyethyl)(methyl)amino)methyl)-3-(3-methoxy-6-methyl-2-pyridinyl)-2,4-dioxo-1,2,3,4-tetrahydrothieno[2,3-d]pyrimidin-6-yl)phenyl)-N'-ethylurea

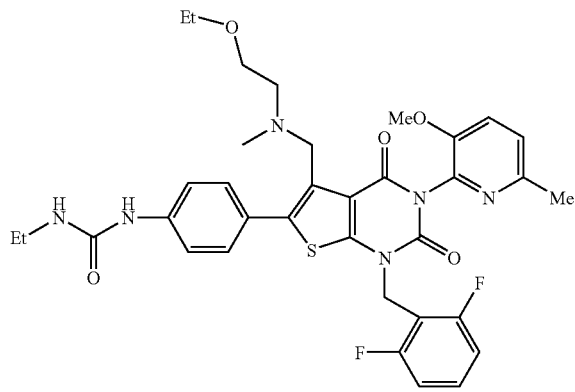

The similar reaction to that of Example 133 was performed to obtain the crude amide product (265 mg) from the compound obtained in Reference Example 9 (464 mg), diethyl phosphorocyanidate (228 μl), N-ethyl diisopropylamine (310 μl) and 2-amino-3-methoxy-6-methylpyridine (208 mg), and then methanol (17.5 ml) and a 28% solution of sodium methoxide in methanol (135 mg) were used to give the title compound (217 mg) as colorless powder.

Elemental analysis for $C_{35}H_{38}N_6O_5SF_2 \cdot 0.5H_2O$

Calculated: C, 59.90; H, 5.60; N, 11.98. Found: C, 60.11; H, 5.41; N, 12.01.

$^1$H-NMR (CDCl$_3$) δ: 1.08 (3H, t, J=7.2 Hz), 1.10 (3H, t, J=6.9 Hz), 2.15 (3H, s), 2.51 (3H, s), 2.60 (2H, t, J=6.2 Hz), 3.17-3.26 (2H, m), 3.37 (2H, q, J=6.9 Hz), 3.42 (2H, t, J=6.2 Hz), 3.78 (5H, s), 5.15 (1H, d, J=15.9 Hz), 5.20 (1H, t, J=5.7 Hz), 5.41 (1H, d, J=15.9 Hz), 6.88 (2H, t, J=8.1 Hz), 7.19-7.33 (6H, m), 7.47 (2H, d, J=8.7 Hz).

IR (KBr): 2975, 1715, 1672, 1593, 1534, 1470 cm$^{-1}$.

Example 145

Preparation of N-(4-(1-(2,6-difluorobenzyl)-5-(((2-methoxyethyl)(methyl)amino)methyl)-3-(3-methoxy-6-methyl-2-pyridinyl)-2,4-dioxo-1,2,3,4-tetrahydrothieno[2,3-d]pyrimidin-6-yl)phenyl)-N'-ethylurea

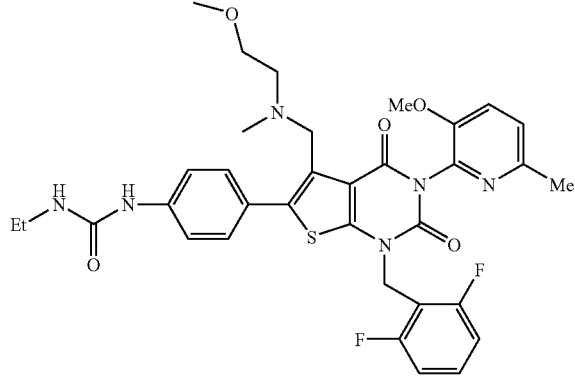

The similar reaction to that of Example 133 was performed to obtain the crude amide product (291 mg) from the compound obtained in Reference Example 9 (454 mg), diethyl phosphorocyanidate (227 μl), N-ethyl diisopropylamine (310 μl) and 2-amino-3-methoxy-6-methylpyridine (208 mg), and then methanol (19 ml) and a 28% solution of sodium methoxide in methanol (147 mg) were used to give the title compound (138 mg) as colorless powder.

Elemental analysis for $C_{34}H_{36}N_6O_5SF_2 \cdot 0.5H_2O$

Calculated: C, 59.38; H, 5.42; N, 12.22. Found: C, 59.24; H, 5.47; N, 11.95.

$^1$H-NMR (CDCl$_3$) δ: 1.05 (3H, t, J=7.2 Hz), 2.12 (3H, s), 2.50 (3H, s), 2.58 (2H, t, J=5.9 Hz), 3.14-3.23 (2H, m), 3.21 (3H, s), 3.37 (2H, t, J=5.9 Hz), 3.74 (1H, d, J=12.3 Hz), 3.78 (3H, s), 3.81 (1H, d, J=12.3 Hz), 5.16 (1H, d, J=15.6 Hz), 5.41 (1H, d, J=15.6 Hz), 5.42 (1H, t, J=5.7 Hz), 6.87 (2H, t, J=8.0 Hz), 7.19-7.28 (3H, m), 7.32 (2H, d, J=8.4 Hz), 7.41 (2H, d, J=8.4 Hz), 7.67 (1H, s).

IR (KBr): 2975, 1715, 1669, 1593, 1532, 1470 cm$^{-1}$.

Example 146

Preparation of N-(4-(1-(2,6-difluorobenzyl)-3-(4,6-dimethyl-2-pyridinyl)-5-(((2-methoxyethyl)(methyl)amino)methyl)-2,4-dioxo-1,2,3,4-tetrahydrothieno[2,3-d]pyrimidin-6-yl)phenyl)-N'-ethylurea

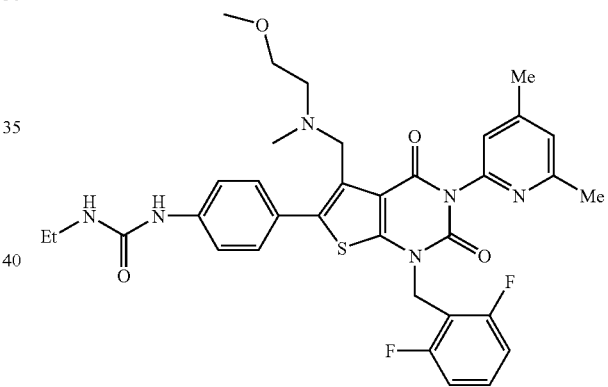

The similar reaction to that of Example 133 was performed to obtain the crude amide product (381 mg) from the compound obtained in Reference Example 9 (454 mg), diethyl phosphorocyanidate (227 μl), N-ethyl diisopropylamine (310 μl) and 2-amino-4,6-dimethylpyridine (184 mg), and then methanol (26 ml) and a 28% solution of sodium methoxide in methanol (200 mg) were used to give the title compound (182 mg) as colorless powder.

Elemental analysis for $C_{34}H_{36}N_6O_5SF_2 \cdot 0.5H_2O$

Calculated: C, 59.38; H, 5.42; N, 12.22. Found: C, 59.24; H, 5.47; N, 11.95.

$^1$H-NMR (CDCl$_3$) δ: 1.05 (3H, t, J=7.2 Hz), 2.12 (3H, s), 2.50 (3H, s), 2.58 (2H, t, J=5.9 Hz), 3.14-3.23 (2H, m), 3.21 (3H, s), 3.37 (2H, t, J=5.9 Hz), 3.74 (1H, d, J=12.3 Hz), 3.78 (3H, s), 3.81 (1H, d, J=12.3 Hz), 5.16 (1H, d, J=15.6 Hz), 5.41 (1H, d, J=15.6 Hz), 5.42 (1H, t, J=5.7 Hz), 6.87 (2H, t, J=8.0 Hz), 7.19-7.28 (3H, m), 7.32 (2H, d, J=8.4 Hz), 7.41 (2H, d, J=8.4 Hz), 7.67 (1H, s).

IR (KBr): 2975, 1715, 1669, 1593, 1532, 1470 cm$^{-1}$.

Example 147

Preparation of N-(4-(1-(2,6-difluorobenzyl)-3-(3-hydroxy-6-methyl-2-pyridinyl)-5-(((2-methoxyethyl)(methyl)amino)methyl)-2,4-dioxo-1,2,3,4-tetrahydrothieno[2,3-d]pyrimidin-6-yl)phenyl)-N'-ethylurea

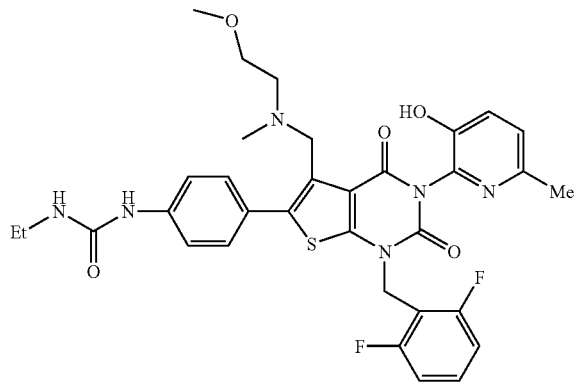

The similar reaction to that of Example 133 was performed to obtain the crude amide product (101 mg) from the compound obtained in Reference Example 9 (454 mg), 1-ethyl-3-(3-dimethylaminopropyl)-carbodiimide hydrochloride (306 mg), 1-hydroxybenzotriazole (288 mg), N-ethyl diisopropylamine (517 μl) and 2-amino-6-methyl-3-hydroxypyridine (187 mg), and then methanol (7 ml) and a 28% solution of sodium methoxide in methanol (54 mg) were used to give the title compound (70 mg) as colorless powder.

Elemental analysis for $C_{33}H_{34}N_6O_5SF_2 \cdot 1.5H_2O$

Calculated: C, 57.30; H, 5.39; N, 12.15. Found: C, 57.31; H, 5.45; N, 12.02.

$^1$H-NMR (CDCl$_3$+CD$_3$OD) δ: 1.13 (3H, t, J=7.3 Hz), 2.06 (3H, s), 2.49 (3H, s), 2.63 (2H, t, J=5.5 Hz), 3.20 (3H, s), 3.24 (2H, q, J=7.3 Hz), 3.40 (2H, t, J=5.5 Hz), 3.53 (1H, d, J=12.4 Hz), 4.18 (1H, d, J=12.4 Hz), 5.09 (1H, d, J=15.8 Hz), 5.30 (1H, d, J=15.8 Hz), 6.89 (2H, t, J=8.0 Hz), 7.15 (2H, d, J=8.4 Hz), 7.15 (1H, d, J=7.6 Hz), 7.22-7.31 (1H, m), 7.33 (1H, d, J=7.6 Hz), 7.41 (2H, d, J=8.4 Hz).

IR (KBr): 2976, 1715, 1669, 1593, 1537, 1472 cm$^{-1}$.

Example 148

Preparation of N-(4-(1-(2,6-difluorobenzyl)-5-(((2-ethoxyethyl)(methyl)amino)methyl)-3-(3-hydroxy-6-methyl-2-pyridinyl)-2,4-dioxo-1,2,3,4-tetrahydrothieno[2,3-d]pyrimidin-6-yl)phenyl)-N'-ethylurea

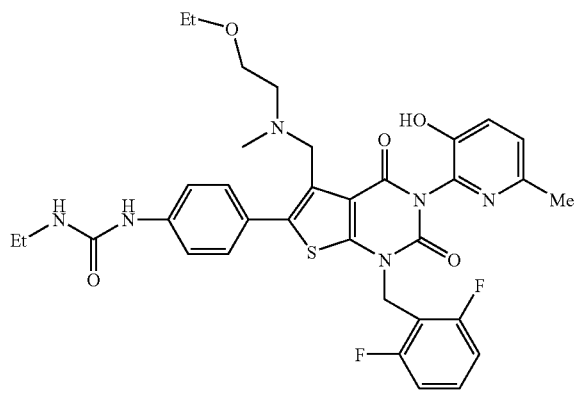

The similar reaction to that of Example 133 was performed to obtain the crude amide product (98 mg) from the compound obtained in Reference Example 24 (464 mg), 1-ethyl-3-(3-dimethylaminopropyl)-carbodiimide hydrochloride (306 mg), 1-hydroxybenzotriazole (288 mg), N-ethyl diisopropylamine (517 μl) and 2-amino-6-methyl-3-hydroxypyridine (187 mg), and then methanol (6.7 ml) and a 28% solution of sodium methoxide in methanol (52 mg) were used to give the title compound (71 mg) as colorless powder.

Elemental analysis for $C_{34}H_{36}N_6O_5SF_2 \cdot 1.5H_2O$

Calculated: C, 57.86; H, 5.57; N, 11.91. Found: C, 58.11; H, 5.47; H, 11.72.

$^1$H-NMR (CDCl$_3$+CD$_3$OD) δ: 1.08 (3H, t, J=6.9 Hz), 1.14 (3H, t, J=7.4 Hz), 2.11 (3H, s), 2.49 (3H, s), 2.69 (2H, t, J=5.7 Hz), 3.25 (2H, q, J=6.9 Hz), 3.36 (2H, q, J=7.4 Hz), 3.46 (2H, t, J=5.7 Hz), 3.58 (1H, d, J=12.6 Hz), 4.22 (1H, d, J=12.6 Hz), 5.12 (1H, d, J=15.4 Hz), 5.29 (1H, d, J=15.4 Hz), 6.90 (2H, t, J=8.0 Hz), 7.15 (2H, d, J=8.4 Hz), 7.16 (1H, d, J=8.0 Hz), 7.22-7.33 (1H, m), 7.34 (1H, d, J=8.0 Hz), 7.43 (2H, d, J=8.4 Hz).

IR (KBr): 1713, 1669, 1593, 1537, 1472 cm$^{-1}$.

Example 149

Preparation of N-(4-(1-(2,6-difluorobenzyl)-5-(((2-methoxyethyl)(methyl)amino)methyl)-3-(3-methoxy-2-pyridinyl)-2,4-dioxo-1,2,3,4-tetrahydrothieno[2,3-d]pyrimidin-6-yl)phenyl)-N'-ethylurea

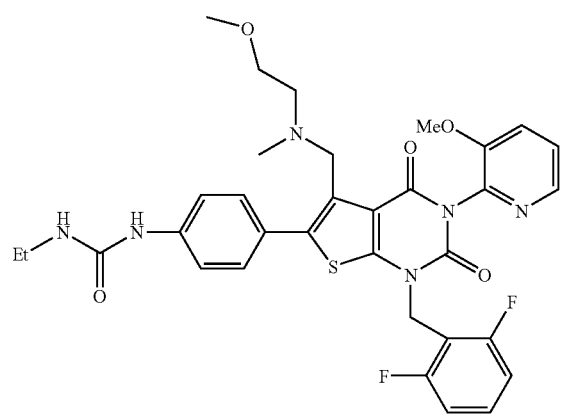

The similar reaction to that of Example 133 was performed to obtain the crude amide product (268 mg) from the compound obtained in Reference Example 9 (454 mg), diethyl phosphorocyanidate (285 μl), N-ethyl diisopropylamine (388 μl) and 2-amino-3-methoxypyridine (233 mg), and then methanol (18.5 ml) and a 28% solution of sodium methoxide in methanol (143 mg) were used to give the title compound (169 mg) as colorless powder.

Elemental analysis for $C_{33}H_{34}N_6O_5SF_2 \cdot 0.5H_2O$

Calculated: C, 58.83; H, 5.24; N, 12.47. Found: C, 58.93; H, 5.39; N, 12.29.

$^1$H-NMR (CDCl$_3$) δ: 1.13 (3H, t, J=7.4 Hz), 2.17 (3H, s), 2.61 (2H, t, J=5.9 Hz), 3.20-3.30 (2H, m), 3.25 (3H, s), 3.39 (2H, t, J=5.9 Hz), 3.81 (2H, s), 3.83 (3H, s), 4.95 (1H, t, J=5.5 Hz), 5.24 (1H, d, J=15.8 Hz), 5.39 (1H, d, J=15.8 Hz), 6.86 (1H, s), 6.90 (2H, t, J=8.1 Hz), 7.22-7.44 (5H, m), 7.55 (2H, d, J=8.4 Hz), 8.22-8.25 (1H, m).

IR (KBr): 1717, 1672, 1593, 1530, 1470 cm$^{-1}$.

Example 150

Preparation of N-(4-(1-(2,6-difluorobenzyl)-5-(((2-methoxyethyl)(methyl)amino)methyl)-3-(4-(1-methoxy-1-methylethyl)phenyl)-2,4-dioxo-1,2,3,4-tetrahydrothieno[2,3-d]pyrimidin-6-yl)phenyl)-N'-ethylurea

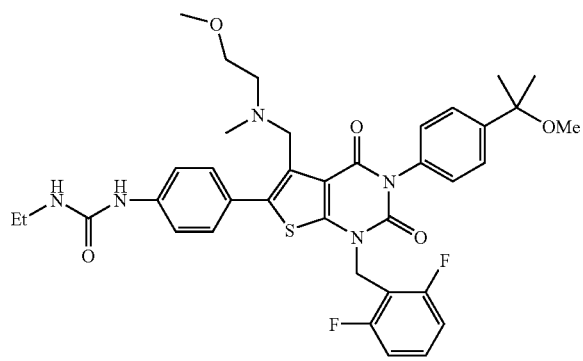

The similar reaction to that of Example 133 was performed to obtain the crude amide product (296 mg) from the compound obtained in Reference Example 9 (363 mg), diethyl phosphorocyanidate (136 µl), N-ethyl diisopropylamine (171 µl) and 4-(1-methoxy-1-methylethyl)aniline (149 mg), and then methanol (19 ml) and a 28% solution of sodium methoxide in methanol (146 mg) were used to give the title compound (143 mg) as colorless powder.

Elemental analysis for $C_{37}H_{41}N_5O_5SF_2 \cdot 0.5H_2O$

Calculated: C, 62.17; H, 5.92; N, 9.80. Found: C, 62.41; H, 5.79; N, 9.83.

$^1$H-NMR (CDCl$_3$) δ: 1.16 (3H, t, J=7.2 Hz), 2.14 (3H, s), 2.62 (2H, t, J=5.9 Hz), 3.10 (3H, s), 3.25 (3H, s), 3.24-3.33 (2H, m), 3.40 (2H, t, J=5.9 Hz), 3.82 (2H, s), 4.78 (1H, t, J=5.1 Hz), 5.35 (2H, s), 6.51 (1H, s), 6.91 (2H, t, J=8.0 Hz), 7.23-7.32 (3H, m), 7.35 (2H, d, J=8.7 Hz), 7.52 (2H, d, J=8.7 Hz), 7.55 (2H, d, J=8.7 Hz).

IR (KBr): 1715, 1672, 1593, 1534, 1470, 1316 cm$^{-1}$.

Example 151

Preparation of N-(4-(1-(2,6-difluorobenzyl)-3-isobutyl-5-(((2-methoxyethyl)(methyl)amino)methyl)-2,4-dioxo-1,2,3,4-tetrahydrothieno[2,3-d]pyrimidin-6-yl)phenyl)-N'-ethylurea

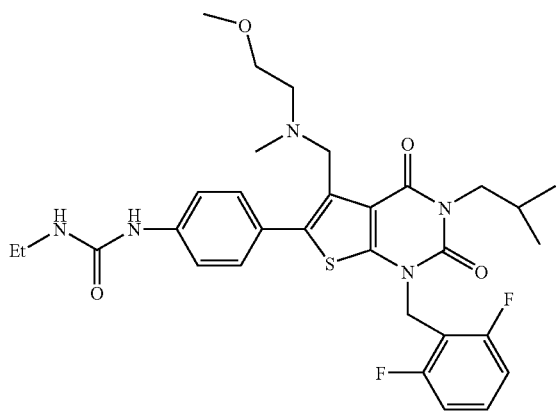

The similar reaction to that of Example 133 was performed to obtain the crude amide product (248 mg) from the compound obtained in Reference Example 9 (454 mg), diethyl phosphorocyanidate (228 µl), N-ethyl diisopropylamine (310 µl) and isobutylamine (117 mg), and then methanol (20 ml) and a 28% solution of sodium methoxide in methanol (154 mg) were reacted at 50° C. for 12 hours and were subject to the treatment as described previously to give the title compound (73 mg) as colorless powder.

Calculated: C, 60.67; H, 6.08; N, 11.41. Found: C, 60.28; H, 6.08; N, 11.31.

$^1$H-NMR (CDCl$_3$) δ: 0.94 (6H, d, J=6.9 Hz), 1.18 (3H, t, J=7.2 Hz), 2.16 (3H, s), 2.15-2.23 (2H, m), 2.65 (2H, t, J=5.9 Hz), 3.26-3.35 (2H, m), 3.29 (3H, s), 3.44 (2H, t, J=5.9 Hz), 3.85 (2H, s), 3.91 (2H, d, J=7.5 Hz), 4.71 (1H, t, J=5.7 Hz), 5.33 (2H, s), 6.37 (1H, s), 6.89 (2H, t, J=8.3 Hz), 7.23-7.30 (1H, m), 7.34 (2H, d, J=8.7 Hz), 7.55 (2H, d, J=8.7 Hz).

IR (KBr): 2961, 1705, 1661, 1593, 1537, 1472 cm$^{-1}$.

Example 152

Preparation of N-(4-(1-(2,6-difluorobenzyl)-3-(2-isopropoxy ethyl-5-(((2-methoxyethyl)(methyl)amino)methyl)-2,4-dioxo-1,2,3,4-tetrahydrothieno[2,3-d]pyrimidin-6-yl)phenyl)-N'-ethylurea

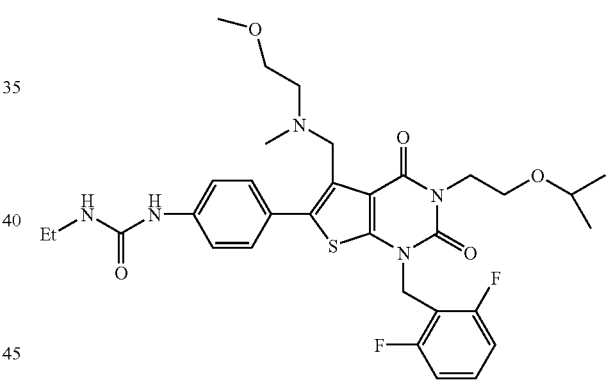

The similar reaction to that of Example 133 was performed to obtain the crude amide product (310 mg) from the compound obtained in Reference Example 9 (454 mg), diethyl phosphorocyanidate (228 µl), N-ethyl diisopropylamine (310 µl) and 2-isopropoxy ethylamine (155 mg), and then methanol (22 ml) and a 28% solution of sodium methoxide in methanol (170 mg) were used to give the title compound (150 mg) as colorless powder.

Elemental analysis for $C_{32}H_{39}N_5O_5SF_2 \cdot 0.5H_2O$

Calculated: C, 58.88; H, 6.18; N, 10.73. Found: C, 58.98; H, 6.27; N, 10.66.

$^1$H-NMR (CDCl$_3$) δ: 1.11 (6H, d, J=6.3 Hz), 1.17 (3H, t, J=7.2 Hz), 2.14 (3H, s), 2.65 (2H, t, J=5.7 Hz), 3.26-3.35 (2H, m), 3.29 (3H, s), 3.45 (2H, t, J=5.7 Hz), 3.60-3.69 (3H, m), 3.84 (2H, s), 4.26 (2H, d, J=5.7 Hz), 4.77 (1H, t, J=5.7 Hz), 5.30 (2H, s), 6.48 (1H, s), 6.88 (2H, t, J=8.3 Hz), 7.23-7.30 (1H, m), 7.34 (2H, d, J=8.7 Hz), 7.51 (2H, d, J=8.7 Hz).

IR (KBr): 2973, 1707, 1663, 1593, 1534, 1472 cm$^{-1}$.

Example 153

Preparation of N-(4-(1-(2,6-difluorobenzyl)-5-(((2-methoxyethyl)(methyl)amino)methyl)3-(1-methyl-1H-imidazol-2-yl)-2,4-dioxo-1,2,3,4-tetrahydrothieno[2,3-d]pyrimidin-6-yl)phenyl)-N'-ethylurea

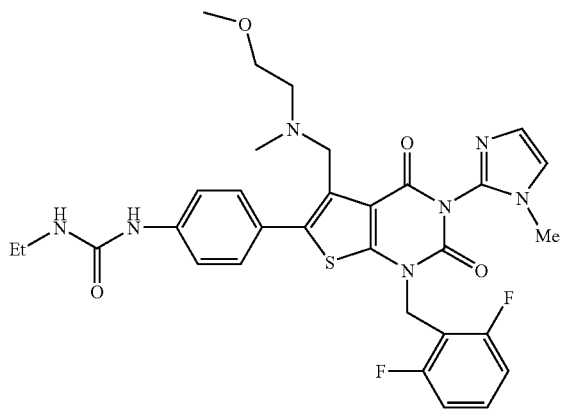

The similar reaction to that of Example 133 was performed to obtain the crude amide product (56 mg) from the compound obtained in Reference Example 9 (454 mg), diethyl phosphorocyanidate (228 µl), N-ethyl diisopropylamine (586 µl) and 2-amino-1-methylimidazole.hydrochloride (214 mg), and then methanol (3.8 ml) and a 28% solution of sodium methoxide in methanol (30 mg) were used to give the title compound (28 mg) as colorless powder.

$^1$H-NMR (CDCl$_3$) δ: 1.09 (3H, d, J=7.2 Hz), 2.09 (3H, s), 2.60 (2H, t, J=5.9 Hz), 3.18-3.27 (2H, m), 3.25 (3H, s), 3.39 (2H, t, J=5.9 Hz), 3.56 (1H, d, J=12.6 Hz), 3.56 (3H, s), 3.88 (1H, d, J=12.6 Hz), 4.70 (1H, t, J=15.6 Hz), 5.31 (1H, t, J=5.6 Hz), 5.60 (1H, d, J=15.6 Hz), 6.90 (2H, t, J=8.1 Hz), 7.06 (1H, d, J=1.5 Hz), 7.16 (1H, d, J=1.5 Hz), 7.18 (2H, d, J=8.7 Hz), 7.24-7.33 (1H, m), 7.34 (2H, d, J=8.7 Hz), 8.32 (1H, s).

IR (KBr): 1726, 1682, 1593, 1531, 1470 cm$^{-1}$.

Example 154

Preparation of N-(4-(1-(2,6-difluorobenzyl)-5-(((2-methoxyethyl)(methyl)amino)methyl)3-(6-methoxy-3-pyridanyl)-2,4-dioxo-1,2,3,4-tetrahydrothieno[2,3-d]pyrimidin-6-yl)phenyl)-N'-ethylurea

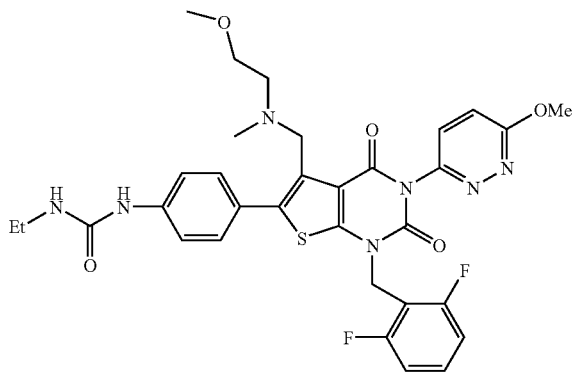

The similar reaction to that of Example 133 was performed to obtain the crude amide product (313 mg) from the compound obtained in Reference Example 9 (454 mg), diethyl phosphorocyanidate (285 µl), N-ethyl diisopropylamine (388 µl) and 3-amino-6-chloropyridazine (243 mg), and then methanol (22 ml) and a 28% solution of sodium methoxide in methanol (166 mg) were used to give the title compound (224 mg) as colorless powder.

$^1$H-NMR (CDCl$_3$) δ: 1.17 (3H, t, J=7.2 Hz), 2.05 (3H, s), 2.58 (2H, t, J=5.6 Hz), 3.22 (3H, s), 3.26-3.45 (5H, m), 3.94 (1H, brs), 4.20 (3H, s), 5.09 (1H, brs), 5.30 (1H, brs), 6.01 (1H, t, J=5.1 Hz), 6.87 (2H, t, J=8.1 Hz), 6.97 (2H, d, J=8.7 Hz), 7.25 (1H, d, J=9.0 Hz), 7.25-7.34 (1H, m), 7.36 (2H, d, J=8.7 Hz), 7.58 (2H, d, J=9.0 Hz), 8.24 (1H, s).

IR (KBr): 2975, 1717, 1674, 1593, 1532, 1462 cm$^{-1}$.

Example 155

Preparation of N-(4-(1-(2,6-difluorobenzyl)-5-(((2-ethoxyethyl)(methyl)amino)methyl)-3-(6-methoxy-3-pyridanyl)-2,4-dioxo-1,2,3,4-tetrahydrothieno[2,3-d]pyrimidin-6-yl)phenyl)-N'-ethylurea

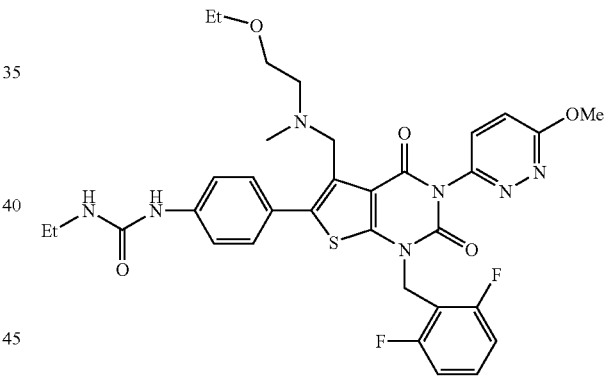

The similar reaction to that of Example 133 was performed to obtain the crude amide product (359 mg) from the compound obtained in Reference Example 24 (464 mg), diethyl phosphorocyanidate (285 µl), N-ethyl diisopropylamine (388 µl) and 3-amino-6-chloropyridazine (243 mg), and then methanol (24 ml) and a 28% solution of sodium methoxide in methanol (187 mg) were used to give the title compound (257 mg) as colorless powder.

$^1$H-NMR (CDCl$_3$) δ: 1.09 (3H, t, J=6.9 Hz), 1.17 (3H, t, J=7.2 Hz), 2.09 (3H, s), 2.62 (2H, t, J=5.7 Hz), 3.25-3.50 (7H, m), 3.95 (1H, brs), 4.20 (3H, s), 5.12 (1H, brs), 5.29 (1H, brs), 5.95 (1H, t, J=5.1 Hz), 6.87 (2H, t, J=8.0 Hz), 7.00 (2H, d, J=8.7 Hz), 7.25 (1H, d, J=9.3 Hz), 7.25-7.32 (1H, m), 7.36 (2H, d, J=8.7 Hz), 7.58 (2H, d, J=9.3 Hz), 8.16 (1H, s).

IR (KBr): 2975, 1717, 1674, 1593, 1532, 1462 cm$^{-1}$.

Example 156

Preparation of N-(4-(1-(2,6-difluorobenzyl)-5-(((2-methoxyethyl)(methyl)amino)methyl)-2,4-dioxo-3-(3-pyridanyl)-1,2,3,4-tetrahydrothieno[2,3-d]pyrimidin-6-yl)phenyl)-N'-ethylurea

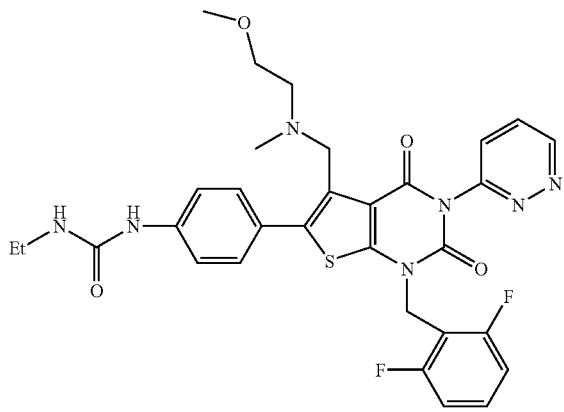

The similar reaction to that of Example 133 was performed to obtain the crude amide product (93 mg) from the compound obtained in Reference Example 9 (363 mg), diethyl phosphorocyanidate (182 μl), N-ethyl diisopropylamine (414 μl) and 3-aminopyridazine-hydrochloride (158 mg), and then ethanol (6.6 ml) and a 28% solution of sodium methoxide in methanol (51 mg) were used to give the title compound (45 mg) as colorless powder.

$^1$H-NMR (CDCl$_3$) δ: 1.21 (3H, t, J=7.2 Hz), 2.02 (3H, s), 2.54 (2H, t, J=5.9 Hz), 3.20 (3H, s), 3.25-3.37 (5H, m), 3.90 (1H, brs), 5.12 (1H, brs), 5.35 (1H, brs), 6.33 (1H, t, J=5.1 Hz), 6.87 (2H, t, J=8.1 Hz), 6.95 (2H, d, J=8.7 Hz), 7.25-7.34 (1H, m), 7.40 (2H, d, J=8.7 Hz), 7.78 (1H, dd, J=1.8 Hz, 8.4 Hz), 7.83 (1H, dd, J=4.5 Hz, 8.4 Hz), 8.27 (1H, s), 9.29 (1H, dd, J=1.8 Hz, 4.5 Hz).

IR (KBr): 2973, 1717, 1674, 1593, 1532, 1470 cm$^{-1}$.

Example 157

Preparation of N-(4-(1-(2,6-difluorobenzyl)-5-(((2-ethoxyethyl)(methyl)amino)methyl)-2,4-dioxo-3-(3-pyridanyl)-1,2,3,4-tetrahydrothieno[2,3-d]pyrimidin-6-yl)phenyl)-N'-ethylurea

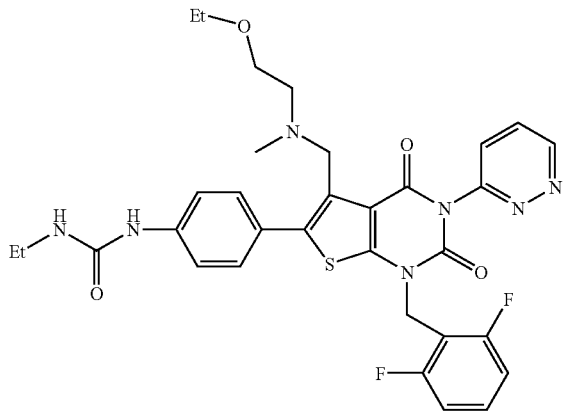

The similar reaction to that of Example 133 was performed to obtain the crude amide product (93 mg) from the compound obtained in Reference Example 24 (372 mg), diethyl phosphorocyanidate (182 μl), N-ethyl diisopropylamine (414 μl) and 3-aminopyridazine-hydrochloride (158 mg), and then methanol (6.5 ml) and a 28% solution of sodium methoxide in methanol (50 mg) were used to give the title compound (32 mg) as colorless powder.

$^1$H-NMR (CDCl$_3$) δ: 1.08 (3H, t, J=6.9 Hz), 1.20 (3H, t, J=7.3 Hz), 2.03 (3H, s), 2.55 (2H, t, J=5.8 Hz), 3.27-3.41 (7H, m), 3.89 (1H, brs), 5.14 (1H, brs), 5.34 (1H, brs), 6.39 (1H, t, J=5.3 Hz), 6.87 (2H, t, J=8.1 Hz), 6.95 (2H, d, J=8.7 Hz), 7.25-7.34 (1H, m), 7.39 (2H, d, J=8.4 Hz), 7.78 (1H, dd, J=1.8 Hz, 8.7 Hz), 7.84 (1H, dd, J=4.5 Hz, 8.7 Hz), 8.34 (1H, s), 9.29 (1H, dd, J=1.8 Hz, 4.5 Hz).

IR (KBr): 2973, 1717, 1674, 1593, 1532, 1470 cm$^{-1}$.

Example 158

Preparation of N-(4-(1-(2,6-difluorobenzyl)-5-(((2-ethoxyethyl)(methyl)amino)methyl)-2,4-dioxo-3-(2-pyrazinyl)-1,2,3,4-tetrahydrothieno[2,3-d]pyrimidin-6-yl)phenyl)-N'-ethylurea

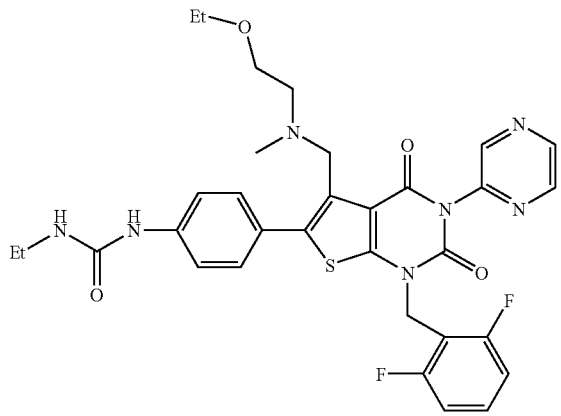

The similar reaction to that of Example 133 was performed to obtain the crude amide product (357 mg) from the compound obtained in Reference Example 24 (619 mg), diethyl phosphorocyanidate (303 μl), N-ethyl diisopropylamine (380 μl) and 2-aminopyrazine (190 mg), and then methanol (25 ml) and a 28% solution of sodium methoxide in methanol (193 mg) were used to give the title compound (170 mg) as colorless powder.

$^1$H-NMR (CDCl$_3$) δ: 1.11 (3H, t, J=6.9 Hz), 1.15 (3H, t, J=7.2 Hz), 2.14 (3H, s), 2.62 (2H, t, J=6.0 Hz), 3.24-3.33 (2H, m), 3.35-3.46 (4H, m), 3.80 (2H, s), 4.99 (1H, t, J=5.1 Hz), 5.33 (2H, s), 6.83 (1H, s), 6.92 (2H, t, J=8.3 Hz), 7.28-7.36 (1H, m), 7.38 (2H, d, J=8.7 Hz), 7.50 (2H, d, J=8.7 Hz), 8.65 (1H, s), 8.66 (1H, d, J=3.3 Hz), 8.67 (1H, d, J=3.3 Hz).

IR (KBr): 1719, 1676, 1534, 1464 cm$^{-1}$.

Preparation Example 1

Using of the compound of Example 110 (100 mg), lactose (165 mg), corn starch (25 mg), polyvinyl alcohol (4 mg) and magnesium stearate (1 mg), tablets are produced by a conventional method.

Preparation Example 2

The compound of Example 110 (5 g) is dissolved in distilled water for injection to make a total volume of 100 ml. This solution is aseptically filtered through a 0.22 μm membrane filter (produced by Sumitomo Electric Industries, Ltd. or Sartorius Corp.) and dispensed by 2 ml per washed sterile vial, followed by freeze-drying by a conventional method, to yield a 100 mg/vial of freeze-dried injectable preparation.

Preparation Example 3

Using the compound of Example 112 (100 mg), lactose (165 mg), corn starch (25 mg), polyvinyl alcohol (4 mg) and magnesium stearate (1 mg), tablets are produced by a conventional method.

Preparation Example 4

The compound of Example 112 (5 g) is dissolved in distilled water for injection to make a total volume of 100 ml. This solution is aseptically filtered through a 0.22 μm membrane filter (produced by Sumitomo Electric Industries, Ltd. or Sartorius Corp.) and dispensed by 2 ml per washed sterile vial, followed by freeze-drying by a conventional method, to yield a 100 mg/vial of freeze-dried injectable preparation.

Preparation Example 5

| (1) | The compound of Example 110 or 112 | 5 g |
|---|---|---|
| (2) | Lactose/crystalline cellulose (particles) | 330 g |
| (3) | D-mannitol | 29 g |
| (4) | Low-substituted hydroxypropyl cellulose | 20 g |
| (5) | Talc | 25 g |
| (6) | Hydroxypropyl cellulose | 50 g |
| (7) | Aspartame | 3 g |
| (8) | Dipotassium glycyrrhizinate | 3 g |
| (9) | Hydroxypropylmethyl cellulose 2910 | 30 g |
| (10) | Titanium oxide | 3.5 g |
| (11) | Yellow iron sesquioxide | 0.5 g |
| (12) | Light silicic anhydride | 1 g |

Components (1), (3), (4), (5), (6), (7) and (8) are suspended or dissolved in purified water and coated on the core particles of (2) to yield base granula subtilae, which are then further coated with components (9) through (11) to yield coated granula subtilae, which are then mixed with component (12) to yield 500 g of 1% granula subtilae of the compound KM05283. These are divided to 500 mg.

Experimental Example 1

(1) Preparation of $^{125}$I-Leuprorelin

To a tube containing 10 μl of a $3\times10^{-4}$ M aqueous solution of leuprorelin and 10 μl of 0.01 mg/ml lactoperoxidase, 10 μl (37 MBq) of a solution of Na$^{125}$I was added. After stirring, 10 μl of 0.001% H$_2$O$_2$ was added, and a reaction was carried out at room temperature for 20 minutes. By adding 700 μl of a 0.05% TFA (trifluoroacetic acid) solution, the reaction was stopped, and the solution was purified by reversed-phase HPLC. The HPLC conditions are shown below. $^{125}$I-leuprorelin was eluted at a retention time of 26 to 27 minutes.

Column: TSKgel ODS-80™ (™ indicates a registered trademark; this is true of the followings)

CTR (4.6 mm×10 cm) eluents:

Solvent A (0.05% TFA)

Solvent B (40% CH$_3$CN-0.05% TFA)

0 minute (100% Solvent A)–3 minutes (100% Solvent A)–7 minutes (50% Solvent A+50% Solvent B)–40 minutes (100% Solvent B)

Eluting temperature: Room temperature

Elution rate: 1 ml/min (2) Preparation of a Pituitary Anterior Lobe Membrane Fraction Containing Rat GnRH Receptor Anterior lobes of the pituitary glands were isolated from forty Wistar rats (8 weeks old, male), and washed with ice-cooled homogenate buffer {25 mM Tris [tris(hydroxymethyl)aminomethane]-HCl}, 0.3 M sucrose, 1 mM EGTA (glycol-etherdiamin-tetraacetic acid), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide, pH 7.5]. The pituitary gland was suspended in 2 ml of the homogenate buffer and homogenized using a Polytron homogenizer. The homogenate was centrifuged at 700×g for 15 minutes. The supernatant was taken in an ultracentrifuge tube and centrifuged at 100,000×g for 1 hour to give a membrane fraction precipitate. This precipitate was suspended in 2 ml of assay buffer (25 mM Tris-HCl, 1 mM EDTA (ethylenediamine tetraacetic acid), 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5) and the suspension was centrifuged at 100,000×g for 1 hour. The membrane fraction recovered as a precipitate was resuspended in 10 ml of assay buffer, dispensed and stored at −80° C. until it is used upon thawing.

(3) Preparation of a CHO (Chinese Hamster Ovarian) Cell Membrane Fraction Containing Human GnRH Receptor Human GnRH receptor-expressing CHO cells ($10^9$ cells) were suspended in phosphate-buffered saline supplemented with 5 mM EDTA (PBS-EDTA) and centrifuged at 100×g for 5 minutes. To the cell pellet, 10 ml of a cell homogenate buffer (10 mM NaHCO$_3$, 5 mM EDTA, pH 7.5) was added, and the mixture was homogenized using the Polytron homogenizer. After centrifugation at 400×g for 15 minutes, the supernatant was transferred to an ultracentrifugation tube and centrifuged at 100,000×g for 1 hour to give a membrane fraction precipitate. This precipitate was suspended in 2 ml of an assay buffer and centrifuged at 100,000×g for 1 hour. The membrane fraction recovered as a precipitate was resuspended in 20 ml of the assay buffer, dispensed and stored at −80° C. until it is used upon thawing.

(4) Determination of $^{125}$I-Leuprorelin Binding Inhibition Rate

The rat and human membrane fractions prepared in the above (2) and (3) were diluted with the assay buffer to give a 200 μg/ml dilution, which was then dispensed by 188 μl to each tube. When the rat pituitary anterior lobe membrane fraction was used, 2 μl of a solution of 0.1 mM compound in 60% DMSO (dimethyl sulfoxide) and 10 μl of 38 nM $^{125}$I-leuprorelin were added to each tube simultaneously. When the cell membrane fraction of the human GnRH receptor-expressing CHO cell was used, 2 μl of a solution of 2 mM compound in 60% DMSO and 10 μl of 38 nM $^{125}$I-leuprorelin were added to each tube simultaneously. To determine maximum binding amount, 2 μl of 60% DMSO and 10 μl of 38 nM $^{125}$I-leuprorelin were added to prepare a reaction solution. In addition, to determine non-specific binding amount, a reaction solution of 2 μl of 100 μM leuprorelin in 60% DMSO and 10 μl of 38 nM $^{125}$I-leuprorelin were added to prepare another reaction solution.

When the rat pituitary anterior lobe membrane fraction was used, the reaction was conducted at 4° C. for 90 minutes. When the membrane fraction of the human GnRH receptor-expressing CHO cells was used, the reaction was carried out at 25° C. for 60 minutes. After each reaction, the reaction solution was aspirated and filtered through a polyethyleneimine-treated Whatman glass filter (GF-F). After the filtration, the radioactivity of $^{125}$I-leuprorelin remaining on the filter paper was measured with a γ-counter.

(TB−SB)/(TB−NSB)×100 (SB: radioactivity when the compound is added, TB: maximum binding radioactivity, NSB: non-specific binding radioactivity) was calculated to find the binding inhibition rate (%) of each test substance. Furthermore, the inhibition rate was determined by varying the concentration of the test substance and the concentration inhibiting 50% binding ($IC_{50}$ value) of the compound was calculated from Hill plot. The results are shown as follows.

TABLE 1

| Test Substance | $IC_{50}$ value (μM) | |
| --- | --- | --- |
|  | Rat | Human |
| Compound of Ex. 110 | 0.2 | <0.0001 |
| Compound of Ex. 112 | 0.2 | 0.0001 |

INDUSTRIAL APPLICABILITY

A compound of the present invention possesses excellent gonadotropin-releasing hormone antagonizing activity. It is also good in oral absorption and excellent in stability and pharmacokinetics. With low toxicity, it is also excellent in safety. Therefore, the compound of the present invention can be used as an agent for preventing or treating hormone-dependent diseases and the like. Specifically, it is effective as an agent for preventing or treating sex hormone-dependent cancers (e.g., prostatic cancer, uterine cancer, breast cancer, pituitary tumor etc.), prostatic hypertrophy, hysteromyoma, endometriosis, uterine fibroid, precocious puberty, amenorrhea, premenstrual syndrome, multilocular ovary syndrome, polycystic ovary syndrome, pimple, alopecia, Alzheimer's disease and the like. The compound of the present invention is also useful as pregnancy regulating agent (e.g., contraceptive), an agent for treating infertility, an agent for regulating menstrual cycle, an agent for preventing and/or treating irritable bowel syndrome or an agent for preventing recurrence of post-operative sex hormone-dependent cancers. In addition, the compound of the present invention is useful for regulation of animal estrous, improvement of food meat quality and promotion of animal growth in the field of animal husbandry. The compound of the present invention is also useful as a fish spawning promoter in the field of fishery.

The invention claimed is:

1. A compound represented by the formula

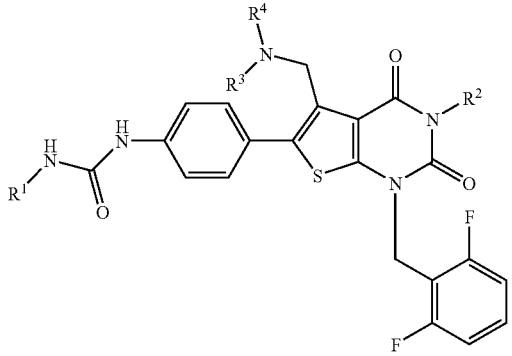

wherein $R^1$ is $C_{1-4}$ alkyl, $R^2$ is (I) phenyl optionally having 1 to 3 substituents selected from (1) amino, (2) —$NR^5COR^6$ ($R^5$ is a hydrogen atom, and $R^6$ is $C_{1-4}$ alkyl, or mono $C_{1-4}$ alkylamino), (3) —$CONR^9R^{10}$ ($R^9$ is a hydrogen atom, $C_{1-4}$ alkyl or $C_{3-8}$ cycloalkyl, $R^{10}$ is a hydrogen atom or $C_{1-4}$ alkyl), (4) —$CO_2R^{13}$ ($R^{13}$ is $C_{1-4}$ alkyl), (5) $C_{1-4}$ alkoxy optionally having a hydroxyl group, $C_{1-4}$ alkoxy, $C_{1-4}$ alkyl-carbonyloxy, —$NR^7SO_2R^8$ ($R^7$ is a hydrogen atom and $R^8$ is $C_{1-4}$alkyl), —$CONR^9R^{10}$ ($R^9$ is a hydrogen atom or $C_{1-4}$ alkyl and $R^{10}$ is a hydrogen atom or $C_{1-4}$ alkyl, or $R^9$ and $R^{10}$ form a ring together with the adjacent nitrogen atom) or —$CO_2R^{13}$ ($R^{13}$ is $C_{1-4}$ alkyl), (6) $C_{1-4}$ alkyl optionally having a hydroxyl group, —$CONR^9R^{10}$ ($R^9$ is a hydrogen atom or $C_{1-4}$ alkyl and $R^{10}$ is $C_{1-4}$ alkyl) or $C_{1-4}$ alkoxy, (7) a halogen atom, (8) a hydroxyl group and (9) nitro (II) a heterocyclic group optionally having 1 to 3 substituents selected from $C_{1-4}$ alkoxy, $C_{1-4}$ alkyl, a halogen atom, a hydroxyl group and oxo, (III) $C_{3-8}$ cycloalkyl optionally having a hydroxyl group, or (IV) $C_{1-4}$ alkyl optionally having 1 to 3 substituents selected from (1) a 5 to 7-membered nitrogen-containing heterocyclic group, (2) a hydroxyl group and (3) $C_{1-4}$ alkoxy, $R^3$ is a hydrogen atom or $C_{1-4}$ alkyl, and $R^4$ is (I) $C_{1-4}$ alkyl having 1 to 3 substituents selected from (1)—$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (2) a 5 to 7-membered nitrogen-containing heterocyclic group optionally having (1') hydroxy-$C_{1-4}$ alkyl, (2') $C_{1-4}$ alkoxy-carbonyl or (3') mono $C_{1-4}$ alkyl-carbamoyl, (3) $C_{1-4}$ alkoxy-carbonyl, (4) carboxyl and (5) N—$C_{1-4}$ alkyl-N—$C_{7-10}$ aralkylamino or (II) $C_{3-8}$ cycloalkyl, or a salt thereof.

2. The compound according to claim 1, or a salt thereof, wherein $R^1$ is $C_{1-4}$ alkyl, $R^2$ is (I) phenyl optionally having 1 to 3 substituents selected from (1) amino, (2) —$NR^5COR^6$ ($R^5$ is a hydrogen atom, and $R^6$ is $C_{1-4}$ alkyl or mono $C_{1-4}$ alkylamino), (3) —$CONR^9R^{10}$ ($R^9$ is a hydrogen atom, $C_{1-4}$ alkyl, or $C_{3-8}$ cycloalky, $R^{10}$ is a hydrogen atom or $C_{1-4}$ alkyl), (4) —$CO_2R^{13}$ ($R^{13}$ is $C_{1-4}$ alkyl), (5) $C_{1-4}$ alkoxy optionally having a hydroxyl group, $C_{1-4}$ alkoxy, $C_{1-4}$ alkyl-carbonyloxy, —$NR^7SO_2R^8$ ($R^7$ is a hydrogen atom and $R^8$ is $C_{1-4}$ alkyl), —$CONR^9R^{10}$ ($R^9$ is a hydrogen atom or $C_{1-4}$ alkyl and $R^{10}$ is a hydrogen atom or $C_{1-4}$ alkyl, or $R^9$ and $R^{10}$ form a ring together with the adjacent nitrogen atom) or —$CO_2R^{13}$ ($R^{13}$ is $C_{1-4}$ alkyl), (6) $C_{1-4}$ alkyl optionally having a hydroxyl group, —$CONR^9R^{10}$ ($R^9$ is a hydrogen atom or $C_{1-4}$ alkyl and $R^{10}$ is $C_{1-4}$ alkyl) or $C_{1-4}$ alkoxy, (7) a halogen atom, (8) a hydroxyl group and (9) nitro, (II) a heterocyclic group optionally having 1 to 3 substituents selected from $C_{1-4}$ alkoxy, $C_{1-4}$ alkyl, a halogen atom, a hydroxyl group and oxo, or (III) $C_{3-8}$ cycloalkyl optionally having a hydroxyl group, $R^3$ is a hydrogen atom or $C_{1-4}$ alkyl, and $R^4$ is (I) $C_{1-4}$ alkyl having 1 to 3 substituents selected from (1) —$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (2) a 5 to 7-membered nitrogen-containing heterocyclic group, (3) $C_{1-4}$ alkoxy-carbonyl, (4) carboxyl and (5) N-$C_{1-4}$ alkyl-N-$C_{7-10}$ aralkylamino or (II) $C_{3-8}$ cycloalkyl.

3. The compound according to claim 1, or a salt thereof, wherein
R$^1$ is C$_{1-4}$ alkyl,
R$^2$ is
(I) phenyl optionally having 1 to 3 substituents selected from (1)amino, (2) —NHCOR$^{6'}$ (R$^{6'}$ is C$_{1-4}$ alkyl or mono C$_{1-4}$ alkylamino), (3) —CONR$^9$R$^{10}$ (R$^9$ is a hydrogen atom, or C$_{1-4}$ alkyl or C$_{3-8}$ cycloalkyl, R$^{10}$ is a hydrogen atom or C$_{1-4}$ alkyl), (4) —CO$_2$R$^{13}$ (R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy, —NHSO$_2$R$^{8'}$ (R$^{8'}$ is C$_{1-4}$ alkyl) or —CONR$^9$R$^{10}$ (R$^9$ is a hydrogen atom or C$_{1-4}$ alkyl and R$^{10}$ is a hydrogen atom or C$_{1-4}$" alkyl, or R$^9$ and R$^{10}$ form a ring together with the adjacent nitrogen atom), (6) C$_{1-4}$ alkyl optionally having a hydroxyl group, —CONR$^9$R$^{10}$ (R$^9$ is a hydrogen atom or C$_{1-4}$ alkyl and R$^{10}$ is C$_{1-4}$ alkyl) or C$_{1-4}$ alkoxy, (7) a halogen atom, (8) a hydroxyl group and (9) nitro,
(II) a 5 to 8-membered nitrogen-containing heterocyclic group optionally having (1) C$_{1-4}$ alkyl, (2) C$_{1-4}$ alkoxy, (3) a halogen atom, (4) a hydroxyl group or (5) oxo,
(III) C$_{3-8}$ cycloalkyl optionally having a hydroxyl group or
(IV) C$_{1-4}$ alkyl optionally having 1 to 3 substituents selected from (1) a 5 to 7-membered nitrogen-containing heterocyclic group, (2) a hydroxyl group and (3) C$_{1-4}$ alkoxy,
R$^3$ is a hydrogen atom or C$_{1-4}$ alkyl, and
R$^4$ is
(I) C$_{1-4}$ alkyl having 1 to 3 substituents selected from (1) —CONR$^{18}$R$^{19}$ R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (2) a 5 to 7-membered nitrogen-containing heterocyclic group optionally having (1') hydroxy-C$_{1-4}$ alkyl, (2') C$_{1-4}$ alkoxy-carbonyl or (3') mono C$_{1-4}$ alkyl-carbamoyl, (3) C$_{1-4}$ alkoxy-carbonyl, (4) carboxyl and (5) N—C$_{1-4}$ alkyl-N—C$_{7-10}$ aralkylamino or
(II) C$_{3-8}$ cycloalkyl.

4. The compound according to claim 1, or a salt thereof, wherein R$^1$ is ethyl.

5. The compound according to claim 1, or a salt thereof, wherein R$^2$ is phenyl optionally having 1 to 3 substituents selected from (1)amino, (2) —NHCOR$^{6'}$ (R$^{6'}$ is C$_{1-4}$ alkyl or mono C$_{1-4}$ alkylamino), (3) —CONR$^{9'}$R$^{10'}$ (R$^{9'}$ is a hydrogen atom, C$_{1-4}$ alkyl or C$_{3-8}$ cycloalkyl, R$^{10'}$ is a hydrogen atom or C$_{1-4}$ alkyl), (4) —CO$_2$R$^{13}$ (R$^{13}$ is C$_{1-4}$alkyl), (5) C$_{1-4}$ alkoxy optionally having a hydroxyl group, C$_{1-4}$ alkoxy, or —CONR$^{9'}$R$^{10'}$ (R$^{9'}$ is a hydrogen atom or C$_{1-4}$ alkyl and R$^{10}$' is a hydrogen atom or C$_{1-4}$ alkyl, or R$^{9'}$ and R$^{10'}$ form a ring together with the adjacent nitrogen atom), (6) C$_{1-4}$ alkyl optionally having a hydroxyl group or —CONR$^{9'\ R10'}$ (R$^{9'}$ is a hydrogen atom or C$_{1-4}$ alkyl and R$^{10'}$ is C$_{1-4}$ alkyl), (7) a halogen atom, (8) a hydroxyl group and (9) nitro.

6. The compound according to claim 1, or a salt thereof, wherein R$^3$ is methyl.

7. The compound according to claim 1, or a salt thereof, wherein R$^4$ is C$_{1-4}$ alkyl having 1 to 3 substituents selected from (1) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (2) a 5 to 7-membered nitrogen-containing heterocyclic group, (3) C$_{1-4}$ alkoxy-carbonyl, (4) carboxyl and (5) N—C$_{1-4}$ alkyl-N—C$_{7-10}$ aralkylamino.

8. The compound according to claim 1, or a salt thereof, wherein
R$^1$ is ethyl,
R$^2$ is phenyl optionally having 1 to 3 substituents selected from (1)amino, (2) —NHCOR$^{6'}$ (R$^{6'}$ is C$_{1-4}$ alkyl or mono C$_{1-4}$ alkylamino), (3) —CONR$^{9'}$ R$^{10'}$ (R$^{9'}$ is a hydrogen atom, C$_{1-4}$ alkyl or C$_{3-8}$ cycloalkyl, R$^{10'}$ is a hydrogen atom or C$_{1-4}$ alkyl), (4) —CO$_2$R$^{13}$ (R$^{13}$ is C$_{1-4}$ alkyl), (5)C$_{1-4}$ alkoxy optionally having a hydroxyl group, C$_{1-4}$ alkoxy, C$_{1-4}$ alkyl-carbonyloxy or —CONR$^{9'}$R$^{10'}$ (R$^{9'}$ is a hydrogen atom or C$_{1-4}$ alkyl and R$^{10}$ ' is a hydrogen atom or C$_{1-4}$ alkyl, or R$^{9'}$ and R$^{10'}$ form a ring together with the adjacent nitrogen atom), (6) C$_{1-4}$ alkyl optionally having a hydroxyl group or —CONR$^{9'}$R$^{10'}$(R$^{9'}$ is a hydrogen atom or C$_{1-4}$ alkyl and R$^{10'}$ is C$_{1-4}$ alkyl), (7) a halogen atom, (8) a hydroxyl group and (9)nitro,
R$^3$ is methyl, and
R$^4$ is C$_{1-4}$ alkyl having 1 to 3 substituents selected from (1) —CONR$^{18}$R$^{19}$ (R$^{18}$ is a hydrogen atom or C$_{1-4}$ alkyl, R$^{19}$ is C$_{1-4}$ alkyl optionally having C$_{1-4}$ alkoxy, or R$^{18}$ and R$^{19}$ may form a ring together with the adjacent nitrogen atom), (2) a 5 to 7-membered nitrogen-containing heterocyclic group, (3) C$_{1-4}$ alkoxy-carbonyl, (4) carboxyl and (5) N—C$_{1-4}$ alkyl-N—C$_{7-10}$ aralkylamino.

9. N-{4-[1-(2,6-difluorobenzyl)-3-(4-fluorophenyl)-5-({methy[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea or N-{4-[1-(2,6-difluorobenzyl)-3-[4-(2-methoxyethoxy)phenyl]-5-({methyl[2-(2-oxo-1-piperidinyl)ethyl]amino}methyl)-2,4-dioxo-1,2,3,4-tetrahydrothieno[2,3-d]pyrimidin-6-yl]phenyl}-N'-ethylurea, or a salt thereof.

10. A pharmaceutical composition comprising a compound represented by the formula

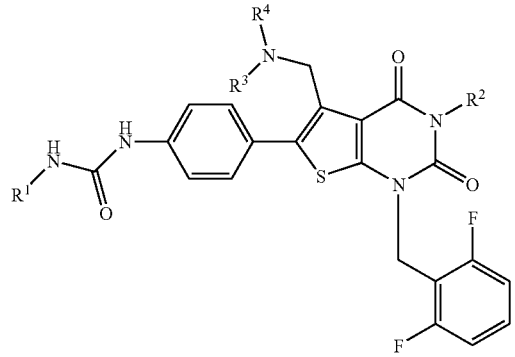

wherein
R$^1$ C$_{1-4}$
R$^2$ is
(I) phenyl optionally having 1 to 3 substituents selected from (1) amino, (2) —NR$_5$COR6 (R$^5$ is a hydrogen atom, and R$^6$ is C$_{14}$ alkyl or mono C$_{1-4}$ alkylamino), (3) —CONR$^9$R$^{10}$(R is a hydrogen atom, C$_{1-4}$ alkyl or C$_{3-8}$ cycloalkyl, R$^{10}$ is a hydrogen atom or C$_{1-4}$ alkyl), (4) —CO$_2$R$^{13}$(R$^{13}$ is C$_{1-4}$ alkyl), (5) C$_{1-4}$ alkoxy optionally having a hydroxyl group, C$_{1-4}$ alkoxy, C$_{1-4}$ alkyl-carbonyloxy, —NR$^7$SO$_2$R$^{8(R}$7 is a hydrogen atom and R$^8$ is C$_{1-4}$ alkyl), —CONR$^9$R$^{10}$(R is a hydrogen atom or C$_{1-4}$ alkyl and R$^{10}$is a hydrogen atom or C$_{1-4}$ alkyl, or R$_9$ and R$_{10}$ form a ring together with the adjacent nitrogen atom) or —CO$_2$R$^{13}$ (R$^{13}$ is C$_{1-4}$ alkyl), (6) C$_{1-4}$ alkyl optionally having a hydroxyl group, —CONR$^9$R$^{10}$ (R$^9$ is a hydrogen atom or $C_{1-4}$ alkyl and $R^{10}$ is $C_{1-4}$ alkyl) or $C_{1-4}$ alkoxy, (7) a halogen atom, (8) a hydroxyl group and (9) nitro (II) a heterocyclic group optionally having 1 to 3 substituents selected from $C_{1-4}$ alkoxy, $C_{1-4}$ alkyl, a halogen atom, a hydroxyl group and oxo, (III) $C_{3-8}$ cycloalkyl optionally having a hydroxyl group, or (IV) $C_{1-4}$ alkyl optionally having 1 to 3 substituents selected from (1) a 5 to 7-membered nitrogen-containing heterocyclic group, (2) a hydroxyl group and (3) $C_{1-4}$ alkoxy, $R^3$ is a hydrogen atom or $C_{1-4}$ alkyl, and R4 is (I) $C_{1-4}$ alkyl having 1 to 3 substituents selected from 1) —$CONR^{18}R^{19}$ ($R^{18}$ is a hydrogen atom or $C_{1-4}$ alkyl, $R^{19}$ is $C_{1-4}$ alkyl optionally having $C_{1-4}$ alkoxy, or $R^{18}$ and $R^{19}$ may form a ring together with the adjacent nitrogen atom), (2) a 5 to 7-membered nitrogen-containing heterocyclic group optionally having (1') hydroxy-$C_{1-4}$ alkyl, (2') $C_{1-4}$ alkoxy-carbonyl or (3') mono $C_{1-4}$ alkyl-carbamoyl, (3) $C_{1-4}$ alkoxy-carbonyl, (4) carboxyl and (5) N—$C_{1-4}$ alkyl-N—$C_{7-10}$ aralkylamino or (II) $C_{3-8}$ cycloalkyl (provided that when $R^2$ is phenyl which is mono-substituted with a halogen atom, $R^4$ is not $C_{1-4}$ alkyl which is substituted with $C_{1-4}$ alkoxy), or a salt thereof, and a pharmaceutically acceptable carrier, excipient or diluent.

11. A method for manufacturing an agent for antagonizing gonadotropin-releasing hormone, which comprises incorporating the compound according to claim 1 or a salt thereof into a pharmaceutically acceptable carrier, excipient or diluent.

* * * * *